(12) United States Patent
Brown et al.

(10) Patent No.: US 12,378,551 B2
(45) Date of Patent: Aug. 5, 2025

(54) MULTIMERIC OLIGONUCLEOTIDES HAVING DECREASED KIDNEY CLEARANCE

(71) Applicant: MPEG LA, L.L.C., Chevy Chase, MD (US)

(72) Inventors: Jonathan Miles Brown, Larchmont, NY (US); Kristin K. H. Neuman, Chevy Chase, MD (US); Hans-Peter Vornlocher, Kulmbach (DE); Philipp Hadwiger, Kulmbach (DE)

(73) Assignee: MPEG LA, L.L.C., Chevy Chase, MD (US)

( * ) Notice: Subject to any disclaimer, the term of this patent is extended or adjusted under 35 U.S.C. 154(b) by 27 days.

(21) Appl. No.: 17/305,225

(22) Filed: Jul. 1, 2021

(65) Prior Publication Data

US 2021/0380979 A1    Dec. 9, 2021

Related U.S. Application Data

(62) Division of application No. 15/889,975, filed on Feb. 6, 2018, now Pat. No. 11,078,484.

(60) Provisional application No. 62/561,853, filed on Sep. 22, 2017, provisional application No. 62/522,363, filed on Jun. 20, 2017, provisional application No. 62/455,231, filed on Feb. 6, 2017.

(51) Int. Cl.
| | |
|---|---|
| C07H 21/04 | (2006.01) |
| A61K 31/713 | (2006.01) |
| C12N 15/11 | (2006.01) |
| C12N 15/113 | (2010.01) |

(52) U.S. Cl.
CPC .......... *C12N 15/113* (2013.01); *A61K 31/713* (2013.01); *C12N 15/111* (2013.01); *C12N 2310/14* (2013.01); *C12N 2310/315* (2013.01); *C12N 2310/351* (2013.01); *C12N 2310/3519* (2013.01); *C12N 2310/51* (2013.01); *C12N 2320/32* (2013.01); *C12N 2320/53* (2013.01)

(58) Field of Classification Search
None
See application file for complete search history.

(56) References Cited

U.S. PATENT DOCUMENTS

| | | | |
|---|---|---|---|
| 5,552,535 A | 9/1996 | McLean et al. |
| 6,218,371 B1 | 4/2001 | Krieg et al. |
| 8,106,173 B2 | 1/2012 | Kandimalla et al. |
| 8,110,674 B2 | 2/2012 | Manoharan et al. |
| 8,188,261 B2 | 5/2012 | Kandimalla et al. |
| 8,362,233 B2 | 1/2013 | Kandimalla et al. |
| 8,431,544 B1 | 4/2013 | Agrawal et al. |
| 8,580,946 B2 | 11/2013 | Park et al. |
| 8,759,310 B2 | 6/2014 | Kandimalla et al. |
| 9,243,050 B2 | 1/2016 | Kandimalla et al. |
| 9,255,269 B2 | 2/2016 | Park et al. |
| 9,616,085 B2 | 4/2017 | Hong et al. |
| 9,644,209 B2 | 5/2017 | Park et al. |
| 10,597,659 B2 | 3/2020 | Park et al. |
| 11,078,484 B2 | 8/2021 | Brown et al. |
| 11,352,629 B2 | 6/2022 | Hadwiger et al. |
| 11,767,531 B2 | 9/2023 | Hadwiger et al. |
| 11,859,184 B2 | 1/2024 | Park et al. |
| 2004/0235773 A1 | 11/2004 | Zhao et al. |
| 2007/0287681 A1 | 12/2007 | Jeong et al. |
| 2008/0108801 A1 | 5/2008 | Manoharan et al. |
| 2008/0214436 A1 | 9/2008 | Yu et al. |
| 2008/0287383 A1 | 11/2008 | Quay et al. |
| 2008/0311040 A1 | 12/2008 | Berry et al. |
| 2009/0126038 A1 | 5/2009 | Van De craen et al. |
| 2012/0065243 A1 | 3/2012 | Woolf et al. |
| 2013/0064786 A1 | 3/2013 | Hong et al. |
| 2013/0330293 A1 | 12/2013 | Long et al. |
| 2014/0066592 A1 | 3/2014 | Yu et al. |
| 2014/0194610 A1 | 7/2014 | Verdine et al. |
| 2014/0309281 A1 | 10/2014 | Park et al. |
| 2015/0197754 A9 | 7/2015 | Park et al. |
| 2015/0299695 A1 | 10/2015 | Uhlmann et al. |
| 2015/0315585 A1 | 11/2015 | Uhlmann et al. |
| 2016/0193354 A1 | 7/2016 | Noe et al. |
| 2016/0298124 A1 | 10/2016 | Borodovsky et al. |
| 2016/0347780 A1 | 12/2016 | Wada et al. |
| 2017/0189525 A1 | 7/2017 | Brunskill et al. |

(Continued)

FOREIGN PATENT DOCUMENTS

| | | |
|---|---|---|
| JP | 2009-502198 | 1/2009 |
| JP | 2014-527819 | 10/2014 |

(Continued)

OTHER PUBLICATIONS

Lee et al. ("Dual gene targeted multimeric siRNA for combinatorial gene silencing." Biomaterials 32.9 (2011): 2359-2368).*
Kim, Dajeong, et al. ("Multimeric RNAs for efficient RNA-based therapeutics and vaccines." Journal of Controlled Release 345 (2022): 770-785).*
Examination Report in Australian Application No. 2018215684, dated Jan. 8, 2024, in 4 pages.
Brown, JM et al., Ligan Conjugated Multimeric siRNAs Enable Enhanced Uptake and Multiplexed Gene Silencing. Nucieic Acid Therapeutics, Sep. 26, 2019, vol. 29, No. 5, pp. 231-244; entire document. DOI: 10.1089/nat.2019.0782.

(Continued)

*Primary Examiner* — Kimberly Chong
(74) *Attorney, Agent, or Firm* — KNOBBE, MARTENS, OLSON & BEAR, LLP

(57) ABSTRACT

The present invention relates to methods of administering to a subject multimeric oligonucleotides having monomeric subunits joined by linkers. The multimeric oligonucleotides have a molecular weight of at least about 45 kD and other characteristics, such that their clearance due to glomerular filtration is reduced. The present invention also relates to such multimeric oligonucleotides and methods of synthesizing such multimeric oligonucleotides.

19 Claims, 51 Drawing Sheets

Specification includes a Sequence Listing.

(56) References Cited

U.S. PATENT DOCUMENTS

| | | |
|---|---|---|
| 2017/0204408 A9 | 7/2017 | Lewis |
| 2017/0349896 A1 | 12/2017 | Albaek et al. |
| 2018/0080028 A1 | 3/2018 | Park et al. |
| 2018/0312839 A1 | 11/2018 | Bhat et al. |
| 2019/0062743 A1 | 2/2019 | Uhlmann et al. |
| 2019/0085331 A1* | 3/2019 | Hadwiger ............. C12N 15/111 |
| 2020/0239892 A1 | 7/2020 | Park et al. |
| 2020/0308578 A1 | 10/2020 | Woolf et al. |
| 2022/0290148 A1 | 9/2022 | Hadwiger et al. |
| 2023/0114023 A1 | 4/2023 | Brown et al. |
| 2023/0279390 A1 | 9/2023 | Brown |
| 2023/0287406 A1 | 9/2023 | Brown et al. |
| 2024/0150766 A1 | 5/2024 | Park et al. |
| 2024/0191240 A1 | 6/2024 | Hadwiger et al. |

FOREIGN PATENT DOCUMENTS

| | | |
|---|---|---|
| JP | 2017-565893 A | 7/2018 |
| JP | 2011-518784 | 10/2019 |
| KR | 10-2011-0083919 A | 7/2011 |
| WO | WO 2004/030634 A2 | 4/2004 |
| WO | WO 2004/090108 A2 | 10/2004 |
| WO | WO 2004/091515 A2 | 10/2004 |
| WO | WO 2004/094345 A2 | 11/2004 |
| WO | WO 2004/094595 A2 | 11/2004 |
| WO | WO 2007/117686 A2 | 10/2007 |
| WO | WO 2008/109105 A2 | 9/2008 |
| WO | WO 2009/014887 A2 | 1/2009 |
| WO | WO 2009/126933 A2 | 10/2009 |
| WO | WO2010/021720 A1 | 2/2010 |
| WO | WO 2010/064146 | 6/2010 |
| WO | WO 2011/031520 A1 | 3/2011 |
| WO | WO 2011/109380 A1 | 9/2011 |
| WO | WO 2013/040429 A1 | 3/2013 |
| WO | WO 2014/043544 A1 | 3/2014 |
| WO | WO 2014/113802 A1 | 7/2014 |
| WO | WO 2014/208973 | 12/2014 |
| WO | WO 2015/001336 | 1/2015 |
| WO | WO 2016/110691 | 7/2016 |
| WO | WO 2017/004357 | 1/2017 |
| WO | WO 2018/030338 | 2/2018 |
| WO | WO 2018/223073 | 12/2018 |
| WO | WO 2019/105421 A1 | 6/2019 |

OTHER PUBLICATIONS

Elbashir et al. (2001), "Duplexes of 21-nucleotide RNAs mediate RNA interference in cultured mammalian cells," Nature, 411: 494-498.

Jeong, J.H., et al., siRNA conjugate delivery systems. Bioconjug Chem. Jan. 2009;20(1):5-14. doi: 10.1021/bc800278e.

Kang et al. "HER2 RNA Aptamerand Cell Penetrating Peptide-Mediated Delivery of Multimeric Antisense Strands of siRNAs for Gene Silencing: Multimeric antisense strands of siRNAS", bull. Korean chem. Soc., vol. 37, No. 9, Aug. 29, 2016, pp. 1440-1444, XPO55746857, ISSN: 1229-5949, DOI: 10.1002/bkcs.10886.

Kim, S.H., et al., Local and systemic delivery of VEGF siRNA using polyelectrolyte complex micelles for effective treatment of cancer. J Control Release. Jul. 14, 2008;129(2): 107-16. doi: 10.1016/j.jconrel.2008.03.008. Epub Mar. 14, 2008.

Kim, S.H., et al., LHRH receptor-mediated delivery of siRNA using polyelectrolyte complex micelles self-assembled rom siRNA-PEG-LHRH conjugate and PEI. Bioconjug Chem. Nov. 19, 2008;19(11):2156-62. doi: 10.1021/bc800249n.

Kim et al. (2006) "PEG conjugated VEGF siRNA for anti-angiogenic gene therapy," Journal of Controlled Release, 116:123-129.

Lee et al., (2012) "Molecularly Self-Assembled Nucleic-Acid Nanoparticles for Targeted in Vivo siRNA Delivery," Nature Nanotechnology, 7(6):389-393.

Lee et al., (2012) "Small-Interfering RNA (siRNA)-Based Functional Micro-and Nanostructures for Efficient and Selective Gene Silencing," Accounts of Chemical Research, 45(7):1014-1025.

Mok et al., "Self-crosslinked and reducible fusogenic peptides for intracellular delivery of siRNA", Biopolymers. J008 Ocl;89(10):881-8. doi: 10.1002/bip.21032.

Mok et al., "Multimeric small interfering ribonucleic acid for highly efficient sequence-specific gene silencing", Natural Materials, vol. 9(3):272-278 (2010).

Moschos, S.A, et al., Lung delivery studies using siRNA conjugated to TAT(48-60) and penetralin reveal peptide nduced reduction in gene expression and induction of innate immunity. Bioconjug Chem. Sep. 2007-Ocl;18(5):1450-9. Epub Aug. 21, 2007.

Muratovska, A., et al., Conjugate for efficient delivery of short interfering RNA (siRNA) into mammalian cells. FEBS Lett. Jan. 30, 2004;558(1-3):63-8.

Schiffelers RM, et al. "Cancer siRNA therapy by tumor selective delivery with ligand-targeted sterically stabilized nanoparticle", Nucleic Acids Res. 32 (2004) e149. Published Oct. 1, 2004.

Subramanian et al., "Enhancing Antisense Efficacy with Multimers and Multi-Targeting Oligonucleotides (MTOs) Using Cleavable Linkers," Nucleic Acids Research, Oct. 7, 2015, vol. 43, Issue 19, pp. 9123-9132.

Sugo, T. et al., Development of antibody-siRNA conjugate targeted to cardiac and skeletal muscles, Journal of Controlled Release, 237 (2016) 1-13.

Sun et al., (1997) "Synthesis of 3'-thioribonucleosides and their incorporation into oligoribonucleotides via phosphoramidite chemistry," RNA, 3(11 ):1352-63.

Tai, Wanyi, Bin Qin, and Kun Cheng. "Inhibition of breast cancer cell growth and invasiveness by dual silencing of HER-2 and VEGF." Molecular pharmaceutics 7.2 (2010): 543-556.

Xu, et al., "Delivery systems for siRNA drug development in cancer therapy", Asian Journal of Pharmaceutical Sciences, Aug. 28, 2014, vol. 10, No. 1, pp. 1-12.

Yoo et al., "Multivalent comb-type aptamer-siRNA conjugates for efficient and selective intracellular delivery", Chemical Communications, vol. 50, No., 51, May 8, 2014, pp. 6765-6767, XP055747253.

Notice of Allowance in U.S. Appl. No. 15/889,975 dated Mar. 29, 2021, 9 pages.

International Preliminary Report on Patentability for International Application No. PCT/US2018/017062, mailing date of Aug. 6, 2019, in 10 pages.

Extended European Search Report for European Application No. 18747398, mailing date of Nov. 16, 2020, in 12 pages.

International Search Report and Written Opinion for Singapore Application No. 11201906728T, mailing date Nov. 24, 2020, in 12 pages.

Hong et al., "Gene Silencing by siRNA Microhydrogels via Polymeric Nanoscale Condensation", Aug. 2011, JAGS, 133: 13914-13917.

Kashihara et al, "Analysis of Renal Microcirculation and Permeability-Change with Bio-Imaging Techniques", Kenbikyo, 2011, vol. 46, No. 3, p. 181-187.

Motoyashi et al., "Glomerular Disease and tubule injury", Japanese Journal of Pediatric Nephrology, 2009, vol. 22, No. 2, p. 76-81.

Rinsho Yakuri, Japanese Journal of Clinical Pharmacology and Therapeutics, 2016, vol. 47, No. 2, p. 56-61.

Zhang et al., "Synthesis and Biological Evaluation of Bivalent Ligands for the Cannabinoid 1 Receptor" Journal of Medicinal Chemistry, 53, pp. 7048-7060.

Office Action in Chinese Application 201880010283.4 dated Jun. 6, 2022, in 11 pages.

International Search Report and Written Opinion for International Application No. PCT/US2018/017062, mailing date of Apr. 13, 2018, in 3 pages.

Notice of Reasons for Rejection in Japanese Application 2019-542485 dated Feb. 24, 2022, in 10 pages.

Written Opinion for Singapore Application No. 11201906728T, mailing date Feb. 21, 2022, in 7 pages.

Office Action in Israel Application No. 267806, dated Nov. 2, 2022, with English translation.

Office Action in Korean Application No. 10-2019-1083090, dated Jan. 10, 2023, 6 pages.

English Translation of Office Action in Chinese Application No. 201880010283.1, issued on Feb. 11, 2023.

(56) References Cited

OTHER PUBLICATIONS

Examination Report in Australian Application No. 2018215684, dated Mar. 10, 2023, in 4 pages.
English Translation of Office Action in Chinese Application No. 201880010283.4, dated Aug. 17, 2023.
Bolcato-Bellemin et al. (2007), "Sticky overhangs enhance siRNA-mediated gene silencing," Proc. Natl. Acad. Sci. USA, 104:41: 16050-16055.
Bonger, K. M., "Dimeric ligands for GPCRs involved in human reproduction: synthesis and biological evaluation" pp. 1-217, Dec. 19, 2008.
Cellamare et al., "Design, synthesis, and biological evaluation of glycine-based molecular tongs as inhibitors of AB1-40 aggregation in vitro", Bioorganic & Medicinal Chemistry, vol. 16, 2008, pp. 4810-4822.
Endoh et al., "Cellular siRNA delivery using cell-penetrating peptides modified for endosomal escape", Advanced Drug Delivery Reviews, vol. 61(9):704-709 (2009).
Gary et al. (2007), "Polymer-based siRNA delivery: Perspective on the fundamental and phenomenological distinctions from polymer-based DNA delivery," J. Controlled Release, 121: 64-73.
Nechaev et al., "Intracellular processing of immunostimulatory CpG-siRNA: Toll-like receptor 9 facilitates siRNA dicing and dndosomal escape", Journal of Controlled Release, vol. 170:307-315 (2013).
Nechaev et a l., "Supplementary Data", 2013, XP093087395, retrieved from the internet: https://www.sciencedirect.com/science/article/pii/S0016836591303416?via%3Dihub#s0090, retrieved on Sep. 29, 2023.
Takei et al., "5'-,3'-inverted thymidine-modified antisense oligodeoxynucleotide targeting midkine", Journal of Biological Chemistry, vol. 277(26):23800-23806 (2002).
Office Action in Canadian application no. 3,051,480, dated Feb. 5, 2024, in 5 pages.
Notice of Allowance in Australian application No. 2018215684, dated Feb. 23, 2024, in 3 pages.
Office Action with English translation in Korean application no. 10-2024-7000303, dated Mar. 7, 2024, in 10 pages.
Adamus et al., "The revival of CpG oligonucleotide-based cancer immunotherapies", Contemporary Oncology/Wspolczesna Onkologia, pp. 56-60 (2018).
Antopolsky et al., "Peptide-oligonucleotide phosphorothioate conjugates with membrane translocation and nuclear localization properties", Bioconjugate Chemistry, vol. 10(4):598-606, (1999).
Hansen et al., "Natural RNA circles function as efficient microRNA sponges", Nature, vol. 495(7441):384-388 (2013).
Huang et al., "Non-reducible disulfide bond replacement implies that disulfide exchange is not required for hepcidin-ferroportin interaction", Chemical Communications, vol. 55(19):2821-2824, XP93161113, XP93161114 (2019).
Kortylewski et al., "In vivo delivery of siRNA to immune cells by conjugation to a TLR9 agonist enhances antitumor immune responses", Nature Biotechnology, vol. 27(10):925-932 (2009).
Stasinska et al., "Disulfide bridge as a linker in nucleic acids, Bioconjugation Part 1: An overview of synthetic strategies", Bioorganic Chemistry, vol. 92 (2019).
European Search Report in application No. 18747398.8, dated Jul. 25, 2024, in 7 pages.

* cited by examiner

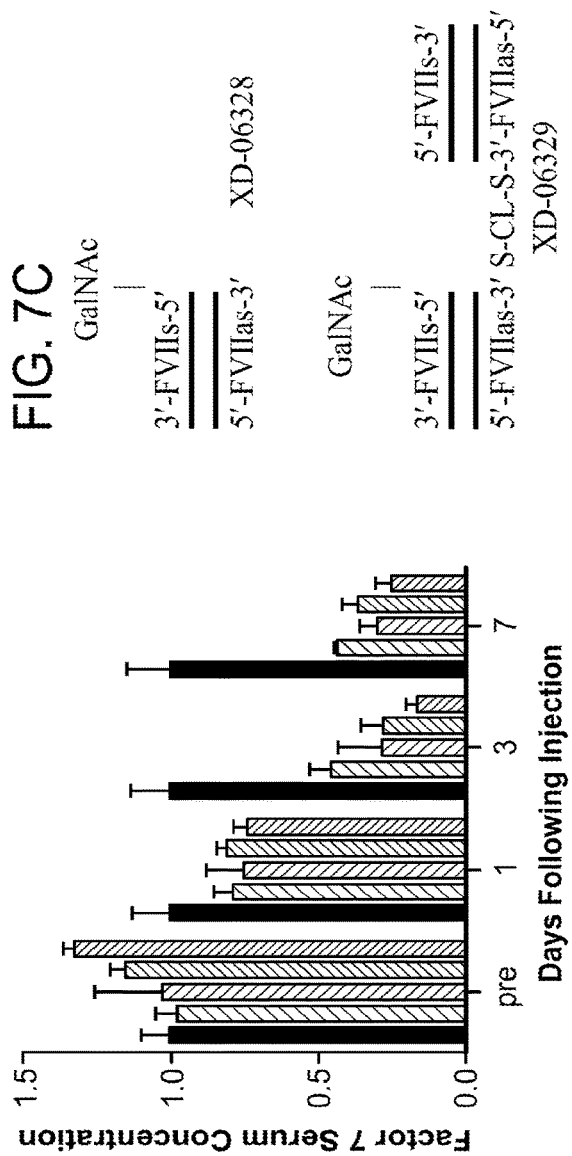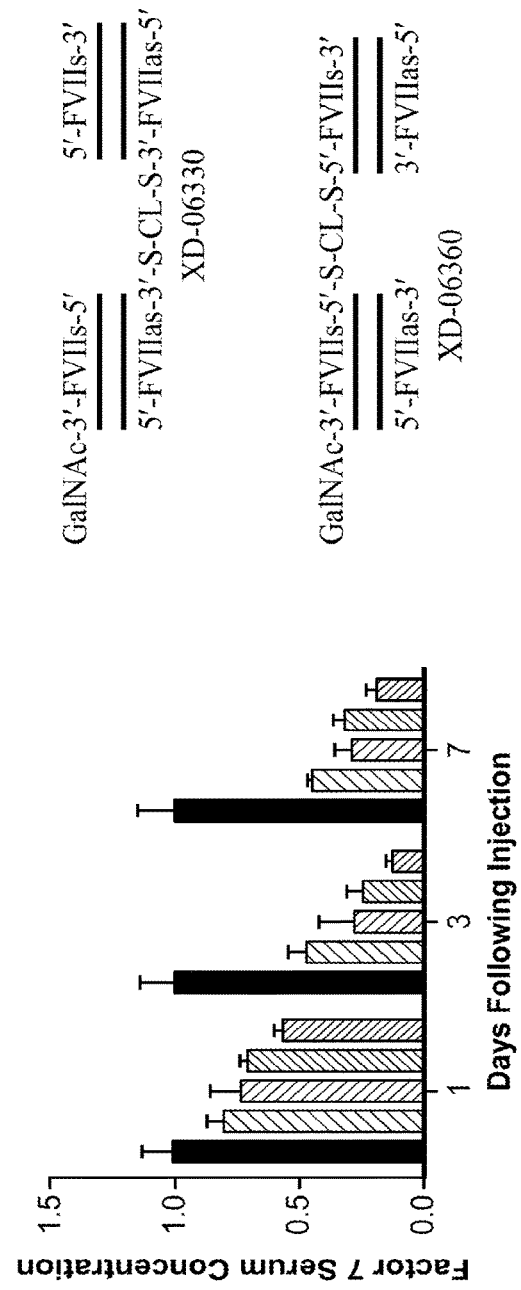

FIG. 8

```
            GalNAc
              |
3'-GeneFVIIs-5'
═══════════════
5'-GeneFVIIas-3'        (XD-06328)
```

```
            GalNAc
              |
3'-GeneApoBs-5'
═══════════════
5'-GeneApoBas-3'        (XD-06728)
```

```
            GalNAc
              |
3'-GeneTTRs-5'
═══════════════
5'-GeneTTRas-3'         (XD-06386)
```

FIG. 9

GalNAc-3'-GeneAs-5'-S-CL-S-5'-GeneBs-3'-S-S-5'-GeneCs-3'
═══════════════      ═══════════════   ═══════════════
5'-GeneAas-3'        3'-GeneBas-5'     3'-GeneCas-5'

MULTIMERIC OLIGONUCLEOTIDES HAVING DECREASED KIDNEY CLEARANCE

CROSS-REFERENCE TO RELATED APPLICATIONS

This application claims the benefits of U.S. Provisional Application No. 62/455,231, filed on Feb. 6, 2017, U.S. Provisional Application No. 62/522,363, filed on Jun. 20, 2017, and U.S. Provisional Application No. 62/561,853, filed on Sep. 22, 2017, the disclosures of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Feb. 5, 2018 is named 116244_604_Sequence_Listing.txt and is 24,828 bytes in size.

FIELD OF THE INVENTION

The present invention relates to multimeric oligonucleotides having improved pharmacodynamics and/or pharmacokinetics and methods of administering such multimeric oligonucleotides to a subject. For example, the multimeric oligonucleotides of the present invention can have molecular weights of at least about 45 kD and/or other characteristics that result in their reduced kidney clearance.

BACKGROUND

Oligonucleotides are now a well-established class of therapeutics with multiple applications (e.g., RNA interference, or RNAi) and ongoing clinical trials. However, many factors still limit oligonucleotide therapeutics, for example, the delivery of the oligonucleotide to a target cell and the subsequent internalization of the oligonucleotide into the target cell.

In an attempt to address these delivery and internalization limitations, many parties have investigated lipid nanoparticles (LNPs, e.g., lipid spheroids including positively charged lipids to neutralize the negative charge of the oligonucleotide and to facilitate target cell binding and internalization). While LNPs can in some cases facilitate delivery and internalization, they suffer from major drawbacks, for example poor targeting and toxicity, resulting in a narrowed therapeutic window.

Due at least in part to the limitations of LNPs, ligands targeting specific cell surface receptors have been also investigated. The use of one such ligand, N-acetylgalactosamine (GalNAc), has become a method of choice for oligonucleotide delivery to hepatocytes. However, while the toxicological profiles of GalNAc-conjugates can be better than LNPs, delivery is not as efficient. This limitation necessitates increased dosages, often by an order of magnitude or more. Increased dosages can be undesirable due to toxicity, side effects, and/or cost.

Accordingly, these and other prior art approaches do not fully solve the problems and limitations of oligonucleotide delivery. Thus, there remains a need for improved oligonucleotide compositions.

SUMMARY OF THE INVENTION

The present invention relates to methods of administering to a subject oligonucleotides in the form of a multimeric oligonucleotide having monomeric subunits of oligonucleotide joined by covalent linkers. A multimeric oligonucleotide of the invention has a molecular weight of at least about 45 kD and is configured such that its clearance due to glomerular filtration is reduced. The present invention also relates to the multimeric oligonucleotide and methods of synthesizing the multimeric oligonucleotide. For example, whereas a typical siRNA (e.g., double stranded monomer) may have a molecular weight of about 15 kD and relatively low circulation half-life (e.g., have a glomerular filtration rate similar to urea or glucose), an oligonucleotide multimer according to the invention may have a molecular weight of at least about 45 kD and have a relatively higher circulation half-life (e.g., have a lower clearance rate due to glomerular filtration rate). The improved and advantageous properties of the multimers according to the invention can be described in terms of increased in vivo circulation half-life. They may also be described in terms of increased in vivo activity.

When combined with a targeting ligand, the multi-conjugate (also referred to as "multimeric oligonucleotide" or "multimer") can also deliver a higher payload per ligand/receptor binding event than the monomeric equivalent. The present invention also relates to new synthetic intermediates and methods of synthesizing the multi-conjugate oligonucleotides. The present invention also relates to methods of using the multi-conjugate oligonucleotides, for example in reducing gene expression, biological research, treating or preventing medical conditions, and/or to produce new or altered phenotypes.

In various aspects, the invention provides a method of administering a multimeric oligonucleotide to a subject in need thereof, the method comprising administering an effective amount of the multimeric oligonucleotide to the subject, the multimeric oligonucleotide comprising subunits ⎯⎯⎯⎯, wherein:

each of the subunits ⎯⎯⎯⎯ is independently a single or double stranded oligonucleotide, and each of the subunits ⎯⎯⎯⎯ is joined to another subunit by a covalent linker ●;

the multimeric oligonucleotide has a molecular weight and/or size configured to decrease its clearance due to glomerular filtration; and the molecular weight of the multimeric oligonucleotide is at least about 45 kD.

In various aspects, the invention provides a multimeric oligonucleotide comprising subunits ⎯⎯⎯⎯, wherein:

each of the subunits ⎯⎯⎯⎯ is independently a single or double stranded oligonucleotide, and each of the subunits ⎯⎯⎯⎯ is joined to another subunit by a covalent linker ●;

the multimeric oligonucleotide has a molecular weight and/or size configured to decrease its clearance due to glomerular filtration; and the molecular weight of the multimeric oligonucleotide is at least about 45 kD.

In various aspects, the invention provides a method of synthesizing a multimeric oligonucleotide comprising Structure 51:

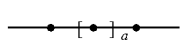

(Structure 51)

wherein each ⎯⎯⎯⎯ is a single stranded oligonucleotide, each ● is a covalent linker joining adjacent single stranded oligonucleotides, and a is an integer ≥ 1, the method comprising the steps of:

(i) reacting

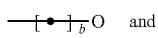 O   and   (Structure 52)

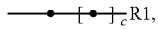 R1,   (Structure 53)

wherein ○ is a linking moiety, R1 is a chemical group capable of reacting with the linking moiety ○, b and c are each independently an integer ≥0, b and c cannot both simultaneously be zero, and b+c=a, thereby forming Structure 51:

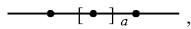   (Structure 51)

and (ii) optionally annealing Structure 51:

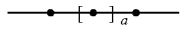   (Structure 51)

with complementary single stranded oligonucleotides ———, thereby forming Structure 54:

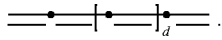   (Structure 54)

In various aspects, the invention provides a method of synthesizing a multimeric oligonucleotide comprising Structure 54:

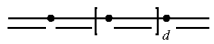   (Structure 54)

wherein each ——— is a single stranded oligonucleotide, each ● is a covalent linker joining adjacent single stranded oligonucleotides, and a≥1, the method comprising the steps of:

(i) annealing Structure 51:

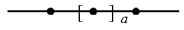   (Structure 51)

with complementary single stranded oligonucleotides ———, thereby forming Structure 54:

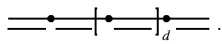   (Structure 54)

In various aspects, the invention provides a multimeric oligonucleotide comprising Structure 21:

   (Structure 21)

wherein each ------ is a single or double stranded oligonucleotide, each ● is a covalent linker joining adjacent oligonucleotides, m is an integer ≥0, and wherein the multimeric oligonucleotide has molecular size and/or weight configured to decrease glomerular filtration in vivo.

In various aspects, the invention provides a multimeric oligonucleotide comprising Structure 22 or 23:

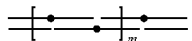   (Structure 22)

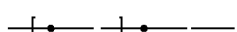   (Structure 23)

wherein ═══ each is a double stranded oligonucleotide, each ● is a covalent linker joining single strands of adjacent oligonucleotides, and m is an integer ≥1 and n is an integer ≥0, and wherein the multimeric oligonucleotide has molecular size and/or weight configured to decrease glomerular filtration in vivo.

In various aspects, the invention provides a plurality of the multimeric oligonucleotides as described above, wherein substantially all of the multimeric oligonucleotides have a molecular size and/or weight configured to decrease glomerular filtration in vivo.

In various aspects, the invention provides a plurality of the multimeric oligonucleotides as described above, wherein substantially all of the multimeric oligonucleotides have a predetermined value of m or n.

In various aspects, the invention provides a plurality of the multimeric oligonucleotides as described herein, wherein substantially all of the multimeric oligonucleotides are defined multimers (e.g., multi-conjugates) having the same value of m or n.

In various aspects, the invention provides a plurality of the multimeric oligonucleotides as described herein, wherein substantially all of the multimeric oligonucleotides are defined tetramers (m=1) (e.g., tetraconjugates).

In various aspects, the invention provides a plurality of the multimeric oligonucleotides as described herein, wherein substantially all of the multimeric oligonucleotides are defined pentamers (e.g., pentaconjugates) or longer (m>1 or n≥1).

In various aspects, the invention provides a composition comprising the multimeric oligonucleotide of the invention and a pharmaceutically acceptable excipient.

In various aspects, the invention provides a method for reducing gene expression comprising administering an effective amount of the multimeric oligonucleotide of the invention or composition comprising the multimeric oligonucleotide of the invention to a subject in need thereof.

In various aspects, the invention provides a method for treating a subject comprising administering an effective amount of the multimeric oligonucleotide of the invention or composition comprising the multimeric oligonucleotide of the invention to a subject in need thereof.

In various aspects, the invention provides a method of synthesizing a multimeric oligonucleotide comprising Structure 22 or 23:

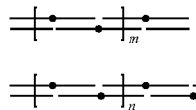
(Structure 22)

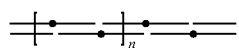
(Structure 23)

wherein each ═══ is a double stranded oligonucleotide, each ● is a covalent linker joining single strands of adjacent oligonucleotides, and m is an integer ≥1 and n is an integer ≥0, the method comprising the steps of:

(i) annealing a first single stranded oligonucleotide ——— and a complementary second single stranded oligonucleotide comprising a linking moiety

——O, thereby forming

══O;

(ii) reacting

══O and a third single stranded oligonucleotide

——$R_1$, wherein $R_1$ is a chemical group capable of reacting with the linking moiety ○ thereby forming

;

(iii) annealing

══●—— and a fourth complementary single stranded oligonucleotide comprising a linking moiety

——O, thereby forming

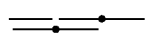;

(iv) reacting

and a fifth single stranded oligonucleotide

——$R_1$, thereby forming

══●——

(v) annealing

══●—— and a sixth complementary single stranded oligonucleotide comprising a linking moiety

——O, thereby forming

;

(vi) reacting

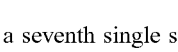

and a seventh single stranded oligonucleotide

——$R_1$, thereby forming

(Structure 24);

(vii) optionally annealing one or more (a) additional single stranded oligonucleotide(s) comprising a linking moiety

——O and (b) single stranded oligonucleotide(s)

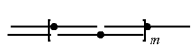

thereby forming

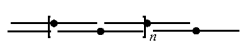 (Structure 25)

wherein m is an integer ≥2 or

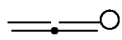 (Structure 26)

wherein n is an integer ≥1; and (viii) annealing a final complementary single stranded oligonucleotide ——— with Structure 24, 25, or 26, thereby forming the multimeric oligonucleotide comprising Structure 22 or 23.

The invention further provides a multimeric oligonucleotide comprising Structure 24, 25, 26, or 27:

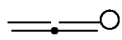 (Structure 24)

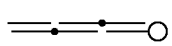 (Structure 25)

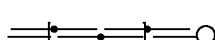 (Structure 26)

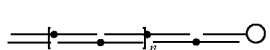 (Structure 27)

wherein each ═══ is a double stranded oligonucleotide, each ● is a covalent linker joining single strands of adjacent single stranded oligonucleotides, each ○ is a linking moiety; and m is an integer ≥1 and n is an integer ≥1.

In various aspects, the invention provides a multimeric oligonucleotide comprising Structure 21:

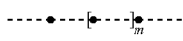 (Structure 21)

wherein each monomeric subunit ------- is independently a single or double stranded oligonucleotide, m is an integer ≥1, each ● is a covalent linker joining adjacent monomeric subunits -------, and at least one of the monomeric subunits ------- comprises a single strand having one of the covalent linkers ● joined to its 3' terminus and another of the covalent linkers joined to its 5' terminus.

In various aspects, the invention provides a multimeric oligonucleotide comprising Structure 21:

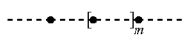 (Structure 21)

wherein each monomeric subunit ------- is independently a single or double stranded oligonucleotide, each ● is a covalent linker joining adjacent monomeric subunits -------, and m is an integer ≥0 selected to (a) increase in vivo circulation half-life of the multimeric oligonucleotide relative to that of the individual monomeric subunits ------- and/or (b) increase in vivo activity of the multimeric oligonucleotide relative to that of the individual monomeric subunits -------.

A multimeric oligonucleotide comprising Structure 21:

 (Structure 21)

wherein each monomeric subunit ------- is independently a single or double stranded oligonucleotide, each ● is a covalent linker joining adjacent monomeric subunits -------, m is an integer ≥0, and wherein the multimeric oligonucleotide has molecular size and/or weight configured to (a) increase in vivo circulation half-life of the multimeric oligonucleotide relative to that of the individual monomeric subunits ------- and/or (b) increase in vivo activity of the multimeric oligonucleotide relative to that of the individual monomeric subunits -------.

A method for increasing in vivo circulation half-life and/or in vivo activity of one or more oligonucleotides, the method comprising administering to a subject the one or more oligonucleotides in the form of a multimeric oligonucleotide comprising Structure 21:

 (Structure 21)

wherein each monomeric subunit ------- is independently a single or double stranded oligonucleotide, each ● is a covalent linker joining adjacent monomeric subunits -------, and m is an integer ≥0 selected to (a) increase in vivo circulation half-life of the multimeric oligonucleotide relative to that of the individual monomeric subunits ------- and/or (b) increase in vivo activity of the multimeric oligonucleotide relative to that of the individual monomeric subunits -------.

A method for increasing in vivo circulation half-life and/or in vivo activity of one or more oligonucleotides, the method comprising administering to a subject the one or more oligonucleotides in the form of a multimeric oligonucleotide comprising Structure 21:

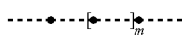 (Structure 21)

wherein each monomeric subunit ------- is independently a single or double stranded oligonucleotide, each ● is a covalent linker joining adjacent monomeric subunits -------, m is an integer ≥0, and wherein the multimeric oligonucleotide has molecular size and/or weight configured to (a) increase in vivo circulation half-life of the multimeric oligonucleotide relative to that of the individual monomeric subunits ------- and/or (b) increase in vivo activity of the multimeric oligonucleotide relative to that of the individual monomeric subunits -------.

In various aspects, the invention provides a composition comprising the multimeric oligonucleotides as described herein and a pharmaceutically acceptable excipient.

In various aspects, the invention provides a method for reducing gene expression comprising administering an effective amount of the multimeric oligonucleotide as described herein to a subject in need thereof.

In various aspects, the invention provides a method for treating a subject comprising administering an effective amount of the multimeric oligonucleotide to a subject in need thereof.

In various aspects, the invention provides a multimeric oligonucleotide comprising m monomeric subunits ───────, wherein each of the monomeric subunits ─────── is independently a single or double stranded oligonucleotide, each of the monomeric subunits ─────── is joined to another monomeric subunit by a covalent linker ●, and m is an integer ≥3 selected to (a) increase in vivo circulation half-life of the multimeric oligonucleotide relative to that of the individual monomeric subunits ─────── and/or (b) increase in vivo activity of the multimeric oligonucleotide relative to that of the individual monomeric subunits ───────.

In various aspects, the invention provides a multimeric oligonucleotide comprising m monomeric subunits ───────, wherein each of the monomeric subunits ─────── is independently a single or double stranded oligonucleotide, each of the monomeric subunits ─────── is joined to another monomeric subunit by a covalent linker ●, m is an integer ≥3, and the multimeric oligonucleotide has molecular size and/or weight configured to (a) increase in vivo circulation half-life of the multimeric oligonucleotide relative to that of the individual monomeric subunits ─────── and/or (b) increase in vivo activity of the multimeric oligonucleotide relative to that of the individual monomeric subunits ───────.

In various aspects, the invention provides a method of synthesizing a multimeric oligonucleotide comprising Structure 34:

─●─●─  (Structure 34)

wherein each ─── is a single stranded oligonucleotide and each ● is a covalent linker joining adjacent single stranded oligonucleotides, the method comprising the steps of:

(i) reacting

─●─○  and  ─●─R1, wherein ○ is a linking moiety and R₁ is a chemical group capable of reacting with the linking moiety ○, thereby forming ─●─●─,  (Structure 34)

and
(ii) optionally annealing

─●─●─  (Structure 34)

with complementary single stranded oligonucleotides, thereby forming (Structure 28)

In various aspects, the invention provides a method of synthesizing a multimeric oligonucleotide comprising Structure 35:

─●─●─●─  (Structure 35)

wherein each ─── is a single stranded oligonucleotide and each ● is a covalent linker joining adjacent single stranded oligonucleotides, the method comprising the steps of:

(i) reacting

─●─●─○  and  ─●─R1, wherein ○ is a linking moiety and R₁ is a chemical group capable of reacting with the linking moiety ○, thereby forming ─●─●─●─,  (Structure 35)

and
(ii) optionally annealing

─●─●─●─  (Structure 35)

with complementary single stranded oligonucleotides, thereby forming (Structure 36)

In various aspects, the invention provides a method of synthesizing a multimeric oligonucleotide comprising Structure 37:

─●─●─●─●─  (Structure 37)

wherein each ─── is a single stranded oligonucleotide and each ● is a covalent linker joining adjacent single stranded oligonucleotides, the method comprising the steps of:

(i) reacting

─●─●─○  and  ─●─●─R1, wherein ○ is a linking moiety and $R_1$ is a chemical group capable of reacting with the linking moiety ○, thereby forming

 (Structure 37)

and
(ii) optionally annealing

 (Structure 37)

with complementary single stranded oligonucleotides, thereby forming

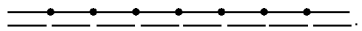 (Structure 38)

One skilled in the art will recognize that these and other aspects of the invention can be combined with one or more suitable features described herein.

In various embodiments, the multimeric oligonucleotides of the invention, for example, those comprising Structure 21, have a molecular weight of at least about 40, 41, 42, 43, 44, 45, 46, 47, 48, 49, 50, 51, 52, 53, 54, 55, 56, 57, 58, 59, 60, 61, 62, 63, 64, or 65 kD.

In various embodiments, the multimeric oligonucleotides of the invention, including those comprising Structure 21, have a molecular weight of at least about 40-45, 45-50, 50-55, 55-60, 60-65, 65-70, or 70-75 kD.

In one aspect, the invention provides a method of administering a multimeric oligonucleotide to a subject in need thereof, wherein the number of subunits contained in the multimeric oligonucleotide is m, m being an integer selected to enable the multimeric oligonucleotide to have the molecular weight and/or size configured to decrease its clearance due to glomerular filtration. In various aspects, m is, for example, (i) ≥2; (ii) ≥3; (iii) ≥4; (iv) ≥4 and ≤17; (v) ≥4 and ≤8; or (vi) 4, 5, 6, 7, or 8.

In one aspect, the invention provides a method of administering a multimeric oligonucleotide to a subject in need thereof, in which the multimeric oligonucleotide comprises Structure 21:

 (Structure 21)

and n is an integer ≥0.

In one aspect, the invention provides a method of administering a multimeric oligonucleotide to a subject in need thereof, in which the subunits are single-stranded oligonucleotides.

In one aspect, the invention provides a method of administering a multimeric oligonucleotide to a subject in need thereof, wherein n is ≥1.

In one aspect, the invention provides a method of administering a multimeric oligonucleotide to a subject in need thereof, in which the subunits are double-stranded oligonucleotides.

In one aspect, the invention provides a method of administering a multimeric oligonucleotide to a subject in need thereof, wherein:

when n=0, the clearance of the multimeric oligonucleotide due to glomerular filtration is decreased relative to that of a monomeric subunit  and/or a dimeric subunit

of the multimeric oligonucleotide; and when n≥1, the clearance of the multimeric oligonucleotide due to glomerular filtration is decreased relative to that of a monomeric subunit , a dimeric subunit

, and/or a trimeric subunit

of the multimeric oligonucleotide.

In one aspect, the invention provides a method of administering a multimeric oligonucleotide to a subject in need thereof, in which the decreased clearance due to glomerular filtration results in increased in vivo circulation half-life of the multimeric oligonucleotide.

In one aspect, the invention provides a method of administering a multimeric oligonucleotide to a subject in need thereof, in which the decreased clearance due to glomerular filtration is determined by measuring the in vivo circulation half-life of the multimeric oligonucleotide after administering the multimeric oligonucleotide to the subject.

In one aspect, the invention provides a method of administering a multimeric oligonucleotide to a subject in need thereof, in which the decreased clearance due to glomerular filtration is determined by measuring the time required for the serum concentration of the multimeric oligonucleotide to decrease to a predetermined value.

In one aspect, the invention provides a method of administering a multimeric oligonucleotide to a subject in need thereof, in which the decreased clearance due to glomerular filtration is determined by measuring the serum concentration of the multimeric oligonucleotide at a predetermined time after administering the multimeric oligonucleotide to the subject.

In one aspect, the invention provides a method of administering a multimeric oligonucleotide to a subject in need thereof, in which the decreased clearance due to glomerular filtration is determined by measuring the area under the curve of a graph representing serum concentration of the multimeric oligonucleotide over time after administering the multimeric oligonucleotide to the subject.

In one aspect, the invention provides a method of administering a multimeric oligonucleotide to a subject in need thereof, in which the decreased clearance due to glomerular filtration increases in vivo bioavailability of the multimeric oligonucleotide.

In one aspect, the invention provides a method of administering a multimeric oligonucleotide to a subject in need thereof, in which the decreased clearance due to glomerular filtration increases in vivo cellular uptake of the multimeric oligonucleotide.

In one aspect, the invention provides a method of administering a multimeric oligonucleotide to a subject in need thereof, in which the decreased clearance due to glomerular filtration increases in vivo therapeutic index/ratio of the multimeric oligonucleotide.

In one aspect, the invention provides a multimeric oligonucleotide comprising subunits -------, wherein the number of subunits contained in the multimeric oligonucleotide is m, m being an integer selected to enable the multimeric oligonucleotide to have the molecular weight and/or size configured to decrease its clearance due to glomerular filtration. In various aspects, m is, for example, (i) ≥2; (ii) ≥3; (iii) ≥4; (iv) ≥4 and ≤17; (v) ≥4 and ≤8; or (vi) 4, 5, 6, 7, or 8.

In one aspect, the invention provides a multimeric oligonucleotide comprising Structure 21:

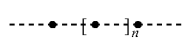
(Structure 21)

wherein at least one of the subunits ------- comprises a single strand having one of the covalent linkers ● joined to its 3' terminus and another of the covalent linkers joined to its 5' terminus, and n is an integer ≥0.

In one aspect, the invention provides a multimeric oligonucleotide comprising subunits -------, in which each subunit ------- is 15-30, 17-27, 19-26, or 20-25 nucleotides in length.

In one aspect, the invention provides a multimeric oligonucleotide wherein n≥1 and n≤17.

In one aspect, the invention provides a multimeric oligonucleotide in which n≥1 and n≤5.

In one aspect, the invention provides a multimeric oligonucleotide in which n is, for example, 1, 2, 3, 4, or 5.

In one aspect, the invention provides a multimeric oligonucleotide wherein each subunit is a double-stranded RNA and n≥1.

In one aspect, the invention provides a multimeric oligonucleotide in which each subunit is a single-stranded oligonucleotide.

In one aspect, the invention provides a multimeric oligonucleotide in which each subunit is a double-stranded oligonucleotide.

In one aspect, the invention provides a multimeric oligonucleotide in which the subunits comprise a combination of single-stranded and double-stranded oligonucleotides.

In one aspect, the invention provides a multimeric oligonucleotide in which each subunit is an RNA, a DNA, or an artificial or non-natural nucleic acid analog.

In one aspect, the invention provides a multimeric oligonucleotide in which the multimeric oligonucleotide further comprises one or more targeting ligands.

In one aspect, the invention provides a multimeric oligonucleotide in which at least one of the subunits is a targeting ligand.

In one aspect, the invention provides a multimeric oligonucleotide in which the targeting ligand is an aptamer.

In one aspect, the invention provides a multimeric oligonucleotide in which each subunit is a RNA.

In one aspect, the invention provides a multimeric oligonucleotide in which each subunit is a siRNA, a saRNA, or a miRNA.

In one aspect, the invention provides a multimeric oligonucleotide in which each subunit is a double-stranded siRNA and each of the covalent linkers joins sense strands of the siRNA.

In one aspect, the invention provides a multimeric oligonucleotide in which one or more of the covalent linkers ● comprise a cleavable covalent linker.

In one aspect, the invention provides a multimeric oligonucleotide in which the cleavable covalent linker contains an acid cleavable bond, a reductant cleavable bond, a biocleavable bond, or an enzyme cleavable bond.

In one aspect, the invention provides a multimeric oligonucleotide in which the cleavable covalent linker is cleavable under intracellular conditions.

In one aspect, the invention provides a multimeric oligonucleotide in which each covalent linker ● is the same.

In one aspect, the invention provides a multimeric oligonucleotide in which the covalent linkers ● comprise two or more different covalent linkers.

In one aspect, the invention provides a multimeric oligonucleotide in which each covalent linker ● joins two monomeric subunits -------.

In one aspect, the invention provides a multimeric oligonucleotide in which at least one covalent linker ● joins three or more monomeric subunits -------.

In one aspect, the invention provides a multimeric oligonucleotide in which the multimeric oligonucleotide comprises a homo-multimer of substantially identical subunits -------.

In one aspect, the invention provides a multimeric oligonucleotide in which the multimeric oligonucleotide comprises a hetero-multimer of two or more substantially different subunits -------.

In one aspect, the invention provides a multimeric oligonucleotide in which the multimeric oligonucleotide is at least 75, 80, 85, 90, 95, 96, 97, 98, 99, or 100% pure.

In one aspect, the invention provides a multimeric oligonucleotide wherein each subunit ------- is independently a double stranded oligonucleotide ═══, and wherein n is an integer ≥1.

In one aspect, the invention provides a multimeric oligonucleotide wherein each subunit ------- is independently a double-stranded oligonucleotide ═══, wherein n is an integer ≥1, and wherein each covalent linker ● is on the same strand:

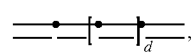
(Structure 54)

wherein d is an integer ≥1.

In one aspect, the invention provides a multimeric oligonucleotide comprising Structure 22 or 23:

(Structure 22)

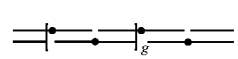
(Structure 23)

where each ═══ is a double stranded oligonucleotide, each ● is a covalent linker joining adjacent double stranded oligonucleotides, f is an integer ≥1, and g is an integer ≥0.

In one aspect, the invention provides a multimeric oligonucleotide wherein the decreased glomerular filtration is relative to the rate of glomerular filtration for a monomeric, dimeric, and/or trimeric oligonucleotide subunit of the multimeric oligonucleotide.

In one aspect, the invention provides a multimeric oligonucleotide wherein the decreased glomerular filtration increases in vivo circulation half-life of the multimeric oligonucleotide.

In one aspect, the invention provides a multimeric oligonucleotide wherein the decreased glomerular filtration increases in vivo bio-availability of the multimeric oligonucleotide.

In one aspect, the invention provides a multimeric oligonucleotide wherein the decreased glomerular filtration increases in vivo cellular uptake of the multimeric oligonucleotide.

In one aspect, the invention provides a multimeric oligonucleotide wherein the decreased glomerular filtration increases in vivo therapeutic index/ratio of the multimeric oligonucleotide.

In one aspect, the invention provides a multimeric oligonucleotide wherein each oligonucleotide ------- is a single stranded oligonucleotide.

In one aspect, the invention provides a multimeric oligonucleotide wherein each oligonucleotide ------- is a double stranded oligonucleotide.

In one aspect, the invention provides a multimeric oligonucleotide wherein the oligonucleotides ------ comprise a combination of single and double stranded oligonucleotides.

In one aspect, the invention provides a multimeric oligonucleotide comprising a homo-multimer of substantially identical oligonucleotides.

In one aspect, the invention provides a multimeric oligonucleotide wherein the substantially identical oligonucleotides each comprise an siRNA targeting the same molecular target in vivo.

In one aspect, the invention provides a multimeric oligonucleotide comprising a hetero-multimer of two or more substantially different oligonucleotides.

In one aspect, the invention provides a multimeric oligonucleotide wherein the substantially different oligonucleotides each comprise an siRNA targeting a different molecular target in vivo.

In one aspect, the invention provides a multimeric oligonucleotide wherein the multimeric oligonucleotide does not comprise PEG.

In one aspect, the invention provides a multimeric oligonucleotide further comprising a targeting ligand.

In one aspect, the invention provides a multimeric oligonucleotide wherein the targeting ligand is conjugated to an oligonucleotide.

In one aspect, the invention provides a multimeric oligonucleotide wherein the targeting ligand is conjugated to the oligonucleotide through its 3' or 5' terminus.

In one aspect, the invention provides a multimeric oligonucleotide wherein each covalent linker ● is the same.

In one aspect, the invention provides a multimeric oligonucleotide comprising two or more different covalent linkers ●.

In one aspect, the invention provides a multimeric oligonucleotide wherein one or more of ● comprises a cleavable covalent linker.

In one aspect, the invention provides a multimeric oligonucleotide wherein the compound is at least 75, 80, 85, 90, 95, 96, 97, 98, 99, or 100% pure.

In one aspect, the invention provides a multimeric oligonucleotide wherein each oligonucleotide is RNA, DNA, or comprises an artificial or non-natural nucleic acid analog.

In one aspect, the invention provides a multimeric oligonucleotide wherein at least one oligonucleotide is an siRNA.

In one aspect, the invention provides a multimeric oligonucleotide wherein each oligonucleotide is 15-30, 17-27, 19-26, or 20-25 nucleotides in length.

In one aspect, the invention provides a method of synthesizing a multimeric oligonucleotide further comprising the step of conjugating a targeting ligand to the multimeric oligonucleotide comprising Structure 22 or 23.

In one aspect, the invention provides a method of synthesizing a multimeric oligonucleotide further comprising the step of conjugating a targeting ligand to the first single stranded oligonucleotide ——— .

In one aspect, the invention provides a multimeric oligonucleotide wherein m is, for example, 1, 2, 3, 4, 5, 6, 7, 8, 9, 10, 11, or 12.

In one aspect, the invention provides a multimeric oligonucleotide wherein each of the monomeric subunits ------- comprises an siRNA and each of the covalent linkers joins sense strands of the siRNA.

In one aspect, the invention provides a multimeric oligonucleotide wherein each of the covalent linkers ● joins two monomeric subunits -------.

In one aspect, the invention provides a multimeric oligonucleotide wherein at least one of the covalent linkers ● joins three or more monomeric subunits -------.

In one aspect, the invention provides a multimeric oligonucleotide wherein each monomeric subunit ------- is independently a double stranded oligonucleotide ═══, and wherein m is 1:

(Structure 28)
(Structure 29)

In one aspect, the invention provides a multimeric oligonucleotide wherein each monomeric subunit ------- is independently a double stranded oligonucleotide ═══, wherein m is 1, and wherein each covalent linker ● is on the same strand:

(Structure 28)

In one aspect, the invention provides a multimeric oligonucleotide wherein each monomeric subunit ------- is independently a double stranded oligonucleotide ═══, and wherein m is 2:

(Structure 30)
(Structure 31)
(Structure 32)
(Structure 33)

In one aspect, the invention provides a multimeric oligonucleotide wherein each monomeric subunit ------- is independently a double stranded oligonucleotide ═══, and wherein m is 2, and wherein each covalent linker ● is on the same strand:

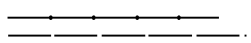

(Structure 33)

In one aspect, the invention provides a multimeric oligonucleotide wherein each monomeric subunit ------- is independently a double stranded oligonucleotide ═══, and wherein m is 3, 4, 5, 6, 7, 8, 9, 10, 11, or 12.

In one aspect, the invention provides a multimeric oligonucleotide wherein each monomeric subunit ------- is independently a double stranded oligonucleotide ═══, wherein m is 3, 4, 5, 6, 7, 8, 9, 10, 11, or 12, and wherein each covalent linker ● is on the same strand.

In one aspect, the invention provides a multimeric oligonucleotide wherein each monomeric subunit ------- is independently a double stranded oligonucleotide ═══, and wherein m is ≥13.

In one aspect, the invention provides a multimeric oligonucleotide wherein each monomeric subunit ------- is independently a double stranded oligonucleotide ═══, wherein m is ≥13, and wherein each covalent linker ● is on the same strand.

In one aspect, the invention provides a multimeric oligonucleotide or a method for increasing in vivo circulation half-life of the multimeric oligonucleotide, wherein m is 0, 1, 2, 3, 4, 5, 6, 7, 8, 9, 10, 11, or 12.

In one aspect, the invention provides a multimeric oligonucleotide or a method for increasing in vivo circulation half-life of the multimeric oligonucleotide, wherein Structure 21 is Structure 22 or 23:

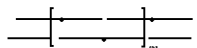

(Structure 22)

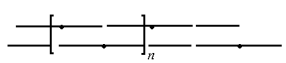

(Structure 23)

where each ═══ is a double stranded oligonucleotide, each ● is a covalent linker joining adjacent double stranded oligonucleotides, m is an integer ≥1, and n is an integer ≥0.

In one aspect, the invention provides a multimeric oligonucleotide or a method for increasing in vivo circulation half-life of the multimeric oligonucleotide, wherein Structure 21 is not a structure which is the same and/or substantially the same as any structure disclosed in PCT/US2016/037685.

In one aspect, the invention provides a multimeric oligonucleotide or a method for increasing in vivo circulation half-life of the multimeric oligonucleotide, wherein the in vivo circulation half-life increases by a factor of at least 2, 3, 4, 5, 6, 7, 8, 9, 10, 20, 30, 40, 50, 60, 70, 80, 90, 100, 150, 200, 250, 500, or 1,000.

In one aspect, the invention provides a multimeric oligonucleotide or a method for increasing in vivo circulation half-life of the multimeric oligonucleotide, wherein the in vivo circulation half-life increases by about 10%, 20%, 30%, 40%, 50%, 60%, 70%, 80%, 90%, or 100%.

In one aspect, the invention provides a multimeric oligonucleotide or a method for increasing in vivo circulation half-life of the multimeric oligonucleotide, wherein the increase in in vivo activity is measured as the ratio of in vivo activity at $t_{max}$.

In one aspect, the invention provides a multimeric oligonucleotide or a method for increasing in vivo circulation half-life of the multimeric oligonucleotide, wherein the in vivo activity increases by a factor of at least 2, 3, 4, 5, 6, 7, 8, 9, 10, 20, 30, 40, 50, 60, 70, 80, 90, 100, 150, 200, 250, 500, or 1,000.

In one aspect, the invention provides a multimeric oligonucleotide or a method for increasing in vivo circulation half-life of the multimeric oligonucleotide, wherein each oligonucleotide ------- is a single stranded oligonucleotide.

In one aspect, the invention provides a multimeric oligonucleotide or a method for increasing in vivo circulation half-life of the multimeric oligonucleotide, wherein each oligonucleotide ------- is a double stranded oligonucleotide.

In one aspect, the invention provides a multimeric oligonucleotide or a method for increasing in vivo circulation half-life of the multimeric oligonucleotide, wherein the oligonucleotides ------- comprise a combination of single and double stranded oligonucleotides.

In one aspect, the invention provides a multimeric oligonucleotide or a method for increasing in vivo circulation half-life of the multimeric oligonucleotide, comprising a homo-multimer of substantially identical oligonucleotides.

In one aspect, the invention provides a multimeric oligonucleotide wherein the substantially identical oligonucleotides are:

(a) siRNA targeting the same molecular target in vivo;
(b) miRNA targeting the same molecular target in vivo;
(c) antisense RNA targeting the same molecular target in vivo; or
(d) a combination of siRNA, miRNA, and/or antisense RNA targeting the same molecular target in vivo.

In one aspect, the invention provides a multimeric oligonucleotide or a method for increasing in vivo circulation half-life of the multimeric oligonucleotide, comprising a hetero-multimer of two or more substantially different oligonucleotides.

In one aspect, the invention provides a multimeric oligonucleotide wherein the substantially different oligonucleotides are:

(a) siRNA targeting different molecular targets in vivo;
(b) miRNA targeting different molecular targets in vivo;
(c) antisense RNA targeting different molecular targets in vivo; or
(d) a combination of siRNA, miRNA, and/or antisense RNA targeting different molecular targets in vivo.

In one aspect, the invention provides a multimeric oligonucleotide or a method for increasing in vivo circulation half-life of the multimeric oligonucleotide, wherein the multimeric oligonucleotide does not comprise: PEG, a polyether compound, and/or a polymer other than oligonucleotide.

In one aspect, the invention provides a multimeric oligonucleotide or a method for increasing in vivo circulation half-life of the multimeric oligonucleotide, wherein the multimeric oligonucleotide is not formulated in a nanoparticle (NP) or more specifically in a lipid nanoparticle (LNP).

In one aspect, the invention provides a multimeric oligonucleotide or a method for increasing in vivo circulation half-life of the multimeric oligonucleotide, wherein the multimeric oligonucleotide consists essentially of Structure 21 and an optional targeting ligand.

In one aspect, the invention provides a multimeric oligonucleotide or a method for increasing in vivo circulation half-life of the multimeric oligonucleotide, wherein the multimeric oligonucleotide further comprises a targeting ligand.

In one aspect, the invention provides a multimeric oligonucleotide wherein the targeting ligand is conjugated to an oligonucleotide.

In one aspect, the invention provides a multimeric oligonucleotide wherein the targeting ligand is conjugated to the oligonucleotide through its 3' or 5' terminus.

In one aspect, the invention provides a multimeric oligonucleotide or a method for increasing in vivo circulation half-life of the multimeric oligonucleotide, wherein each covalent linker ● is the same.

In one aspect, the invention provides a multimeric oligonucleotide or a method for increasing in vivo circulation half-life of the multimeric oligonucleotide, comprising two or more different covalent linkers ●.

In one aspect, the invention provides a multimeric oligonucleotide or a method for increasing in vivo circulation half-life of the multimeric oligonucleotide, wherein one or more of ● comprises a cleavable covalent linker.

In one aspect, the invention provides a multimeric oligonucleotide comprising a linear structure wherein each of the covalent linkers ● joins two monomeric subunits --------.

In one aspect, the invention provides a multimeric oligonucleotide comprising a branched structure wherein at least one of the covalent linkers ● joins three or more monomeric subunits --------.

In one aspect, the invention provides a multimeric oligonucleotide wherein each monomeric subunit -------- is independently a single stranded oligonucleotide ———.

In one aspect, the invention provides a multimeric oligonucleotide wherein:

m is 1

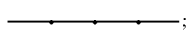  (Structure 34)

m is 2

  (Structure 39)

m is 3

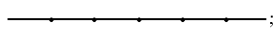  (Structure 35)

m is 4

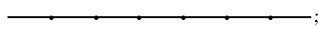  (Structure 40)

or m is 5

___•___•___•___.  (Structure 37)

In one aspect, the invention provides a multimeric oligonucleotide wherein m is 6, 7, 8, 9, 10, 11, or 12.

In one aspect, the invention provides a multimeric oligonucleotide wherein m is an integer ≥13.

In one aspect, the invention provides a multimeric oligonucleotide wherein at least one single stranded oligonucleotide ——— is an antisense oligonucleotide.

In one aspect, the invention provides a multimeric oligonucleotide wherein each single stranded oligonucleotide ——— is independently an antisense oligonucleotide.

These and other advantages of the present technology will be apparent when reference is made to the accompanying drawings and the following description.

BRIEF DESCRIPTION OF THE DRAWINGS

FIGS. 7A and 7B and 7C present data showing FVII activity in mouse serum (knockdown by FVII homodimeric GalNAc conjugates normalized for GalNAc content), which is discussed in connection with Example 13.

FIG. 8 presents canonical GalNAc-siRNAs independently targeting FVII, ApoB and TTR, which are discussed in connection with Example 14.

FIG. 9 presents a GalNAc-heterotrimer conjugate (XD-06726), which is discussed in connection with Example 15. Key: In this Example, "GeneA" is siFVII; "GeneB" is siApoB; and "GeneC" is siTTR.

Figure 1A:
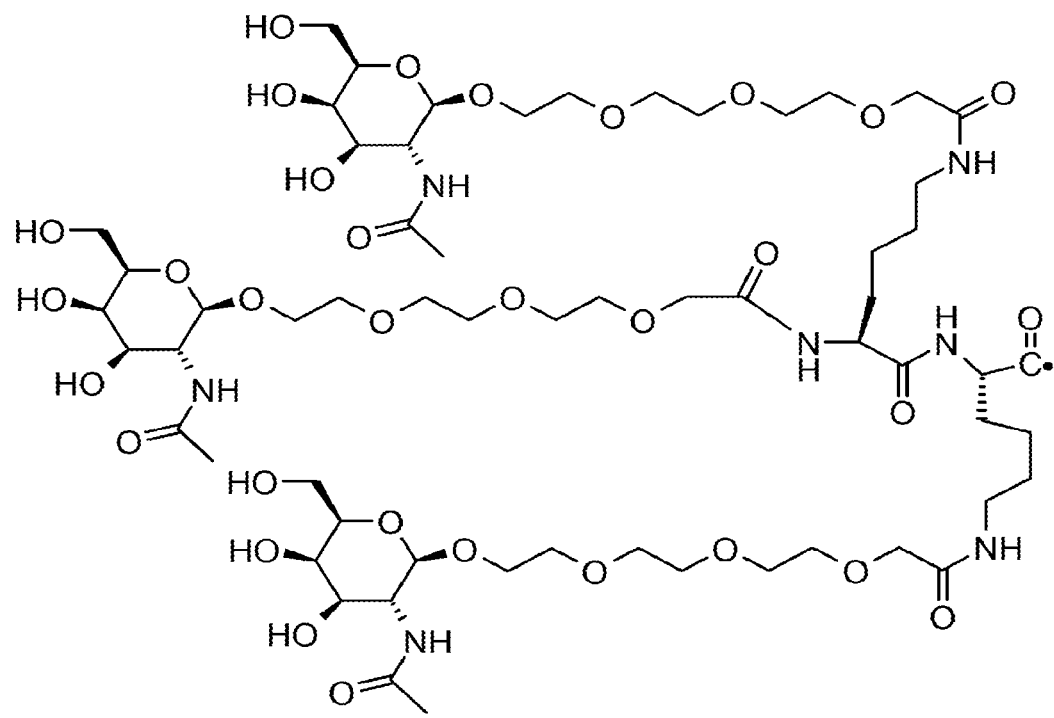
FIG. 1A presents the chemical structure of a tri-antennary N-acetylgalactosamine ligand.

While the invention comprises embodiments in many different forms, there are shown in the drawings and will herein be described in detail several specific embodiments with the understanding that the present disclosure is to be considered as an exemplification of the principles of the technology and is not intended to limit the invention to the embodiments illustrated.

DETAILED DESCRIPTION

The present invention relates to methods of administering to a subject multimeric oligonucleotides having monomeric subunits joined by covalent linkers. The multimeric oligonucleotide can have a molecular weight of at least about 45 kD, such that clearance due to glomerular filtration of the multimeric oligonucleotide is reduced. The present invention also relates to the multimeric oligonucleotide and methods of synthesizing the multimeric oligonucleotide. For example, whereas a typical siRNA (e.g., double stranded monomer) may have a molecular weight of about 15 kD and relatively low circulation half-life (e.g., have a glomerular filtration rate similar to urea or glucose), an oligonucleotide multimer according to the invention may have a molecular weight of at least about 45 kD and have a relatively higher circulation half-life (e.g., have a lower rate of clearance due to glomerular filtration rate). The improved and advantageous properties of the multimers according to the invention can be described in terms of increased in vivo circulation half-life. They may also be described in terms of increased in vivo activity.

When combined with a targeting ligand, the multi-conjugate can also deliver a higher payload per ligand/receptor binding event than the monomeric equivalent. The present invention also relates to new synthetic intermediates and methods of synthesizing the multi-conjugate oligonucleotides. The present invention also relates to methods of using the multi-conjugate oligonucleotides, for example in reducing gene expression, biological research, treating or preventing medical conditions, and/or to produce new or altered phenotypes.

Methods of Administering Multimeric Oligonucleotide to a Subject

In various aspects, the invention provides a method of administering a multimeric oligonucleotide to a subject in need thereof, the method comprising administering an effective amount of the multimeric oligonucleotide to the subject, the multimeric oligonucleotide comprising subunits ▬▬▬▬, wherein:

each of the subunits ▬▬▬▬ is independently a single or double stranded oligonucleotide, and each of the subunits ▬▬▬▬ is joined to another subunit by a covalent linker ●;

the multimeric oligonucleotide has a molecular weight and/or size configured to decrease its clearance due to glomerular filtration; and the molecular weight of the multimeric oligonucleotide is at least about 45 kD.

In one aspect, the invention provides a method of administering a multimeric oligonucleotide to a subject in need thereof, wherein the number of subunits contained in the multimeric oligonucleotide is m, m being an integer selected to enable the multimeric oligonucleotide to have the molecular weight and/or size configured to decrease its clearance due to glomerular filtration. In various aspects, m is (i) ≥2; (ii) ≥3; (iii) ≥4; (iv) ≥4 and ≤17; (v) ≥4 and ≤8; or (vi) 4, 5, 6, 7, or 8.

In one aspect, the invention provides a method of administering a multimeric oligonucleotide to a subject in need thereof, in which the multimeric oligonucleotide comprises Structure 21:

(Structure 21)

and n is an integer ≥0.

In one aspect, the invention provides a method of administering a multimeric oligonucleotide to a subject in need thereof, in which the subunits are single-stranded oligonucleotides.

In one aspect, the invention provides a method of administering a multimeric oligonucleotide to a subject in need thereof, wherein n is ≥1.

In one aspect, the invention provides a method of administering a multimeric oligonucleotide to a subject in need thereof, in which the subunits are double-stranded oligonucleotides.

In one aspect, the invention provides a method of administering a multimeric oligonucleotide to a subject in need thereof, wherein:

when n=0, the clearance of the multimeric oligonucleotide due to glomerular filtration is decreased relative to that of a monomeric subunit ▬▬▬▬ and/or a dimeric subunit

of the multimeric oligonucleotide; and when n≥1, the clearance of the multimeric oligonucleotide due to glomerular filtration is decreased relative to that of a monomeric subunit ▬▬▬▬, a dimeric subunit

, and/or a trimeric subunit

of the multimeric oligonucleotide.

Methods of Measuring Decreased Clearance of Multimeric Oligonucleotide

In one aspect, the invention provides a method of administering a multimeric oligonucleotide to a subject in need thereof, in which the decreased clearance due to glomerular filtration results in increased in vivo circulation half-life of the multimeric oligonucleotide.

In one aspect, the invention provides a method of administering a multimeric oligonucleotide to a subject in need thereof, in which the decreased clearance due to glomerular filtration is determined by measuring the in vivo circulation half-life of the multimeric oligonucleotide after administering the multimeric oligonucleotide to the subject.

In one aspect, the invention provides a method of administering a multimeric oligonucleotide to a subject in need thereof, in which the decreased clearance due to glomerular filtration is determined by measuring the time required for the serum concentration of the multimeric oligonucleotide to decrease to a predetermined value. The predetermined value can be 90%, 80%, 70%, 60%, 55%, 50%, 45%, 40%, 35%, 30%, 25%, 20%, 15%, 10%, 5%, 4%, 3%, 2%, or 1% of the administered dose.

In one aspect, the invention provides a method of administering a multimeric oligonucleotide to a subject in need thereof, in which the decreased clearance due to glomerular filtration is determined by measuring the serum concentration of the multimeric oligonucleotide at a predetermined time after administering the multimeric oligonucleotide to the subject.

In one aspect, the invention provides a method of administering a multimeric oligonucleotide to a subject in need thereof, in which the decreased clearance due to glomerular filtration is determined by measuring the area under a curve of a graph representing serum concentration of the multimeric oligonucleotide over time after administering the multimeric oligonucleotide to the subject.

Effects of Decreased Clearance of Multimeric Oligonucleotide Administered to Subjects In one aspect, the invention provides a method of administering a multimeric oligonucleotide to a subject in need thereof, in which the decreased clearance due to glomerular filtration increases in vivo bioavailability of the multimeric oligonucleotide.

In one aspect, the invention provides a method of administering a multimeric oligonucleotide to a subject in need thereof, in which the decreased clearance due to glomerular filtration increases in vivo cellular uptake of the multimeric oligonucleotide.

In one aspect, the invention provides a method of administering a multimeric oligonucleotide to a subject in need thereof, in which the decreased clearance due to glomerular filtration increases in vivo therapeutic index/ratio of the multimeric oligonucleotide.

In one aspect, the invention provides a method of administering a multimeric oligonucleotide to a subject in need thereof, wherein the measured parameter has a sigmoidal relationship with respect to the number of subunits in a monomeric, dimeric, trimeric and higher number multimeric oligonucleotides, for example, as shown in FIGS. 37A-37D.

Figure 38A:
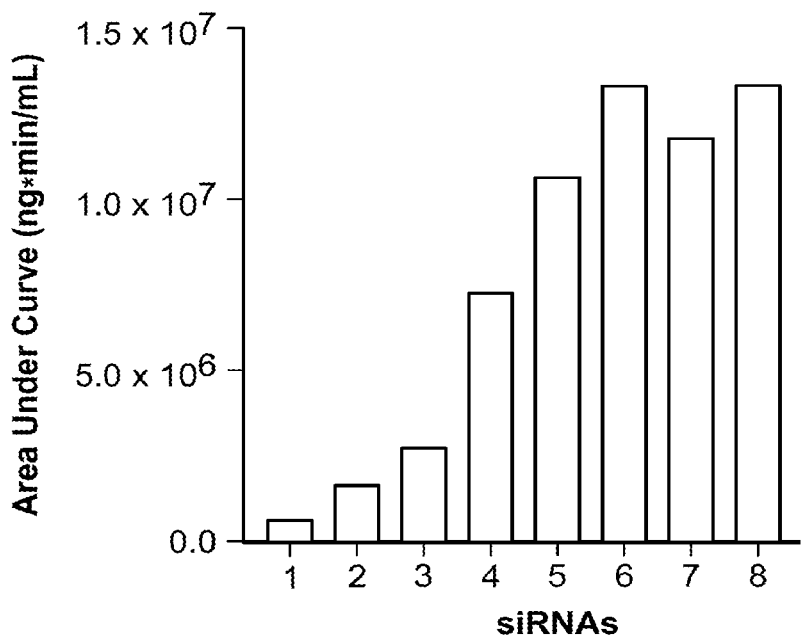
FIG. 38A presents a bar chart of FVII siRNA exposure levels in serum (area under the curve) for FVII multimers, which is discussed in connection with Example 37.
Figure 38B:
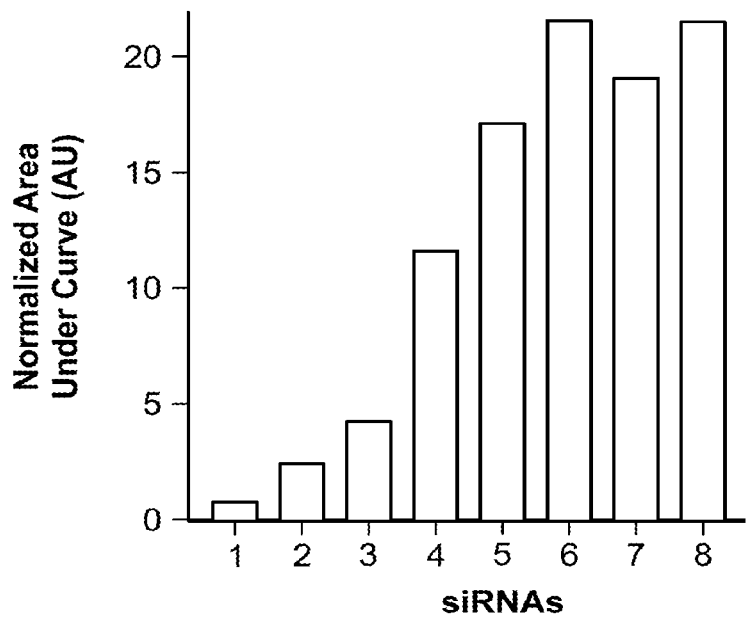
FIG. 38B presents a bar chart of total FVII siRNA levels in serum (area under the curve) for FVII multimers normalized to monomer, which is discussed in connection with Example 37.

In one aspect, the invention provides a method of administering a multimeric oligonucleotide to a subject in need thereof, wherein the measured parameter for the multimeric oligonucleotide and each of its subunits starting with a monomeric subunit, when plotted, define a sigmoidal curve, for example, as shown in FIGS. 38A-38B.

Multimeric Oligonucleotide

In various aspects, the invention provides a multimeric oligonucleotide comprising subunits ------- , wherein:

each of the subunits ------- is independently a single or double stranded oligonucleotide, and each of the subunits ------- is joined to another subunit by a covalent linker ●;

the multimeric oligonucleotide has a molecular weight and/or size configured to decrease its clearance due to glomerular filtration; and the molecular weight of the multimeric oligonucleotide is at least about 45 kD.

In one aspect, the invention provides a multimeric oligonucleotide wherein the number of subunits contained in the multimeric oligonucleotide is m, m being an integer selected to enable the multimeric oligonucleotide to have the molecular weight and/or size configured to decrease its clearance due to glomerular filtration. In various aspects, m is (i) ≥2; (ii) ≥3; (iii) ≥4; (iv) ≥4 and ≤17; (v) ≥4 and ≤8; or (vi) 4, 5, 6, 7, or 8.

A multimeric oligonucleotide as in any one of claims 16 and 17 comprising Structure 21:

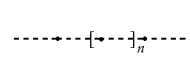

(Structure 21)

wherein at least one of the subunits ------- comprises a single strand having one of the covalent linkers ● joined to its 3' terminus and another of the covalent linkers joined to its 5' terminus, and n is an integer ≥0.

In one aspect, the invention provides a multimeric oligonucleotide in which each subunit ------- is 15-30, 17-27, 19-26, or 20-25 nucleotides in length.

In one aspect, the invention provides a multimeric oligonucleotide wherein n≥1 and n≤17.

In one aspect, the invention provides a multimeric oligonucleotide in which n≥1 and n≤5.

In one aspect, the invention provides a multimeric oligonucleotide in which n is 1, 2, 3, 4, or 5.

In one aspect, the invention provides a multimeric oligonucleotide wherein each subunit is a double-stranded RNA and n≥1.

In one aspect, the invention provides a multimeric oligonucleotide in which each subunit is a single-stranded oligonucleotide.

In one aspect, the invention provides a multimeric oligonucleotide in which each subunit is a double-stranded oligonucleotide.

In one aspect, the invention provides a multimeric oligonucleotide in which the subunits comprise a combination of single-stranded and double-stranded oligonucleotides.

In one aspect, the invention provides a multimeric oligonucleotide in which each subunit is an RNA, a DNA, or an artificial or non-natural nucleic acid analog.

In one aspect, the invention provides a multimeric oligonucleotide in which each subunit is a RNA.

In one aspect, the invention provides a multimeric oligonucleotide in which each subunit is a siRNA, a saRNA, or a miRNA.

In one aspect, the invention provides a multimeric oligonucleotide in which each subunit is a double-stranded siRNA and each of the covalent linkers joins sense strands of the siRNA.

In one aspect, the invention provides a multimeric oligonucleotide in which the multimeric oligonucleotide comprises a homo-multimer of substantially identical subunits -------.

In one aspect, the invention provides a multimeric oligonucleotide in which the multimeric oligonucleotide comprises a hetero-multimer of two or more substantially different subunits -------.

In one aspect, the invention provides a multimeric oligonucleotide in which the multimeric oligonucleotide is at least 75, 80, 85, 90, 95, 96, 97, 98, 99, or 100% pure.

In one aspect, the invention provides a multimeric oligonucleotide wherein each subunit ------- is independently a double stranded oligonucleotide ═══, and wherein n is an integer ≥1.

In one aspect, the invention provides a multimeric oligonucleotide wherein each subunit ------- is independently a double-stranded oligonucleotide ═══, wherein n is an integer ≥1, and wherein each covalent linker ● is on the same strand:

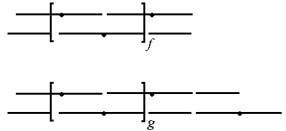
(Structure 54)

wherein d is an integer ≥1.

In one aspect, the invention provides a multimeric oligonucleotide comprising Structure 22 or 23:

(Structure 22)
(Structure 23)

where each ═══ is a double stranded oligonucleotide, each ● is a covalent linker joining adjacent double stranded oligonucleotides, f is an integer ≥1, and g is an integer ≥0.

In one aspect, the invention provides a plurality of a multimeric oligonucleotide wherein substantially all of the multimeric oligonucleotides have a predetermined value of n and/or predetermined molecular weight.

Target Ligands and Aptamers

In one aspect, the invention provides a multimeric oligonucleotide in which the multimeric oligonucleotide further comprises one or more targeting ligands.

In one aspect, the invention provides a multimeric oligonucleotide in which at least one of the subunits is a targeting ligand.

In one aspect, the invention provides a multimeric oligonucleotide in which the targeting ligand is an aptamer.

Linkers

In one aspect, the invention provides a multimeric oligonucleotide in which one or more of the covalent linkers ● comprise a cleavable covalent linker and include nucleotide linkers, for example, as discussed in Examples 20, 22B and 27. Nucleotide linker is a linker that contains one or more nucleotides and it can be chosen such that it does not carry out any other designated function.

In one aspect, the invention provides a multimeric oligonucleotide in which the cleavable covalent linker contains an acid cleavable bond, a reductant cleavable bond, a biocleavable bond, or an enzyme cleavable bond.

In one aspect, the invention provides a multimeric oligonucleotide in which the cleavable covalent linker is cleavable under intracellular conditions.

In one aspect, the invention provides a multimeric oligonucleotide in which each covalent linker ● is the same.

In one aspect, the invention provides a multimeric oligonucleotide in which the covalent linkers ● comprise two or more different covalent linkers.

In one aspect, the invention provides a multimeric oligonucleotide in which each covalent linker ● joins two monomeric subunits -------.

In one aspect, the invention provides a multimeric oligonucleotide in which at least one covalent linker ● joins three or more monomeric subunits -------.

Method of Synthesis of Multimeric Oligonucleotide

In various aspects, the invention provides a method of synthesizing a multimeric oligonucleotide comprising Structure 51:

(Structure 51)

wherein each ——— is a single stranded oligonucleotide, each ● is a covalent linker joining adjacent single stranded oligonucleotides, and a is an integer ≥1, the method comprising the steps of:
(i) reacting

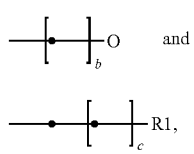
(Structure 52)

and (Structure 53)

wherein ○ is a linking moiety, R1 is a chemical group capable of reacting with the linking moiety ○, b and c are each independently an integer ≥0, b and c cannot both simultaneously be zero, and b+c=a, thereby forming Structure 51:

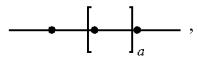
(Structure 51)

and (ii) optionally annealing Structure 51:

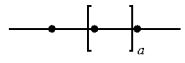
(Structure 51)

with complementary single stranded oligonucleotides ———, thereby forming Structure 54:

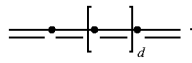
(Structure 54)

In various aspects, the invention provides a method of synthesizing a multimeric oligonucleotide comprising Structure 54:

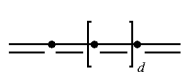
(Structure 54)

wherein each ——— is a single stranded oligonucleotide, each ● is a covalent linker joining adjacent single stranded oligonucleotides, and a≥1, the method comprising the steps of:

(i) annealing Structure 51:

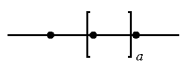
(Structure 51)

with complementary single stranded oligonucleotides ———, thereby forming Structure 54:

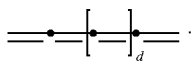
(Structure 54)

Subjects

In one aspect, the invention provides a method of administering a multimeric oligonucleotide to a subject in need thereof, wherein the subject is a rodent, for example, a mouse or a rat.

In one aspect, the invention provides a method of administering a multimeric oligonucleotide to a subject in need thereof, wherein the subject is a primate, for example, a human.

Mouse glomerular filtration rate (GFR) can be about 0.15-0.25 ml/min Human GFR can be about 1.8 ml/min/kg (Mahmood I: (1998) Interspecies scaling of renally secreted drugs. Life Sci 63:2365-2371).

Mice can have about 1.46 ml of blood. Therefore, the time for glomerular filtration of total blood volume in mice can be about 7.3 minutes (1.46/0.2). Humans can have about 5 liters of blood and weigh about 70 kg. Therefore, the time for glomerular filtration of total blood volume in humans can be 39.7 mins [5000/126(1.8*70)].

A person of ordinary skill in the art would recognize that different species can have different rates of clearance by glomerular filtration, at least for the above reasons. A person of ordinary skill in the art can infer that a ratio of rate of clearance by glomerular filtration between human and mouse times can be about 1:5 or 1:6. In other words, the rate of clearance of a certain substance (e.g., a particular oligonucleotide) by humans can be 5-6 times slower than that of a mouse.

In one aspect, the invention provides a method of administering a multimeric oligonucleotide to a subject in need thereof, wherein the in vivo circulation half-life is measured between 30 and 120 minutes after administering the multimeric oligonucleotide to the subject.

In one aspect, the invention provides a method of administering a multimeric oligonucleotide to a subject in need thereof, wherein the predetermined time is between 30 and 120 minutes after administering the multimeric oligonucleotide to the subject.

In one aspect, the invention provides a method of administering a multimeric oligonucleotide to a subject in need thereof, wherein the area under the curve is calculated based on serum concentration of the multimeric oligonucleotide between x and y minutes after administering the multimeric oligonucleotide to the subject. In some embodiments, x can be 1, 2, 3, 4, 5, 10, 20, 30, 40, 50, 60, 75, 90, 120, 180, 240, or 300 minutes and y can be 90, 120, 180, 240, 300, 360, 420, 480, 540, 600, 720, 840, 960, 1080, 1200, 1320, 1440, or 1600 minutes. For example, the time range can be 30-120 minutes, 1-1600 minutes, or 300-600 minutes.

In one aspect, the invention provides a multimeric oligonucleotide or a method for increasing in vivo circulation half-life of the multimeric oligonucleotide, wherein the multimeric oligonucleotide is not formulated in a nanoparticle (NP) or a lipid nanoparticle (LNP).

The present invention also relates to multi-conjugate oligonucleotides having improved pharmacodynamics and/or pharmacokinetics. For example, the multi-conjugate oligonucleotides (e.g., multimeric oligonucleotide including 3, 4, 5, 6, 7, 8, 9, 10, 11, 12 or more siRNA) can have increased in vivo circulation half-life and/or increased in vivo activity, relative to that of the individual monomeric subunits. When conjugated to a targeting ligand, the multi-conjugate can also deliver a higher oligonucleotide payload per ligand/receptor binding event than the monomeric equivalent. The present invention also relates to new synthetic intermediates and methods of synthesizing the multi-conjugate oligonucleotides. The present invention also relates to methods of using the multi-conjugate oligonucleotides, for example in reducing gene expression, biological research, treating or preventing medical conditions, and/or to produce new or altered phenotypes.

Various features of the invention are discussed, in turn, below.

Nucleic Acids

In various embodiments, the nucleic acid or oligonucleotide is RNA, DNA, or comprises an artificial or non-natural nucleic acid analog. In various embodiments, the nucleic acid or oligonucleotide is single stranded. In various embodiments, the nucleic acid or oligonucleotide is double stranded (e.g., antiparallel double stranded).

In various embodiments, the nucleic acid or oligonucleotide is RNA, for example an antisense RNA (aRNA), CRISPR RNA (crRNA), long noncoding RNA (lncRNA), microRNA (miRNA), piwi-interacting RNA (piRNA), small interfering RNA (siRNA), messenger RNA (mRNA), short hairpin RNA (shRNA), small activating (saRNA), or ribozyme.

In one embodiment, the RNA is siRNA. For example, each double stranded oligonucleotide is an siRNA and/or has a length of 15-30 base pairs.

In various embodiments, the nucleic acid or oligonucleotide is an aptamer.

siRNA (small interfering RNA) is a short double-stranded RNA composed of 19-22 nucleic acids, which targets mRNA (messenger RNA) of a gene whose nucleotide sequence is identical with its sense strand in order to suppress expression of the gene by decomposing the target gene (Elbashir, S. M., Harborth, J., Lendeckel, W., Yalcin, A., Weber, K., and Tuschl, T. (2001) Duplexes of 21-nucleotide RNAs mediate RNA interference in cultured mammalian cells. Nature 411: 494-8).

Another class of nucleic acid, useful in the methods of the invention, are miRNAs. MiRNAs are non-coding RNAs that play key roles in post-transcriptional gene regulation. miRNA can regulate the expression of 30% of all mammalian protein-encoding genes. Specific and potent gene silencing by double stranded RNA (RNAi) was discovered, plus additional small noncoding RNA (Canver, M. C. et al., Nature (2015)). Pre-miRNAs are short stem loops ~70 nucleotides in length with a 2-nucleotide 3'-overhang that are exported, into the mature 19-25 nucleotide duplexes. The miRNA strand with lower base pairing stability (the guide strand) can be loaded onto the RNA-induced silencing complex (RISC). The passenger guide strand can be functional but is usually degraded. The mature miRNA tethers RISC to partly complementary sequence motifs in target mRNAs predominantly found within the 3' untranslated regions (UTRs) and induces posttranscriptional gene silencing (Bartel, D. P. Cell, 136: 215-233 (2009); Saj, A. & Lai, E. C. Curr Opin Genet Dev, 21: 504-510 (2011)). MiRNAs mimics are described for example, in U.S. Pat. No. 8,765,709.

In some embodiments, the RNA can be short hairpin RNA (shRNA), for example, as described in U.S. Pat. Nos. 8,202,846 and 8,383,599.

In some embodiments, the RNA can be CRISPR RNA (crRNA), for example, CRISPR array of Type V can be processed into short mature crRNAs of 42-44 nucleotides in length, with each mature crRNA beginning with 19 nucleotides of direct repeat followed by 23-25 nucleotides of spacer sequence. Alternatively, mature crRNAs in Type II systems can start with 20-24 nucleotides of spacer sequence followed by about 22 nucleotides of direct repeat. CRISPR systems are described for example, in U.S. Pat. No. 8,771,945, Jinek et al., Science, 337(6096): 816-821 (2012), and International Patent Application Publication No. WO 2013/176772.

In various embodiments, the nucleic acid or oligonucleotide is 15-30, 17-27, 19-26, 20-25, 40-50, 40-150, 100-300, 1000-2000, or up to 10000 nucleotides in length.

In various embodiments, the oligonucleotide is double stranded and complementary. Complementarity can be 100% complementary, or less than 100% complementary where the oligonucleotide nevertheless hybridizes and remains double stranded under relevant conditions (e.g., physiologically relevant conditions). For example, a double stranded oligonucleotide can be at least about 80, 85, 90, or 95% complementary.

In some embodiments, RNA is long noncoding RNA (lncRNA), lncRNAs are a large and diverse class of transcribed RNA molecules with a length of more than 200 nucleotides that do not encode proteins (or lack >100 amino acid open reading frame). lncRNAs are thought to encompass nearly 30,000 different transcripts in humans, hence lncRNA transcripts account for the major part of the non-coding transcriptome (see, e.g., Derrien et al., The GENCODE v7 catalog of human long noncoding RNAs: analysis of their gene structure, evolution, and expression. Genome Res, 22(9): 1775-89 (2012)).

In yet other embodiments, RNA is messenger RNA (mRNA). mRNA and its application as a delivery method for in-vivo production of proteins, is described, for example, in International Patent Application Publication No. WO 2013/151736.

In other embodiments, RNA can be small activating (saRNA) (e.g., as described in Chappell et al., Nature Chemical Biology, 11: 214-220 (2015)), or ribozyme (Doherty et al., Ann Rev Biophys Biomo Struct, 30: 457-475 (2001)).

In some embodiments, the nucleic acid or oligonucleotide is DNA, for example an antisense DNA (aDNA) (e.g., antagomir) or antisense gapmer. Examples of aDNA, including gapmers and multimers, are described for example in Subramanian et al., Nucleic Acids Res, 43(19): 9123-9132 (2015) and International Patent Application Publication No. WO 2013/040429. Examples of antagomirs are described for example, in U.S. Pat. No. 7,232,806.

In various embodiments, the oligonucleotide has a specific sequence, for example any one of the sequences disclosed herein.

A general procedure for oligonucleotide synthesis is provided in the examples below. Other methods that can be adapted for use with the invention are known in the art.

Modifications to Nucleic Acids

In various embodiments, the nucleic acid or oligonucleotide further comprises a chemical modification. The chemical modification can comprise a modified nucleoside, modified backbone, modified sugar, or modified terminus.

Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3' alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'.

The oligonucleotides contained in the multi-conjugates of this invention may be modified using various strategies known in the art to produce a variety of effects, including, e.g., improved potency and stability in vitro and in vivo. Among these strategies are: artificial nucleic acids, e.g., 2'-O-methyl-substituted RNA; 2'-fluro-2'deoxy RNA, peptide nucleic acid (PNA); morpholinos; locked nucleic acid (LNA); Unlocked nucleic acids (UNA); bridged nucleic acid (BNA); glycol nucleic acid (GNA); and threose nucleic acid (TNA); or more generally, nucleic acid analogs, e.g., bicyclic and tricyclic nucleoside analogs, which are structurally similar to naturally occurring RNA and DNA but have alterations in one or more of the phosphate backbone, sugar, or nucleobase portions of the naturally-occurring molecule. Typically, analogue nucleobases confer, among other things, different base pairing and base stacking properties. Examples include universal bases, which can pair with all four canon bases. Examples of phosphate-sugar backbone analogues include PNA. Morpholino-based oligomeric compounds are described in Braasch et al., Biochemistry, 41(14): 4503-4510 (2002) and U.S. Pat. Nos. 5,539,082; 5,714,331; 5,719,262; and 5,034,506.

In the manufacturing methods described herein, some of the oligonucleotides are modified at a terminal end by substitution with a chemical functional group. The substitution can be performed at the 3' or 5' end of the oligonucleotide, and is preferably performed at the 3' ends of both the sense and antisense strands of the monomer, but is not always limited thereto. The chemical functional groups may include, e.g., a sulfhydryl group (—SH), a carboxyl group (—COOH), an amine group (—NH2), a hydroxy group (—OH), a formyl group (—CHO), a carbonyl group (—CO—), an ether group (—O—), an ester group (—COO—), a nitro group (—NO$_2$), an azide group (—N$_3$), or a sulfonic acid group (—SO$_3$H).

The oligonucleotides contained in the multi-conjugates of this invention may be modified to also include, additionally or alternatively, nucleobase (often referred to in the art simply as "base") modifications or substitutions. Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6

(6-aminohexyl)adenine, and 2,6-diaminopurine. Kornberg, A., DNA Replication, W. H. Freeman & Co., San Francisco, pp 75-77 (1980); Gebeyehu et al., Nucl. Acids Res, 15: 4513 (1997). A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, pp 276-278 (1993) and are aspects of base substitutions. Modified nucleobases can include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine. Hydroxy group (—OH) at a terminus of the nucleic acid can be substituted with a functional group such as sulfhydryl group (—SH), carboxyl group (—COOH) or amine group (—NH$_2$). The substitution can be performed at the 3' end or the 5' end.

Linkers

In various aspects and embodiments of the invention, oligonucleotides are linked covalently. Linkers may be cleavable (e.g., under intracellular conditions, to facilitate oligonucleotide delivery and/or action) or non-cleavable. Although generally described below and in the Examples in the context of linkers using nucleophile-electrophile chemistry, other chemistries and configurations are possible. And, as will be understood by those having ordinary skill, various linkers, including their composition, synthesis, and use are known in the art and may be adapted for use with the invention.

In various embodiments, a covalent linker can comprise the reaction product of nucleophilic and electrophilic groups. For example, a covalent linker can comprise the reaction product of a thiol and maleimide, a thiol and vinylsulfone, a thiol and pyridyldisulfide, a thiol and iodoacetamide, a thiol and acrylate, an azide and alkyne, or an amine and carboxyl group. As described herein, one of these groups is connected to an oligonucleotide (e.g., thiol (—SH) functionalization at the 3' or 5' end) and the other group is encompassed by a second molecule (e.g., linking agent) that ultimately links two oligonucleotides (e.g., maleimide in DTME).

In various embodiments, a covalent linker can comprise an unmodified di-nucleotide linkage or a reaction product of thiol and maleimide.

In various embodiments, two or more linkers of a multimeric oligonucleotide can comprise two orthogonal types of bio-cleavable linkages. In a preferred embodiment, the two orthogonal bio-cleavable linkages can comprise an unmodified di-nucleotide and a reaction product of thiol and maleimide.

In various embodiments, the nucleic acid or oligonucleotide is connected to the linker via a phosphodiester or thiophosphodiester (e.g., R1 in Structure 1 is a phosphodiester or thiophosphodiester). In various embodiments, the nucleic acid or oligonucleotide is connected to the linker via a C1-8 alkyl, C2-8 alkenyl, C2-8 alkynyl, heterocyclyl, aryl, and heteroaryl, branched alkyl, aryl, halo-aryl, and/or other carbon-based connectors. In various embodiments, the nucleic acid or oligonucleotide is connected to the linker via a C2-C10, C3-C6, or C6 alkyl (e.g., R2 in Structure 1 is a C2-C10, C3-C6, or C6 alkyl). In a preferred embodiment, the nucleic acid or oligonucleotide is connected to the linker via a C6 alkyl. Alternatively, these moieties (e.g., R1 and/or R2 in Structure 1) are optional and a direct linkage is possible.

In various embodiments, the nucleic acid or oligonucleotide is connected to the linker via the reaction product of a thiol and maleimide group. (e.g., A in Structure 1 is the reaction product of a thiol and maleimide group). Preferred linking agents utilizing such chemistry include DTME (dithiobismaleimidoethane), BM(PEG)2 (1,8-bis(maleimido)diethylene glycol), BM(PEG)3 (1,11-bismaleimido-triethyleneglycol), BMOE (bismaleimidoethane), BMH (bismaleimidohexane), or BMB (1,4-bismaleimidobutane).

Again, the Examples are illustrative and not limiting. In various embodiments, oligonucleotides can be linked together directly, via functional end-substitutions, or indirectly by way of a linking agent. In various embodiments, the oligonucleotide can be bound directly to a linker (e.g., R1 and R2 of Structure 1 are absent). Such bonding can be achieved, for example, through use of 3'-thionucleosides, which can be prepared according to the ordinary skill in the art. See, e.g., Sun et al. "Synthesis of 3'-thioribonucleosides and their incorporation into oligoribonucleotides via phosphoramidite chemistry" RNA. 1997 Nov.; 3(11):1352-63. In various embodiments, the linking agent may be a non-ionic hydrophilic polymer such as polyethyleneglycol (PEG), polyvinylpyrolidone and polyoxazoline, or a hydrophobic polymer such as PLGA and PLA.

A polymer linking agent used as a mediator for a covalent bond may be non-ionic hydrophilic polymers including PEG, Pluronic, polyvinylpyrolidone, polyoxazoline, or copolymers thereof; or one or more biocleavable polyester polymers including poly-L-lactic acid, poly-D-lactic acid, poly-D,L-lactic acid, poly-glycolic acid, poly-D-lactic-co-glycolic acid, poly-L-lactic-co-glycolic acid, poly-D,L-lactic-co-glycolic acid, polycaprolactone, polyvalerolactone, polyhydroxybutyrate, polyhydroxyvalerate, or copolymers thereof, but is not always limited thereto.

The linking agent may have a molecular weight of 100-10,000 Daltons. Examples of such linking agent include dithio-bis-maleimidoethane (DTME), 1,8-bis-maleimidodiethyleneglycol (BM(PEG)2), tris-(2-maleimidoethyl)-amine (TMEA), tri-succinimidyl aminotriacetate (TSAT), 3-arm-poly(ethylene glycol) (3-arm PEG), maleimide, N-hydroxysuccinimide (NHS), vinylsulfone, iodoacetyl, nitrophenyl azide, isocyanate, pyridyldisulfide, hydrazide, and hydroxyphenyl azide.

A linking agent having cleavable bonds (such as a reductant bond that is cleaved by the chemical environment of the cytosol) or a linking agent having non-cleavable bonds can be used herein. For example, the linking agent of the foregoing aspects of present invention can have non-cleavable bonds such as an amide bond or a urethane bond. Alternatively, the linking agent of the foregoing aspects of the present invention can have cleavable bonds such as an acid cleavable bond (e.g., a covalent bond of ester, hydrazone, or acetal), a reductant cleavable bond (e.g., a disulfide bond), a bio-cleavable bond, or an enzyme cleavable bond. In one embodiment, the cleavable covalent linker is cleavable under intracellular conditions. Additionally, any linking agent available for drug modification can be used in the foregoing aspects of the invention without limitation.

Further, combinations of functional groups and linking agents may include: (a) where the functional groups are amino and thiol, the linking agent may be Succinimidyl 3-(2-pyridyldithio)propionate, or Succinimydyl 6-([3(2-pyridyldithio)propioamido]hexanoate; (b) where the functional group is amino, the linking agent may be 3,3'dithiodipropionic acid di-(N-succinimidyl ester), Dithio-bis(ethyl 1H-imidazole-1-carboxylate), or Dithio-bis(ethyl 1H-imidazole-1-carboxylate); (c) where the functional groups are amino and alkyne, the linking agent may be Sulfo-N-succinimidyl3-[[2-(p-azidosalicylamido)ethyl]-1,3'-dithio]propionate; and (d) where the functional group y is thiol, the linking agent is dithio-bis-maleimidoethane (DTME); 1,8-Bis-maleimidodiethyleneglycol (BM(PEG)2); or dithiobis(sulfosuccinimidyl propionate) (DTSSP).

In the foregoing methods of preparing compounds, an additional step of activating the functional groups can be included. Compounds that can be used in the activation of the functional groups include but are not limited to 1-ethyl-3,3-dimethylaminopropyl carbodiimide, imidazole, N-hydroxysuccinimide, dichlorohexylcarbodiimide, N-beta-Maleimidopropionic acid, N-beta-maleimidopropyl succinimide ester or N-Succinimidyl 3-(2-pyridyldithio)propionate.

Monomeric Intermediate Compounds

In various aspects, the invention provides an oligonucleotide coupled to a covalent linker, which can be used, for example, in the synthesis of defined multi-conjugate oligonucleotides having predetermined sizes and compositions.

In one aspect, the invention provides a compound according to Structure 1:

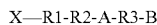     (Structure 1)

wherein:
X is a nucleic acid bonded to R1 through its 3' or 5' terminus;
R1 is a derivative of phosphoric acid, a derivative of thiophosphoric acid, a sulfate, amide, glycol, or is absent;
R2 is a C2-C10 alkyl, alkoxy, or aryl group, or is absent;
A is the reaction product of a nucleophile and an electrophile;
R3 is a C2-C10 alkyl, alkoxy, aryl, alkyldithio group, ether, thioether, thiopropionate, or disulfide; and
B is a nucleophile or electrophile (e.g., a thiol, maleimide, vinylsulfone, pyridyldisulfide, iodoacetamide, acrylate, azide, alkyne, amine, or carboxyl group).

In one aspect, the invention provides a compound according to Structure 2:

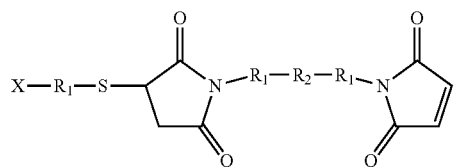

(Structure 2)

wherein:
X is a nucleic acid bonded to R1 via a phosphate or derivative thereof, or thiophosphate or derivative thereof at its 3' or 5' terminus;
each R1 is independently a C2-C10 alkyl, alkoxy, or aryl group; and
R2 is a thiopropionate or disulfide group.

In one aspect, the invention provides a compound according to Structure 3:

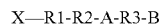     (Structure 3)

wherein:
X is a nucleic acid bonded to R1 through its 3' or 5' terminus;
R1 is a derivative of phosphoric acid such as phosphate, phosphodiester, phosphotriester, phosphonate, phosphoramidate and the like, a derivative of thiophosphoric acid such as thiophosphate, thiophosphodiester, thiophosphotriester, thiophosphoramidate and the like, a sulfate, amide, glycol, or is absent;
R2 is a C2-C10 alkyl, alkoxy, or aryl group, or is absent;
A is the reaction product of a first and a second reactive moiety;
R3 is an C2-C10 alkyl, alkoxy, aryl, alkyldithio group, ether, thioether, thiopropionate, or disulfide; and
B is a third reactive moiety.

In various aspects, the invention also provides methods for synthesizing an oligonucleotide coupled to a covalent linker.

In one aspect, the invention provides a method for synthesizing a compound according to Structure 1 (or adapted for synthesizing a compounds according to Structure 2 or 3), the method comprising:
reacting a functionalized nucleic acid X—R1-R2-A' and a covalent linker A"-R3-B, wherein A' and A" comprise a nucleophile and an electrophile, in a dilute solution of X—R1-R2-A' and with a stoichiometric excess of A"-R3-B, thereby forming the compound X—R1-R2-A-R3-B (Structure 1), wherein:
X is a nucleic acid bonded to R1 through its 3' or 5' terminus;
R1 a phosphodiester, thiophosphodiester, sulfate, amide, glycol, or is absent;
R2 is a C2-C10 alkyl, alkoxy, or aryl group, or is absent;
A is the reaction product of a nucleophile and an electrophile;
R3 is a C2-C10 alkyl, alkoxy, aryl, alkyldithio group, ether, thioether, thiopropionate, or disulfide; and
B is a nucleophile or electrophile (e.g., a thiol, maleimide, vinylsulfone, pyridyldisulfide, iodoacetamide, acrylate, azide, alkyne, amine, or carboxyl group).

The method can further comprise the step of synthesizing the functionalized nucleic acid X—R1-R2-A', wherein A' comprises a thiol (—SH) by (i) introducing the thiol during solid phase synthesis of the nucleic acid using phosphoramidite oligomerization chemistry or (ii) reduction of a disulfide introduced during the solid phase synthesis.

In various embodiments, the method for synthesizing the compound of Structure 1 further comprises synthesizing the compound of Structure 2.

The oligonucleotide coupled to a covalent linker can include any one or more of the features described herein, including in the Examples. For example, the compounds can include any one or more of the nucleic acids (with or without modifications), targeting ligands, and/or linkers described herein, or any of the specific structures or chemistries shown in the summary, description, or Examples. Example 1 provides an example methodology for generating thiol terminated oligonucleotides. Example 2 provides an example methodology for preparing an oligonucleotide coupled to a linker.

In various embodiments, the method for synthesizing the compound of Structure 1, 2 or 3 is carried out under conditions that substantially favor the formation of Structure 1, 2 or 3 and substantially prevent dimerization of X. The conditions can improve the yield of the reaction (e.g., improve the purity of the product).

In various embodiments, the method for synthesizing the compound of Structure 1, 2 or 3, the step of reacting the functionalized nucleic acid X—R1-R2-A' and the covalent linker A"-R3-B is carried out at a X—R1-R2-A' concentration of below about 1 mM, 500 µM, 250 µM, 100 µM, or 50 µM. Alternatively, the X—R1-R2-A' concentration can be about 1 mM, 500 µM, 250 µM, 100 µM, or 50 µM.

In various embodiments, the method for synthesizing the compound of Structure 1, 2 or 3, the step of reacting the functionalized nucleic acid X—R1-R2-A' and the covalent linker A"-R3-B is carried out with a molar excess of A"-R3-B of at least about 5, 10, 15, 20, 25, 30, 35, 40, 45, 50, or 100. Alternatively, the molar excess of A"-R3-B can be about 5, 10, 15, 20, 25, 30, 35, 40, 45, 50, or 100.

In various embodiments, the method for synthesizing the compound of Structure 1, 2 or 3, the step of reacting the functionalized nucleic acid X—R1-R2-A' and the covalent linker A"-R3-B is carried out at a pH of below about 7, 6, 5, or 4. Alternatively, the pH can be about 7, 6, 5, or 4.

In various embodiments, the method for synthesizing the compound of Structure 1, 2 or 3, the step of reacting the functionalized nucleic acid X—R1-R2-A' and the covalent linker A"-R3-B is carried out in a solution comprising water and a water miscible organic co-solvent. The water miscible organic co-solvent can comprise DMF (dimethylformamide), NMP (N-methyl-2-pyrrolidone), DMSO (dimethyl sulfoxide), or acetonitrile. The water miscible organic co-solvent can comprise about 10, 15, 20, 25, 30, 40, or 50% V (v/v) of the solution.

In various embodiments, the compound is isolated or substantially pure. For example, the compound can be at least 75, 80, 85, 90, 95, 96, 97, 98, 99, or 100% pure. In one embodiment, the compound is about 85-95% pure. Likewise, the methods for synthesizing the compounds and compositions according to the invention can result in a product that is at least 75, 80, 85, 90, 95, 96, 97, 98, 99, or 100% pure. In one embodiment, the product is about 85-95% pure. Preparations can be greater than or equal to 50% pure; preferably greater than or equal to 75% pure; more preferably greater than or equal to 85% pure; and still more preferably, greater than or equal to 95% pure.

As used herein, the term about is used in accordance with its plain and ordinary meaning of approximately. For example, "about X" encompasses approximately the value X as stated, including similar amounts that are within the measurement error for the value of X or amounts that are approximately the same as X and have essentially the same properties as X.

As used herein, isolated includes compounds that are separated from other, unwanted substances. The isolated compound can be synthesized in a substantially pure state or separated from the other components of a crude reaction mixture, except that some amount of impurities, including residual amounts of other components of the crude reaction mixture, may remain. Similarly, pure or substantially pure means sufficiently free from impurities to permit its intended use (e.g., in a pharmaceutical formulation or as a material for a subsequent chemical reaction). X % pure means that the compound is X % of the overall composition by relevant measure, which can be for example by analytical methods such as HPLC.

Dimeric Compounds and Intermediates

In various aspects, the invention provides dimeric defined multi-conjugate oligonucleotides. These compounds include homodimers (e.g., two oligonucleotides that are substantially the same, for example targeting the same gene in vivo) and heterodimers (e.g., two oligonucleotides that are substantially different, for example different sequences or targeting different genes in vivo)

In one aspect, the invention provides an isolated compound according to Structure 4:

(Structure 4)

wherein:

each  is a double stranded oligonucleotide designed to react with the same molecular target in vivo, and ● is a covalent linker joining single strands of adjacent single stranded oligonucleotides at their 3' or 5' termini, and having the structure —R1-R2-A-R3-A-R2-R1- wherein:
each R1 is a derivative of phosphoric acid such as phosphate, phosphodiester, phosphotriester, phosphonate, phosphoramidate and the like, a derivative of thiophosphoric acid such as thiophosphate, thiophosphodiester, thiophosphotriester, thiophosphoramidate and the like, a sulfate, amide, glycol, or is absent;

each R2 is independently a C2-C10 alkyl, alkoxy, or aryl group, or is absent;

each A is independently the reaction product of a nucleophile and an electrophile, and R3 is a C2-C10 alkyl, alkoxy, aryl, alkyldithio group, ether, thioether, thiopropionate, or disulfide.

In one aspect, the invention provides an isolated compound according to Structure 5:

(Structure 5)

wherein:

 is a first single stranded oligonucleotide

 is a second single stranded oligonucleotide having a different sequence from the first, and ● is a covalent linker joining single strands of adjacent single stranded oligonucleotides at their 3' or 5' termini, and having the structure —R1-R2-A-R3-A-R2-R1- wherein:
each R1 is a derivative of phosphoric acid such as phosphate, phosphodiester, phosphotriester, phosphonate, phosphoramidate and the like, a derivative of thiophosphoric acid such as thiophosphate, thiophosphodiester, thiophosphotriester, thiophosphoramidate and the like, a sulfate, amide, glycol, or is absent;

each R2 is independently a C2-C10 alkyl, alkoxy, or aryl group, or is absent;

each A is independently the reaction product of a thiol and maleimide, a thiol and vinylsulfone, a thiol and pyridyldisulfide, a thiol and iodoacetamide, a thiol and acrylate, an azide and alkyne, or an amine and carboxyl group, and R3 is an C2-C10 alkyl, alkoxy, aryl, alkyldithio group, ether, thioether, thiopropionate, or disulfide.

In one aspect, the invention provides an isolated compound according to Structure 6:

 (Structure 6)

wherein:
===== is a first double stranded oligonucleotide
∿∿∿ is a second double stranded oligonucleotide having a different sequence from the first, and
● is a covalent linker joining single strands of adjacent single stranded oligonucleotides at their 3' or 5' termini, and having the structure —R1-R2-A-R3-A-R2-R1-
wherein:
each R1 is a derivative of phosphoric acid such as phosphate, phosphodiester, phosphotriester, phosphonate, phosphoramidate and the like, a derivative of thiophosphoric acid such as thiophosphate, thiophosphodiester, thiophosphotriester, thiophosphoramidate and the like, a sulfate, amide, glycol, or is absent;
each R2 is independently a C2-C10 alkyl, alkoxy, or aryl group, or is absent;
each A is independently the reaction product of a thiol and maleimide, a thiol and vinylsulfone, a thiol and pyridyldisulfide, a thiol and iodoacetamide, a thiol and acrylate, an azide and alkyne, or an amine and carboxyl group, and
R3 is an C2-C10 alkyl, alkoxy, aryl, alkyldithio group, ether, thioether, thiopropionate, or disulfide.

In one aspect, the invention provides an isolated compound according to Structure 11:

 (Structure 11)

wherein:
===== is a double stranded oligonucleotide,
——— is a single stranded oligonucleotide, and
● is a covalent linker joining single strands of adjacent single stranded oligonucleotides.

In various aspects, the invention provides methods for synthesizing dimeric defined multi-conjugate oligonucleotides.

In one aspect, the invention provides a method for synthesizing a compound of Structure 5:

 (Structure 5)

wherein ——— is a first single stranded oligonucleotide, ∿∿∿ is a second single stranded oligonucleotide having a different sequence from the first, and ● is a covalent linker joining single strands of adjacent single stranded oligonucleotides at their 3' or 5' termini, the method comprising the steps of:

(i) reacting a first single stranded oligonucleotide

with a bifunctional linking moiety ○, wherein R1 is a chemical group capable of reacting with ○ under conditions that produce the mono-substituted product

(ii) reacting

with a second single stranded oligonucleotide

wherein R2 is a chemical group capable of reacting with ○, thereby forming

The method can further comprise the step of annealing complementary ——— and ∿∿∿ to yield Structure 6:

 (Structure 6)

In one aspect, the invention provides a method for synthesizing an isolated compound of Structure 4:

 (Structure 4)

wherein each ===== is a double stranded oligonucleotide and ● is a covalent linker joining single strands of adjacent single stranded oligonucleotides at their 3' or 5' termini, the method comprising the steps of:

(i) reacting a first single stranded oligonucleotide

with a bifunctional linking moiety ○, wherein R1 is a chemical group capable of reacting with ○, thereby forming a mono-substituted product

(ii) reacting

with a second single stranded oligonucleotide

——R₂, wherein R2 is a chemical group capable of reacting with ○, thereby forming a single stranded dimer

———•———;

(iii) annealing single stranded oligonucleotides, at the same time or sequentially, thereby forming

═══•═══.

In one aspect, the invention provides a method for synthesizing an isolated compound of Structure 4:

═══•═══    (Structure 4)

wherein each ═══ is a double stranded oligonucleotide and ● is a covalent linker joining single strands of adjacent single stranded oligonucleotides at their 3' or 5' termini, the method comprising the steps of:

(i) forming

═══•——— by:

(a) annealing a first single stranded oligonucleotide ——— and a second single stranded oligonucleotide

——R₁, thereby forming

═══R₁, and reacting

═══R₁ with a third single stranded oligonucleotide

——R₂, wherein R1 and R2 are chemical moieties capable of reacting directly or indirectly to form a covalent linker ●, thereby forming

═══•———;

or (b) reacting the second single stranded oligonucleotide

——R₁ and the third single stranded oligonucleotide

——R₂, thereby forming

———•———, and annealing the first single stranded oligonucleotide ——— and

———•———, thereby forming

═══•———;

(ii) annealing

═══•——— and a fourth single stranded oligonucleotide ———, thereby forming

═══•═══.

This methodology can be adapted for synthesizing an isolated compound according to ═══•———,    (Structure 11)

for example by omitting step (ii).

In one aspect, the invention provides a method for synthesizing an isolated compound of Structure 4:

 (Structure 4)

wherein each ══ is a double stranded oligonucleotide and ● is a covalent linker joining single strands of adjacent single stranded oligonucleotides at their 3' or 5' termini, the method comprising the steps of:

(a) annealing a first single stranded oligonucleotide ─── and a second single stranded oligonucleotide

thereby forming

(b) annealing a third single stranded oligonucleotide

and a fourth single stranded oligonucleotide ───, thereby forming

(c) reacting

wherein R1 and R2 are chemical moieties capable of reacting directly or indirectly to form a covalent linker ●, thereby forming

.

As with the other compounds and compositions according to the invention, dimeric compounds and intermediates can include any one or more of the features described herein, including in the Examples. For example, the compounds can include any one or more of the nucleic acids (with or without modifications), targeting ligands, and/or linkers described herein, or any of the specific structures or chemistries shown in the summary, description, or Examples.

Example 3 provides an example methodology for preparing dimerized oligocleotides and Example 4 provides an example methodology for annealing single stranded oligonucleotides to form double stranded oligonucleotides. Example 7 provides an example methodology for preparing various oligonucleotide precursors useful in the syntheses above. Example 8 provides an example methodology for preparing various oligonucleotide multimers, which are also useful in the syntheses above.

Examples of heterodimers are provided in Examples 9 and 10.

Examples of homodimers are provided in Examples 12-15.

In various embodiments, R1, R2, and the bifunctional linking moiety ○ can form a covalent linker ● as described and shown herein. For example, in various embodiments, R1 and R2 can each independently comprise a reactive moiety, for example an electrophile or nucleophile. In one embodiment, R1 and R2 can each independently be selected from the group consisting of a thiol, maleimide, vinylsulfone, pyridyldisulfide, iodoacetamide, acrylate, azide, alkyne, amine, and carboxyl group. In various embodiments, the bifunctional linking moiety ○ comprises two reactive moieties that can be sequentially reacted according to steps (i) and (ii) above, for example a second electrophile/nucleophile that can be reacted with an electrophile/nucleophile in R1 and R2. Examples of bifunctional linking moieties ○ include, but are not limited to, DTME, BM(PEG)2, BM(PEG)3, BMOE, BMH, or BMB.

These, as well as all other synthetic methods of the invention, can further comprise the step of adding a targeting ligand to the molecule. Example 6 provides an example methodology for adding a targeting ligand (e.g., GalNAc). Additional methods for adding targeting ligands are known in the art and can be adapted for the present invention by those skilled in the art.

Multimeric (n>2) Compounds and Intermediates

In various aspects, the invention provides multimeric (n>2) defined multi-conjugate oligonucleotides, including defined tri-conjugates and defined tetraconjugates.

In one aspect, the invention provides a compound according to Structure 7 or 8:

 (Structure 7)

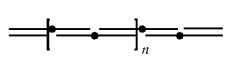 (Structure 8)

wherein:
each ─── is a double stranded oligonucleotide,
each ● is a covalent linker joining single strands of adjacent single stranded oligonucleotides, and
m is an integer ≥1 and n is an integer ≥0.

In one aspect, the invention provides a compound according to Structure 9 and wherein n=0:

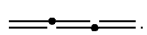 (Structure 9)

In one aspect, the invention provides a compound according to Structure 10 and wherein m=1:

 (Structure 10)

In one aspect, the invention provides a compound according to Structure 12, 13, 14, or 15:

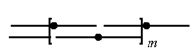 (Structure 12)

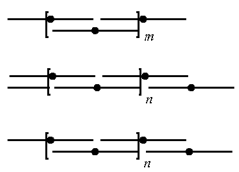
(Structure 13)

(Structure 14)

(Structure 15)

wherein:
each === is a double stranded oligonucleotide,
each ——— is a single stranded oligonucleotide,
each ● is a covalent linker joining single strands of adjacent single stranded oligonucleotides, and m is an integer ≥1 and n is an integer ≥0.

In various aspects, the invention provides methods for synthesizing multimeric (n>2) defined multi-conjugate oligonucleotides, including defined tri-conjugates and defined tetraconjugates.

In one aspect, the invention provides a method for synthesizing a compound according to Structure 7 or 8:

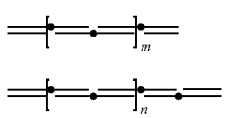
(Structure 7)

(Structure 8)

wherein: each === is a double stranded oligonucleotide, each ● is a covalent linker joining single strands of adjacent single stranded oligonucleotides, and m is an integer ≥1 and n is an integer ≥0, the method comprising the steps of:

(i) forming

by:
(a) annealing a first single stranded oligonucleotide ——— and a second single stranded oligonucleotide

———$R_1$, thereby forming

===$R_1$, and reacting

===$R_1$ with a third single stranded oligonucleotide

———$R_2$, wherein R1 and R2 are chemical moieties capable of reacting directly or indirectly to form a covalent linker ●, thereby forming

;

or
(b) reacting the second single stranded oligonucleotide

———$R_1$ and the third single stranded oligonucleotide

———$R_2$, thereby forming

———●———, and annealing the first single stranded oligonucleotide ——— and

———●———, thereby forming

;

(ii) annealing

and a second single stranded dimer

———●———, thereby forming

and, optionally, annealing one or more additional single stranded dimers

———●——— to 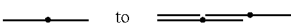

thereby forming,

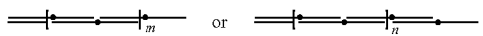

wherein m is an integer ≥1 and n is an integer ≥0; and
(iii) annealing a fourth single stranded oligonucleotide ——— to the product of step (ii), thereby forming structure 7 or 8.

In one aspect, the invention provides a method for synthesizing a compound according to Structure 7 or 8:

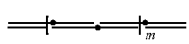 (Structure 7)

 (Structure 8)

wherein: each ═══ is a double stranded oligonucleotide, each ● is a covalent linker joining single strands of adjacent single stranded oligonucleotides, and m is an integer ≥1 and n is an integer ≥0, the method comprising the steps of:
(i) annealing a first single stranded oligonucleotide ——— and a first single stranded dimer

, thereby forming

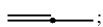;

(ii) annealing

and a second single stranded dimer

, thereby forming

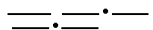

and, optionally, annealing one or more additional single stranded dimers

thereby forming,

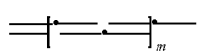 or 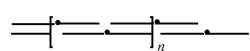

wherein m is an integer ≥1 and n is an integer ≥0; and
(iii) annealing a second single stranded oligonucleotide ——— to the product of step (ii), thereby forming structure 7 or 8.

In one aspect, the invention provides a method for synthesizing a compound of Structure 9:

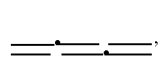 (Structure 9)

wherein each ═══ is a double stranded oligonucleotide, each ● is a covalent linker joining single strands of adjacent single stranded oligonucleotides, the method comprising the steps of:
(i) forming

by:
(a) annealing a first single stranded oligonucleotide ——— and a second single stranded oligonucleotide

—$R_1$, thereby forming

═$R_1$, and reacting

═$R_1$ with a third single stranded oligonucleotide

—$R_2$, wherein $R_1$ and $R_2$ are chemical moieties capable of reacting directly or indirectly to form a covalent linker ●, thereby forming

;

or
(b) reacting the second single stranded oligonucleotide

—$R_1$ and the third single stranded oligonucleotide

—R₂, thereby forming

——•——, and annealing the first single stranded oligonucleotide ———— and

——•——, thereby forming

══•——;

(ii) annealing

══•—— and a single stranded dimer

——•——, thereby forming

══ ══•——;

and
(iii) annealing

══ ══•—— and a fourth single stranded oligonucleotide ————, thereby forming

══ ══•══.

In one aspect, the invention provides a method for synthesizing a compound of Structure 10:

══•══ ══•══,  (Structure 10)

wherein each ══ is a double stranded oligonucleotide, each ● is a covalent linker joining single strands of adjacent single stranded oligonucleotides, the method comprising the steps of:

(i) forming

══•—— by:

(a) annealing a first single stranded oligonucleotide ———— and a second single stranded oligonucleotide

—R₁, thereby forming

══R₁, and reacting

══R₁ with a third single stranded oligonucleotide

—R₂, wherein R1 and R2 are chemical moieties capable of reacting directly or indirectly to form a covalent linker ●, thereby forming

══•—— ;

or (b) reacting the second single stranded oligonucleotide

—R₁ and the third single stranded oligonucleotide

—R₂, thereby forming

——•——, and annealing the first single stranded oligonucleotide  and

, thereby forming

;

(ii) annealing

and a single stranded dimer

, thereby forming

;

(iii) annealing

and a second single stranded dimer

, thereby forming

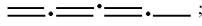;

and
(iv) annealing

and a fourth single stranded oligonucleotide , thereby forming

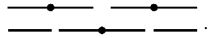.

As with the other compounds and compositions according to the invention, dimeric compounds and intermediates can include any one or more of the features described herein, including in the Examples. For example, the compounds can include any one or more of the nucleic acids (with or without modifications), targeting ligands, and/or linkers described herein, or any of the specific structures or chemistries shown in the summary, description, or Examples.

Example 7 provides an example methodology for preparing various oligonucleotide precursors useful in the syntheses above. Example 8 provides an example methodology for preparing various oligonucleotide multimers, which are also useful in the syntheses above.

In various embodiments, R1, R2, and the bifunctional linking moiety ○ can form a covalent linker ● as described and shown herein. For example, in various embodiments, R1 and R2 can each independently comprise a reactive moiety, for example an electrophile or nucleophile. In one embodiment, R1 and R2 can each independently be selected from the group consisting of a thiol, maleimide, vinylsulfone, pyridyldisulfide, iodoacetamide, acrylate, azide, alkyne, amine, and carboxyl group. In various embodiments, the bifunctional linking moiety ○ comprises two reactive moieties that can be sequentially reacted according to steps (i) and (ii) above, for example a second electrophile/nucleophile that can be reacted with an electrophile/nucleophile in R1 and R2. Examples of bifunctional linking moieties ○ include, but are not limited to, DTME, BM(PEG)2, BM(PEG)3, BMOE, BMH, or BMB.

In various embodiments comprising two or more covalent linkers ● (e.g., in Structures 7-16), the linkers are all the same. Alternatively, the compound or composition can comprise two or more different covalent linkers ●.

In various embodiments, each

may independently comprise two sense or two antisense oligonucleotides. For example, in the case of siRNA, a

may comprise two active strands or two passenger strands.
In various embodiments, each

may independently comprise one sense and one antisense oligonucleotide. For example, in the case of siRNA, a

may comprise one active strand and one passenger strand.

In various embodiments, the compound or composition comprises a homo-multimer of substantially identical double stranded oligonucleotides. The substantially identical double stranded oligonucleotides can each comprise an siRNA targeting the same molecular target in vivo.

In various embodiments, the compound or composition comprises a hetero-multimer of two or more substantially different double stranded oligonucleotides. The substantially different double stranded oligonucleotides can each comprise an siRNA targeting different genes.

In various embodiments, the compound comprises Structure 9 and n=0:

(Structure 9). The compound can further comprise a targeting ligand. The compound can further comprise 2 or 3 substantially different double stranded oligonucleotides ══ each comprising an siRNA targeting a different molecular target in vivo. The compound can further comprise a targeting ligand, one ══ comprising a first siRNA guide strand targeting Factor VII and a first passenger strand hybridized to the guide strand, one ══ comprising a second siRNA guide strand targeting Apolipoprotein B and a second passenger strand hybridized to the second guide strand, and one ══ comprising a third siRNA guide strand targeting TTR and a third passenger strand hybridized to the third guide strand. The targeting ligand can comprise N-Acetylgalactosamine (GalNAc).

Examples of trimers are provided in Examples 17, 18, and 20.

In various embodiments, the compound comprises Structure 10 and m=1:

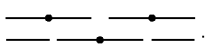

(Structure 10)

The compound can further comprise a targeting ligand. The compound can further comprise 2, 3, or 4 substantially different double stranded oligonucleotides ══ each comprising an siRNA targeting a different molecular target in vivo. The compound can further comprise a targeting ligand, one ══ comprising a first siRNA guide strand targeting Factor VII and a first passenger strand hybridized to the guide strand, one ══ comprising a second siRNA guide strand targeting Apolipoprotein B and a second passenger strand hybridized to the second guide strand, and one ══ comprising a third siRNA guide strand targeting TTR and a third passenger strand hybridized to the third guide strand. The targeting ligand can comprise N-Acetylgalactosamine (GalNAc).

Examples of tetramers are provided in Example 21.

In various embodiments, each double stranded oligonucleotide (e.g., ══, for example in Structure 4) comprises an siRNA guide strand targeting Factor VII and a passenger strand hybridized to the guide strand.

In various embodiments (e.g., in Structure 4), the compound further comprises a targeting ligand, each double stranded oligonucleotide (e.g., ══) comprises an siRNA guide strand and a passenger strand hybridized to the guide strand, and the compound is at least 75, 80, 85, 90, 95, 96, 97, 98, 99, or 100% pure.

In various embodiments, at least one double stranded oligonucleotide (e.g., ══, for example in Structure 6) comprises a first siRNA guide strand targeting Factor VII and a first passenger strand hybridized to the guide strand, and at least one double stranded oligonucleotide (e.g., ∿∿∿, for example in Structure 6) comprises a second siRNA guide strand targeting Apolipoprotein B and a second passenger strand hybridized the second guide strand.

Oligonucleotides Having Increased Circulation Half-Life and/or Activity In Vivo

The invention provides multimeric oligonucleotides having increased circulation half-life and/or activity in vivo, as well as compositions including the multimeric oligonucleotides and methods for their synthesis and use.

In various aspects, the invention provides a multimeric oligonucleotide comprising Structure 21:

(Structure 21)

wherein each monomeric subunit ------- is independently a single or double stranded oligonucleotide, m is an integer ≥1, each ● is a covalent linker joining adjacent monomeric subunits -------, and at least one of the monomeric subunits ------- comprises a single strand having one of the covalent linkers ● joined to its 3' terminus and another of the covalent linkers joined to its 5' terminus.

In various aspects, the invention provides a multimeric oligonucleotide comprising Structure 21:

(Structure 21)

wherein each monomeric subunit ------- is independently a single or double stranded oligonucleotide, each ● is a covalent linker joining adjacent monomeric subunits -------, and m is an integer ≥0 selected to (a) increase in vivo circulation half-life of the multimeric oligonucleotide relative to that of the individual monomeric subunits ------- and/or (b) increase in vivo activity of the multimeric oligonucleotide relative to that of the individual monomeric subunits -------.

In various aspects, the invention provides a multimeric oligonucleotide comprising Structure 21:

(Structure 21)

wherein each monomeric subunit ------- is independently a single or double stranded oligonucleotide, each ● is a covalent linker joining adjacent monomeric subunits -------, m is an integer ≥0, and
wherein the multimeric oligonucleotide has molecular size and/or weight configured to (a) increase in vivo circulation half-life of the multimeric oligonucleotide relative to that of the individual monomeric subunits ------- and/or (b) increase in vivo activity of the multimeric oligonucleotide relative to that of the individual monomeric subunits -------.

In various aspects, the invention provides a method for increasing in vivo circulation half-life and/or in vivo activity of one or more oligonucleotides, the method comprising administering to a subject the one or more oligonucleotides in the form of a multimeric oligonucleotide comprising Structure 21:

(Structure 21)

wherein each monomeric subunit ------- is independently a single or double stranded oligonucleotide, each ● is a covalent linker joining adjacent monomeric subunits -------, and m is an integer ≥0 selected to (a) increase in vivo circulation half-life of the multimeric oligonucleotide relative to that of the individual monomeric subunits ------- and/or (b) increase in vivo activity of the multimeric oligonucleotide relative to that of the individual monomeric subunits -------.

In various aspects, the invention provides a method for increasing in vivo circulation half-life and/or in vivo activity of one or more oligonucleotides, the method comprising administering to a subject the one or more oligonucleotides in the form of a multimeric oligonucleotide comprising Structure 21:

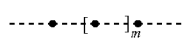

(Structure 21)

wherein each monomeric subunit ------- is independently a single or double stranded oligonucleotide, each ● is a covalent linker joining adjacent monomeric subunits -------, m is an integer ≥0, and wherein the multimeric oligonucleotide has molecular size and/or weight configured to (a) increase in vivo circulation half-life of the multimeric oligonucleotide relative to that of the individual monomeric subunits ------- and/or (b) increase in vivo activity of the multimeric oligonucleotide relative to that of the individual monomeric subunits -------.

In various aspects, the invention provides a multimeric oligonucleotide comprising m monomeric subunits -------, wherein each of the monomeric subunits ------- is independently a single or double stranded oligonucleotide, each of the monomeric subunits ------- is joined to another monomeric subunit by a covalent linker ●, and m is an integer ≥3 selected to (a) increase in vivo circulation half-life of the multimeric oligonucleotide relative to that of the individual monomeric subunits ------- and/or (b) increase in vivo activity of the multimeric oligonucleotide relative to that of the individual monomeric subunits -------.

In various aspects, the invention provides a multimeric oligonucleotide comprising m monomeric subunits -------, wherein each of the monomeric subunits ------- is independently a single or double stranded oligonucleotide, each of the monomeric subunits ------- is joined to another monomeric subunit by a covalent linker ●, m is an integer ≥3, and the multimeric oligonucleotide has molecular size and/or weight configured to (a) increase in vivo circulation half-life of the multimeric oligonucleotide relative to that of the individual monomeric subunits ------- and/or (b) increase in vivo activity of the multimeric oligonucleotide relative to that of the individual monomeric subunits -------.

In various embodiments, the increase is relative to the circulation half-life and/or activity for a monomeric subunit of the multimeric oligonucleotide. Circulation half-life (and its relationship to other properties such as glomerular filtration) is discussed in further detail in the Oligonucleotide Uptake and Clearance section and in Examples 25 and 37 below. In various embodiments, the in vivo circulation half-life increases by a factor of at least 2, 3, 4, 5, 6, 7, 8, 9, 10, 20, 30, 40, 50, 60, 70, 80, 90, 100, 150, 200, 250, 500, or 1,000. The in vivo circulation half-life can increase by a factor of at least 2. The in vivo circulation half-life can increase by a factor of at least 10. In various embodiments, the increase in in vivo activity is measured as the ratio of in vivo activity at $t_{max}$. In various embodiments, the in vivo activity increases by a factor of at least 2, 3, 4, 5, 6, 7, 8, 9, 10, 20, 30, 40, 50, 60, 70, 80, 90, 100, 150, 200, 250, 500, or 1,000. The in vivo activity can increase by a factor of at least 2. The in vivo activity can increase by a factor of at least 10. In one embodiment, the increase is in a mouse. In one embodiment, the increase is in a human.

In various embodiments, m is 1, 2, 3, 4, 5, 6, 7, 8, 9, 10, 11, or 12.

In various embodiments, m is 0, 1, 2, 3, 4, 5, 6, 7, 8, 9, 10, 11, or 12.

In various embodiments, each of the monomeric subunits ------- comprises an siRNA and each of the covalent linkers joins sense strands of the siRNA.

In various embodiments, each of the covalent linkers ● joins two monomeric subunits -------.

In various embodiments, at least one of the covalent linkers ● joins three or more monomeric subunits -------.

In various embodiments, each monomeric subunit ------- is independently a double stranded oligonucleotide ═══, and m is 1:

 or (Structure 28)

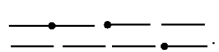 . (Structure 29)

In various embodiments, each monomeric subunit ------- is independently a double stranded oligonucleotide ═══, m is 1, and each covalent linker ● is on the same strand:

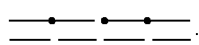 . (Structure 28)

In various embodiments, each monomeric subunit ------- is independently a double stranded oligonucleotide ═══, and m is 2:

 , (Structure 30)

 , (Structure 31)

 , or (Structure 32)

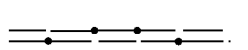 . (Structure 33)

In various embodiments, each monomeric subunit ------- is independently a double stranded oligonucleotide ═══, and m is 2, and each covalent linker ● is on the same strand:

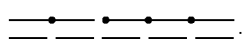 . (Structure 33)

In various embodiments, each monomeric subunit ------- is independently a double stranded oligonucleotide ====, and m is 3, 4, 5, 6, 7, 8, 9, 10, 11, or 12.

In various embodiments, each monomeric subunit ------- is independently a double stranded oligonucleotide ====, m is 3, 4, 5, 6, 7, 8, 9, 10, 11, or 12, and each covalent linker ● is on the same strand.

In various embodiments, each monomeric subunit ------- is independently a double stranded oligonucleotide ====, and m is ≥13.

In various embodiments, each monomeric subunit ------- is independently a double stranded oligonucleotide ====, m is ≥13, and each covalent linker ● is on the same strand. In various embodiments, Structure 21 is Structure 22 or 23:

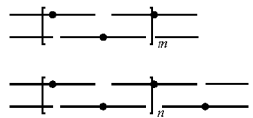

(Structure 22)

(Structure 23)

where ==== each is a double stranded oligonucleotide, each ● is a covalent linker joining adjacent double stranded oligonucleotides, m is an integer ≥1, and n is an integer ≥0.

In various embodiments, Structure 21 is not a structure disclosed in PCT/US2016/037685.

In various embodiments, each oligonucleotide ------- is a single stranded oligonucleotide.

In various embodiments, each oligonucleotide ------- is a double stranded oligonucleotide.

In various embodiments, the oligonucleotides ------- comprise a combination of single and double stranded oligonucleotides.

In various embodiments, the multimeric oligonucleotide comprises a linear structure wherein each of the covalent linkers ● joins two monomeric subunits -------.

In various embodiments, the multimeric oligonucleotide comprises a branched structure wherein at least one of the covalent linkers ● joins three or more monomeric subunits -------. For example, Structure 21 could be Structure 41

In various embodiments, each monomeric subunit ------- is independently a single stranded oligonucleotide ====. In some such embodiments, m is 1

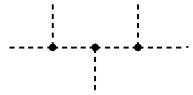

(Structure 34)

m is 2

(Structure 39)

m is 3

(Structure 35)

m is 4

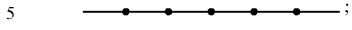

(Structure 40)

or m is 5

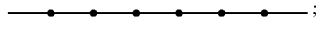

(Structure 37)

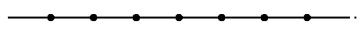

In some such embodiments, m is 6, 7, 8, 9, 10, 11, or 12. In some such embodiments, m is an integer ≥13. In one such embodiment, at least one single stranded oligonucleotide ==== is an antisense oligonucleotide. In one such embodiment, each single stranded oligonucleotide ==== is independently an antisense oligonucleotide.

In various embodiments, the multimeric oligonucleotide comprises a homo-multimer of substantially identical oligonucleotides. The substantially identical oligonucleotides can be siRNA targeting the same molecular target in vivo. The substantially identical oligonucleotides can be miRNA targeting the same molecular target in vivo. The substantially identical oligonucleotides can be antisense RNA targeting the same molecular target in vivo. The substantially identical oligonucleotides can be a combination of siRNA, miRNA, and/or or antisense RNA targeting the same molecular target in vivo.

In various embodiments, the multimeric oligonucleotide comprises a hetero-multimer of two or more substantially different oligonucleotides. The substantially different oligonucleotides can be siRNA targeting different molecular targets in vivo. The substantially different oligonucleotides can be miRNA targeting different molecular targets in vivo. The substantially different oligonucleotides can be antisense RNA targeting different molecular targets in vivo. The substantially different oligonucleotides can be a combination of siRNA, miRNA, and/or or antisense RNA targeting different molecular targets in vivo.

Polymer linkers such as polyethylene glycol (PEG) have been used in attempts to increase the circulation half-life of certain drugs. Such approaches can have drawbacks, including "diluting" the therapeutic agent (e.g., less active agent per unit mass). The present invention can be distinguished from such approaches. For example, in various embodiments, the multimeric oligonucleotide does not comprise PEG. In various embodiments, the multimeric oligonucleotide does not comprise a polyether compound. In various embodiments, the multimeric oligonucleotide does not comprise a polymer other than the oligonucleotides.

Nanoparticles (NP), such as lipid nanoparticles (LNP) have been used in attempts to increase the circulation half-life of certain drugs. Such approaches can have drawbacks, including increased toxicity (e.g., from cationic lipids). The present invention can be distinguished from such approaches. For example, in various embodiments, the multimeric oligonucleotide is not formulated in an NP or LNP.

Phosphorothioate groups have been used in attempts to increase the circulation half-life of certain drugs. Such approaches can have the drawbacks, including lower activity (e.g., due to oligonucleotide/plasma protein aggregation). The present invention can be distinguished from such approaches. For example, in various embodiments, the multimeric oligonucleotide does not comprise a phosphorothioate.

In various embodiments, the multimeric oligonucleotide further comprises a targeting ligand. In various embodiments, the multimeric oligonucleotide consists essentially of Structure 21 and an optional targeting ligand. The multimeric oligonucleotide can use any of the targeting ligands discussed herein (see, e.g., the Targeting Ligands section below). In various embodiments, the targeting ligand is conjugated to an oligonucleotide, for example, the targeting ligand can be conjugated to the oligonucleotide through its 3' or 5' terminus.

The multimeric oligonucleotide can use any of the linkers discussed herein (see, e.g., the Linkers section above). In various embodiments, each covalent linker ● is the same. In various embodiments, the multimeric oligonucleotide comprises two or more different covalent linkers ●. In various embodiments, one or more of ● comprises a cleavable covalent linker. Cleavable linkers can be particularly advantageous in some situations. For example, intracellular cleavage can convert a single multimeric oligonucleotide into multiple biologically active oligonucleotides after cellular targeting and entry (e.g., a single siRNA construct can deliver four or more active siRNA), increasing potency and decreasing undesired side effects.

In various embodiments, one or more of ● comprises nucleotide linker (e.g., a cleavable nucleotide linker such as UUU). Alternatively, in some embodiments, the multimeric oligonucleotide expressly excludes nucleotide linkers.

In various embodiments, the compound is isolated or substantially pure. For example, the compound can be at least 75, 80, 85, 90, 95, 96, 97, 98, 99, or 100% pure. In one embodiment, the compound is about 85-95% pure. Likewise, the methods for synthesizing the compounds and compositions according to the invention can result in a product that is at least 75, 80, 85, 90, 95, 96, 97, 98, 99, or 100% pure. In one embodiment, the product is about 85-95% pure. Preparations can be greater than or equal to 50% pure; preferably greater than or equal to 75% pure; more preferably greater than or equal to 85% pure; and still more preferably, greater than or equal to 95% pure.

In various embodiments, each oligonucleotide is RNA, DNA, or comprises an artificial or non-natural nucleic acid analog. In various embodiments, at least one oligonucleotide is an siRNA, miRNA, or antisense oligonucleotide. Various other possible oligonucleotides and substitutions are discussed, for example, in the Nucleic Acids section above.

In various embodiments, each oligonucleotide is 15-30, 17-27, 19-26, or 20-25 nucleotides in length. In various embodiments, the nucleic acid or oligonucleotide is 15-30, 17-27, 19-26, 20-25, 40-50, 40-150, 100-300, 1000-2000, or up to 10000 nucleotides in length.

In various embodiments, the multimeric oligonucleotides comprising structure 21 have a molecular weight of at least about 40, 41, 42, 43, 44, 45, 46, 47, 48, 49, 50, 51, 52, 53, 54, 55, 56, 57, 58, 59, 60, 61, 62, 63, 64, or 65 kD. In various embodiments, the multimeric oligonucleotides comprising structure 21 have a molecular weight of at least about 40-45, 45-50, 50-55, 55-60, 60-65, 65-70, or 70-75 kD. Molecular weight can include everything covalently bound to the multimeric oligonucleotide, such a targeting ligands and linkers.

Although the multimeric oligonucleotides comprising Structure 21 can be synthesized by various methods (e.g., those described herein for making tetrameric or greater multimers), certain results may call for specific methodologies. For example, the following method (as well as those shown in Example 22) is designed to efficiently produce multimers having each covalent linker ● on the same strand.

For example, in one aspect, the invention provides a method of synthesizing a multimeric oligonucleotide comprising structure 34:

(Structure 34)

wherein each ─── is a single stranded oligonucleotide and each ● is a covalent linker joining adjacent single stranded oligonucleotides, the method comprising the steps of:

(i) reacting

───●───○ and ───●───R1, wherein ○ is a linking moiety and $R_1$ is a chemical group capable of reacting with the linking moiety ○, thereby forming (Structure 34)

and (ii) optionally annealing (Structure 34)

with complementary single stranded oligonucleotides, thereby forming (Structure 28)

For example, in one aspect, the invention provides a method of synthesizing a multimeric oligonucleotide comprising structure 35:

(Structure 35)

wherein each ─── is a single stranded oligonucleotide and each ● is a covalent linker joining adjacent single stranded oligonucleotides, the method comprising the steps of:

(i) reacting

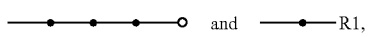 and 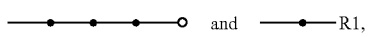—R1, wherein ○ is a linking moiety and $R_1$ is a chemical group capable of reacting with the linking moiety ○, thereby forming

 (Structure 35)

and (ii) optionally annealing

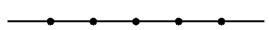 (Structure 35)

with complementary single stranded oligonucleotides, thereby forming

 (Structure 36)

For example, in one aspect, the invention provides a method of synthesizing a multimeric oligonucleotide comprising structure 37:

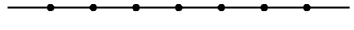 (Structure 37)

wherein each ——— is a single stranded oligonucleotide and each ● is a covalent linker joining adjacent single stranded oligonucleotides, the method comprising the steps of:

(i) reacting

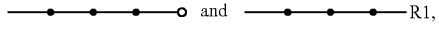 and 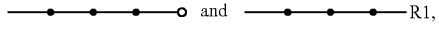—R1, wherein ○ is a linking moiety and $R_1$ is a chemical group capable of reacting with the linking moiety ○, thereby forming

 (Structure 37)

(ii) optionally annealing

 (Structure 37)

with complementary single stranded oligonucleotides, thereby forming

 (Structure 38)

The invention also provides methods for synthesizing single stranded multimeric oligonucleotides, for example wherein m is 2

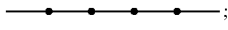 (Structure 39)

m is 4

 (Structure 40)

m is 6, 7, 8, 9, 10, 11, or 12; or m is ≥13 (see Example 22 below).

The multimeric compounds can include any one or more of the features disclosed herein. For example, the compounds can include any one or more of the nucleic acids (with or without modifications), targeting ligands, and/or linkers described herein, or any of the specific structures or chemistries shown in the summary, description, or Examples. Likewise, the compounds can be prepared in an of the compositions (e.g., for experimental or medical use) shown in the summary, description, or Examples. Illustrative examples are provided in the Pharmaceutical Compositions section below.

Oligonucleotide Uptake and Clearance

The bioavailability of a drug in the blood stream can be characterized as the balance between target cell uptake versus kidney clearance. From a practical perspective, in vivo circulation half-life and/or in vivo activity are good proxies for kidney clearance/glomerular filtration because they can be readily quantified and measured and because their improvement (e.g., increase) can correlate with improved pharmacodynamics and/or pharmacokinetics.

The uptake rate of a therapeutic agent such as an oligonucleotide (ONT) in the blood is a function of a number of factors, which can be represented as: Rate of Uptake=f{(ONT Concentration)×(Rate Blood Flow)×(Receptor Copy Number/cell)×(Number of Cells)×(equilibrium dissociation constant $K_d$)×(Internalization Rate)}. For a given ligand/receptor pair, the Copy Number, KD, Number of cells and Internalization Rate will be constant. This can explain why the GalNAc ligand system is so effective for hepatocytes—it targets the ASGP receptor, which is present at high copy number. The KD of some ASGP/GalNAc variants is in the nanomolar range and the internalization rate is very high.

However, effective targeting is also dependent on the ONT concentration, which rapidly decreases over time due to clearance from the blood stream. The rate of clearance of a therapeutic can be represented as: Rate of Clearance=f{(Blood Flow Rate)×(Kidney Filtration Rate)×(Other clearance mechanisms)}. The resulting concentration of ONT at time t can be represented as: (ONT Concentration)t=f{(Initial Concentration)−(Rate of Clearance×t)}.

In humans, clearance is mainly due to glomerular filtration in the kidney. In general, molecules less than about 45 kD have a half-life of about 30 minutes. In mice, the rate of clearance is even faster, the circulation half-life being about 5 minutes. Without wishing to be bound by any particular theory, it is believed that the invention can reduce glomerular filtration using specifically configured multimeric oligonucleotides (e.g., specific composition, size, weight, etc.), leading to a lower rate of clearance, resulting in a higher concentration of ONT in circulation at a given time t (e.g., increased serum half-life, higher overall uptake, and higher activity).

Again, without wishing to bound by any particular theory, actual glomerular filtration rates can be difficult to measure directly. For example, compounds that pass through the glomerular capillaries are readily absorbed by cells such as tubular epithelial cells, which can retain compounds like siRNA for significant periods of time (see, e.g., Henry, S. P. et al; Toxicology, 301, 13-20 (2012) and van de Water, F. M et al; Drug metabolism and Disposition, 34, No 8, 1393-1397 (2006)). In addition, absorbed compounds can be metabolized to breakdown products, which are then secreted in urine. Thus, the concentration (e.g., in urine) of a therapeutic agent such as an siRNA at a specific time point may not necessarily be representative of the glomerular filtration rate. However, serum half-life, which is related to glomerular filtration and which is directly measurable, may be considered to be a suitable proxy for glomerular filtration.

The following table shows the dramatic effect increasing the circulation half-life ($t_{1/2}$) of a component can have on the resulting concentration of the component at time t:

| t (min): | 0 | 30 | 60 | 90 | 120 | 150 | 180 | 210 | 240 |
|---|---|---|---|---|---|---|---|---|---|
| 30 min $t_{1/2}$ | 100 | 50 | 25 | 12.5 | 6.25 | 3.13 | 1.56 | 0.78 | 0.4 |
| 60 min $t_{1/2}$ | 100 |  | 50 |  | 25 |  | 12.5 |  | 6.25 |
| 90 min $t_{1/2}$ | 100 |  |  | 50 |  |  | 25 |  |  |
| 120 min $t_{1/2}$ | 100 |  |  |  | 50 |  |  |  | 25 |

Values are presented as % initial dose at time t.

Thus, increasing the half-life of a component by a factor of 2 increases its residual concentration at 2 hours by a factor of 4. Increasing the half-life by a factor of four leads to even more dramatic improvements in residual concentration—by factors of eight and greater than sixty at 2 and 4 hours, respectively.

A typical siRNA (e.g., double stranded monomer) has a molecular weight of about 15 kD. A siRNA tetramer according to the invention can have a molecular weight of about 60 kD. Without wishing to be bound by any particular theory, it is believed that such multimers (tetramers, pentamers, etc.) can be configured to have a molecular size and/or weight resulting in decreased glomerular filtration in vivo. Such multimers would have an increased circulation half-life. Thus, multimers according to the invention can be configured to have increased in vivo circulation half-life and/or increased in vivo activity, relative to that of the individual monomeric subunits. Further, if directed by a suitable targeting ligand the multimer (e.g., tetramer) would deliver many (e.g., four) times the payload per ligand/receptor binding event than the monomeric equivalent. In combination, these effects can lead to a dramatic increase in the bio-availability and uptake of the therapeutic agent. This can be especially advantageous in cases where some combination of the copy number, KD, number of target cells and internalization rate of a given ligand/receptor pair are suboptimal.

Accordingly, the multimeric oligonucleotide has a structure selected to (a) increase in vivo circulation half-life of the multimeric oligonucleotide relative to that of the individual monomeric subunits and/or (b) increase in vivo activity of the multimeric oligonucleotide relative to that of the individual monomeric subunits. For example, the multimeric oligonucleotide can have a molecular size and/or weight configured for this purpose.

Pharmaceutical Compositions

In various aspects, the invention provides pharmaceutical compositions including any one or more of the compounds or compositions described above. As used herein, pharmaceutical compositions include compositions of matter, other than foods, that can be used to prevent, diagnose, alleviate, treat, or cure a disease. Similarly, the various compounds or compositions according to the invention should be understood as including embodiments for use as a medicament and/or for use in the manufacture of a medicament.

A pharmaceutical composition can include a compound or composition according to the invention and a pharmaceutically acceptable excipient. As used herein, an excipient can be a natural or synthetic substance formulated alongside the active ingredient. Excipients can be included for the purpose of long-term stabilization, increasing volume (e.g., bulking agents, fillers, or diluents), or to confer a therapeutic enhancement on the active ingredient in the final dosage form, such as facilitating drug absorption, reducing viscosity, or enhancing solubility. Excipients can also be useful manufacturing and distribution, for example, to aid in the handling of the active ingredient and/or to aid in vitro stability (e.g., by preventing denaturation or aggregation). As will be understood by those skilled in the art, appropriate excipient selection can depend upon various factors, including the route of administration, dosage form, and active ingredient(s).

Oligonucleotides can be delivered locally or systemically, and the pharmaceutical compositions of the invention can vary accordingly. For example, administration is not necessarily limited to any particular delivery system and may include, without limitation, parenteral (including subcutaneous, intravenous, intramedullary, intraarticular, intramuscular, or intraperitoneal injection), rectal, topical, transdermal, or oral. Administration to an individual may occur in a single dose or in repeat administrations, and in any of a variety of physiologically acceptable salt forms, and/or with an acceptable pharmaceutical carrier and/or additive as part of a pharmaceutical composition. Physiologically acceptable formulations and standard pharmaceutical formulation techniques, dosages, and excipients are well known to persons skilled in the art (see, e.g., Physicians' Desk Reference (PDR®) 2005, 59th ed., Medical Economics Company, 2004; and Remington: The Science and Practice of Pharmacy, eds. Gennado et al. 21th ed., Lippincott, Williams & Wilkins, 2005).

Pharmaceutical compositions can include an effective amount of the compound or composition according to the invention. As used herein, effective amount can be a concentration or amount that results in achieving a particular stated purpose, or more amount means an amount adequate to cause a change, for example in comparison to a placebo. Where the effective amount is a therapeutically effective amount, it can be an amount adequate for therapeutic use, for example and amount sufficient to prevent, diagnose, alleviate, treat, or cure a disease. An effective amount can be determined by methods known in the art. An effective amount can be determined empirically, for example by human clinical trials. Effective amounts can also be extrapolated from one animal (e.g., mouse, rat, monkey, pig, dog) for use in another animal (e.g., human), using conversion factors known in the art. See, e.g., Freireich et al., Cancer Chemother Reports 50(4):219-244 (1966).

Delivery Vehicles and Targeting Ligands

In various aspects, the invention provides any one or more of the compounds or compositions described above formulated in a delivery vehicle. For example, the delivery vehicle can be a lipid nanoparticle (LNP), exosome, microvesicle, or viral vector. Similarly, in various aspects, the invention provides any one or more of the compounds or compositions described above and further comprising a targeting ligand. For example, the targeting ligand comprises N-Acetylgalactosamine (GalNAc), cholesterol, tocopherol, folate, 2-[3-(1, 3-dicarboxypropyl)-ureido]pentanedioic acid (DUPA), or anisamide. The targeting ligand can be bound (e.g., directly) to the nucleic acid, for example through its 3' or 5' terminus. In some embodiments, two targeting ligands are conjugated to the oligonucleotide, where one ligand is conjugated through the 3' terminus and the other ligand is conjugated through the 5' terminus of the oligonucleotide. One or more targeting ligands can be conjugated to the sense strand or the anti-sense strand of the oligonucleotide, or both the sense-strand and the anti-sense strand. Additional examples that may be adapted for use with the invention are discussed below.

As will be understood by those skilled in the art, regardless of biological target or mechanism of action, therapeutic oligonucleotides must overcome a series of physiological hurdles to access the target cell in an organism (e.g., animal, such as a human, in need of therapy). For example, a therapeutic oligonucleotide generally must avoid clearance in the bloodstream, enter the target cell type, and then enter the cytoplasm, all without eliciting an undesirable immune response. This process is generally considered inefficient, for example, 95% or more of siRNA that enters the endosome in vivo may be degraded in lysosomes or pushed out of the cell without affecting any gene silencing.

To overcome these obstacles, scientists have designed numerous drug delivery vehicles. These vehicles have been used to deliver therapeutic RNAs in addition to small molecule drugs, protein drugs, and other therapeutic molecules. Drug delivery vehicles have been made from materials as diverse as sugars, lipids, lipid-like materials, proteins, polymers, peptides, metals, hydrogels, conjugates, and peptides. Many drug delivery vehicles incorporate aspects from combinations of these groups, for example, some drug delivery vehicles can combine sugars and lipids. In some other examples, drugs can be directly hidden in 'cell like' materials that are meant to mimic cells, while in other cases, drugs can be put into, or onto, cells themselves. Drug delivery vehicles can be designed to release drugs in response to stimuli such as pH change, biomolecule concentration, magnetic fields, and heat.

Much work has focused on delivering oligonucleotides such as siRNA to the liver. The dose required for effective siRNA delivery to hepatocytes in vivo has decreased by more than 10,000 fold in the last ten years—whereas delivery vehicles reported in 2006 could require more than 10 mg/kg siRNA to target protein production, with new delivery vehicles target protein production can now be reduced after a systemic injection of 0.001 mg/kg siRNA. The increase in oligonucleotide delivery efficiency can be attributed, at least in part, to developments in delivery vehicles.

Another important advance has been an increased understanding of the way helper components influence delivery. Helper components can include chemical structures added to the primary drug delivery system. Often, helper components can improve particle stability or delivery to a specific organ. For example, nanoparticles can be made of lipids, but the delivery mediated by these lipid nanoparticles can be affected by the presence of hydrophilic polymers and/or hydrophobic molecules. One important hydrophilic polymer that influences nanoparticle delivery is poly(ethylene glycol). Other hydrophilic polymers include non-ionic surfactants. Hydrophobic molecules that affect nanoparticle delivery include cholesterol, 1-2-Distearoyl-sn-glyerco-3-phosphocholine (DSPC), 1-2-di-O-octadecenyl-3-trimethylammonium propane (DOTMA), 1,2-dioleoyl-3-trimethylammonium-propane (DOTAP), and others.

Drug delivery systems have also been designed using targeting ligands or conjugate systems. For example, oligonucleotides can be conjugated to cholesterols, sugars, peptides, and other nucleic acids, to facilitate delivery into hepatocytes and/or other cell types. Such conjugate systems may facilitate delivery into specific cell types by binding to specific receptors.

One skilled in the art will appreciate that known delivery vehicles and targeting ligands can generally be adapted for use according to the present invention. Examples of delivery vehicles and targeting ligands, as well as their use, can be found in: Sahay, G., et al. Efficiency of siRNA delivery by lipid nanoparticles is limited by endocytic recycling. Nat Biotechnol, 31: 653-658 (2013); Wittrup, A., et al. Visualizing lipid-formulated siRNA release from endosomes and target gene knockdown. Nat Biotechnol (2015); Whitehead, K. A., Langer, R. & Anderson, D. G. Knocking down barriers: advances in siRNA delivery. Nature reviews. Drug Discovery, 8: 129-138 (2009); Kanasty, R., Dorkin, J. R., Vegas, A. & Anderson, D. Delivery materials for siRNA therapeutics. Nature Materials, 12: 967-977 (2013); Tibbitt, M. W., Dahlman, J. E. & Langer, R. Emerging Frontiers in Drug Delivery. J Am Chem Soc, 138: 704-717 (2016); Akinc, A., et al. Targeted delivery of RNAi therapeutics with endogenous and exogenous ligand-based mechanisms. Molecular therapy: the journal of the American Society of Gene Therapy 18, 1357-1364 (2010); Nair, J. K., et al. Multivalent N-acetylgalactosamine-conjugated siRNA localizes in hepatocytes and elicits robust RNAi-mediated gene silencing. J Am Chem Soc, 136: 16958-16961 (2014); Ostergaard, M. E., et al. Efficient Synthesis and Biological Evaluation of 5'-GalNAc Conjugated Antisense Oligonucleotides. Bioconjugate chemistry (2015); Sehgal, A., et al. An RNAi therapeutic targeting antithrombin to rebalance the coagulation system and promote hemostasis in hemophilia. Nature Medicine, 21: 492-497 (2015); Semple, S. C., et al. Rational design of cationic lipids for siRNA delivery. Nat Biotechnol, 28: 172-176 (2010); Maier, M. A., et al. Biodegradable lipids enabling rapidly eliminated lipid nanoparticles for systemic delivery of RNAi therapeutics. Molecular therapy: the journal of the American Society of Gene Therapy, 21: 1570-1578 (2013); Love, K. T., et al. Lipid-like materials for low-dose, in vivo gene silencing. Proc Nat Acad USA, 107: 1864-1869 (2010); Akinc, A., et al. A combinatorial library of lipid-like materials for delivery of RNAi therapeutics. Nat Biotechnol, 26: 561-569 (2008); Eguchi, A., et al. Efficient siRNA delivery into primary cells by a peptide transduction domain-dsRNA binding domain fusion protein. Nat Biotechnol, 27: 567-571 (2009); Zuckerman, J. E., et al. Correlating animal and human phase Ia/Ib clinical data with CALAA-01, a targeted, polymer-based nanoparticle containing siRNA. Proc Nat Acad USA, 111: 11449-11454 (2014); Zuckerman, J. E. & Davis, M. E. Clinical experiences with systemically administered siRNA-based therapeutics in cancer. Nature Reviews. Drug Discovery, 14: 843-856 (2015); Hao, J., et al. Rapid Synthesis of a Lipocationic Polyester Library via Ring-Opening Polymerization of Functional Valerolactones for Efficacious siRNA Delivery. J Am Chem Soc, 29: 9206-9209 (2015); Siegwart, D. J., et al. Combinatorial synthesis of chemically diverse core-shell nanoparticles for intracellular delivery. Proc Nat Acad USA, 108: 12996-13001 (2011); Dahlman, J E, et al. In vivo endothelial siRNA delivery using polymeric nanoparticles with low molecular weight. Nat Nano 9, 648-655 (2014); Soppimath, K. S., Aminabhavi, T. M., Kulkarni, A. R. & Rudzinski, W. E. Biodegradable polymeric nanoparticles as drug delivery devices. Journal of controlled release: official journal of the Controlled Release Society 70, 1-20 (2001); Kim, H. J., et al. Precise engineering of siRNA delivery vehicles to tumors using polyion complexes and gold nanoparticles. ACS Nano, 8: 8979-8991 (2014); Krebs, M. D., Jeon, O. & Alsberg, E. Localized and sustained delivery of silencing RNA from macroscopic biopolymer hydrogels. J Am Chem Soc 131, 9204-9206 (2009); Zimmermann, T. S., et al. RNAi-mediated gene silencing in non-human primates. Nature, 441: 111-114 (2006); Dong, Y., et al. Lipopeptide nanoparticles for potent and selective siRNA delivery in rodents and nonhuman primates. Proc Nat Acad USA, 111: 3955-3960 (2014); Zhang, Y., et al. Lipid-modified aminoglycoside derivatives for in vivo siRNA delivery. Advanced Materials, 25: 4641-4645 (2013); Molinaro, R., et al. Biomimetic proteolipid vesicles for targeting inflamed tissues. Nat Mater (2016); Hu, C. M., et al. Nanoparticle biointerfacing by platelet membrane cloaking. Nature, 526: 118-121 (2015); Cheng, R., Meng, F., Deng, C., Klok, H.-A. & Thong, Z. Dual and multi-stimuli responsive polymeric nanoparticles for programmed site-specific drug delivery. Biomaterials, 34: 3647-3657 (2013); Qiu, Y. & Park, K. Environment-sensitive hydrogels for drug delivery. Advanced Drug Delivery Reviews, 64, Supplement, 49-60 (2012); Mui, B. L., et al. Influence of Polyethylene Glycol Lipid Desorption Rates on Pharmacokinetics and Pharmacodynamics of siRNA Lipid Nanoparticles. Mol Ther Nucleic Acids 2, e139 (2013); Draz, M. S., et al. Nanoparticle-Mediated Systemic Delivery of siRNA for Treatment of Cancers and Viral Infections. Theranostics, 4: 872-892 (2014); Otsuka, H., Nagasaki, Y. & Kataoka, K. PEGylated nanoparticles for biological and pharmaceutical applications. Advanced Drug Delivery Reviews, 55: 403-419 (2003); Kauffman, K. J., et al. Optimization of Lipid Nanoparticle Formulations for mRNA Delivery in vivo with Fractional Factorial and Definitive Screening Designs. Nano Letters, 15: 7300-7306 (2015); Zhang, S., Zhao, B., Jiang, H., Wang, B. & Ma, B. Cationic lipids and polymers mediated vectors for delivery of siRNA. Journal of Controlled Release 123, 1-10 (2007); Ilium, L. & Davis, S. S. The organ uptake of intravenously administered colloidal particles can be altered using a non-ionic surfactant (Poloxamer 338). FEBS Letters, 167: 79-82 (1984); Feigner, P. L., et al. Improved Cationic Lipid Formulations for In vivo Gene Therapy. Annals of the New York Academy of Sciences, 772: 126-139 (1995); Meade, B. R. & Dowdy, S. F. Exogenous siRNA delivery using peptide transduction domains/cell penetrating peptides. Advanced Drug Delivery Reviews, 59: 134-140 (2007); Endoh, T. & Ohtsuki, T. Cellular siRNA delivery using cell-penetrating peptides modified for endosomal escape. Advanced Drug Delivery Reviews, 61: 704-709 (2009); and Lee, H., et al. Molecularly self-assembled nucleic acid nanoparticles for targeted in vivo siRNA delivery. Nat Nano, 7: 389-393 (2012).

In various embodiments, the compounds and compositions of the invention can be conjugated to or delivered with other chemical or biological moieties, including, e.g., biologically active moieties. A biologically active moiety is any molecule or agent that has a biological effect, preferably a measurable biological effect. Chemical or biological moieties include, e.g., proteins, peptides, amino acids, nucleic acids (including, e.g., DNA, RNA of all types, RNA and DNA aptamers, antisense oligonucleotides, and antisense miRNA inhibitors), targeting ligands, carbohydrates, polysaccharides, lipids, organic compounds, and inorganic chemical compounds.

As used herein, the term targeting ligand can include a moiety that can be made accessible on the surface of a nanoparticle or as part of a delivery conjugate (e.g., multi-conjugate oligonucleotide, multimeric oligonucleotide) for the purpose of delivering the payload of the nanoparticle or delivery conjugate to a specific target, such as a specific bodily tissue or cell type, for example, by enabling cell receptor attachment of the nanoparticle or delivery conjugate. Examples of suitable targeting ligands include, but are not limited to, cell specific peptides or proteins (e.g., transferrin and monoclonal antibodies), aptamers, cell growth factors, vitamins (e.g., folic acid), monosaccharides (e.g., galactose and mannose), polysaccharides, arginine-glycine-aspartic acid (RGD), and asialoglycoprotein receptor ligands derived from N-acetylgalactosamine (GalNac). The ligand may be incorporated into the foregoing compounds of the invention using a variety of techniques known in the art, such as via a covalent bond such as a disulfide bond, an amide bond, or an ester bond, or via a non-covalent bond such as biotin-streptavidin, or a metal-ligand complex.

Additional biologically active moieties within the scope of the invention are any of the known gene editing materials, including for example, materials such as oligonucleotides, polypeptides and proteins involved in CRISPR/Cas systems, TALES, TALENs, and zinc finger nucleases (ZFNs).

In various embodiments, the compounds and compositions of the invention can be encapsulated in a carrier material to form nanoparticles for intracellular delivery. Known carrier materials include cationic polymers, lipids or peptides, or chemical analogs thereof. Jeong et al., BIOCONJUGATE CHEM., Vol. 20, No. 1, pp. 5-14 (2009). Examples of a cationic lipid include dioleyl phosphatidylethanolamine, cholesterol dioleyl phosphatidylcholine, N-[1-(2,3-dioleoyloxy)propyl]-N,N,N-trimethylammonium chloride (DOTMA), 1,2-dioleoyloxy-3-(trimethylammonio) propane (DOTAP), 1,2-dioleoyl-3-(4'-trimethyl-ammonio) butanoyl-sn-glycerol(DOTB), 1,2-diacyl-3-dimethylammonium-propane (DAP), 1,2-diacyl-3-trimethylammonium-propane (TAP), 1,2-diacyl-sn-glycerol-3-ethylphosphocholin, 3 beta-[N—(N',N'-dimethylaminoethane)-carbamoyl]cholesterol (DC-Cholesterol), dimethyldioctadecylammonium bromide (DDAB), and copolymers thereof. Examples of a cationic polymer include polyethyleneimine, polyamine, polyvinylamine, poly(alkylamine hydrochloride), polyamidoamine dendrimer, diethylaminoethyl-dextran, polyvinylpyrrolidone, chitin, chitosan, and poly(2-dimethylamino)ethyl methacrylate. In one embodiment, the carrier contains one or more acylated amines, the properties of which may be better suited for use in vivo as compared to other known carrier materials.

In one embodiment, the carrier is a cationic peptide, for example KALA (a cationic fusogenic peptide), polylysine, polyglutamic acid or protamine In one embodiment, the carrier is a cationic lipid, for example dioleyl phosphatidylethanolamine or cholesterol dioleyl phosphatidylcholine. In one embodiment, the carrier is a cationic polymer, for example polyethyleneimine, polyamine, or polyvinylamine.

In various embodiments, the compounds and compositions of the invention can be encapsulated in exosomes. Exosomes are cell-derived vesicles having diameters between 30 and 100 nm that are present in biological fluids, including blood, urine, and cultured medium of cell cultures. Exosomes, including synthetic exsosomes and exosome mimetics can be adapted for use in drug delivery according to the skill in the art. See, e.g., "A comprehensive overview of exosomes as drug delivery vehicles—endogenous nanocarriers for targeted cancer therapy" Biochim Biophys Acta. 1846(1):75-87 (2014); "Exosomes as therapeutic drug carriers and delivery vehicles across biological membranes: current perspectives and future challenges" Acta Pharmaceutica Sinica B, Available online 8 Mar. 2016 (In Press); and "Exosome mimetics: a novel class of drug delivery systems" International Journal of Nanomedicine, 7: 1525-1541 (2012).

In various embodiments, the compounds and compositions of the invention can be encapsulated in microvesicles. Microvesicles (sometimes called, circulating microvesicles, or microparticles) are fragments of plasma membrane ranging from 100 nm to 1000 nm shed from almost all cell types and are distinct from smaller intracellularly generated extracellular vesicles known as exosomes. Microvesicles play a role in intercellular communication and can transport mRNA, miRNA, and proteins between cells. Microvesicles, including synthetic microvesicles and microvesicle mimetics can be adapted for use in drug delivery according to the skill in the art. See, e.g., "Microvesicle- and exosome-mediated drug delivery enhances the cytotoxicity of Paclitaxel in autologous prostate cancer cells" Journal of Controlled Release, 220: 727-737 (2015); "Therapeutic Uses of Exosomes" J Circ Biomark, 1:0 (2013).

In various embodiments, the compounds and compositions of the invention can be delivered using a viral vector. Viral vectors are tools commonly used by molecular biologists to deliver genetic material into cells. This process can be performed inside a living organism (in vivo) or in cell culture (in vitro). Viral vectors can be adapted for use in drug delivery according to the skill in the art. See, e.g., "Viruses as nanomaterials for drug delivery" Methods Mol Biol, 26: 207-21 (2011); "Viral and nonviral delivery systems for gene delivery" Adv Biomed Res, 1:27 (2012); and "Biological Gene Delivery Vehicles: Beyond Viral Vectors" Molecular Therapy, 17(5): 767-777 (2009).

General procedures for LNP formulation and characterization are provided in the Examples below, as are working examples of LNP formulations and other in vitro and in vivo tests. Other methods are known in the art and can be adapted for use with the present invention by those of ordinary skill.

Methods of Treatment or Reducing Gene Expression

In various aspects, the invention provides methods for using multi-conjugate oligonucleotides, for example for medical treatments, research, or for producing new or altered phenotypes in animals and plants.

In one aspect, the invention provides a method for treating a subject comprising administering an effective amount of a compound or composition according to the invention to a subject in need thereof. In such therapeutic embodiments, the oligonucleotide will be a therapeutic oligonucleotide, for example an siRNA or miRNA.

In this, and other embodiments, the compositions and compounds of the invention can be administered in the form of a pharmaceutical composition, in a delivery vehicle, or coupled to a targeting ligand.

In one aspect, the invention provides a method for silencing or reducing gene expression comprising administering an effective amount of a compound or composition according to the invention to a subject in need thereof. In such therapeutic embodiments, the oligonucleotide will be an oligonucleotide that silences or reduces gene expression, for example an siRNA or antisense oligonucleotide.

Similarly, the invention provides a method for silencing or reducing expression of two or more genes comprising administering an effective amount of a compound or composition according to the invention to a subject in need thereof, wherein the compound or composition comprises oligonucleotides targeting two or more genes. The compound or composition can comprise oligonucleotides targeting two, three, four, or more genes.

In one aspect, the invention provides a method for delivering two or more oligonucleotides to a cell per targeting ligand binding event comprising administering an effective amount of a compound or composition according to the invention to a subject in need thereof, wherein the compound or composition comprises a targeting ligand.

In one aspect, the invention provides a method for delivering a predetermined stoichiometric ratio of two or more oligonucleotides to a cell comprising administering an effective amount of a compound or composition according to the invention to a subject in need thereof, wherein the compound or composition comprises the predetermined stoichiometric ratio of two or more oligonucleotides.

As used herein, subject includes a cell or organism subject to the treatment or administration. The subject can be an animal, for example a mammal such a laboratory animal (mouse, monkey) or veterinary patient, or a primate such as a human Without limitation, a subject in need of the treatment or administration can include a subject having a disease (e.g., that may be treated using the compounds and compositions of the invention) or a subject having a condition (e.g., that may be addressed using the compounds and compositions of the invention, for example one or more genes to be silenced or have expression reduced).

General procedures for measurement of gene knockdown and animal experiments are provided in the Examples below, as are working examples of other in vitro and in vivo tests. Other methods are known in the art and can be adapted for use with the present invention by those of ordinary skill.

The following Examples are illustrative and not restrictive. Many variations of the technology will become apparent to those of skill in the art upon review of this disclosure. The scope of the technology should, therefore, be determined not with reference to the Examples, but instead should be determined with reference to the appended claims along with their full scope of equivalents.

EXAMPLES

General Procedure 1: Single Chain Oligonucleotide Synthesis

Oligoribonucleotides were assembled on ABI 394 and 3900 synthesizers (Applied Biosystems) at the 10 mol scale, or on an Oligopilot 10 synthesizer at 28 mol scale, using phosphoramidite chemistry. Solid supports were polystyrene loaded with 2'-deoxythymidine (Glen Research, Sterling, Virginia, USA), or controlled pore glass (CPG, 520Å, with a loading of 75 µmol/g, obtained from Prime Synthesis, Aston, PA, USA). Ancillary synthesis reagents, DNA-, 2'-O-Methyl RNA-, and 2'-deoxy-2'-fluoro-RNA phosphoramidites were obtained from SAFC Proligo (Hamburg, Germany) Specifically, 5'-O-(4,4'-dimethoxytrityl)-3'-O-(2-cyanoethyl-N,N-diisopropyl) phosphoramidite monomers of 2'-O-methyl-uridine (2'-OMe-U), 4-N-acetyl-2'-O-methyl-cytidine (2'-OMe-$C^{Ac}$), 6-N-benzoyl-2'-O-methyl-adenosine (2'-OMe-$A^{bz}$) and 2-N-isobutyrlguanosine (2'-OMe-$G^{iBu}$) were used to build the oligomer sequences. 2'-Fluoro modifications were introduced employing the corresponding phosphoramidites carrying the same nucleobase protecting groups as the 2'-OMe RNA building blocks. Coupling time for all phosphoramidites (70 mM in Acetonitrile) was 3 min employing 5-Ethylthio-1H-tetrazole (ETT, 0.5 M in Acetonitrile) as activator. Phosphorothioate linkages were introduced using 50 mM 3-((Dimethylamino-methylidene)amino)-3H-1,2,4-dithiazole-3-thione (DDTT, AM Chemicals, Oceanside, California, USA) in a 1:1 (v/v) mixture of pyridine and Acetonitrile.

Upon completion of the solid phase synthesis including removal of the DMT group ("DMT off synthesis") oligonucleotides were cleaved from the solid support and deprotected using a 1:1 mixture consisting of aqueous methylamine (41%) and concentrated aqueous ammonia (32%) for 3 hours at 25° C. according to published methods (Wincott, F. et al: Synthesis, deprotection, analysis and purification of RNA and ribozymes. Nucleic Acids Res, 23: 2677-2684 (1995).

Subsequently, crude oligomers were purified by anionic exchange HPLC using a column packed with Source Q15 (GE Healthcare) and an AKTA Explorer system (GE Healthcare). Buffer A was 10 mM sodium perchlorate, 20 mM Tris, 1 mM EDTA, pH 7.4 (Fluka, Buchs, Switzerland) in 20% aqueous acetonitrile and buffer B was the same as buffer A with 500 mM sodium perchlorate. A gradient of 22% B to 42% B within 32 column volumes (CV) was employed. UV traces at 280 nm were recorded. Appropriate fractions were pooled and precipitated with 3M NaOAc, pH=5.2 and 70% ethanol. Pellets were collected by centrifugation. Alternatively, desalting was carried out using Sephadex HiPrep columns (GE Healthcare) according to the manufacturer's recommendations.

Oligonucleotides were reconstituted in water and identity of the oligonucleotides was confirmed by electrospray ionization mass spectrometry (ESI-MS). Purity was assessed by analytical anion-exchange HPLC.

General Procedure 2: Lipid Nanoparticle Formulation 1,2-distearoyl-3-phosphatidylcholine (DSPC) was purchased from Avanti Polar Lipids (Alabaster, Alabama, USA). α-[3'-(1,2-dimyristoyl-3-propanoxy)-carboxamide-propyl]-ω-methoxy-polyoxyethylene (PEG-c-DOMG) was obtained from NOF (Bouwelven, Belgium). Cholesterol was purchased from Sigma-Aldrich (Taufkirchen, Germany).

The proprietary aminolipids KL22 and KL52 are disclosed in the patent literature (Constien et al. "Novel Lipids and Compositions for Intracellular Delivery of Biologically Active Compounds" US 2012/0295832 A1). Stock solutions of KL52 and KL22 lipids, DSPC, cholesterol, and PEG-c-DOMG were prepared at concentrations of 50 mM in ethanol and stored at −20° C. The lipids were combined to yield various molar ratios (see individual Examples below) and diluted with ethanol to a final lipid concentration of 25 mM. siRNA stock solutions at a concentration of 10 mg/mL in H$_2$O were diluted in 50 mM sodium citrate buffer, pH 3. KL22 and KL52 are sometimes referred to as XL 7 and XL 10, respectively, in the Examples that follow.

The lipid nanoparticle (LNP) formulations were prepared by combining the lipid solution with the siRNA solution at total lipid to siRNA weight ratio of 7:1. The lipid ethanolic solution was rapidly injected into the aqueous siRNA solution to afford a suspension containing 33% ethanol. The solutions were injected by the aid of a syringe pump (Harvard Pump 33 Dual Syringe Pump Harvard Apparatus Holliston, MA).

Subsequently, the formulations were dialyzed 2 times against phosphate buffered saline (PBS), pH 7.4 at volumes 200-times that of the primary product using a Slide-A-Lyzer cassettes (Thermo Fisher Scientific Inc. Rockford, IL) with a MWCO of 10 kD (RC membrane) to remove ethanol and achieve buffer exchange. The first dialysis was carried out at room temperature for 3 hours and then the formulations were dialyzed overnight at 4° C. The resulting nanoparticle suspension was filtered through 0.2 μm sterile filter (Sarstedt, Nümbrecht, Germany) into glass vials and sealed with a crimp closure.

General Procedure 3: LNP Characterization

Particle size and zeta potential of formulations were determined using a Zetasizer Nano ZS (Malvern Instruments Ltd, Malvern, Worcestershire, UK) in 1×PBS and 15 mM PBS, respectively.

The siRNA concentration in the liposomal formulation was measured by UV-vis. Briefly, 100 μL of the diluted formulation in 1×PBS was added to 900 μL of a 4:1 (v/v) mixture of methanol and chloroform. After mixing, the absorbance spectrum of the solution was recorded between 230 nm and 330 nm on a DU 800 spectrophotometer (Beckman Coulter, Beckman Coulter, Inc., Brea, CA). The siRNA concentration in the liposomal formulation was calculated based on the extinction coefficient of the siRNA used in the formulation and on the difference between the absorbance at a wavelength of 260 nm and the baseline value at a wavelength of 330 nm.

Encapsulation of siRNA by the nanoparticles was evaluated by the Quant-iT™ RiboGreen® RNA assay (Invitrogen Corporation Carlsbad, CA). Briefly, the samples were diluted to a concentration of approximately 5 μg/mL in TE buffer (10 mM Tris-HCl, 1 mM EDTA, pH 7.5). 50 μL of the diluted samples were transferred to a polystyrene 96 well plate, then either 50 μL of TE buffer or 50 μL of a 2% Triton X-100 solution was added. The plate was incubated at a temperature of 37° C. for 15 minutes. The RiboGreen reagent was diluted 1:100 in TE buffer, 100 μL of this solution was added to each well. The fluorescence intensity was measured using a fluorescence plate reader (Wallac Victor 1420 Multilabel Counter; Perkin Elmer, Waltham, MA) at an excitation wavelength of ~480 nm and an emission wavelength of ~520 nm. The fluorescence values of the reagent blank were subtracted from that of each of the samples and the percentage of free siRNA was determined by dividing the fluorescence intensity of the intact sample (without addition of Triton X-100) by the fluorescence value of the disrupted sample (caused by the addition of Triton X-100).

General Procedure 4: Animal Experiments

Mouse strain C57BL/6N was used for all in vivo experiments Animals were obtained from Charles River (Sulzfeld, Germany) and were between 6 and 8 weeks old at the time of experiments. Intravenously administered LNP formulations were injected by infusion of 200 μL into the tail vein. Subcutaneously administered compounds were injected in a volume of 100-200 μL. Blood was collected by submandibular vein bleed the day before injection ("prebleed") and during the experiment post injection at times indicated. Serum was isolated with serum separation tubes (Greiner Bio-One, Frickenhausen, Germany) and kept frozen until analysis. 7 days after compound administration, mice were anaesthetized by $CO_2$ inhalation and killed by cervical dislocation. Blood was collected by cardiac puncture and serum isolated as described above. Tissue for mRNA quantification was harvested and immediately snap frozen in liquid nitrogen.

General Procedure 5: Measurement of Gene Knockdown

Determination of serum protein levels was achieved using the following: Factor VII was analyzed using the chromogenic enzyme activity assay BIOPHEN FVII (#221304, Hyphen BioMed, MariaEnzersdorf, Austria) following the manufacturer's recommendations. Mouse serum was diluted 1:3000 before analysis. Absorbance of colorimetric development at 405 nm was measured using a Victor 3 multilabel counter (Perkin Elmer, Wiesbaden, Germany)

ApoB protein in serum was measured by ELISA (Cloud-Clone Corp./Hoelzel Diagnostics, Cologne, Germany, #SEC003Mu). A 1:5000 dilution of mouse serum was processed according to the manufacturer's instructions and absorbance at 450 nm measured using a Victor 3 multilabel counter (Perkin Elmer, Wiesbaden, Germany).

Transthyretin (TTR, also known as prealbumin) protein in serum was measured by ELISA (#KA2070, Novus Biologicals,/Biotechne, Wiesbaden, Germany). A 1:4000 dilution of mouse serum was processed according to the manufacturer's instructions and absorbance at 450 nm measured using a Victor 3 multilabel counter (Perkin Elmer, Wiesbaden, Germany).

For quantification of mRNA levels, frozen tissue pieces (30-50 mg) were transferred to a chilled 1.5 mL reaction tube. 1 mL Lysis Mixture (Epicenter Biotechnologies, Madison, USA) containing 3.3 µL/ml Proteinase K (50 µg/µL) (Epicenter Biotechnologies, Madison, USA) was added and tissues were lysed by sonication for several seconds using a sonicator (HD2070, Bandelin, Berlin, Germany) and digested with Proteinase K for 30 min at 65° C. in a thermomixer (Thermomixer comfort, Eppendorf, Hamburg, Germany) Lysates were stored at –80° C. until analysis. For mRNA analysis, lysates were thawed and mRNA levels were quantified using either QuantiGene 1.0 (FVII, ApoB and GAPDH) or Quantigene 2.0 (TTR) branched DNA (bDNA) Assay Kit (Panomics, Fremont, Calif., USA, Cat-No: QG0004) according to the manufacturer's recommendations. As assay readout, the chemiluminescence signal was measured in a Victor 2 Light luminescence counter (Perkin Elmer, Wiesbaden, Germany) as relative light units (RLU). The signal for the corresponding mRNA was divided by the signal for GAPDH mRNA from the same lysate. Values are reported as mRNA expression normalized to GAPDH.

Additional General Procedure 1: Single Chain Oligonucleotide Synthesis

Oligoribonucleotides were assembled on ABI 394 and 3900 synthesizers (Applied Biosystems) at the 10 mol scale, or on an Oligopilot 10 synthesizer at 28 mol scale, using phosphoramidite chemistry. Solid supports were polystyrene loaded with 2'-deoxythymidine (Glen Research, Sterling, Virginia, USA), or controlled pore glass (CPG, 520Å, with a loading of 75 µmol/g, obtained from Prime Synthesis, Aston, PA, USA). Ancillary synthesis reagents, DNA-, 2'-O-Methyl RNA-, and 2'-deoxy-2'-fluoro-RNA phosphoramidites were obtained from SAFC Proligo (Hamburg, Germany) Specifically, 5'-O-(4,4'-dimethoxytrityl)-3'-O-(2-cyanoethyl-N,N-diisopropyl) phosphoramidite monomers of 2'-O-methyl-uridine (2'-OMe-U), 4-N-acetyl-2'-O-methyl-cytidine (2'-OMe-CAc), 6-N-benzoyl-2'-O-methyl-adenosine (2'-OMe-Abz) and 2-N-isobutyrlguanosine (2'-OMe-GiBu) were used to build the oligomer sequences. 2'-Fluoro modifications were introduced employing the corresponding phosphoramidites carrying the same nucleobase protecting groups as the 2'-OMe RNA building blocks. Coupling time for all phosphoramidites (70 mM in Acetonitrile) was 3 min employing 5-Ethylthio-1H-tetrazole (ETT, 0.5 M in Acetonitrile) as activator. Phosphorothioate linkages were introduced using 50 mM 3-((Dimethylaminomethylidene)amino)-3H-1,2,4-dithiazole-3-thione (DDTT, AM Chemicals, Oceanside, California, USA) in a 1:1 (v/v) mixture of pyridine and Acetonitrile.

Upon completion of the solid phase synthesis including removal of the DMT group ("DMT off synthesis") oligonucleotides were cleaved from the solid support and deprotected using a 1:1 mixture consisting of aqueous methylamine (41%) and concentrated aqueous ammonia (32%) for 3 hours at 25° C. according to published methods (Wincott, F. et al: Synthesis, deprotection, analysis and purification of RNA and ribozymes. Nucleic Acids Res, 23: 2677-2684 (1995).

Subsequently, crude oligomers were purified by anionic exchange HPLC using a column packed with Source Q15 (GE Healthcare) and an AKTA Explorer system (GE Healthcare). Buffer A was 10 mM sodium perchlorate, 20 mM Tris, 1 mM EDTA, pH 7.4 (Fluka, Buchs, Switzerland) in 20% aqueous acetonitrile and buffer B was the same as buffer A with 500 mM sodium perchlorate. A gradient of 22% B to 42% B within 32 column volumes (CV) was employed. UV traces at 280 nm were recorded. Appropriate fractions were pooled and precipitated with 3M NaOAc, pH=5.2 and 70% ethanol. Pellets were collected by centrifugation. Alternatively, desalting was carried out using Sephadex HiPrep columns (GE Healthcare) according to the manufacturer's recommendations.

Oligonucleotides were reconstituted in water and identity of the oligonucleotides was confirmed by electrospray ionization mass spectrometry (ESI-MS). Purity was assessed by analytical anion-exchange HPLC.

5'-aminohexyl linkers were introduced employing the TFA-protected hexylamino-linker phosphoramidite (Sigma-Aldrich, SAFC, Hamburg, Germany). 3'-hexylamino-linkers were introduced using a phthalimido protected hexylamino-linker immobilized on CPG (Prime Synthesis, Aston, PA, USA). Deprotection and purification was performed as above.

Additional General Procedure 2: Generation of Thiol-Terminated siRNA

3'- or 5'-terminal thiol groups were introduced via 1-O-Dimethoxytrityl-hexyl-disulfide,1'-[(2-cyanoethyl)-(N,N-diisopropyl)]-phosphoramidite linker (NucleoSyn, Olivet Cedex, France). After deprotection and purification as above each disulfide containing oligomer was reduced using Dithiothreitol (DTT) (0.1 M DTT stock solution (Sigma-Aldrich Chemie GmbH, Munich, Germany, #646563) in Triethylammonium bicarbonate buffer (TEABc, 0.1M, pH 8.5, Sigma, #90360). The oligonucleotide was dissolved in TEABc buffer (100 mM, pH 8.5) to yield a 1 mM solution. To accomplish the disulfide reduction a 50-100 fold molar DTT excess was added to the oligonucleotide solution. The progress of the reduction was monitored by analytical AEX HPLC on a Dionex DNA Pac 200 column (4×250 mm) obtained from Thermo Fisher. The reduced material, i.e. the corresponding thiol (C6SH), elutes prior to the starting material. After completion of the reaction, excess reagent is removed by size exclusion chromatography using a HiPrep column from GE Healthcare and water as eluent. Subsequently, the oligonucleotide is precipitated using 3 M NaOAc (pH 5.2) and ethanol and stored at minus 20° C.

Additional General Procedure 3: General Procedure for Annealing of Single Stranded RNAs (ssRNAs) to Form Double Stranded RNA (dsRNA)

dsRNAs were generated from RNA single strands by mixing a slight excess of the required complementary anti-sense strand(s) relative to sense strand and annealing in 20 mM NaCl/4 mM sodium phosphate pH 6.8 buffer. Successful duplex formation was confirmed by native size exclusion HPLC using a Superdex 75 column (10×300 mm) from GE Healthcare. Samples were stored frozen until use.

In the sequences described herein upper case letters "A", "C", "G" and "U" represent RNA nucleotides. Lower case letters "c", "g", "a", and "u" represent 2'-O-methyl-modified nucleotides; "s" represents phosphorothioate; and "dT" represents deoxythymidine residues. Upper case letters A, C, G, U followed by "f" indicate 2'-fluoro nucleotides. "(SHC6)" represents a thiohexyl linker. "(DTME)" represents the cleavable homobifunctional crosslinker dithiobismaleimidoethane, "C6NH2" and "C6NH" are used interchangeably to represent the aminohexyl linker. "C6SSC6" represents the dihexyldisulfide linker. "InvdT" means inverted thymidine.

Additional General Procedure 4: General Procedure to Generate Multimeric siRNAs by Sequential Annealing Preparation of multimeric siRNAs via stepwise annealing was performed in water and utilized stepwise addition of complementary strands. No heating/cooling of the solution was required. After each addition, an aliquot of the annealing solution was removed and monitored for duplex formation using analytical RP HPLC under native conditions (20° C.). The required amounts to combine equimolar amounts of complementary single strands were calculated based on the extinction coefficients for the individual single strands computed by the nearest neighbor method. If the analytical RP HPLC trace showed excess single strand, additional amounts of the corresponding complementary strand were added to force duplex formation ("duplex titration").

Duplex titration was monitored using a Dionex Ultimate 3000 HPLC system equipped with a XBride C18 Oligo BEH (2.5 μm; 2.1×50 mm, Waters) column equilibrated to 20° C. The diagnostic wavelength was 260 nm. Buffer A was 100 mM hexafluoro-isopropanol (HFIP), 16.3 mM triethylamine (TEA) containing 1% methanol. Buffer B had the same composition except MeOH was 95%. A gradient from 5% to 70% buffer B in 30 minutes was applied at a flow rate of 250 μL/min. The two complementary strands were run independently to establish retention times. Then the aliquot containing the duplex solution was analyzed and compared to the retention times of the constituent single strands. In case the duplex solution showed a significant amount of single strand the corresponding complementary strand was added to the duplex solution.

Example 1: Generation of Thiol-Terminated siRNA

Where necessary 3'- or 5'-terminal thiol groups were introduced via 1-O-Dimethoxytrityl-hexyl-disulfide,1'-[(2-cyanoethyl)-(N,N-diisopropyl)]-phosphoramidite linker (NucleoSyn, Olivet Cedex, France). Upon completion of the solid phase synthesis and final removal of the DMT group ("DMT off synthesis") oligonucleotides were cleaved from the solid support and deprotected using a 1:1 mixture consisting of aqueous methylamine (41%) and concentrated aqueous ammonia (32%) for 6 hours at 10° C. Subsequently, the crude oligonucleotides were purified by anion-exchange high-performance liquid chromatography (HPLC) on an AKTA Explorer System (GE Healthcare, Freiburg, Germany). Purified ($C_6SSC_6$)-oligonucleotides were precipitated by addition of ethanol and overnight storage in the freezer. Pellets were collected by centrifugation. Oligonucleotides were reconstituted in water and identity of the oligonucleotides was confirmed by electrospray ionization mass spectrometry (ESI-MS). Purity was assessed by analytical anion-exchange and RP HPLC.

Each disulfide containing oligomer was then reduced using a 100 mM DL-Dithiothreitol (DTT) solution. 1.0 M DTT stock solution (Sigma-Aldrich Chemie GmbH, Munich, Germany, #646563) was diluted with Triethylammonium bicarbonate buffer (TEABc, 1M, pH 8.5, Sigma, #90360) and water to give a solution 100 mM each in DTT and TEABc. The oligonucleotide was dissolved in TEABc buffer (100 mM, pH 8.5) to yield a 1 mM solution. To accomplish the disulfide reduction a 50-100 fold molar DTT excess is added to the oligonucleotide solution. The progress of the reduction was monitored by analytical AEX HPLC on a Dionex DNA Pac 200 column (4×250 mm) obtained from Thermo Fisher. The reduced material, i.e. the corresponding thiol (C6SH), elutes prior to the starting material. After completion of the reaction, excess reagent is removed by size exclusion chromatography using a HiPrep column from GE Healthcare and water as eluent. Subsequently, the oligonucleotide is precipitated using 3 M NaOAc (pH 5.2) and ethanol and stored at minus 20° C.

Example 2: General Procedure for Preparation of Mono-DTME Oligomer

Thiol modified oligonucleotide was dissolved in 300 mM NaOAc (pH 5.2) containing 25% acetonitrile to give a 20 OD/mL solution. 40 equivalents dithiobismaleimidoethane (DTME, Thermo Fisher, #22335) were dissolved in acetonitrile to furnish a 15.6 mM solution. The DTME solution was added to the oligonucleotide-containing solution and agitated at 25° C. on a Thermomixer (Eppendorf, Hamburg, Germany) Progress of the reaction was monitored by analytical AEX HPLC using a Dionex DNA Pac200 column (4×250 mm). Depending on the required purity level excess DTME is either removed by size exclusion HPLC using a HiPrep column (GE Healthcare) or the crude reaction mixture is purified by preparative AEX HPLC using a column packed with Source 15 Q resin commercially available from GE Healthcare.

Example 3: General Procedure for Preparation of Dimer Via DTME Functionality

The DTME modified oligonucleotide prepared according to the procedure in Example 2 was reacted with another oligonucleotide equipped with a thiol linker. This reaction could either be carried out on the single stranded sequence or after prior annealing of the complementary oligonucleotide of one of the reaction partners. Consequently, if desired, the DTME modified oligonucleotide was reacted with the thiol modified oligonucleotide directly, or was annealed with its complementary strand and the resulting duplex reacted with the thiol modified oligonucleotide. Alternatively, the thiol modified oligonucleotide was annealed with its complementary strand and this duplex reacted with the DTME modified single strand. In all cases the reaction was carried out in aqueous solution in the presence of 300 mM NaOAc (pH 5.2).

Example 4: General Procedure for Annealing of Single Stranded RNAs (ssRNAs) to Form Double Stranded RNA (dsRNA)

dsRNAs were generated from RNA single strands by mixing equimolar amounts of complementary sense and antisense strands and annealing in 20 mM NaCl/4 mM sodium phosphate pH 6.8 buffer. Successful duplex formation was confirmed by native size exclusion HPLC using a Superdex 75 column (10×300 mm) from GE Healthcare. Samples were stored frozen until use.

Example 5: General Procedure for Preparation of 3'- or 5'-NH$_2$ Derivatized Oligonucleotides RNA equipped with a C-6-aminolinker at the 5'-end of the sense strand was produced by standard phosphoramidite chemistry on solid phase at a scale of 140 µmol using an ÄKTA Oligopilot 100 (GE Healthcare, Freiburg, Germany) and controlled pore glass (CPG) as solid support (Prime Synthesis, Aston, PA, USA). Oligomers containing 2'-O-methyl and 2'-F nucleotides were generated employing the corresponding 2'-OMe-phosphoramidites, 2'-F-methyl phosphoramidites. The 5'-aminohexyl linker at the 5'-end of the sense strand was introduced employing the TFA-protected hexylaminolinker phosphoramidite (Sigma-Aldrich, SAFC, Hamburg, Germany). In case the hexylamino-linker was needed at the 3'-position, a phtalimido protected hexylamino-linker immobilized on CPG (Prime Synthesis, Aston, PA, USA) was used. Cleavage and deprotection was accomplished using a mixture of 41% methylamine in water and concentrated aqueous ammonia (1:1 v/v). Crude oligonucleotides were purified using anion exchange HPLC and a column (2.5×18 cm) packed with Source 15Q resin obtained from GE Healthcare.

Example 6: General Method for GalNAc Ligand Conjugation

The trivalent GalNAc ligand was prepared as outlined in Hadwiger et al., patent application US2012/0157509 A1. The corresponding carboxylic acid derivative was activated using NHS chemistry according to the following procedure:

3GalNAc-COOH (90 µmol, 206 mg) was dissolved in 2.06 mL DMF. To this solution N-Hydroxysuccinimide (NHS, 14.3 mg (99 µmol, 1.1 eq.) and Diisopropylcarbodiimide (DIC, 18.29 µL, 1.05 eq., 94 µmol) were added at 0° C. This solution was stirred overnight at ambient temperature. Completion of the reaction was monitored by TLC (DCM:MeOH=9:1).

The precursor oligonucleotide equipped with an aminohexyl linker was dissolved in sodium carbonate buffer (pH 9.6):DMSO 2:3 v/v to give a 4.4 mM solution. To this solution an aliquot of the NHS activated GalNAc solution (1.25 eq, 116 µL) was added. After shaking for 1 hour at 25° C., another aliquot (116 µL) of the NHS activated GalNAc was added. Once RP HPLC analysis showed at least more than 85% conjugated material, the crude conjugate was precipitated by addition of ethanol and storage in the freezer overnight. The pellet was collected by centrifugation. The pellet was dissolved in 1 mL concentrated aqueous ammonia and agitated for 4 hours at room temperature in order to remove the O-acetates from the GalNAc sugar residues. After confirmation of quantitative removal of the O-acetates by RP HPLC ESI MS, the material was diluted with 100 mM Triethyl ammonium acetate (TEAA) and the crude reaction mixture was purified by RP HPLC using an XBridge Prep C18 (5 µm, 10×50 mm, Waters) column at 60° C. on an ÄKTA explorer HPLC system. Solvent A was 100 mM aqueous TEAA and solvent B was 100 mM TEAA in 95% CAN, both heated to 60° C. by means of a buffer pre-heater. A gradient from 5% to 25% B in 60 min with a flow rate of 3.5 mL/min was employed. Elution of compounds was observed at 260 and 280 nm. Fractions with a volume of 1.0 mL were collected and analyzed by analytical RP HPLC/ESI-MS. Fractions containing the target conjugate with a purity of more than 85% were combined. The correct molecular weight was confirmed by ESI/MS.

Example 7: Oligonucleotide Precursors

Using the methodologies described in the above Examples the following single-stranded monomers, dimers and GalNAc tagged monomers and dimers were prepared:

TABLE 1

Oligonucleotide Precursors-Single Strands ("X")

| SEQ ID NO: | ID | Sequence |
|---|---|---|
| | | FVII sense strands (5'-3') |
| 1 | X18791 | (C$_6$SSC$_6$)gcAfaAfgGfcGfuGfcCfaAfcUfcAf(invdT)(C$_6$NH$_2$) |
| 2 | X18792 | (C$_6$SSC$_6$)gcAfaAfgGfcGfuGfcCfaAfcUfcAf(invdT)(C$_6$NH)(GalNAc$_3$) |
| 3 | X18793 | (SHC$_6$)gcAfaAfgGfcGfuGfcCfaAfcUfcAf(invdT)(C$_6$NH)(GalNAc$_3$) |
| 4 | X18794 | (C$_6$SSC$_6$)gcAfaAfgGfcGfuGfcCfaAfcUfcAf(invdT) |
| 5 | X19569 | (SHC$_6$)gcAfaAfgGfcGfuGfcCfaAfcUfcAf(invdT) |
| 6 | X19574 | (DTME)(SHC$_6$)gcAfaAfgGfcGfuGfcCfaAfcUfcAf(invdT) |
| | | FVII antisense strands (5'-3') |
| 7 | X18796 | UfsGfaGfuUfgGfcAfcGfcCfuUfuGfcusu(C$_6$SSC$_6$)dT |
| 8 | X18797 | UfsGfaGfuUfgGfcAfcGfcCfuUfuGfcusu(C$_6$SH) |
| 9 | X18798 | UfsGfaGfuUfgGfcAfcGfcCfuUfuGfcusu(C$_6$SH)(DTME) |
| | | ApoB sense strands (5'-3') |
| 10 | X19577 | (C$_6$SSC$_6$)cuAfuUfuGfgAfgAfgAfaAfuCfgAf(invdT) |
| 11 | X19578 | (SHC$_6$)cuAfuUfuGfgAfgAfgAfaAfuCfgAf(invdT) |
| 12 | X19579 | (DTME)(SHC$_6$)cuAfuUfuGfgAfgAfgAfaAfuCfgAf(invdT) |

TABLE 2

Oligonucleotide Single Stranded Sense and Antisense Pairs; and Resulting Duplexes ("XD-") After Annealing.

| Duplex ID | SEQ ID NO: | Single Strand ID | Sequence (5'-3') | Target/strand |
|---|---|---|---|---|
| XD-00376 | 13 | X01162 | GGAUfCfAUfCfUfCfAAGUfCfUfUfACfdTsdT | FVIIs |
|  | 14 | X00549 | GUfAAGACfUfUfGAGAUfGAUfCfCfdTsdT | FVIIas |
| XD-00030 | 16 | X00116 | GcAAAGGcGuGccAAcucAdTsdT | FVIIs |
|  | 17 | X00117 | UGAGUUGGcACGCCUUUGCdTsdT | FVIIas |
| XD-01078 | 19 | X02943 | GGAAUCuuAuAuuuGAUCcAsA | ApoBs |
|  | 20 | X02944 | uuGGAUcAAAuAuAAGAuUCcscsU | ApoBas |
| XD-00194 | 22 | X00539 | cuuAcGcuGAGuAcuucGAdTsdT | LUCs |
|  | 23 | X00540 | UCGAAGuACUcAGCGuAAGdTsdT | LUCas |

TABLE 3

Derivatized Oligonucleotide Single Stranded Sense and Antisense Pairs; and Resulting Duplexes After Annealing.

| Duplex ID | SEQ ID NO: | Single Strand ID | Sequence (5'-3') | Target |
|---|---|---|---|---|
| XD-06328 | 25 | X18790 | (GalNAc3)(NHC₆)gcAfaAfgGfcGfuGfcCfaAfcUfcUfCfAf(invdT) | FVII |
|  | 26 | X18795 | UfsGfaGfuUfgGfcAfcGfcCfuUfuGfcusu |  |
| XD-06728 | 28 | X20124 | (GalNAc3)(NHC₆)cuAfuUfuGfgAfgAfgAfaAfuCfgAf(invdT) | ApoB |
|  | 29 | X19583 | UfsCfgAfuUfuCfuCfuCfuCfAfaAfuAfgusu |  |
| XD-06386 | 31 | X20216 | (GalNAc3)(NHC₆)sAfsasCfaGfuGfuUfCfUfuGfcUfcUfaUfaAf(invdT) | TTR |
|  | 32 | X19584 | usUfsaUfaGfaGfcAfagaAfcAfcUfgUfususu |  |
|  | 34 | X19571 | gcAfaAfgGfcGfuGfcCfaAfcUfcUfCfAf(invdT)(C₆NH)(GalNAc3) | FVII |
| XD-05961 | 35 | X18788 | gcAfaAfgGfcGfuGfcCfaAfcUfcUfCfAf(invdT) | FVII |
|  | 26 | X18795 | UfsGfaGfuUfgGfcAfcGfcCfuUfuGfcusu |  |

TABLE 4

Single Stranded Oligonucleotide Dimers Linked by DTME

| SEQ ID NO: | ID | Sequence (5'-3') | Target/strand |
|---|---|---|---|
| 37 & 125 | X15049 | GGAAUCuuAuAuuuGAUCcAsA(SHC₆)(DTME)GGAUfCfAUfCfUfCfAAGUfCfUfUfACfdTsdT(SHC₆) | ApoBs/F7s |
| 38 & 126 | X12714 | GGAUfCfAUfCfUfCfAAGUfCfUfUfACfdTsdT(SHC₆)(DTME)GUfAAGACfUfUfGAGAUfGAUfCfCfdTsdT(SHC₆) | F7s/F7as |
| 39 & 127 | X19575 | (SHC₆)gcAfaAfgGfcGfuGfcCfaAfcUfcUfCfAf(invdT)(C₆NH)(GalNAc₃)(DTME)(SHC₆)gcAfaAfgGfcGfuGfcCfaAfcUfcUfCfAf(invdT) | F7s/F7s |
| 40 & 128 | X19819 | UfsGfaGfuUfgGfcAfcGfcCfuUfuGfcusu(C₆SH)(DTME)UfsGfaGfuUfgGfcAfcGfcCfuUfuGfcusu(C₆SH) | F7as/F7as |
| 41 & 129 | X20336 | (SHC₆)gcAfaAfgGfcGfuGfcCfaAfcUfcUfCfAf(invdT)(C₆NH)(GalNAc₃)(DTME)(SHC₆)cuAfuUfuGfgAfgAfgAfaAfuCfgAf(invdT) | F7s/ApoBs |

TABLE 5

Single Strand DTME Dimers and Corresponding Monomers; and Resulting Duplexes After Annealing

| Duplex ID | SEQ ID | Single Strand ID | Sequence (5'-3') | Target/ Strand |
|---|---|---|---|---|
| XD-05311 | 37 & 130 | X15049 | GGAAUCuuAuAuuuGAUCcAsA(SHC6)(DTME)GGAUfCfA UfCfUfCfAAGUfCfUfUfACfdTsdT(SHC6) | ApoBs-FVIIs |
|  | 14 | X00549 | 5'-GUfAAGACfUfUfGAGAUfGAUfCfCfdTsdT-3' + | FVIIas |
|  | 20 | X02944 | 5'-uuGGAUcAAAuAuAAGAuUCcscsU-3' | ApoBas |
| XD-05312 | 38 & 131 | X12714 | GGAUfCfAUfCfUfCfAAGUfCfUfUfACfdTsdT(SHC6)(DTME) GUfAAGACfUfUfGAGAUfGAUfCfCfdTsdT(SHC6) | FVIIs-FVIIas |
|  | 13 | X01162 | 5'-GGAUfCfAUfCfUfCfAAGUfCfUfUfACfdTsdT-3' | FVIIs |
|  | 14 | X00549 | 5'-GUfAAGACfUfUfGAGAUfGAUfCfCfdTsdT-3' | FVIIas |

TABLE 6

Chemically Synthesized Disulfide-Linked Dimers and Trimers

| SEQ ID | Single Strand ID | Sequence (5'-3') | Target/ Strand |
|---|---|---|---|
| 44 & 132 | X20366 | usUfsaUfaGfaGfcAfagaAfcAfcUfgUfususu(C6SSC6)UfsCfgAfuUfuCfu CfuCfcAfaAfuAfgusu | TTRas/ ApoBas |
| 45 & 133 | X22413 | AfsasCfaGfuGfuUfCfUfuGfcUfcUfaUfaAf(invdT)(C6SSC6)gcAfaAfgGf cGfuGfcCfaAfcUfcAf(invdT) | FVIIs/ TTRs |
| 46 & 134 & 135 | X20256 | (SHC6)gcAfaAfgGfcGfuGfcCfaAfcUfcAf(invdT)(C6NH)(GalNAc3)(SP DP)(NHC6)cuAfuUfuGfgAfgAfgAfaAfuCfgAf(invdT)(C6SSC6)AfsasCf aGfuGfuUfCfUfuGfcUfcUfaUfaAf(invdT) | FVIIs/ ApoBs/ TTRs |
| 47 & 136 | X20366 | usUfsaUfaGfaGfcAfagaAfcAfcUfgUfususu($C_6SSC_6$)UfsCfgAfuUfuCfuC fuCfcAfaAfuAfgusu | TTRas/ ApoBas |
| 48 & 137 | X22413 | AfsasCfaGfuGfuUfCfUfuGfcUfcUfaUfaAf(invdT)($C_6SSC_6$)gcAfaAfgGf cGfuGfcCfaAfcUfcAf(invdT) | FVIIs/ TTRs |

Figure 1B:
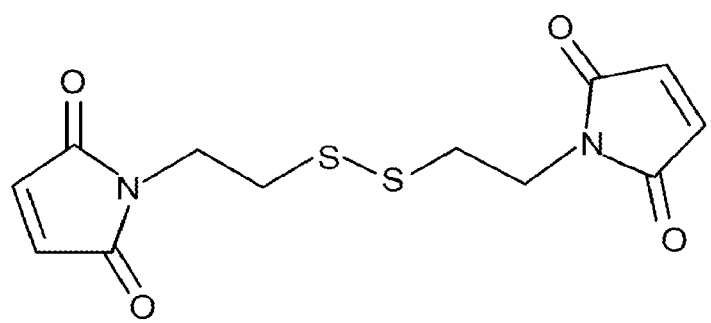
FIG. 1B presents the chemical structure of a dithio-bis-maleimidoethane.

Key: In the Sequence portion of Tables 1-6 above (and those that follow): upper case letters "A", "C", "G" and "U" represent RNA nucleotides. Lower case letters "c", "g", "a", and "u" represent 2'-O-methyl-modified nucleotides; "s" represents phosphorothioate; and "dT" represents deoxythymidine residues. Upper case letters A, C, G, U followed by "f" indicate 2'-fluoro nucleotides. "(SHC6)" represents a thiohexyl linker. "(DTME)" represents the cleavable homobifunctional crosslinker dithiobismaleimidoethane, whose structure is shown in FIG. 1B. "(BMPEG2)" represents the non-cleavable homobifunctional crosslinker 1,8-bismaleimido-diethyleneglycol. "C6NH2" and "C6NH" are used interchangeably to represent the aminohexyl linker. "C6SSC6" represents the dihexyldisulfide linker. "GalNAc3" and "GalNAc" are used interchangeably to represent the tri-antennary N-acetylgalactosamine ligand, whose chemical structure is shown in FIG. 1A. "SPDP" represents the reaction product of the reaction of succinimidyl 3-(2-pyridyldithio)propionate with the aminolinker equipped RNA. "InvdT" means inverted thymidine.

In the Target/Strand portion of the chart: "F7" or "FVII" designates an siRNA sequence targeting the Factor VII transcript (mRNA). "ApoB" designates an siRNA sequence targeting the apolipoprotein B transcript. "TTR" designates an siRNA sequence targeting the transthyretin transcript. Sense strand is designated "s"; antisense strand is designated "as".

Example 8: General Procedure to Generate Dimeric, Trimeric and Tetrameric siRNAs by Sequential Annealing For the preparation of dimeric, trimeric and tetrameric siRNAs, a stepwise annealing procedure was performed. The annealing was performed in water and utilized stepwise addition of complementary strands. No heating/cooling of the solution was required. After each addition, an aliquot of the annealing solution was removed and monitored for duplex formation using analytical RP HPLC under native conditions (20° C.). The required amounts to combine equimolar amounts of complementary single strands were calculated based on the extinction coefficients for the individual single strands computed by the nearest neighbor method. If the analytical RP HPLC trace showed excess single strand, additional amounts of the corresponding complementary strand were added to force duplex formation ("duplex titration").

Duplex titration was monitored using a Dionex Ultimate 3000 HPLC system equipped with a XBride C18 Oligo BEH (2.5 µm; 2.1×50 mm, Waters) column equilibrated to 20° C. The diagnostic wavelength was 260 nm. Buffer A was 100 mM hexafluoro-isopropanol (HFIP), 16.3 mM triethylamine (TEA) containing 1% methanol. Buffer B had the same composition except MeOH was 95%. A gradient from 5% to 70% buffer B in 30 minutes was applied at a flow rate of 250 µL/min. The two complementary strands were run independently to establish retention times. Then the aliquot containing the duplex solution was analyzed and compared to the retention times of the constituent single strands. In case the duplex solution showed a significant amount of single strand the corresponding complementary strand was added to the duplex solution.

Example 9: Preparation of 5'-GalNAc-FVII Canonical Control (XD-06328)

Figure 2:
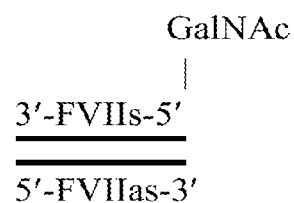
FIG. 2 presents a 5'-GalNAc-FVII canonical control, which is discussed in connection with Example 9.

5'-GalNAc-FVII Canonical Control (XD-06328) (see FIG. 2) was prepared by annealing ssRNA strands X18790 and X18795 by the methods described in Example 4. The product was obtained in 91.6% purity as determined by HPLC analysis.

Example 10: Preparation of 3'-GalNAc-FVII-DTME-FVII Homodimer with Cleavable Linker Joining 3' Antisense Strands and GalNAc Conjugated to External 3' End of Sense Strand (XD-06330)

Figure 3:
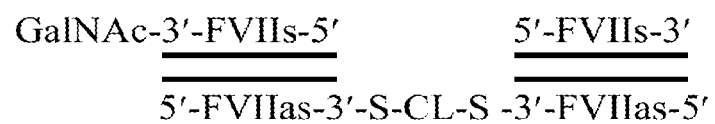
FIG. 3 presents a GalNAc-homodimer conjugate (XD-06330), which is discussed in connection with Example 10.

GalNAc-conjugated homodimeric siRNA XD-06330 targeting FVII (FIG. 3) was prepared (10 mg, 323 nmol) by combining the single stranded dimer X19819 stepwise with X18788 and X19571 according to the duplex titration method described in Example 8. The isolated material was essentially pure by HPLC analysis.

TABLE 8

Stoichiometry of Oligomers Used in Synthesis of GalNAc-FVII-DTME-FVII Homodimer (XD-06330)

| SEQ ID NO: | ID | Target | E (L/mol * cm) | Nmol/ OD | MW (free Acid) | MW Na salt | Req OD |
|---|---|---|---|---|---|---|---|
| 40 | X19819 | FVIIas-FVIIas | 389000 | 2.57 | 14405.6 | 15372.9 | 174 |
| 36 | X18788 | FVIIs | 193000 | 5.18 | 6545.3 | 6962.9 | 62.3 |
| 34 | X19571 | FVIIs | 193000 | 5.18 | 8161.0 | 8600.6 | 62.3 |
| 49 | XD-06330 | | | | 29111.9 | 30936.4 | |

Example 11: Preparation of 3'-GalNAc-FVII-DTME-FVII Homodimer with Cleavable Linker Joining 5' Sense Strands and GalNAc Conjugated to External 3' End of Sense Strand (XD-06360)

Figure 4:
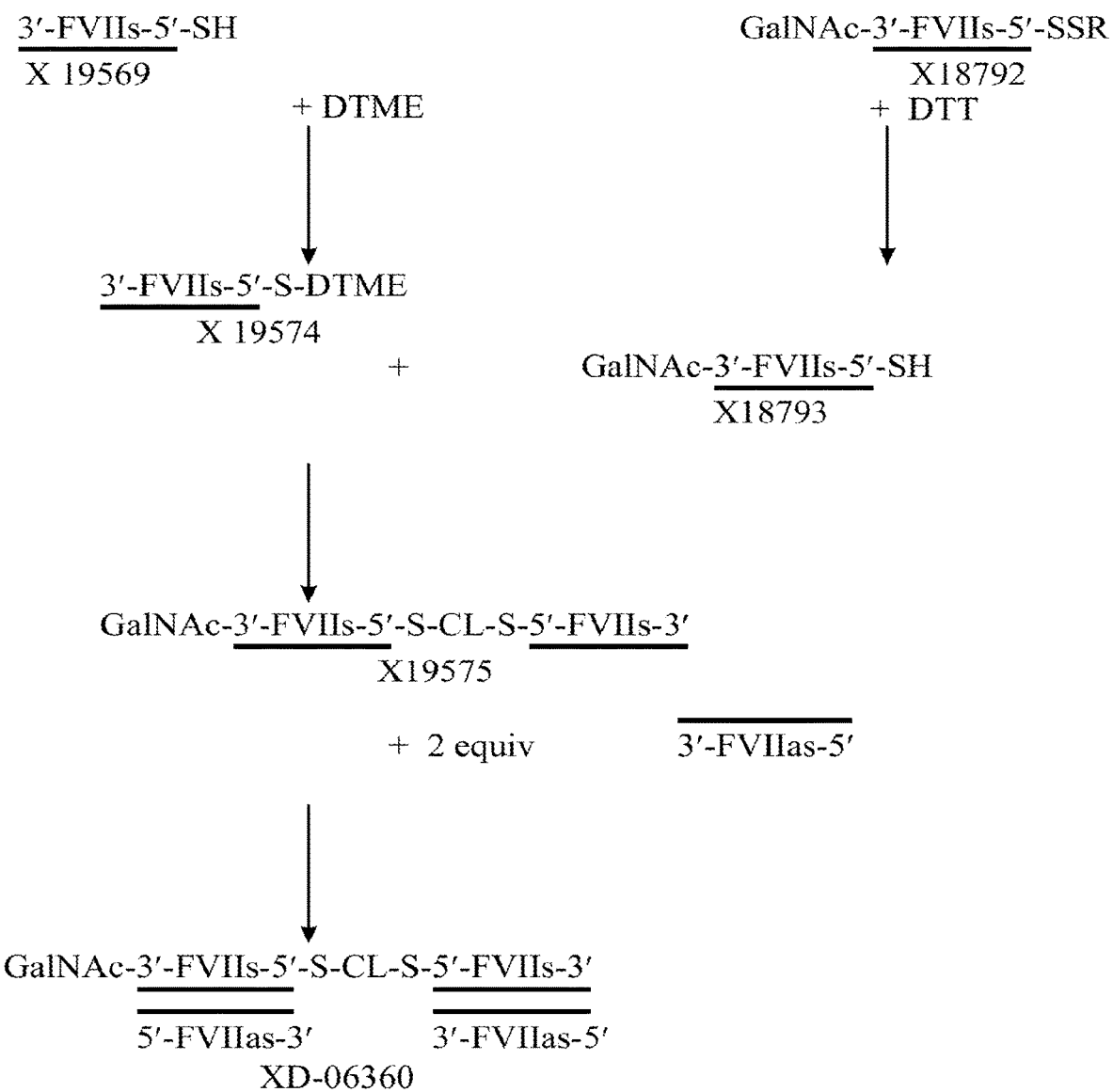
FIG. 4 presents a schematic diagram of a synthesis of a GalNAc-homodimer conjugate (XD-06360), which is discussed in connection with Example 11.

GalNAc-conjugated homodimeric siRNA XD-06360 targeting FVII was prepared (11 mg, 323 nmol) by combining single strands stepwise using the synthesis strategy depicted in FIG. 4 and the methodology described in Example 8.

All reactive steps produced high quality material, with oligomer X19575 being determined to be 91.7 and 93.4% pure by ion exchange and reverse phase chromatography respectively, and oligomer XD-06360 being isolated in 86.8% purity as determined by non-denaturing reverse phase HPLC. The stoichiometry of the various oligomers used in the synthesis are shown in Table 9.

TABLE 9

Stoichiometry of Oligomers Used in Synthesis of GalNAc-FVII-FVII Homodimer (XD-06360)

| SEQ ID NO: | ID | Target | E (L/mol * cm) | Nmol/OD | MW (free Acid) | MW Na salt | Req OD |
|---|---|---|---|---|---|---|---|
| 39 | X19575 | FVIIs-FVIIs | 384800 | 2.60 | 15413.1 | 16314.4 | 137 |
| 26 | X18795 | FVIIas | 194800 | 5.13 | 6849.4 x2 | 7289.1 x2 | 139 |
| 50 | XD-06360 | | | | 29111.9 | 30892.6 | |

Example 12: Preparation of 5'-GalNAc-FVII-DTME-FVII Homodimer with Cleavable Linker Joining 3' Antisense Strands and GalNAc Conjugated to Internal 5' End of Sense Strand (XD-06329)

Figure 5:
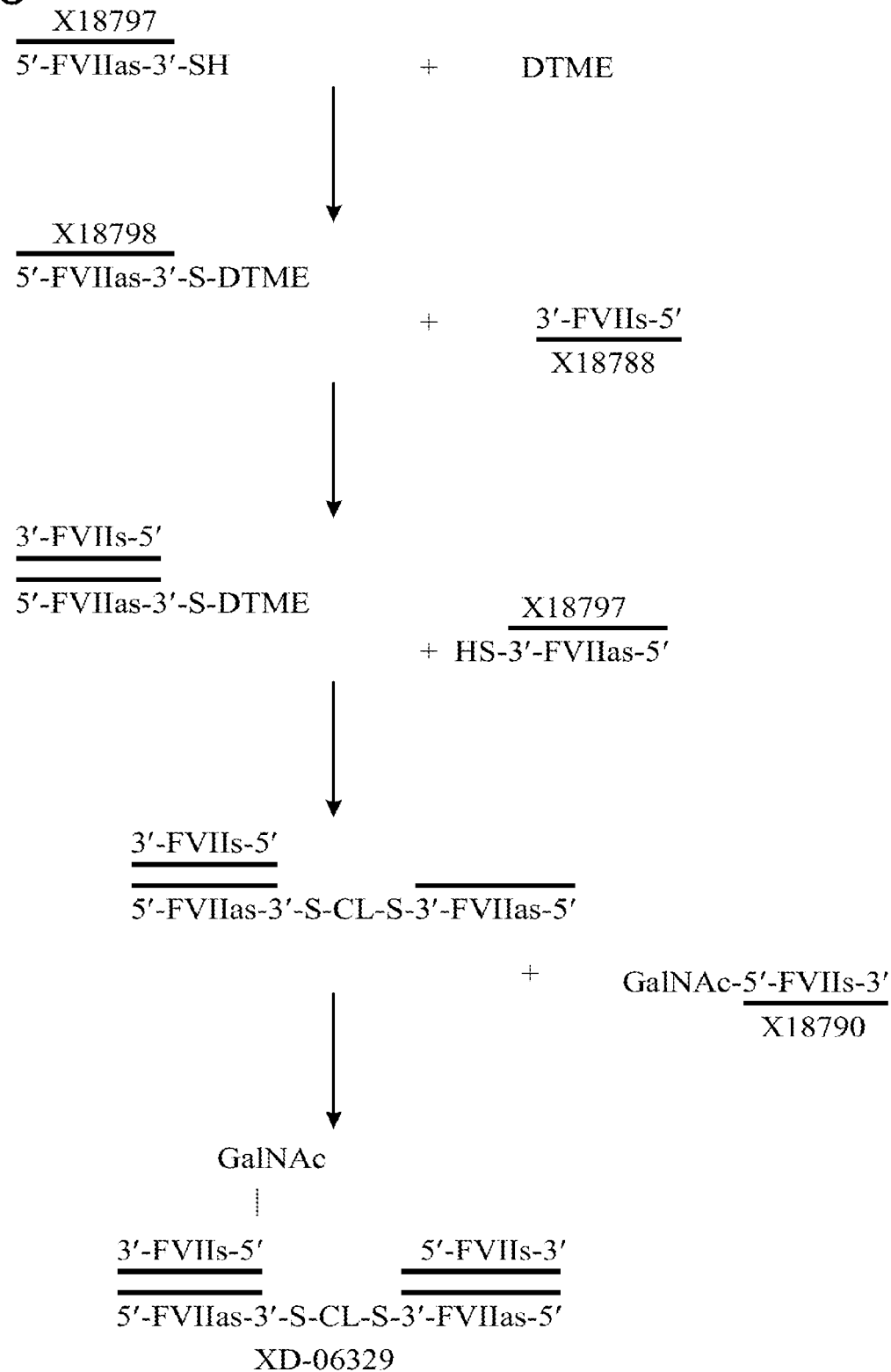
FIG. 5 presents a schematic diagram of a synthesis of a GalNAc-homodimer conjugate (XD-06329), which is discussed in connection with Example 12.

GalNAc-conjugated homodimeric siRNA XD-06329 targeting FVII was prepared as depicted in FIG. 5 by annealing 1150 nmol of X18788 and 1150 nmol X18798. The sum of the ODs of the individual strands was 450 ODs and the combined solution, i.e. the duplex, had 394 ODs due to the hyperchromicity (394 ODs=1150 nmol duplex). This DTME modified duplex was reacted with 1150 nmol X18797 (3'-SH modified FVII antisense) (224 ODs). After HPLC purification, 364 ODs "half-dimer" siRNA was isolated. "Half-dimer" FVII siRNA (10 mg, 323 nmol, 174 ODs) was then annealed with 5'GalNAc-FVII sense (X18790) (323 nmol, 62.3 OD) to yield final product XD-06329.

Example 13: Determination of In Vivo FVII Gene Knockdown by FVII Homodimeric GalNAc Conjugates (XD-06329, XD-06330 and XD-06360)

Figure 6:
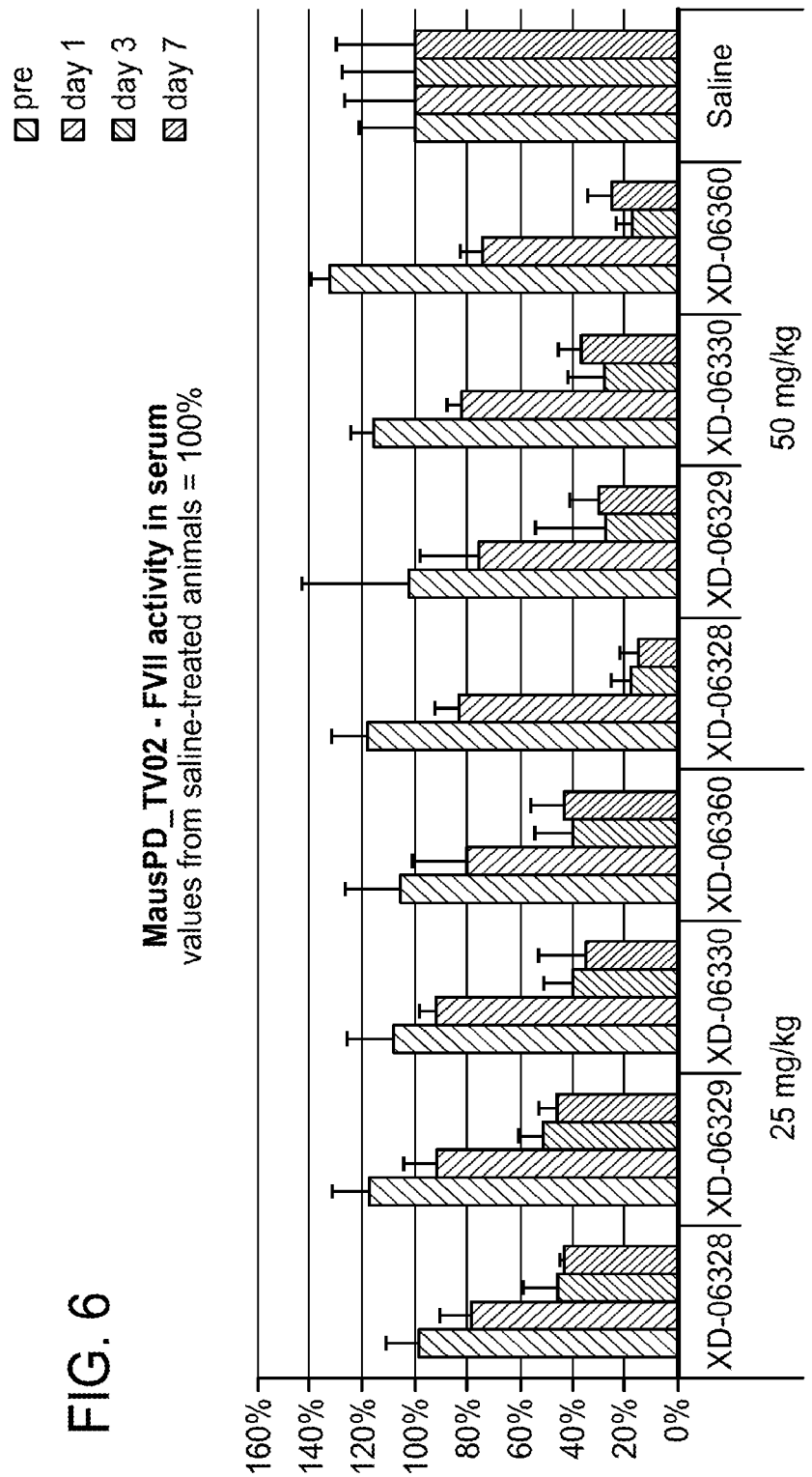
FIG. 6 presents data showing FVII activity in mouse serum (knockdown by FVII homodimeric GalNAc conjugates), which is discussed in connection with Example 13.

Three different variants of homodimeric, GalNAc-conjugated siRNAs targeted against Factor VII (XD-06329, XD-06330 and XD-06360) and a monomeric GalNAc-conjugated FVII-siRNA (XD-06328) were tested for in vivo efficacy in an animal experiment as described above (General Procedure: Animal Experiments). Group size was n=4 mice for treatment groups and n=5 for saline control. All compounds were injected subcutaneously at different doses (25 mg/kg or 50 mg/kg) in a volume of 0.2 mL. Blood was collected 1 day prior to treatment, and at 1, 3 and 7 days post-treatment, and analyzed for FVII enzyme activity. Results are shown in FIG. 6.

Silencing activity, onset of action, and potency of the homodimeric GalNAc-conjugates (XD-06329, XD-06330 and XD-06360) was comparable to the monomeric, canonical control (XD-06328) on a knockdown per unit weight basis. No signs of toxicity were observed (e.g., weight loss, abnormal behavior). However, upon normalizing the data for GalNAc content, the homodimeric GalNAc conjugates were all more effective at FVII knockdown than GalNAc monomer, thereby demonstrating more efficient siRNA uptake per ligand/receptor binding event. These results are shown in FIGS. 7A and 7B.

FIG. 7A. Factor VII serum values at each time point are normalized to control mice injected with 1×PBS. The bars at each datapoint correspond, left to right, to saline, XD-06328, XD-06329, XD-06330, and XD-06360, respectively.

FIG. 7B. Factor VII serum values at each time point are normalized to the prebleed value for each individual group. The bars at each data point correspond, left to right, to saline, XD-06328, XD-06329, XD-06330, and XD-06360, respectively.

Example 14: Preparation of Canonical GalNAc-siRNAs Independently Targeting FVII (XD-06328), ApoB (XD-06728) and TTR (XD-06386)

Three canonical siRNAs independently targeting FVII (XD-06328), ApoB (XD-06728) and TTR (XD-06386) (see FIG. 8) were independently prepared by solid phase synthesis. Three sense strands (X18790, X20124, X20216, respectively) were separately prepared with a 5'-hexylamine linker. Following cleavage and deprotection of the oligonucleotides and HPLC purification of the crude material, conjugation of a per-acetylated GalNAc cluster to each oligo was achieved using NHS chemistry. Removal of the O-acetates by saponification was mediated by aqueous ammonia. The complementary antisense strands (X18795, X19583, and X19584, respectively) were synthesized by standard procedures provided above, followed by annealing to the GalNAc conjugated single strands to yield siRNAs targeting FVII (XD-06328), ApoB (XD-06728) and TTR (XD-06386) in 99.7, 93.1 and 93.8% purity respectively.

TABLE 10

GalNAc-siRNA Conjugates

| Duplex ID | SEQ ID NO: | ssRNA | Sequence 5'-3' | |
|---|---|---|---|---|
| XD-06328 | 138 | X18790 | (GalNAc3)(NHC$_6$)gcAfaAfgGfcGfuGfcCfaAfcUfcAf (invdT) | FVII |
|  | 139 | X18795 | UfsGfaGfuUfgGfcAfcGfcCfuUfuGfcusu | |
| XD-06728 | 140 | X20124 | (GalNAc3)(NHC$_6$)cuAfuUfuGfgAfgAfgAfaAfuCfgAf (invdT) | ApoB |
|  | 141 | X19583 | UfsCfgAfuUfuCfuCfuCfcAfaAfuAfgusu | |
| XD-06386 | 142 | X20216 | (GalNAc3)(NHC$_6$)sAfsasCfaGfuGfuUfCfUfuGfcUfc UfaUfaAf(invdT) | TTR |
|  | 143 | X19584 | usUfsaUfaGfaGfcAfagaAfcAfcUfgUfususu | |

Example 15: Preparation of GalNAc-FVII-ApoB-TTR Trimer with Cleavable Linkages on Sense Strands (XD-06726)

Figure 10:
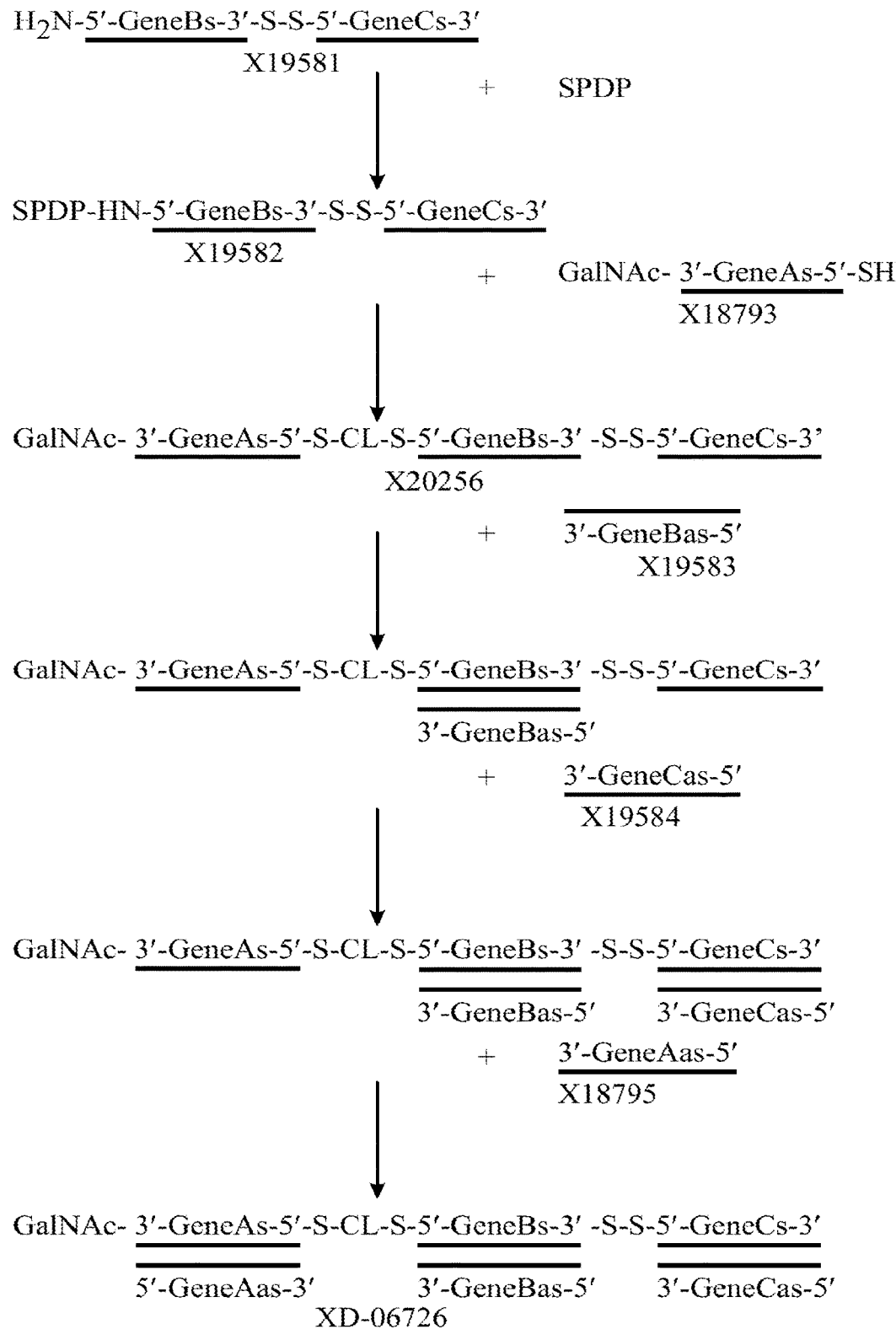
FIG. 10 presents a schematic diagram for a synthesis strategy for a GalNAc-conjugated heterotrimer (XD-06726), which is discussed in connection with Example 15. Key: In this Example, "GeneA" is siFVII; "GeneB" is siApoB; and "GeneC" is siTTR.

A heterotrimer targeting FVII, ApoB and TTR conjugated to GalNAc (see FIG. 9) was synthesized using a hybrid strategy of solid phase and solution phase, as depicted in FIG. 10.

The dimer X19581 was made using solid phase chemistry with an aminohexyl linker on the 5'-end using the corresponding commercially available TFA protected phosphoramidite (SAFC Proligo, Hamburg, Germany). The sequence was cleaved from the solid support, deprotected and purified according to the conditions outlined above. In order to install an additional disulfide linker, the oligonucleotide's 5'-aminohexyllinker was reacted with SPDP (succinimidyl 3-(2-pyridyldithio)propionate)

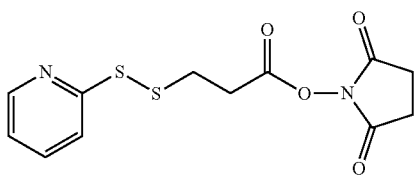 [SMILES: O=C(CCSSc1ccccn1)ON1C(=O)CCC1=O]

available from Sigma (#P3415). 928 nmol (400 OD) oligonucleotide was dissolved in 4.7 mL 100 mM TEAB, pH 8.5, containing 20% Dimethyl formamide (DMF). To this solution was added a solution of 1.4 mg (4.6 µmol, 5 eq) SPDP in 100 µL DMF. Once analytical RP HPLC indicated consumption of the starting material, the crude reaction mixture was purified on a C18 XBridge column (10×50 mm) purchased from Waters. RP purification was performed on an ÄKTA explorer HPLC system. Solvent A was 100 mM aqueous TEAA and solvent B was 100 mM TEAA in 95 ACN. Solvents were heated to 60° C. by means of a buffer pre-heater and the column was kept in an oven at the same temperature. A gradient from 0% to 35% B in 45 min with a flow rate of 4 mL/min was employed. Elution of compounds was observed at 260 and 280 nm. Fractions with a volume of 1.5 mL were collected and analyzed by analytical RP HPLC/ESI-MS. Suitable fractions were combined and the oligonucleotide X19582 precipitated at minus 20° C. after addition of ethanol and 3M NaOAc (pH 5.2). Identity was confirmed by RP-HPLC ESI-MS.

In order to prepare the single stranded trimer, the above oligonucleotide X19582 (255 nmol) was dissolved in 1.3 mL water. To this solution 306 nmol (1.2 eq) of the thiol modified oligonucleotide X18793 was added. The reaction mixture contained 200 mM TEAA and 20% acetonitrile. Progress of the reaction was followed by RP HPLC. Once the starting material was consumed the reaction mixture was purified using the same conditions as described in the previous paragraph, with the exception that the gradient was run from 0% B to 30% B in 45 min.

The single-stranded heterotrimer X20256 (containing linked sense strands of siFVII, siApoB and siTTR) was obtained in high purity. The sequence of X20256 is shown in Table 11.

TABLE 11

Single-Stranded Heterotrimer

| SEQ ID NO: | ID | Sequence | Target/Strand |
|---|---|---|---|
| 52 & 144 & 145 | X20256 | (SHC$_6$) gcAfaAfgGfcGfuGfcCfaAf cUfcAf(invdT) (C$_6$NH) (GalNAc$_3$) (SPDP) (NHC$_6$) cuAfuUfuGfgAfgAf gAfaAfuCfgAf(invdT) (C$_6$SSC$_6$)Af sasCfaGfuGfuUfCfUfuGfcUfcUfa UfaAf(invdT) | FVIIs/ApoBs/TTRs |

Note: In principle the above sequence is accessible through a single solid phase synthesis. In this case, SPDP and C$_6$NH$_2$ would be replaced by the C$_6$SSC$_6$ phosphoramidite. However, due to the sequence length of the entire construct such a synthesis would be challenging.

Thereafter, the heterotrimeric duplex construct (XD-06726), simultaneously targeting FVII, ApoB and TTR, 7 mg (150 nmol), was prepared by sequentially adding the antisense single strands stepwise to the sense-strand heterotrimeric intermediate (X20256) according to the duplex titration method described in Example 8. 7 mg of material was obtained which was essentially pure by HPLC.

TABLE 12

Stoichiometry of Oligomers Used in Synthesis of GalNAc-FVII-ApoB-TTR Trimer (XD-06726).

| SEQ ID NO: | ID | Target | E (L/mol * cm) | Nmol/OD | MW (free Acid) | MW Na salt | Req OD |
|---|---|---|---|---|---|---|---|
| 52 & 144 & 145 | X20256 | FVIIs-ApoBs-TTRs | 623900 | 1.60 | 22690.8 | 24075.7 | 94 |
| 29 | X19583 | ApoBas | 206500 | 4.84 | 6762.4 | 7202.1 | 31 |
| 32 | X19584 | TTRas | 240400 | 4.16 | 7596.1 | 8079.7 | 36 |
| 26 | X18795 | FVIIas | 194800 | 5.13 | 6849.4 | 7289.1 | 29 |
| 53 | XD-06726 | | | | 43898.7 | 46646.6 | |

Example 16: Preparation of GalNAc-FVII-ApoB-TTR Trimer with Cleavable Linkages on Alternating Sense and Antisense Strands (XD-06727)

Figure 11:
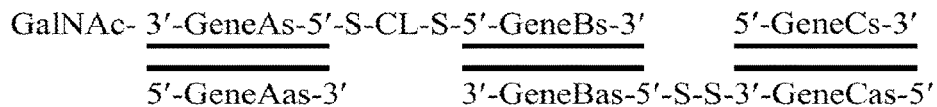
FIG. 11 presents a GalNAc-heterotrimer conjugate (XD-06727), which is discussed in connection with Example 16. Key: In this Example, "GeneA" is siFVII; "GeneB" is siApoB; and "GeneC" is siTTR.
Figure 12:
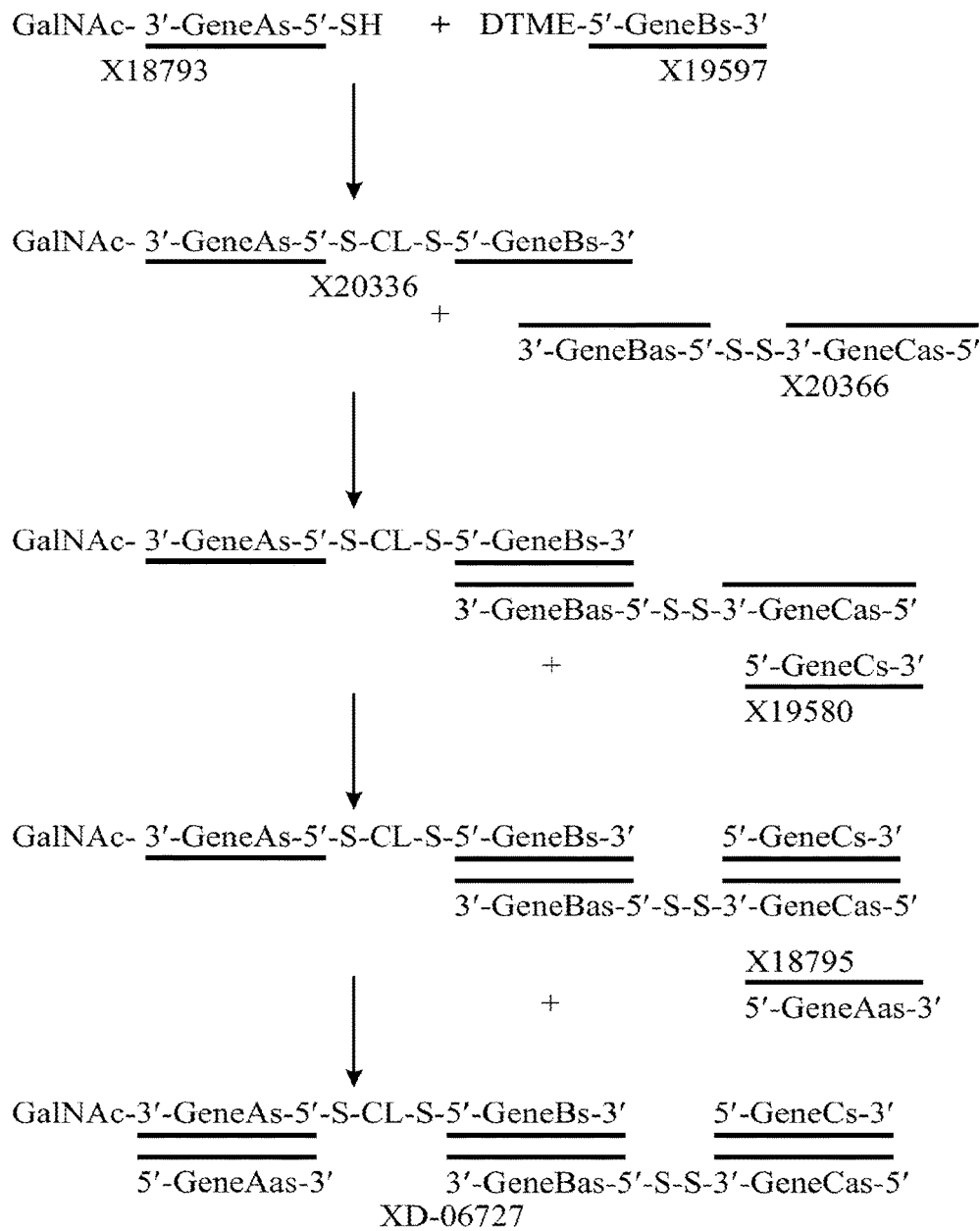
FIG. 12 presents a schematic diagram for a synthesis strategy for GalNAc-conjugated heterotrimer (XD-06727), which is discussed in connection with Example 16. Key: In this Example, "GeneA" is siFVII; "GeneB" is siApoB; and "GeneC" is siTTR.

9 mg (192 nmol) of Trimeric siRNA XD-06727 (see FIG. 11), simultaneously targeting FVII, ApoB and TTR, was prepared in high purity by combining single strands stepwise as depicted in FIG. 12, using the methodology described in Example 8.

TABLE 13A

Stoichiometry of Oligomers used in synthesis of GalNAc-siFVII-siApoB-siTTR Trimer (XD-06727)

| SEQ ID NO: | ID | Target | E (L/mol * cm) | 1 OD | MW (free Acid) | MW Na salt | Req OD |
|---|---|---|---|---|---|---|---|
| 42 | X20336 | FVIIs-ApoBs | 404300 | 2.47 nmol | 15440.1 | 16341.4 | 78 |

TABLE 13A-continued

Stoichiometry of Oligomers used in synthesis of GalNAc-siFVII-siApoB-siTTR Trimer (XD-06727)

| SEQ ID NO: | ID | Target | E (L/mol * cm) | 1 OD | MW (free Acid) | MW Na salt | Req OD |
|---|---|---|---|---|---|---|---|
| 49 | X20366 | ApoBas-TTRas | 446700 | 2.24 nmol | 14748.9 | 15716.1 | 86 |
|  | X19580 | TTRs | 220300 | 4.54 nmol | 7105.6 | 7567.2 | 42 |
| 26 | X18795 | FVIIas | 194800 | 5.13 nmol | 6849.4 | 7289.1 | 37 |
| 54 | XD-06727 |  |  |  | 44144 | 46913.8 |  |

Figure 13:
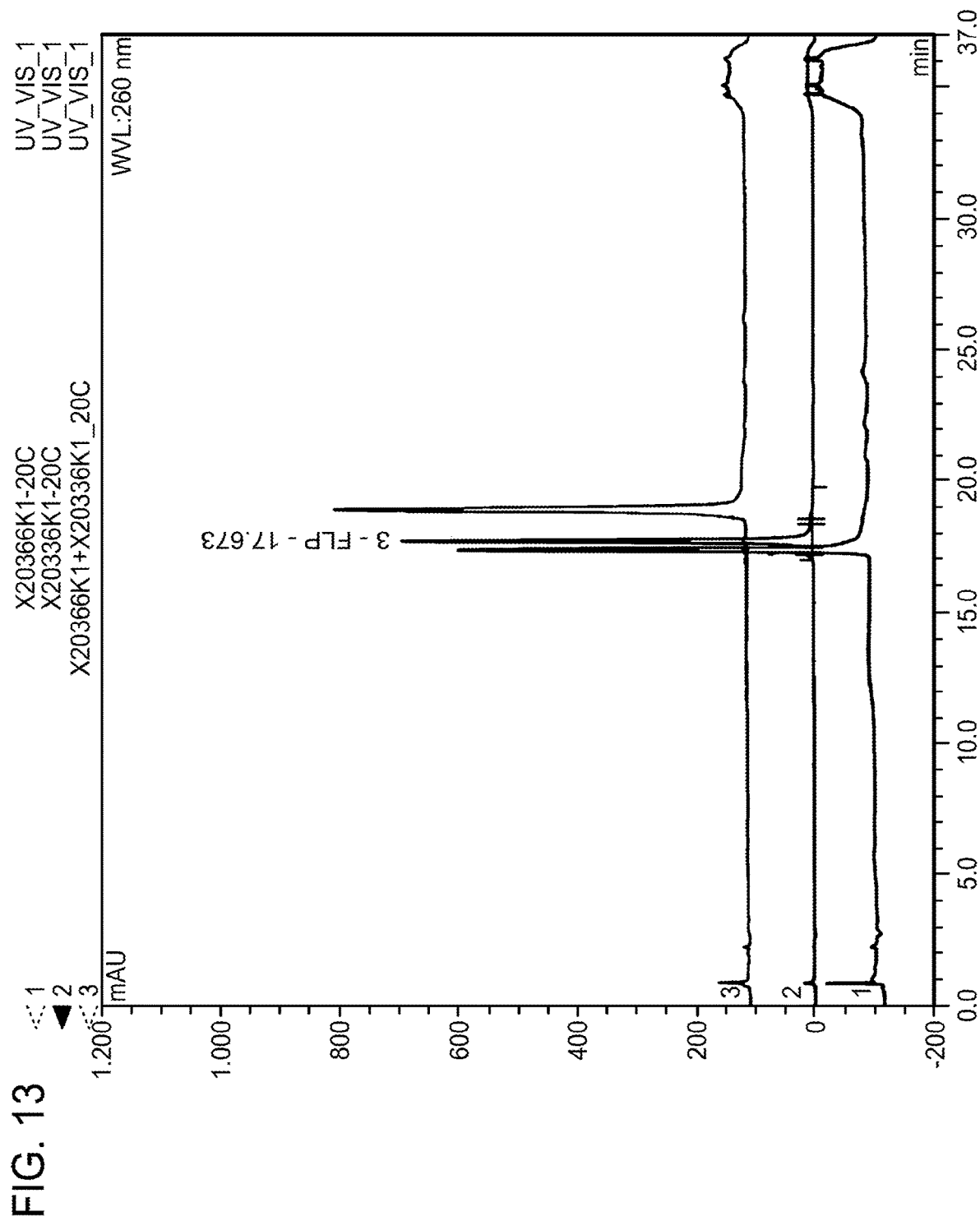
FIG. 13 presents data for an HPLC analysis of the addition of X20336 to X20366, which is discussed in connection with Example 16.
Figure 14:
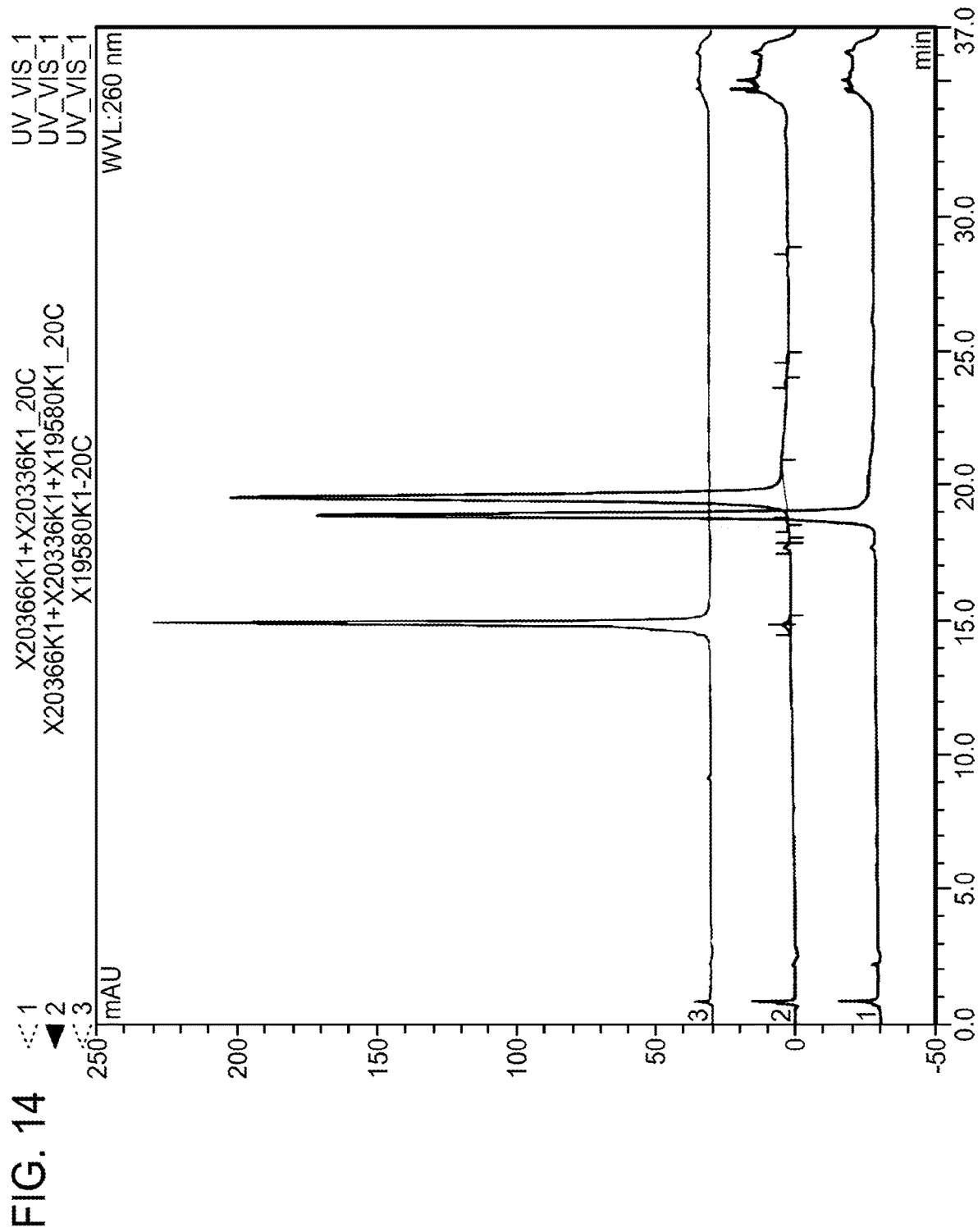
FIG. 14 presents data for an HPLC analysis of the further addition of X19580 to the reaction product of X20336 and X20366, which is discussed in connection with Example 16.
Figure 15:
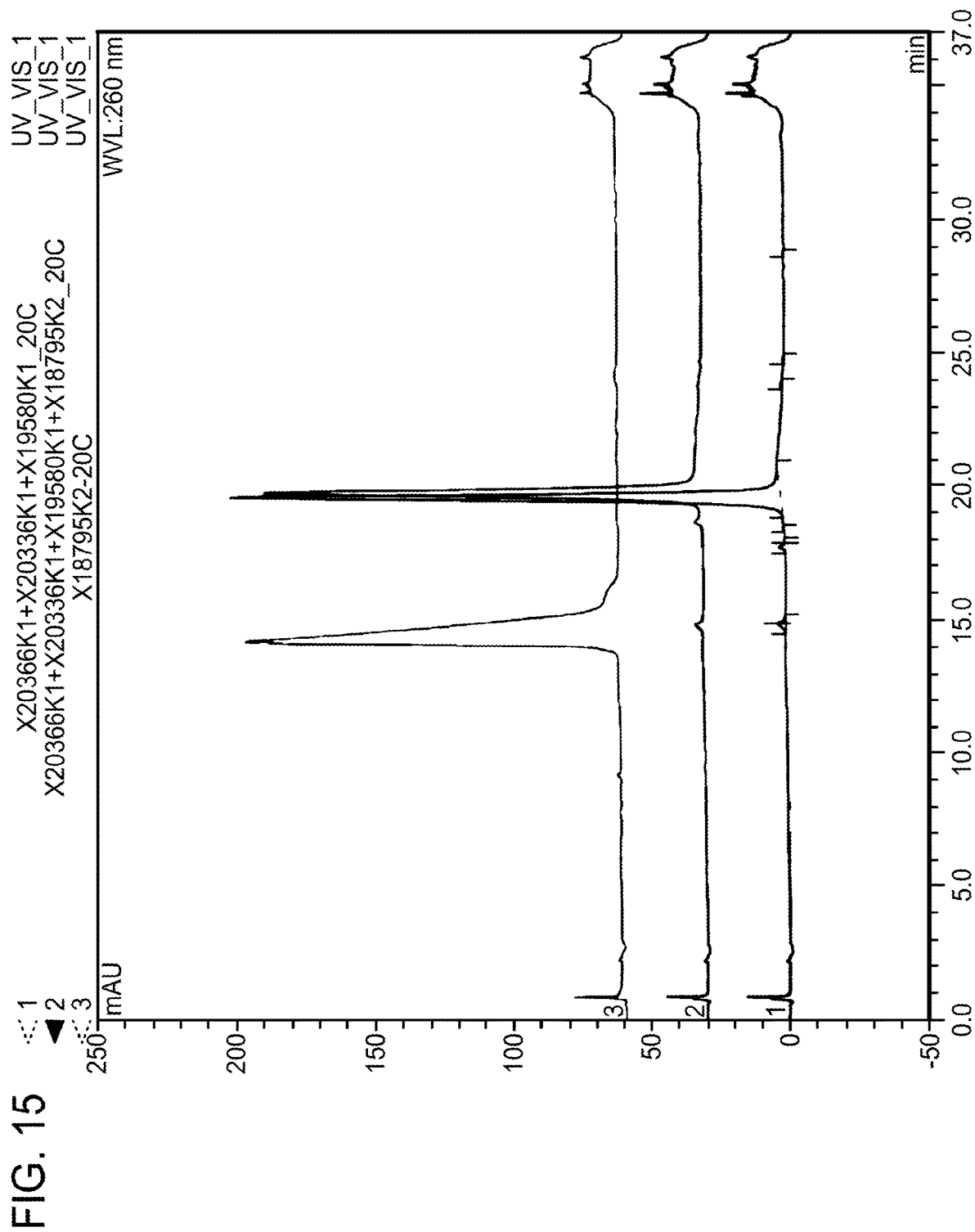
FIG. 15 presents data for an HPLC analysis of the further addition of X18795 (5'-siFVIIantisense-3') to the reaction product of X20336, X20366, and X19580 to yield XD-06727, which is discussed in connection with Example 16.
Figure 16A:
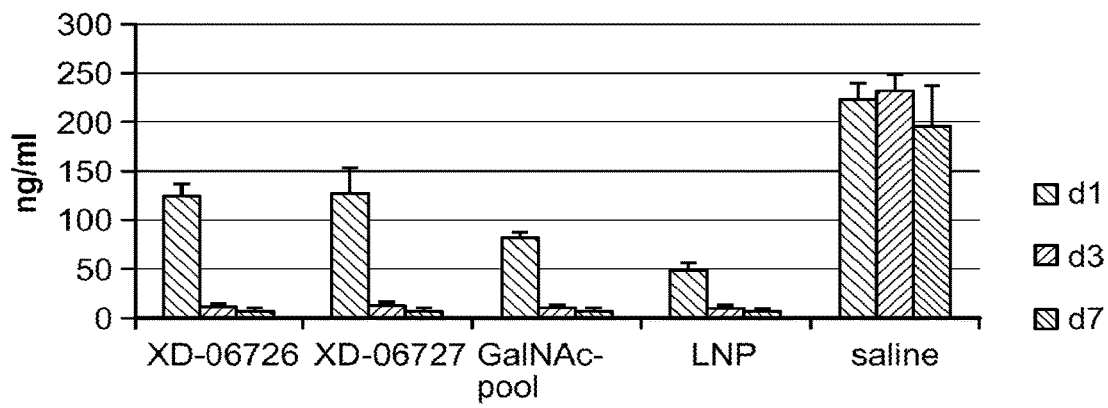
FIGS. 16A and 16B present data for TTR protein levels in serum samples (measured by ELISA), which is discussed in connection with Example 18.
Figure 16B:
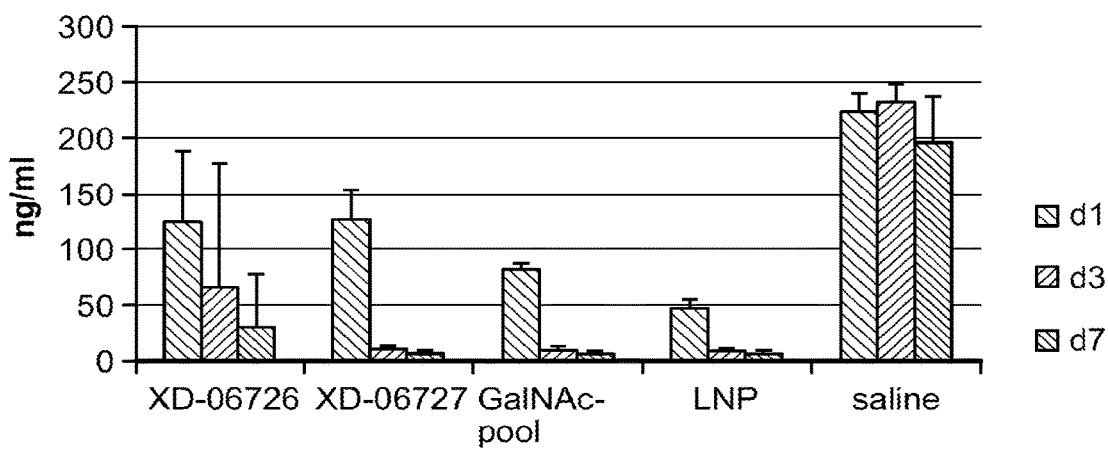
Figure 17A:
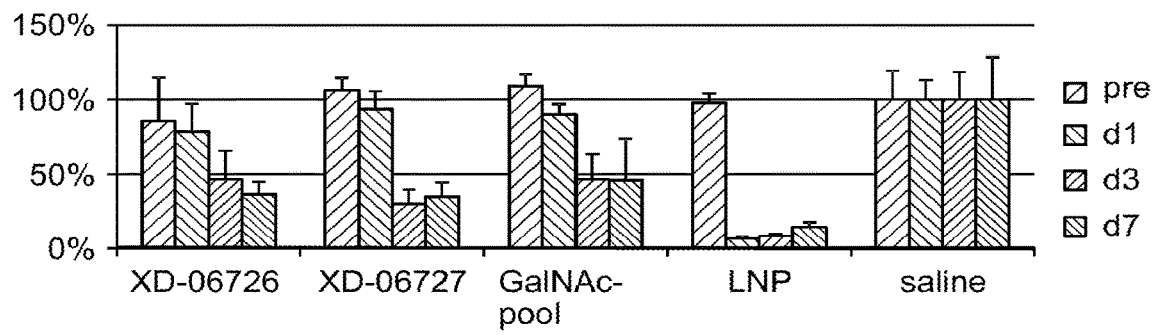
FIGS. 17A and 17B present data for FVII enzymatic activity in serum samples, which is discussed in connection with Example 18.
Figure 17B:
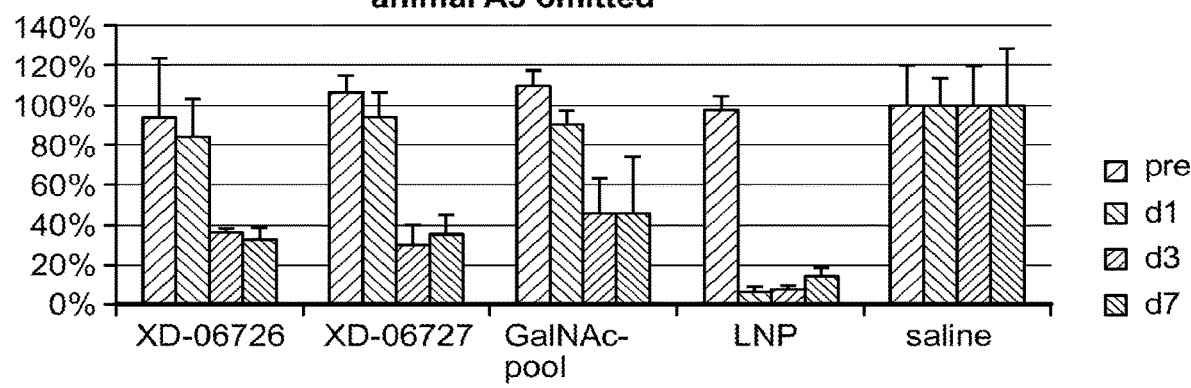
Figure 18A:
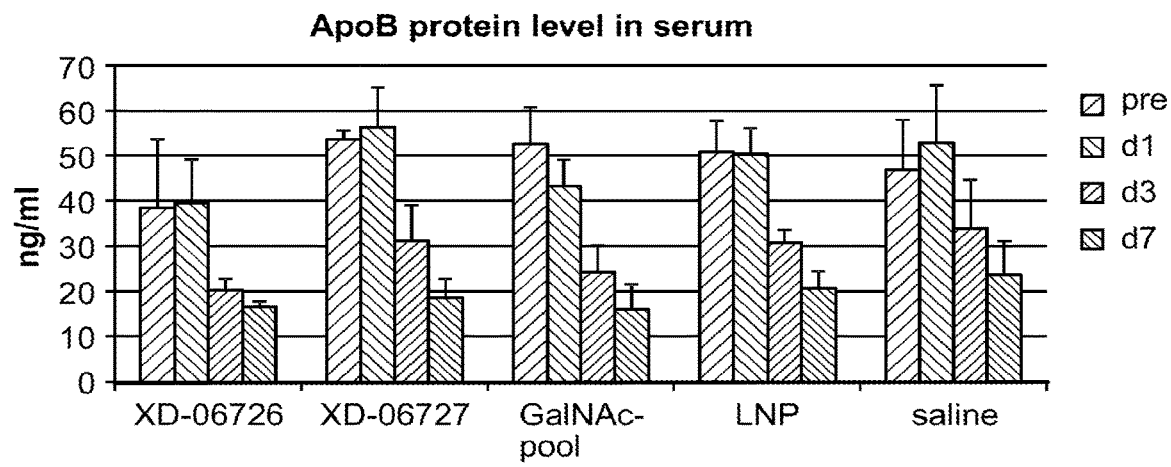
FIGS. 18A and 18B present data for ApoB protein levels in serum samples (measured by ELISA), which is discussed in connection with Example 18.
Figure 18B:
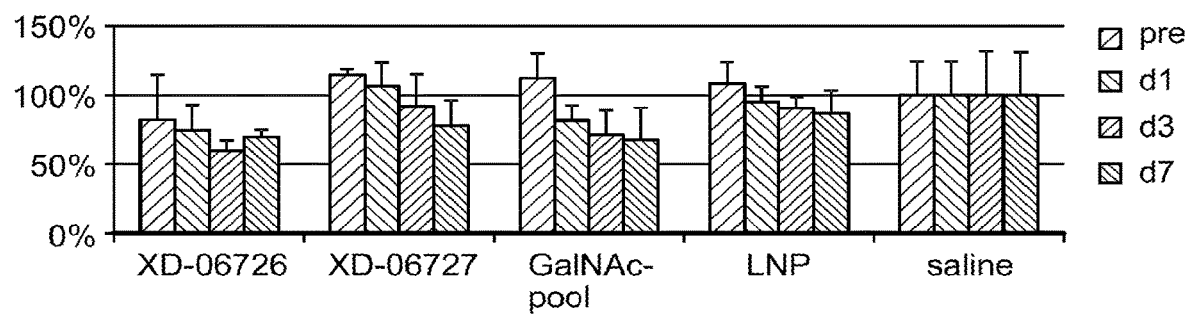

The synthesis that produced the heterotrimer (XD-06727) is highly efficient. In this Example, nearly 100% conversion of the reactants was achieved at each step. See FIGS. 13, 14, and 15.

Example 17: Preparation of LNP Formulation of Pooled siRNAs Individually Targeting FVII, ApoB and TTR Monomeric siRNAs targeting FVII (XD-00030), ApoB (XD-01078) and TTR (XD-06729) were formulated in Lipid Nanoparticles and characterized using the methodologies described in General Procedure: Lipid Nanoparticle Formulation and General Procedure: LNP Characterization. The lipid composition was XL10:DSPC:Cholesterol:PEG-DOMG/50:10:38.5:1.5 molar percent. 88% encapsulation was achieved and the resulting particles were 83 nm in size with a zeta potential of 2.2 mV and a PDI of 0.04.

TABLE 13B

Monomeric siRNA targeting TTR (XD-06729)

| dsRNA ID | ssRNA ID | SEQ ID NO: | Sequence | Target/ Strand |
|---|---|---|---|---|
| XD-06729 | X21072 | 154 | cAGuGuucuuGcucuAuAAd TsdT | TTRs |
|  | X21073 | 155 | UuAuAGAGcAAGAAcACUGd TsdT | TTRas |

Figure 19A:
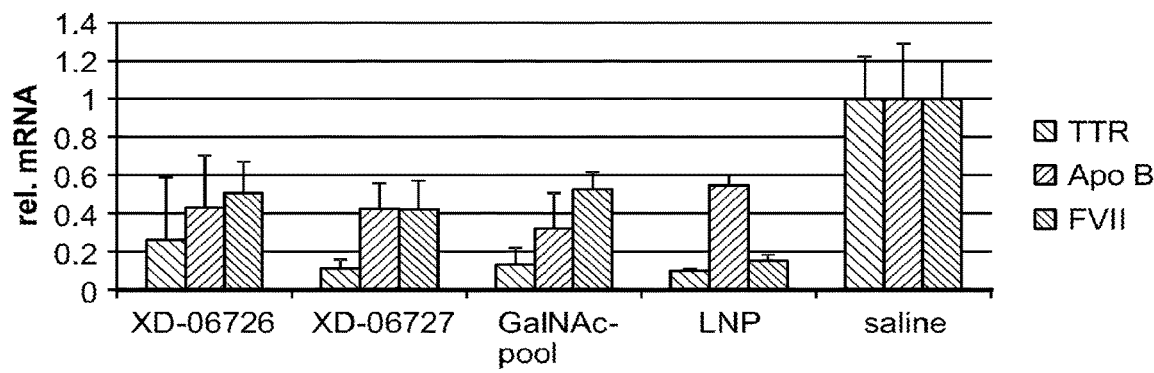
FIGS. 19A and 19B present target knockdown in liver data, which is discussed in connection with Example 18.
Figure 19B:
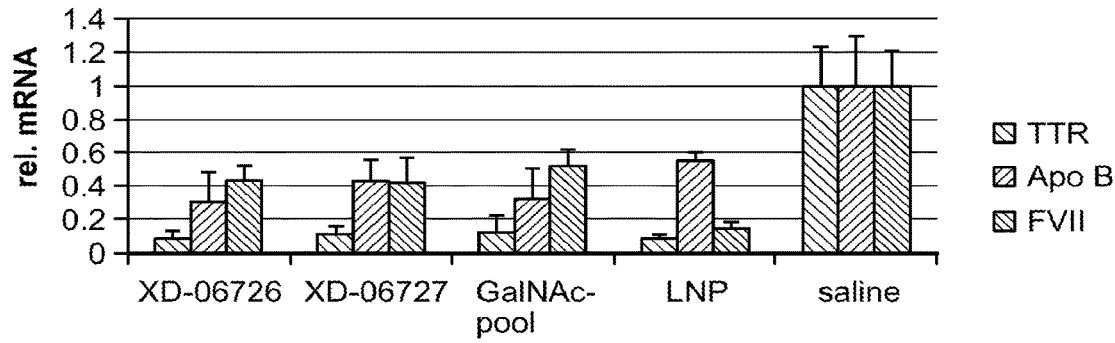

Example 18: Assessment of mRNA Knockdown by GalNAc-Conjugated Heterotrimeric SiRNAs To determine the in vivo efficacy of heterotrimeric GalNAc-conjugated siRNAs (targeted to FVII, ApoB and TTR), an animal experiment was performed as described above (General Procedure: Animal Experiments) using a group size of n=4 mice for treatment groups and n=5 for saline controls. The heterotrimers XD-06726 and XD-06727 as well as a pool of 3 monomeric GalNAc-conjugated siRNAs (XD-06328 targeting FVII; XD-06386 targeting TTR and XD-06728 targeting ApoB) were injected subcutaneously (0.1 mL volume) at a concentration of 50 mg/kg total RNA for the trimers and 17 mg/kg for each of the monomeric conjugates. For comparison, a pool of LNP-formulated siRNAs (NPA-741-1) directed against the same targets (FVII (XD-00030), ApoB (XD-01078) and TTR (XD-06729)) was injected intravenously at 0.5 mg/kg per siRNA. Blood was collected as described above (General Procedure: Animal Experiments) 1 day prior to treatment and at 1, 3 and 7 days post-treatment, and serum levels of FVII, ApoB and TTR measured according to the General Procedures: Measurement of Gene Knockdown. Results are shown in FIGS. 16A and 16B, 17A and 17B, and 18A and 18B. mRNA levels in liver lysates were measured at day 7 post injection (FIGS. 19A and 19B).

One animal in group A (XD-06726) did not show any effect on TTR serum levels. The first of the two TTR protein graphs shows data with values omitted for the non-responding animal.

For comparison, the values from the animal showing poor TTR response have been omitted from the second FVII graph.

ApoB serum levels show a high variation, both within the animals of one group and between the different time-points of the saline control.

Knockdown of all three genes was also measured using a bDNA assay for mRNA from liver tissue according to the General Procedures: Measurement of Gene Knockdown, above. Target gene levels were normalized to the housekeeper GAPDH.

Example 19: Preparation GalNAc-FVII-ApoB-TTR-FVII Tetramer (XD-07140)

Figure 20:
FIG. 20 presents a GalNAc-heterotetramer conjugate (XD-07140), which is discussed in connection with Example 19. Key: In this Example, "GeneA" is siFVII; "GeneB" is siApoB; and "GeneC" is siTTR.
Figure 21:
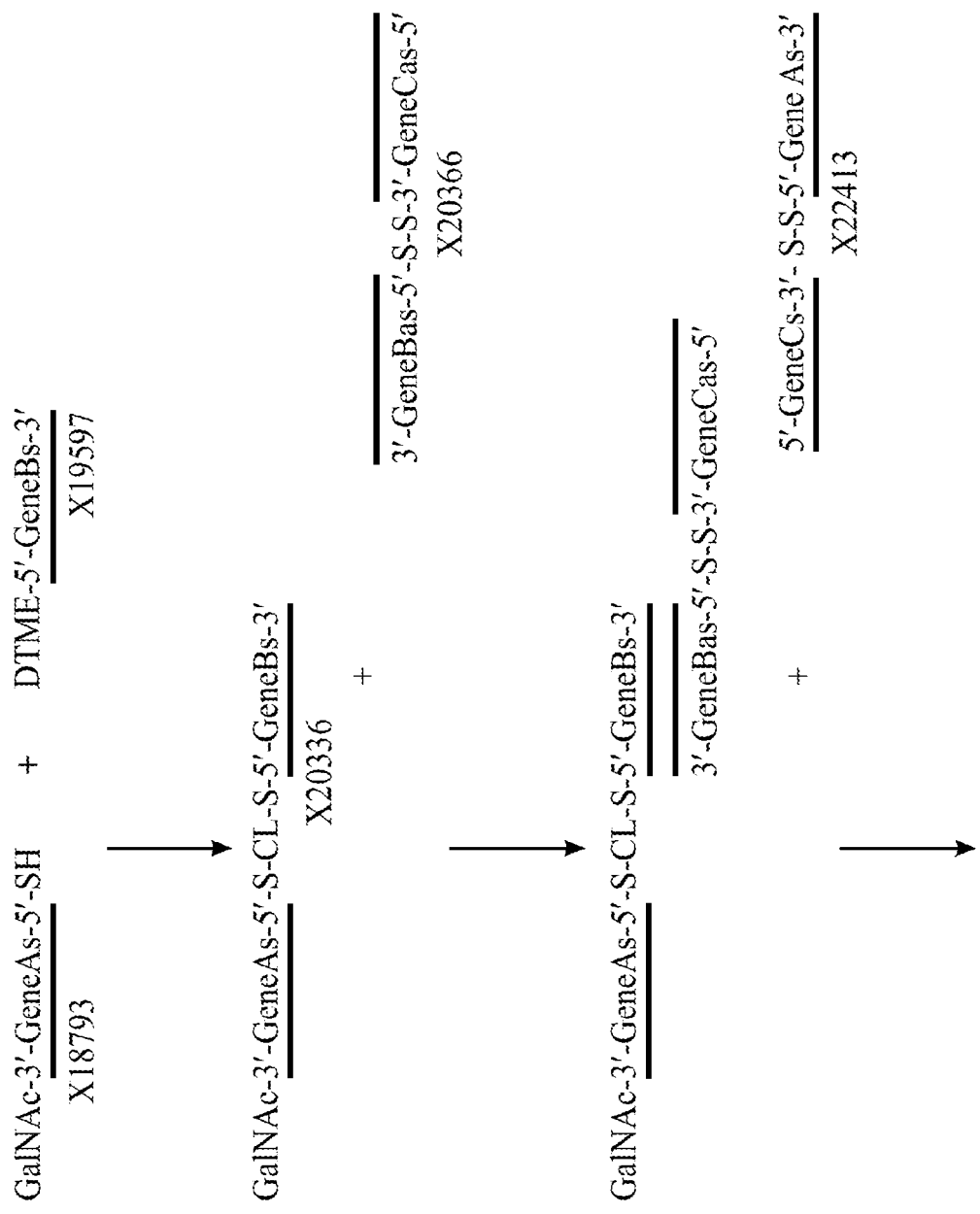
FIG. 21 presents a schematic diagram for synthesis of a GalNAc-heterotetramer conjugate (XD-07140), which is discussed in connection with Example 19. Key: In this Example, "GeneA" is siFVII; "GeneB" is siApoB; and "GeneC" is siTTR.
Figure 21:
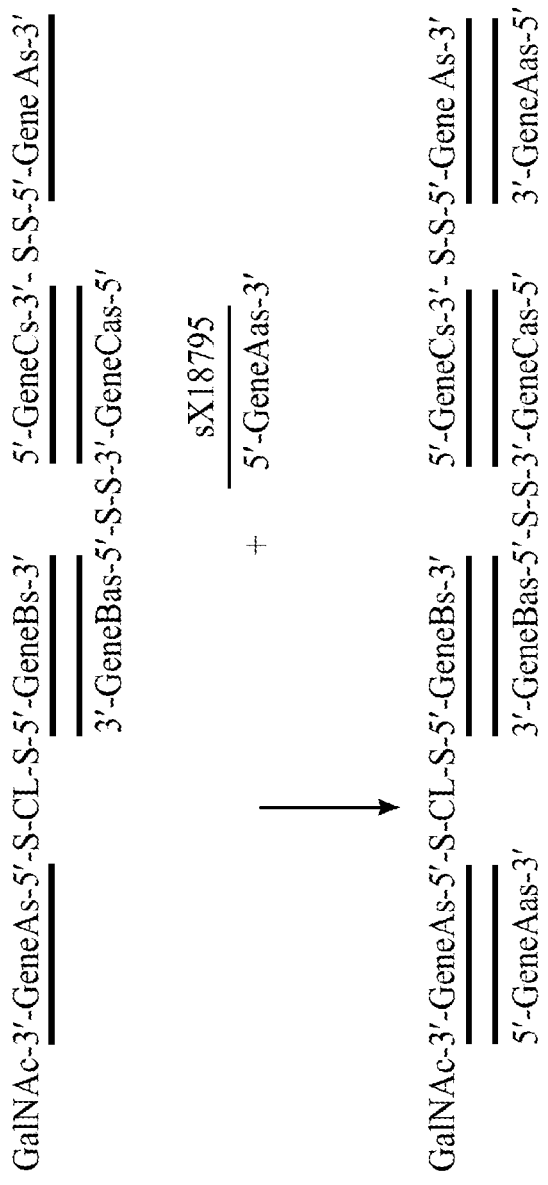
Figure 22:
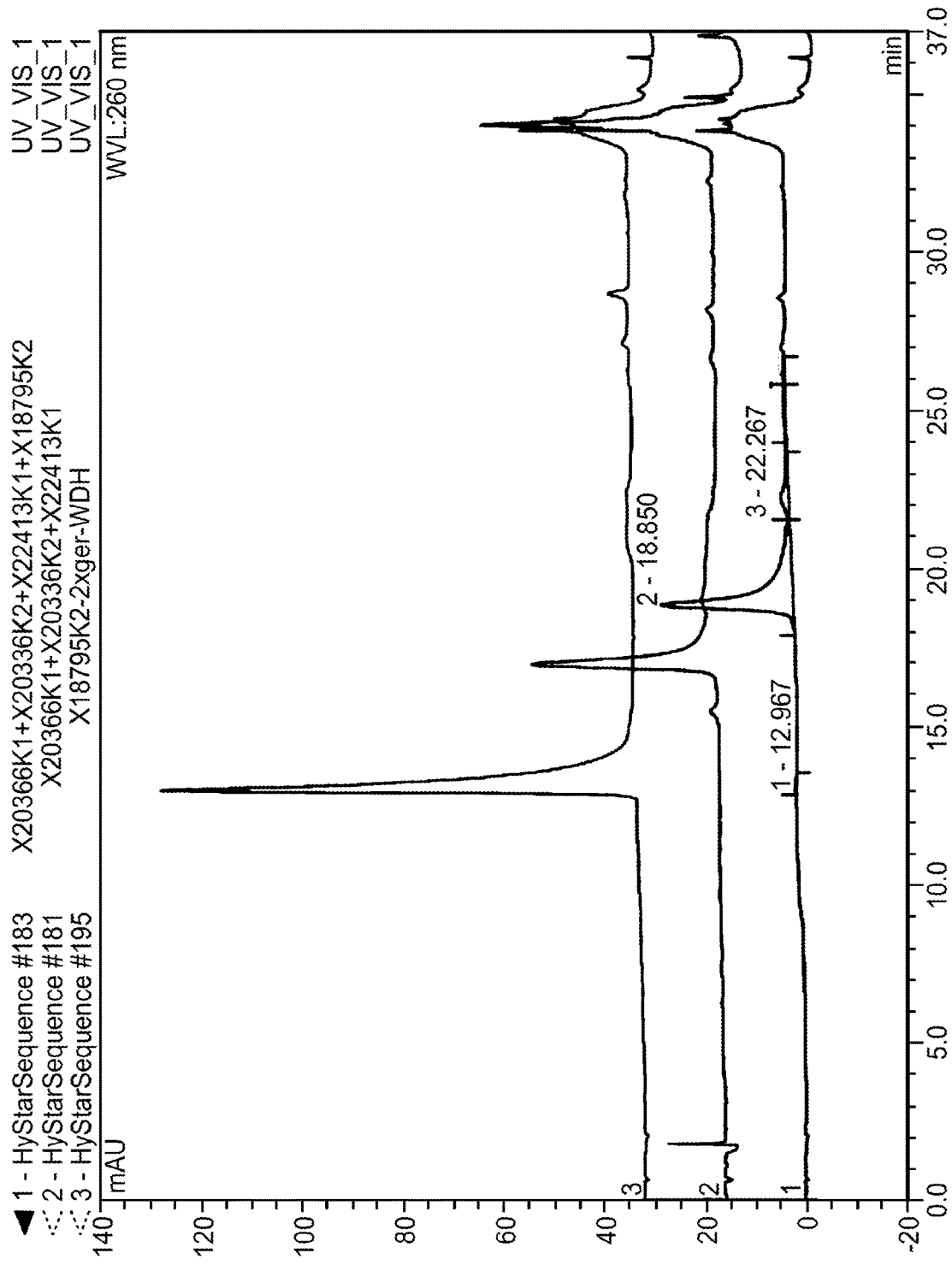
FIG. 22 presents HPLC results of the GalNAc-siFVII-siApoB-siTTR-siFVII Tetramer (XD-07140), which is discussed in connection with Example 19.

12.4 nmol of the tetrameric siRNA XD-07140 (see FIG. 20), simultaneously targeting FVII, ApoB and TTR, was prepared by combining single strands stepwise as depicted in FIG. 21, and according to the duplex titration method described in Example 8. HPLC analysis showed the product was obtained in high purity.

TABLE 14

Stoichiometry of Oligomers used in Synthesis of GalNAc-FVII-ApoB-TTR-FVII Tetramer (XD-07140)

| SEQ ID NO: | ID | Target | E (L/mol * cm) | 1 OD | MW (free Acid) | MW Na salt | Req OD |
|---|---|---|---|---|---|---|---|
| 42 | X20336 | FVIIs-ApoBs | 404300 | 2.47 nmol | 15440.1 | 16341.4 | 5 |

TABLE 14-continued

Stoichiometry of Oligomers used in Synthesis of GalNAc-FVII-ApoB-TTR-FVII Tetramer (XD-07140)

| SEQ ID NO: | ID | Target | E (L/mol * cm) | 1 OD | MW (free Acid) | MW Na salt | Req OD |
|---|---|---|---|---|---|---|---|
| 49 | X20366 | ApoBas-TTRas | 446700 | 2.24 nmol | 14748.9 | 15716.1 | 5.5 |
| 45 | X22413 | TTRs-FVIIs | 412100 | 2.52 nmol | 14041.3 | 14964.5 | 4.9 |
| 26 | X18795 | FVIIas | 194800 | 5.13 nmol | 6849.4 x2 | 7289.1 x2 | 4.8 |
| 55 | XD-07140 | | | | 57929.1 | 61600.2 | |

Example 20: Synthesis of Homo-Tetramer

Multimeric oligonucleotide according to the invention can be synthesized by any of the methods disclosed herein. Two example methods are provided below for homo-tetramers. These Examples can be readily adapted to synthesize longer multimers (e.g., pentamers, hexamers, etc.)

Figure 40:
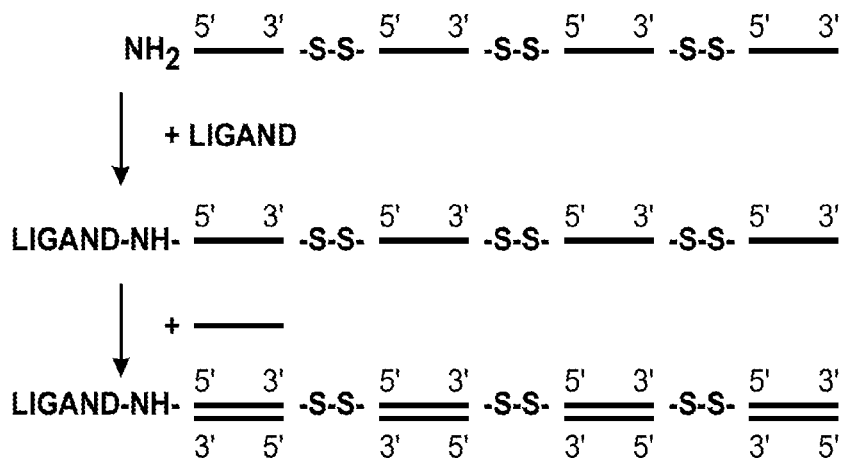
FIG. 40 represents a schematic diagram for a synthesis strategy for homo-tetrameric siRNA, which is discussed in connection with Example 20.

A homo-tetrameric siRNA with linkages on a single strand can be synthesized by preparing a tetramer of the sense strand, each sense strand linked via a cleavable linker, on a synthesizer and then subsequently adding a targeting ligand and annealing the anti-sense strands, as shown in FIG. 40. The cleavable linkers of the sense strand may be disulfides (as shown) or other labile linkages (e.g., chemically unmodified nucleic acid sequences such as UUU/Uridine-Uridine-Uridine).

Variations on the scheme shown in FIG. 40 can include using alternative linkers, linking anti-sense strands and annealing sense strands, synthesizing longer multimers, or where the technical limits of machine-based synthesis are reached, synthesizing one or more multimers and then joining said multimers together using one or more solution phase chemical reactions (e.g., synthesizing two tetramers per scheme 1, one with ligand, the other without, one or both strands modified, as appropriate, with a functional group to facilitate linking, and then linking the two tetramers together via the formation of a covalent bond, with or without the addition of a linking moiety such as, e.g., DTME).

Figure 41:
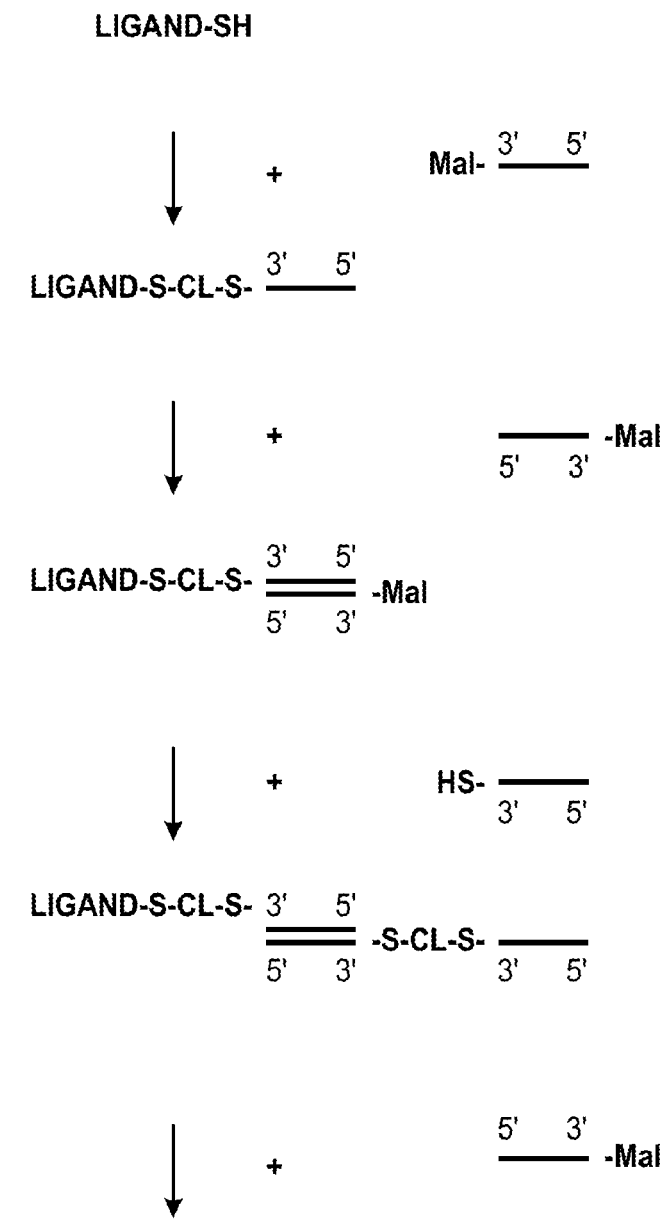
FIG. 41 represents a schematic diagram for a synthesis strategy for homo-tetrameric siRNA having linkages on alternating strands, which is discussed in connection with Example 20.
Figure 41:
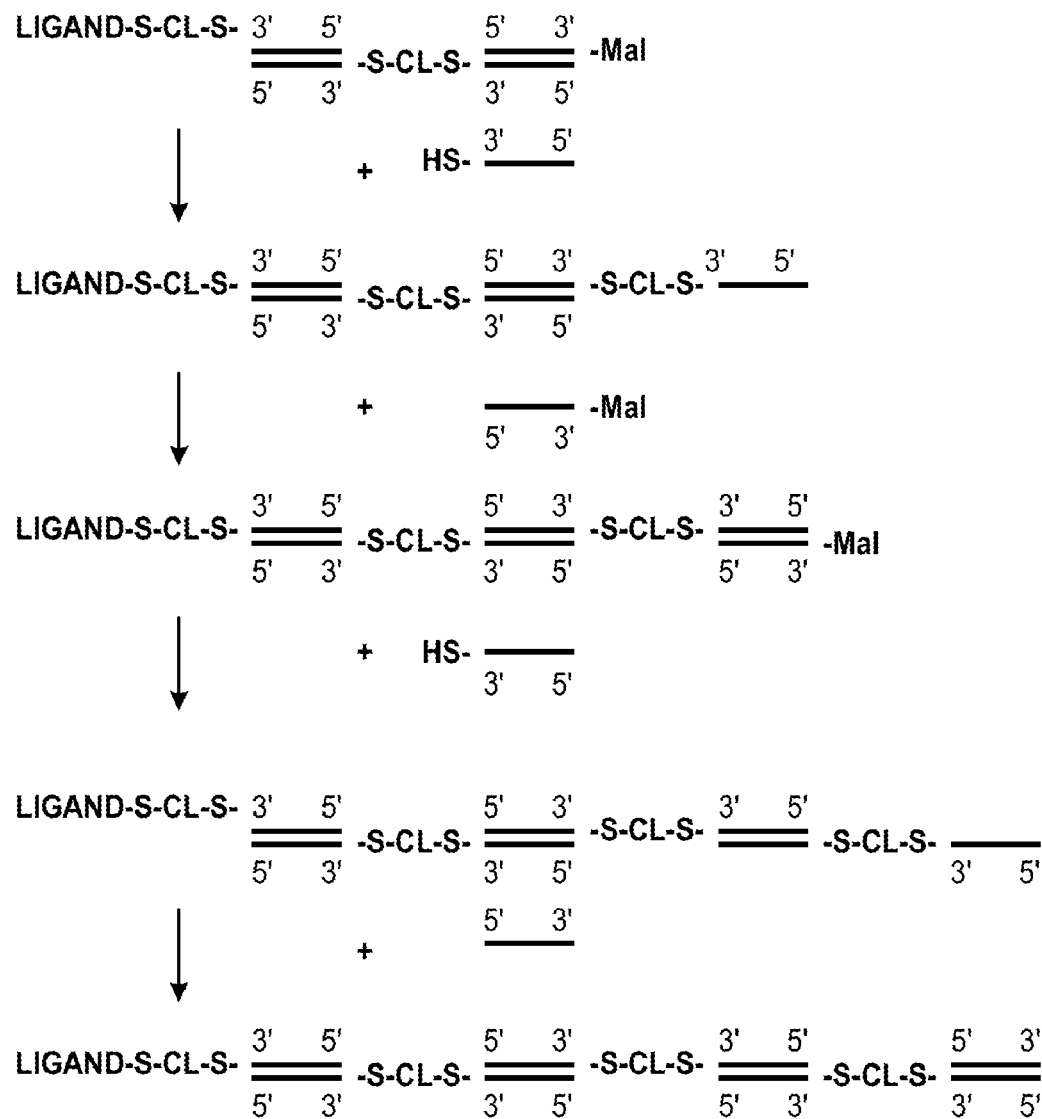

Alternatively, the homo-tetramer could be assembled as shown in FIG. 41 with linkages on alternating strands.

In FIG. 41, "—SH" represents a sulfhydryl group, "Mal" represents DTME, "-CL-" represents a cleavable linker. Variations on the scheme shown in FIG. 41 can include using alternative linkers and synthesizing longer multimers.

Example 21: Synthesis of Ligand Conjugates

The ligand conjugate shown in FIG. 41 can be synthesized as follows:

3'-Sulfydryl derivatives of both sense and antisense strands of the monomer are synthesized:

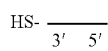
(Structure 61)

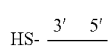
(Structure 62)

Portions of each are converted to the corresponding mono-maleimide derivative:

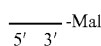
(Structure 63)

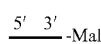
(Structure 64)

A portion of the sense-strand maleimide derivative thus obtained is then treated with a sulfhydryl derivative of the targeting ligand of choice:

(Structure 65)

A slight molar excess of anti-sense-maleimide derivative is then added and the desired ligand-ds-siRNA-maleimide product isolated by preparative chromatography:

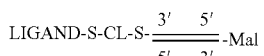
(Structure 66)

A slight molar excess of each of the sense and anti-sense components of the homo-tetramer are then added in the sequence as outlined in FIG. 41, the products at each step being purified by preparative chromatography when required.

Example 22: Synthesis of Multimeric Oligonucleotides

Multimeric oligonucleotide according to the invention can be synthesized by any of the methods disclosed herein or adapted from the art. Example methods are provided below for homo-multimers, but the present synthesis can also be readily adapted to synthesize hetero-multimers.

These Examples can also be adapted to synthesize multimers of different lengths. For example, one can use essentially the same synthesis and linking chemistry to combine a tetramer and monomer (or trimer and dimer) to produce a pentamer. Likewise, one can combine a tetramer and a

Example 22A: Synthesis of Homo-Tetramer of siRNA Via Pre-Synthesized Homodimers Step 1: A sense strand homodimer is synthesized wherein the two sense strands are linked by a nuclease cleavable oligonucleotide (NA) and terminated with an amino function and a disulfide moiety.

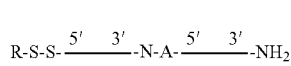
(Structure 67)

Individual strands (for this and other steps) are synthesized as outlined above in the General Procedure: Single Chain Oligonucleotide Synthesis section. Other methods for oligonucleotide strand synthesis, linking, and chemical modification can be adapted from the art.

Step 2: A tri-antennary GalNAc ligand is then added to the terminal amino function of one part of the sense strand homo-dimer via reaction with an acyl activated triantennary GalNAc ligand.

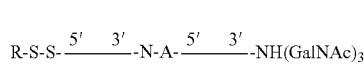
(Structure 68)

Step 3: The remainder of the sense strand homodimer is treated with a molar excess of dithiothreitol to cleave the disulfide group to generate a thiol terminated sense strand homodimer.

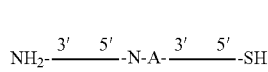
(Structure 69)

Step 4: This material is mono-derivatized with dithiobis-maleimidoethane (DTME) according to the procedure used to prepare hetero-multimers (see above).

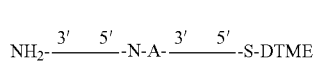
(Structure 70)

Step 5: The disulfide group of the GalNAc derivatized homodimer is also cleaved by treatment with a molar excess of dithiothreitol.

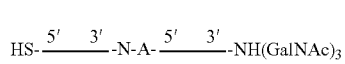
(Structure 71)

Step 6: The GalNAc terminated homodimer is then linked to the mono-DTME derivatized homodimer via reaction of the terminal thiol-group to yield single stranded homo-tetramer. "-S-CL-S-" represents the cleavable disulfide group in DTME, e.g., a Cleavable linker (CL).

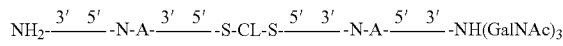
(Structure 72)

Step 7: This material is then annealed with 4 molecular equivalents of antisense monomer to yield the desired double stranded homo-tetramer (this annealing step is optional and can be omitted, for example to prepare single stranded multimers such as antisense oligonucleotides).

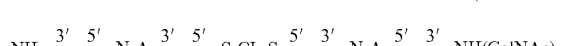
(Structure 73)

Example 22B: Synthesis of Homo-Hexamer of siRNA Via Presynthesized Homodimer and Homo-Tetramer Step 1: A sense strand homo-tetramer is synthesized wherein the four sense strands are linked by a nuclease cleavable oligonucleotide and terminated with an amino function and a disulfide moiety.

(Structure 74)

Step 2: This material is treated with a molar excess of dithiothreitol to cleave the disulfide group

(Structure 75)

Step 3: This material is monoderivatized with dithiobis-maleimidoethane (DTME) according to the procedure used to prepare hetero-multimers (see above).

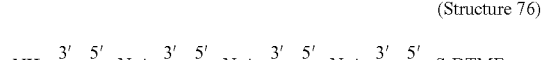
(Structure 76)

Step 4: This material is reacted with the thiol terminated GalNAc homodimer to yield the single stranded homo-hexamer

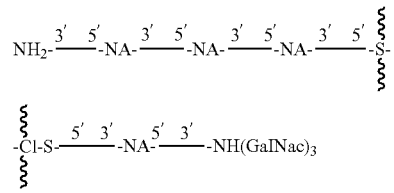
(Structure 77)

Note: In Structures 77, 78, 81, 82, 89, and 91, a single contiguous structure is broken into two parts by the symbol ⸲.

Step 5: This material is then annealed with 6 molecular equivalents of antisense monomer to yield the desired double stranded homo-hexamer (this annealing step is optional and can be omitted, for example to prepare single stranded multimers such as antisense oligonucleotides).

(Structure 78)

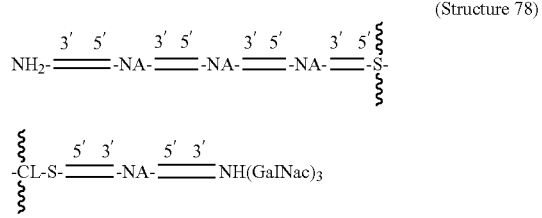

Example 22C: Synthesis of Homo-Octamer of siRNA Via Presynthesized Homo-Tetramer Step 1: One part of the amino-terminal homo-tetramer synthesized above is converted to the corresponding GalNAc derivative by reaction with an acyl activated triantennary GalNAc ligand.

(Structure 79)

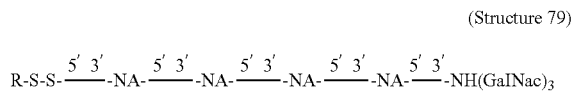

Step 2: This material is treated with a molar excess of dithiothreitol to cleave the disulfide group (Structure 80)

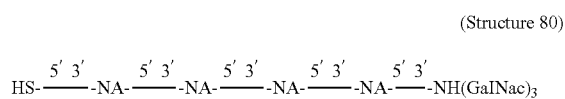

Step 3: This material is reacted with the mono-DTME derivatized tetramer to yield the terminal GalNAc derivatized single-stranded octamer.

(Structure 81)

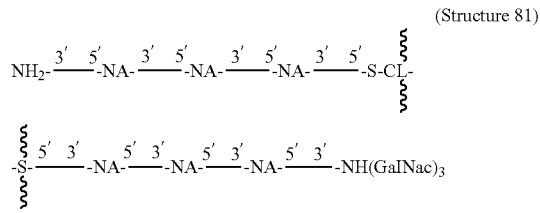

Step 4: This material is then annealed with 8 molecular equivalents of antisense monomer to yield the desired double stranded homo-octamer (this annealing step is optional and can be omitted, for example to prepare single stranded multimers such as antisense oligonucleotides).

(Structure 82)

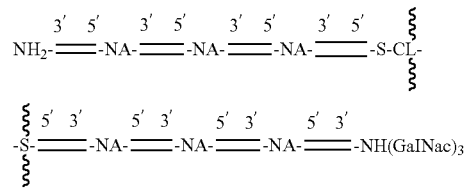

Example 22D: Synthesis of Homo-Dodecamer of Anti-Sense Oligonucleotide Via Pre-synthesized Homo-Tetramers Using Combination of Thiol/Maleimide and Azide/Acetylene ("Click") Linkers Step 1: A homo-tetramer of anti-sense oligonucleotides is synthesized containing 3 nuclease cleavable oligonucleotide linkers and terminal disulfide and amino groups.

(Structure 83)

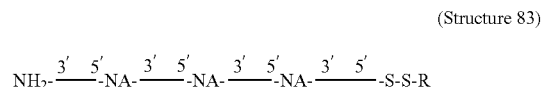

Step 2: This material is converted to the corresponding GalNAc derivative by reaction with an acyl activated triantennary GalNAc ligand.

(Structure 84)

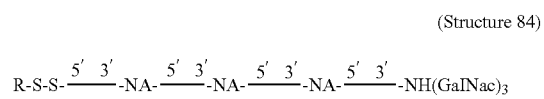

Step 3: This material is treated with a molar excess of dithiothreitol to cleave the disulfide group (Structure 85)

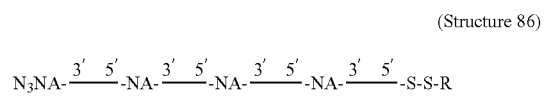

Step 4: Separately, a homo-tetramer of anti-sense oligonucleotides is synthesized containing 3 nuclease cleavable oligonucleotide linkers and terminal disulfide and azide groups.

(Structure 86)

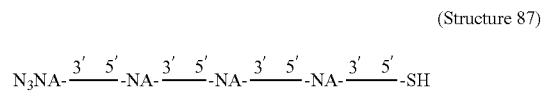

Step 5: This material is treated with a molar excess of dithiothreitol to cleave the disulfide group (Structure 87)

$N_3NA$-———$\frac{3'\quad 5'}{}$-NA-———$\frac{3'\quad 5'}{}$-NA-———$\frac{3'\quad 5'}{}$-NA-———$\frac{3'\quad 5'}{}$-SH Step 6: This material is mono-derivatized with dithiobis-maleimidoethane (DTME) according to the procedure used to prepare siRNA hetero-multimers (see above).

(Structure 88)

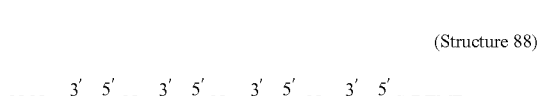

Step 7: This material is reacted with the thiol-terminated GalNAc derivatized tetramer to yield the terminal GalNAc derivatized single-stranded anti-sense octamer.

(Structure 89)

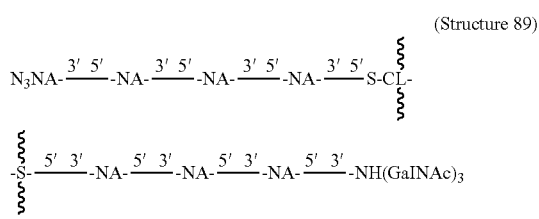

Step 8: Separately, a third homo-tetramer of anti-sense oligonucleotides is synthesized containing 3 nuclease cleavable oligonucleotide linkers and a terminal acetylene group. The latter can be underivatized or a sterically strained derivative such as dibenzocyclooctyne (DBCO, Glen Research, VA, USA)

(Structure 90)

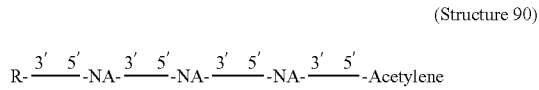

Step 9: This material is then reacted with the azide-terminated octamer prepared in Step 7 to yield the desired Anti-Sense Homo-Dodecamer. If the terminal acetylene on the tetramer is underivatized a metal salt catalyst such as copper 1 chloride will be required to effect the linking. By contrast if the terminal acetylene is DBCO then the coupling reaction will be spontaneous.

(Structure 91)

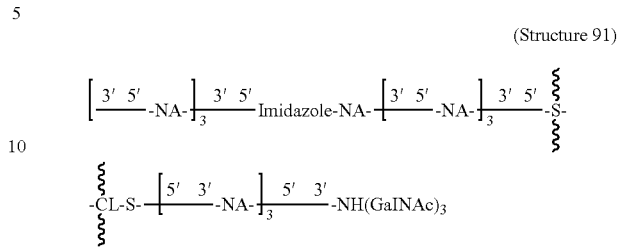

This methodology, or methods using alternative linking chemistry, can also be used to make multimers of other lengths (e.g., 9, 10, 11, 13, 14, 15, . . . oligonucleotides). Such multimers can be made double stranded by annealing the single stranded multimer with complementary oligonucleotides.

Example 23: Synthesis of Homo-Hexamer siRNA

Figure 23:
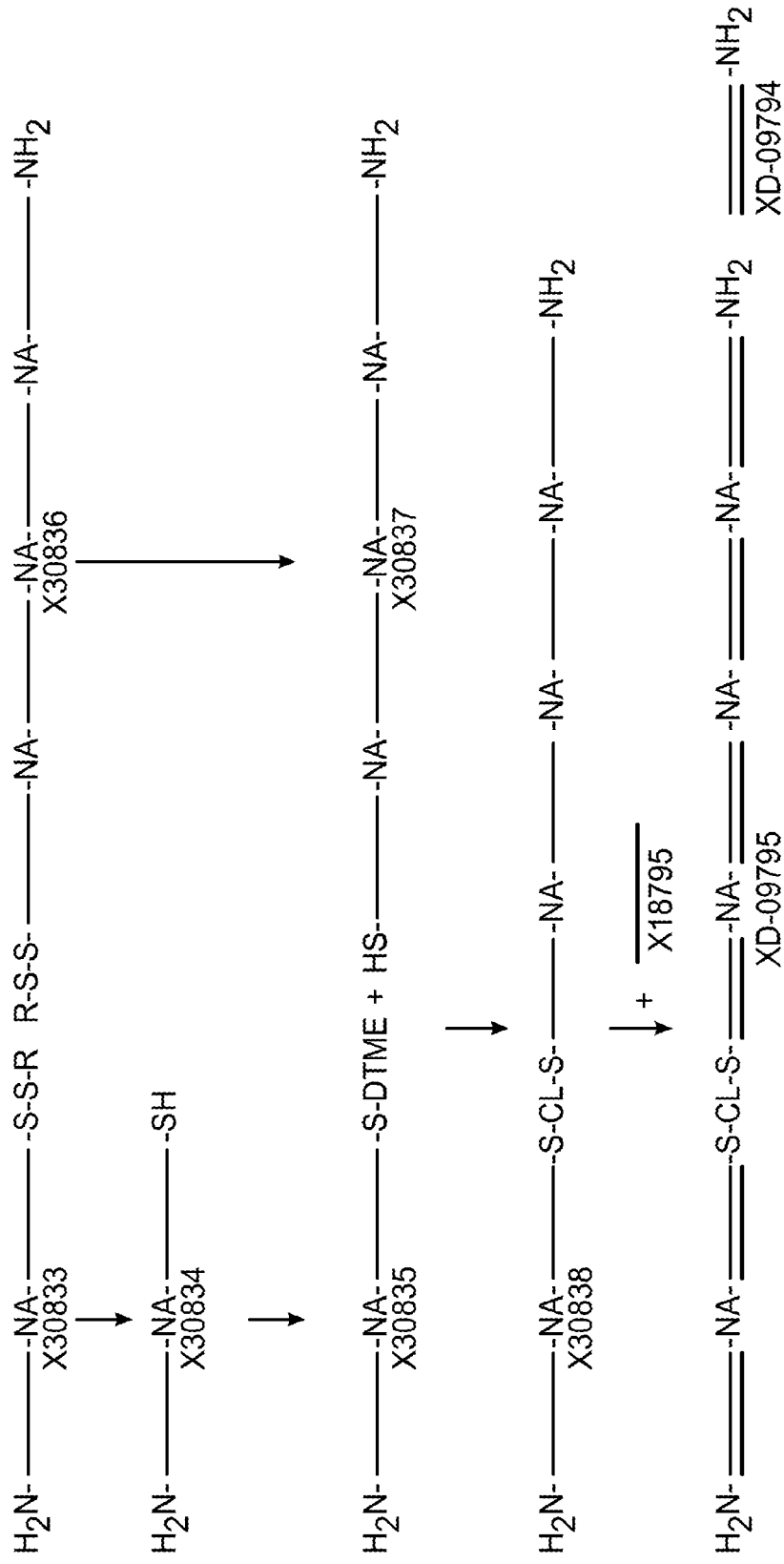
FIG. 23 presents a schematic diagram illustrating the steps for synthesizing a homo-hexamer, which is discussed in connection with Example 23.
Figure 24A:
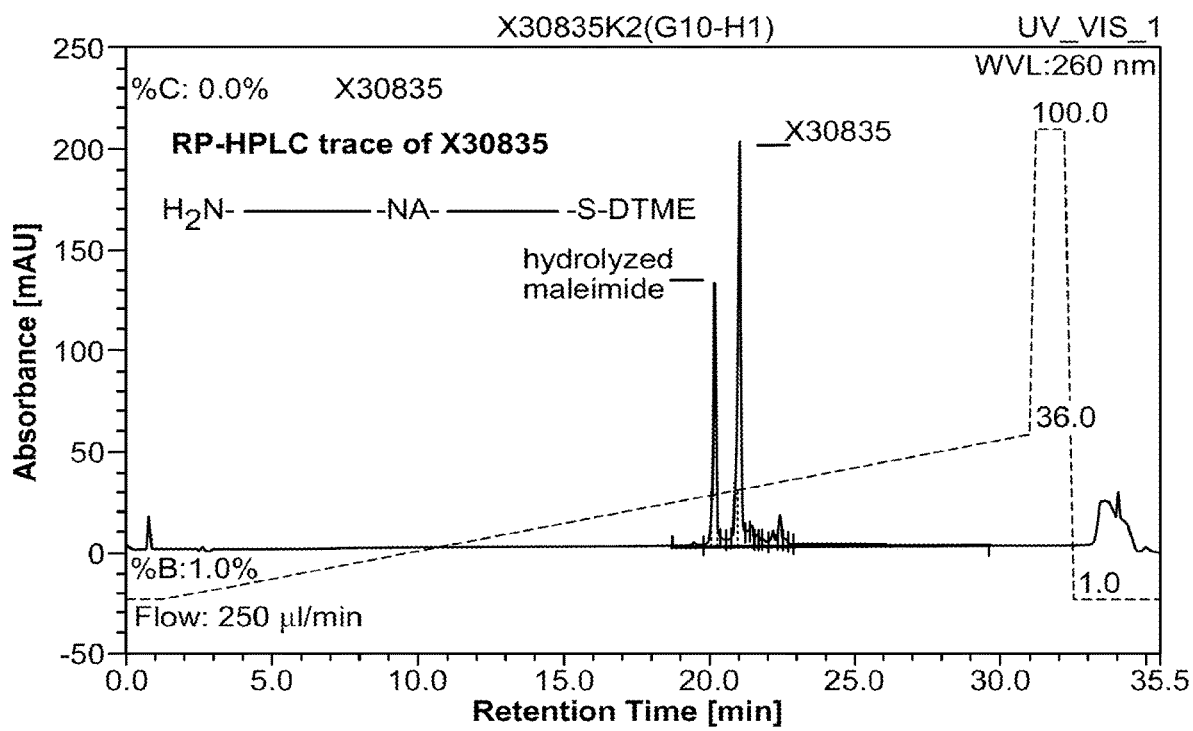
FIGS. 24A and 24B present RP-HPLC results showing yield and purity of the ssRNA X30835, which are discussed in connection with Example 24.
Figure 24B:
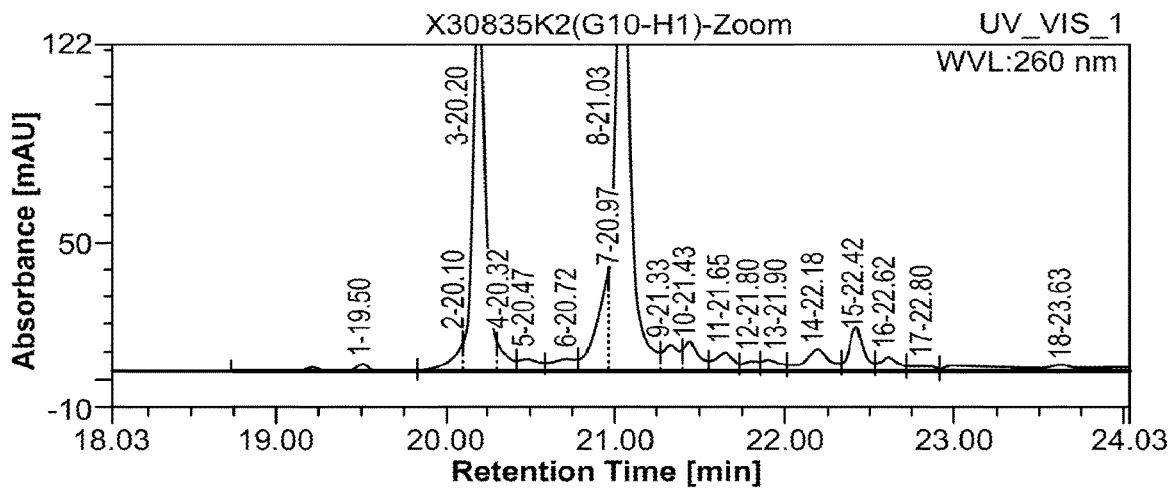
Figure 24C:
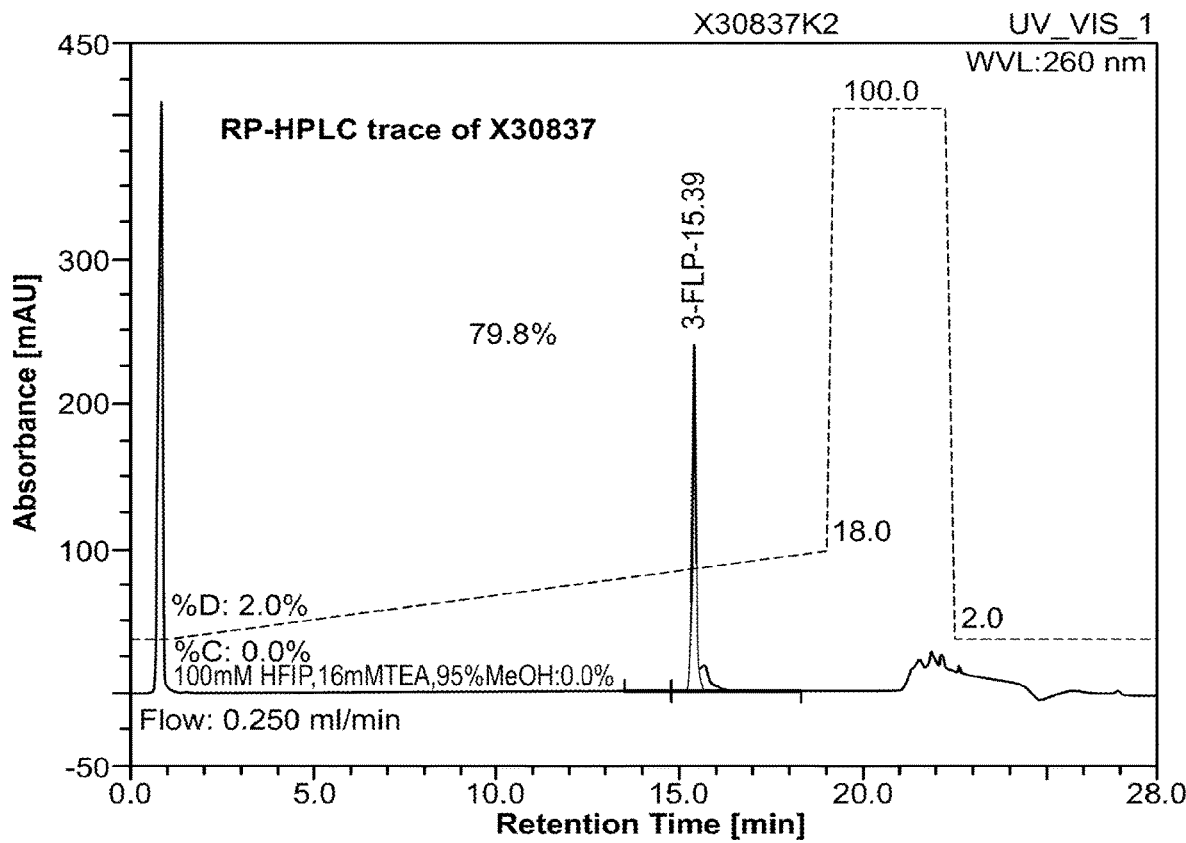
FIGS. 24C and 24D present RP-HPLC results showing yield and purity of the ssRNA X30837, which are discussed in connection with Example 24.
Figure 24D:
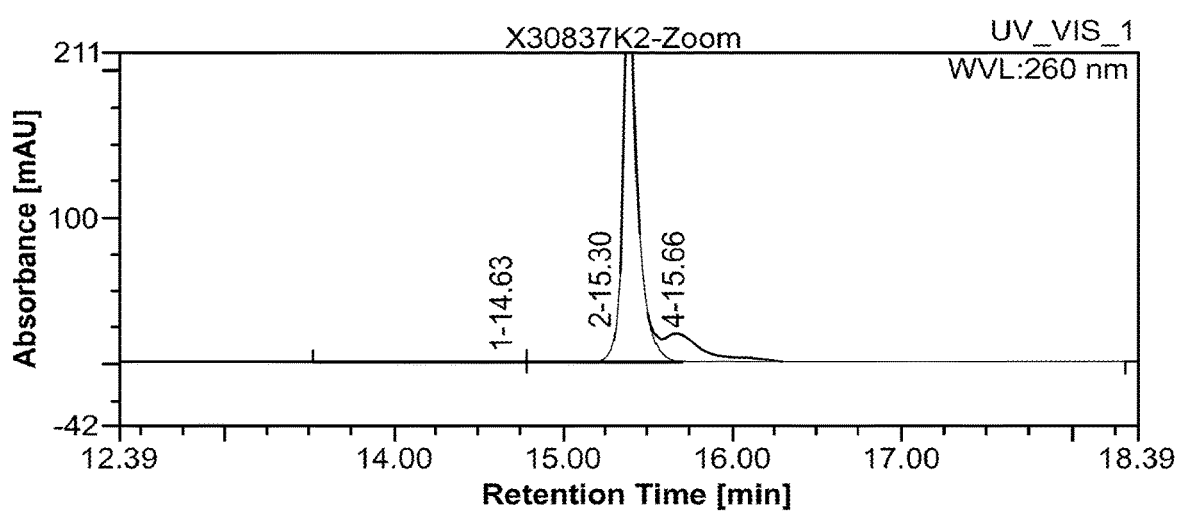
Figure 24E:
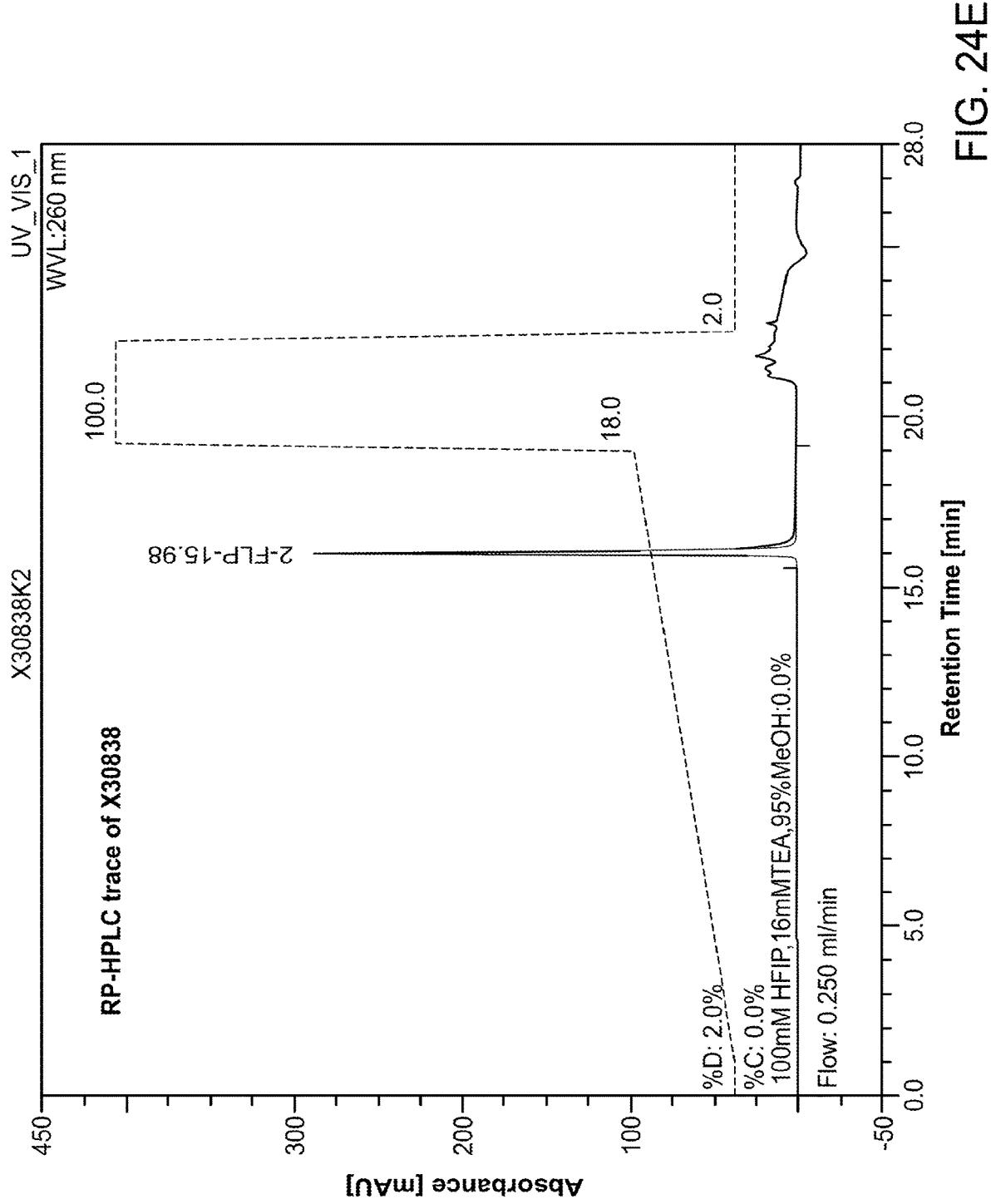
FIG. 24E presents RP-HPLC results for X30838, which is discussed in connection with Example 24.
Figure 24F:
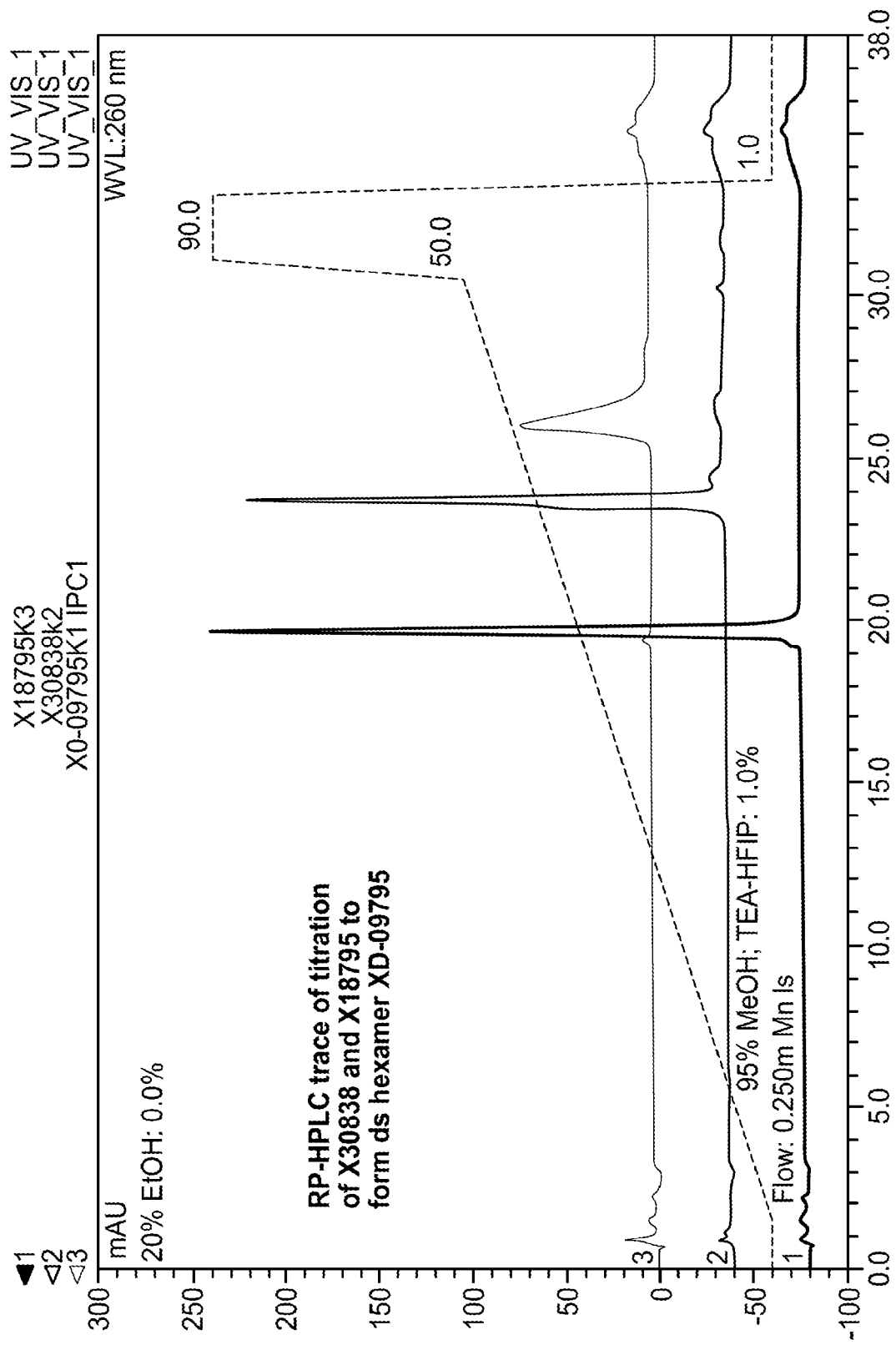
FIG. 24F presents RP-HPLC results for X30838, X18795 and XD-09795, which are discussed in connection with Example 24.

A homo-hexamer of FVII siRNA was constructed containing two orthogonal types of bio-cleavable linkages, i) an unmodified di-nucleotide linkage easily introduced on the synthesizer, and ii) the thiol/maleimide derivative that was introduced post-synthesis. The FVII homo-hexamer (XD-09795) was assembled by combining a homodimer (X30835) and a homo-tetramer (X30837) as illustrated in FIG. 23. Both the homodimer and homo-tetramer synthesized on solid support via standard techniques with an amino- and disulfide group at each terminus. After unblocking and purification the homodimer and homo-tetramer were then linked together via the thiol/maleimide reaction and annealed with antisense strand X18795 to give the FVII homo-hexamer (XD-09795).

The sequences of the single-stranded homodimer X30835, the single-stranded homo-tetramer X30837, the resultant single-stranded homo-hexamer X30838, as well as the double-stranded hexamer XD-09795 and the double-stranded monomer XD-09794 are shown in Table 15.

TABLE 15

Sequences of oligonucleotides in Example 23

| Duplex-ID | SEQ ID NO: | ss-ID | Sequence (5'-3') |
|---|---|---|---|
| | 146 | X30835 | (DTME)(SHC6)gcAfaAfgGfcGfuGfcCfaAfcUfcAf(invdT)dCdAgcAfaAfgGfcGfuGfcCfaAfcUfcAf(invdT)(NH2C6) |
| | 147 | X30837 | (SHC6)gcAfaAfgGfcGfuGfcCfaAfcUfcAf(invdT)dCdAgcAfaAfgGfcGfuGfcCfaAfcUfcAf(invdT)dCdAgcAfaAfgGfcGfuGfcCfaAfcUfcAf(invdT)dCdAgcAfaAfgGfcGfuGfcCfaAfcUfcAf(invdT)(NH2C6) |
| XD09794 | 148 | X18789 | (NH2C6)gcAfaAfgGfcGfuGfcCfaAfcUfcAf(invdT) |
| | 26 | X18795 | UfsGfaGfuUfgGfcAfcGfcCfuUfuGfcusu |
| XD09795 | 146 & 147 | X30838 | [(DTME)(SHC6)gcAfaAfgGfcGfuGfcCfaAfcUfcAf(invdT)dCdAgcAfaAfgGfcGfuGfcCfaAfcUfcAf(invdT)(NH2C6)](SHC6)gcAfaAfgGfcGfuGfcCfaAfcUfcAf(invdT)dCdAgcAfaAfgGfcGfuGfcCfaAfcUfcAf(invdT)dCdAgcAfaAfgGfcGfuGfcCfaAfcUfcAf(invdT)dCdAgcAfaAfgGfcGfuGfcCfaAfcUfcAf(invdT)(NH2C6) |
| | 26 | X18795 | UfsGfaGfuUfgGfcAfcGfcCfuUfuGfcusu |

Example 24: Purity and Yield in Synthesis of Homo-Hexamer siRNA

The synthesis steps described in Example 23 resulted in high yield and purity of the intermediate products, homodimer (X30835), homo-tetramer (X30837), and homo-hexamer (X30878), as well as the resultant dsRNA homo-hexamer (XD-09795), as presented by HPLC trace data in FIGS. 24A-24B, 24C-24D, 24E, and 24F, respectively.

Example 25: Comparison of In Vivo Circulation Half-Life Between Homo-Hexamer siRNA and Corresponding Monomer The serum half-lives of the FVII homo-hexamer XD-09795 and the corresponding FVII monomer XD-09794 were determined in mice. Briefly, the homo-hexamer or the corresponding monomer were administered via intravenous (IV) bolus injection into 3 cohorts of 4 C57/BL6N female mice aged approximately 11 weeks per cohort. Dosage was 20 mg/kg for both FVII monomer and FVII hexamer and blood samples were drawn 5, 30, 60 and 120 minutes after the IV bolus injection. The concentration of FVII antisense was determined at various time-points via a fluorescent PNA probe complementary to the antisense strand and the results are shown in FIG. 25.

Figure 25:
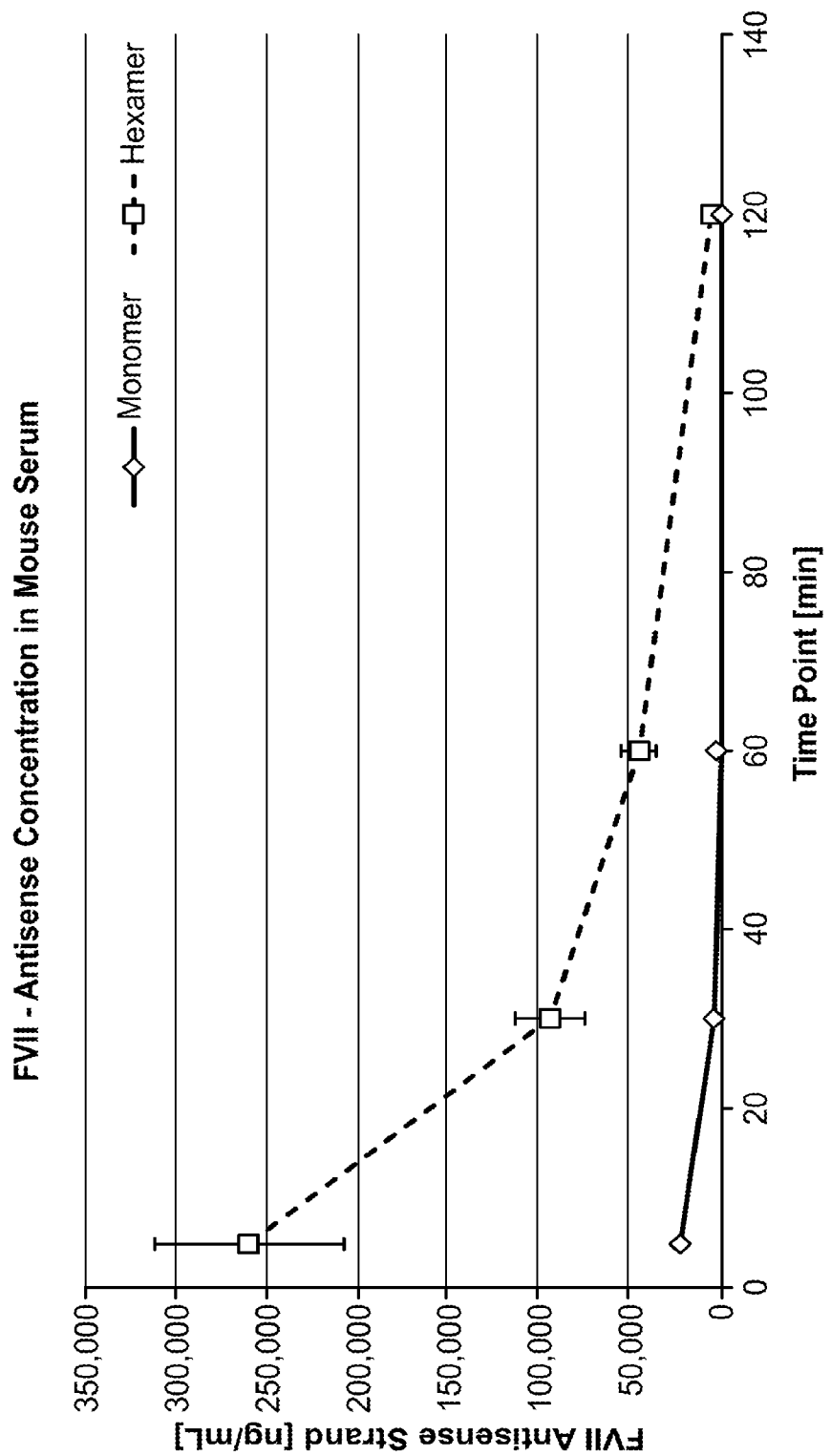
FIG. 25 presents data showing serum concentrations of FVII antisense RNA in mice at various times after injection of XD-09795 or XD-09794, which is discussed in connection with Example 25.
Figure 26A:
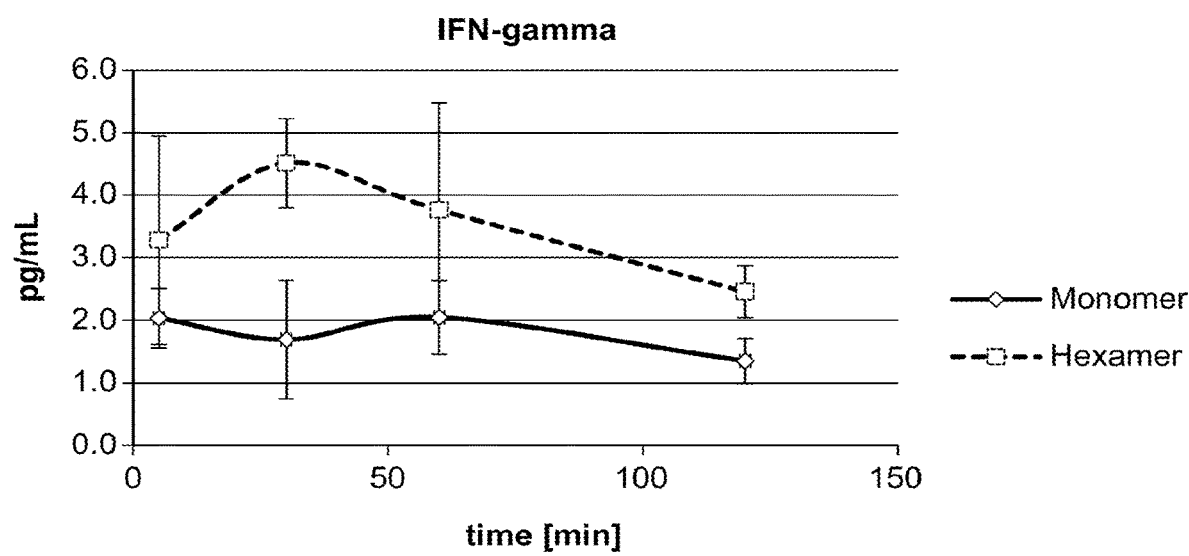
FIGS. 26A-J present data showing serum levels of various cytokines in mice at various times after injection of XD-09795 or XD-09794, which is discussed in connection with Example 26.
Figure 26B:
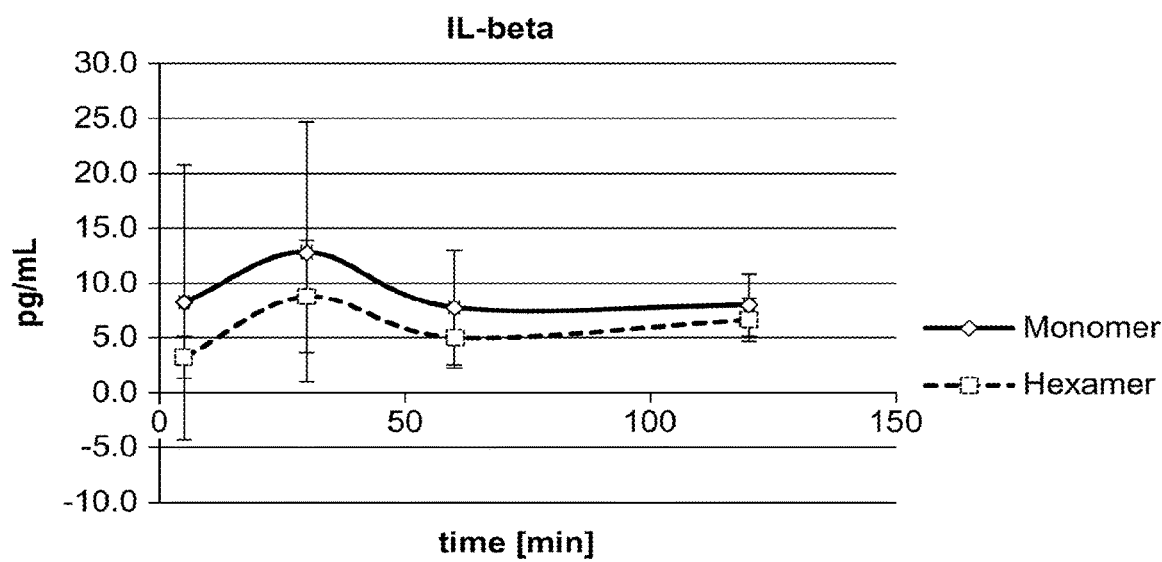
Figure 26C:
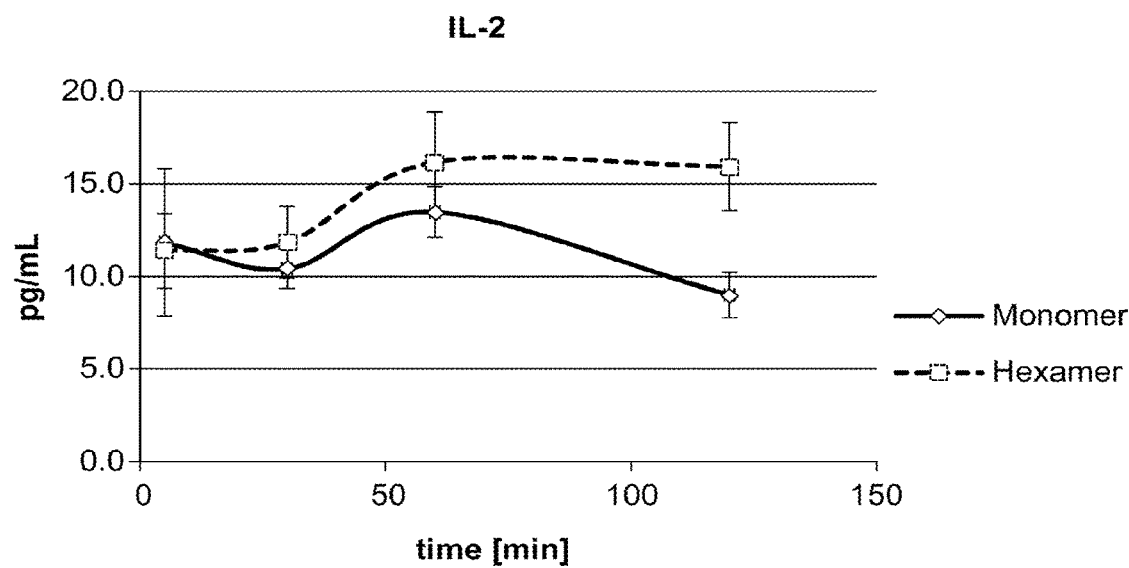
Figure 26D:
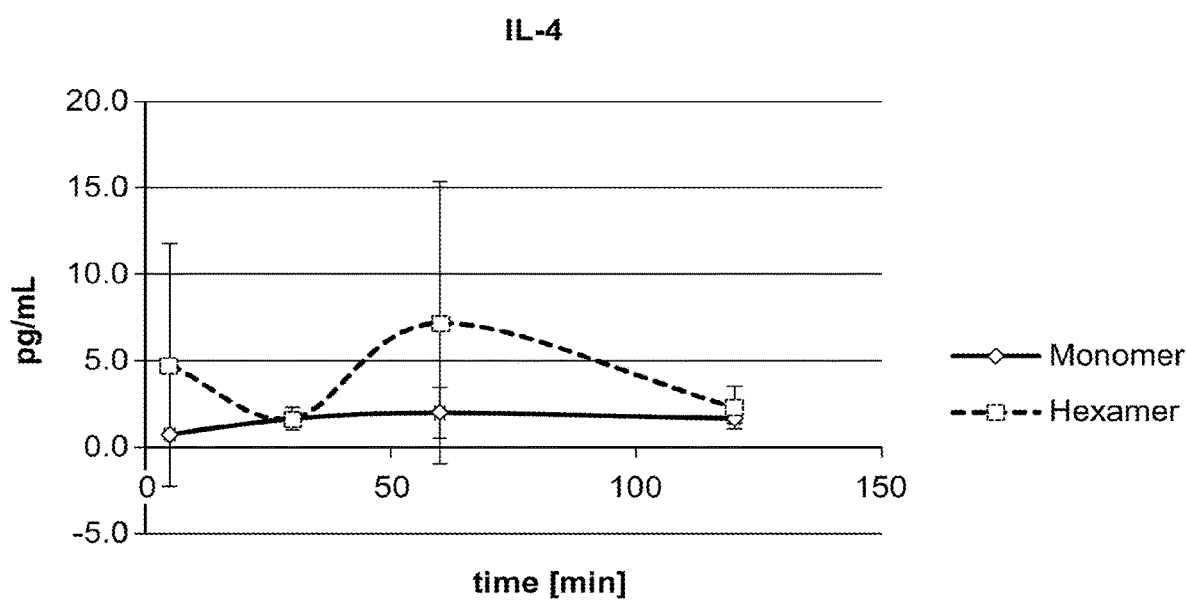
Figure 26E:
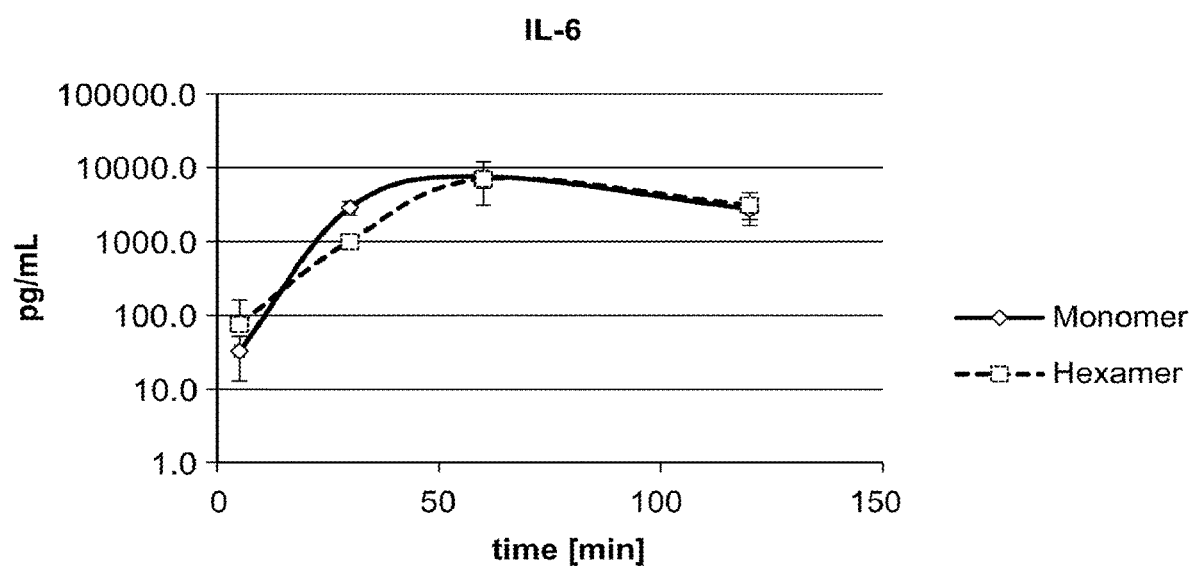
Figure 26F:
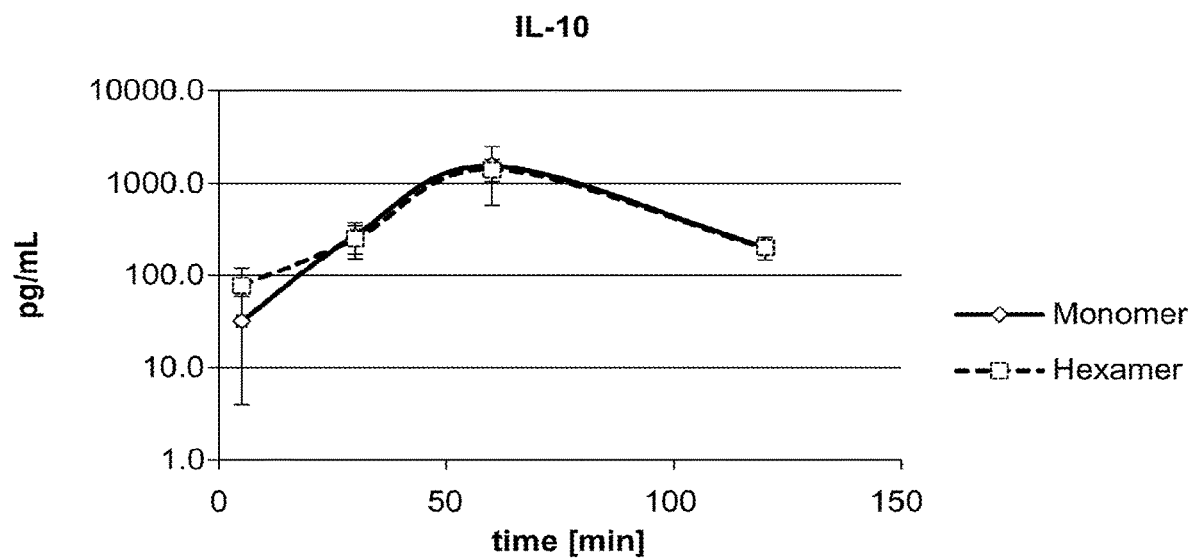
Figure 26G:
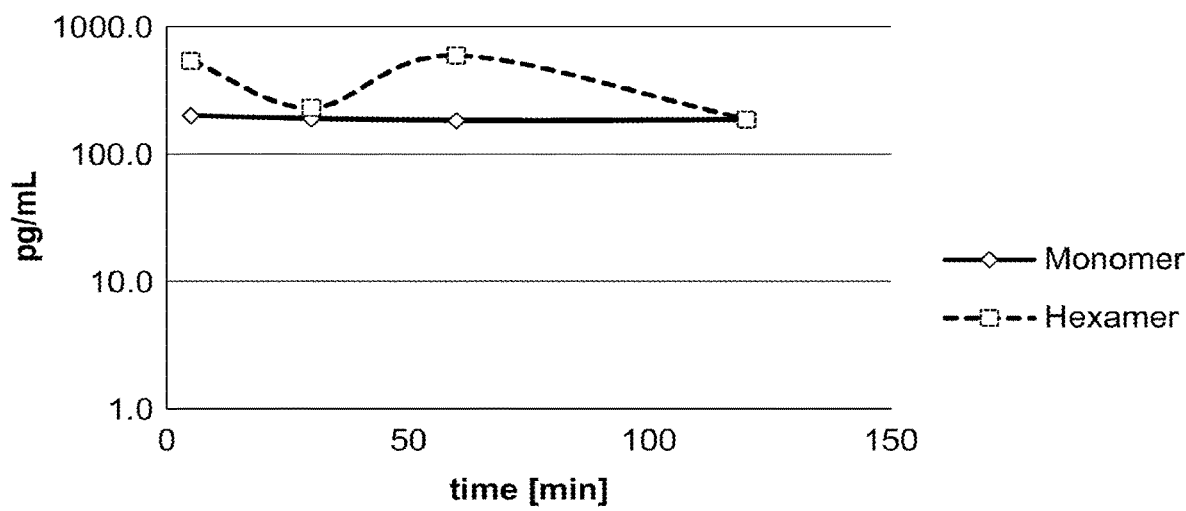
Figure 26H:
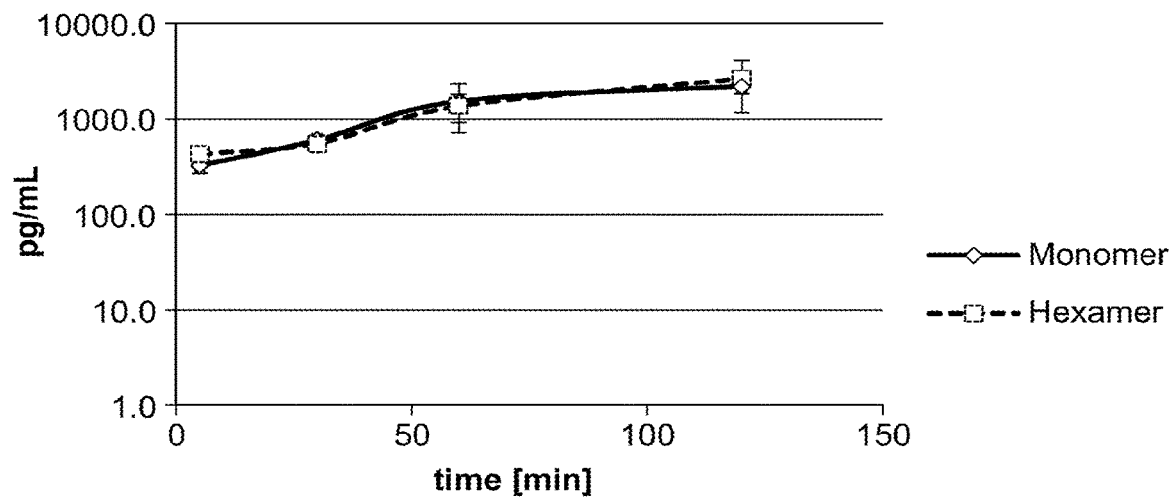
Figure 26I:
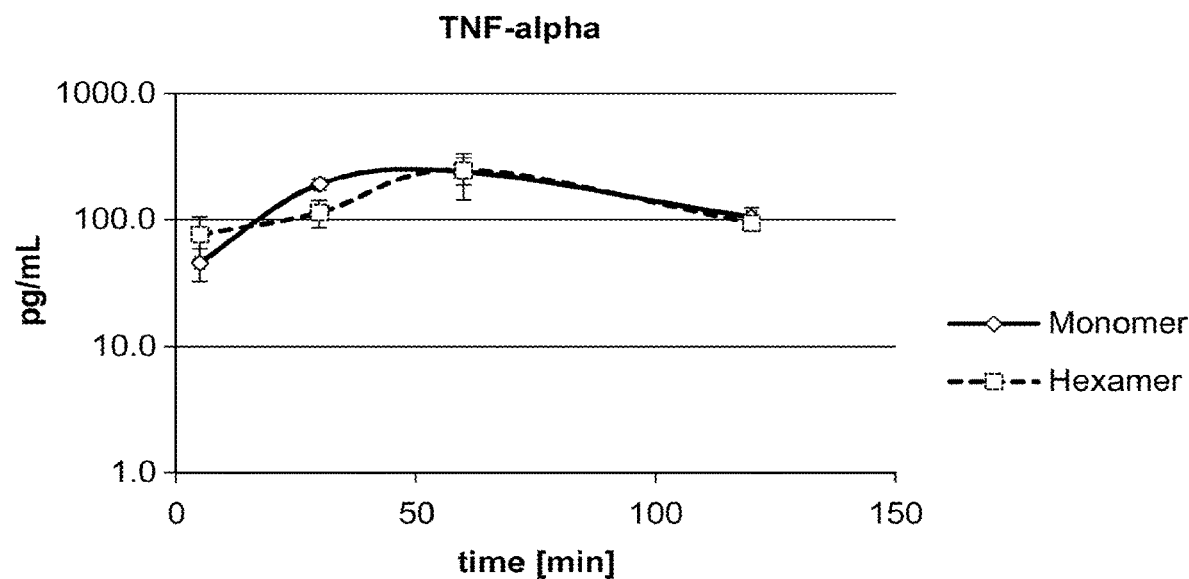
Figure 26J:
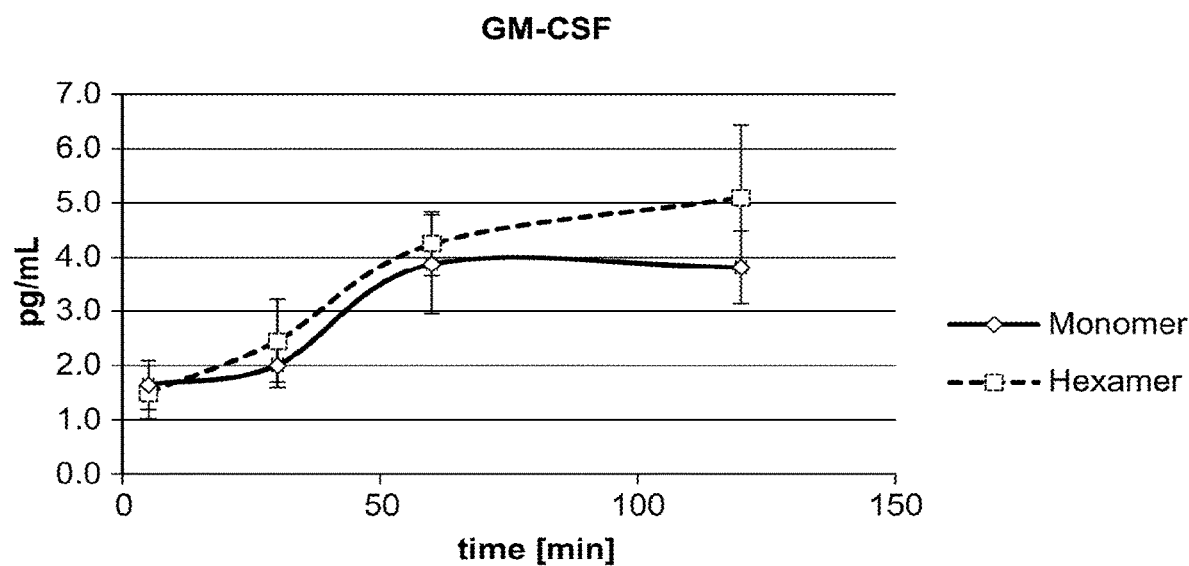

As shown in FIG. 25, only approximately 10% of administered FVII monomer remained in circulation after 5 minutes, and all had essentially disappeared after 30 minutes. By contrast, nearly all of the administered FVII hexamer remained in circulation after 5 minutes with one third of the initial dose remaining after 30 minutes. The data shows that the in-vivo circulation half-life of the hexamer was approximately 30-fold greater than the monomer.

Example 26: Determination of Levels of Cytokines in Blood Samples Taken at t=5, 30, 60, and 120 Minutes Using MSD U-Plex Platform To assess any adverse toxicological response to the hexamer, analysis of cytokine levels in the blood samples was performed using a MSD U-Plex platform. Blood samples from the monomer XD-09794 and homo-hexamer XD-09795 treated cohorts were analyzed for cytokine levels at the various time points. Serum levels of ten cytokines (IFN-γ, IL-1β, IL-2, IL-4, IL-6, IL-10, IL-12p70, KC-GRO, TNF-α, and GM-CSF) were assayed and shown in FIGS. 26 A-J. Of the ten cytokines assayed, the serum levels of 4 cytokines were unchanged between monomer and hexamer, and the serum levels were virtually identical in the remaining 6.

Example 27: Synthesis Homo-Multimers

Homo-multimers of an siRNA directed against FVII mRNA were prepared via the above methodologies using the following sequences:

```
FVII sense:
                                      (SEQ ID NO: 35)
5'-gcAfaAfgGfcGfuGfcCfaAfcUfcAf(invdT)-3'

FVII anti-sense:
                                      (SEQ ID NO: 26)
5'-UfsGfaGfuUfgGfcAfcGfcCfuUfuGfcusu-3',
``` linked via the endonuclease cleavable linkers dCdA and the reductively cleavable linker DTME as follows:

TABLE 16A

| Oligonucleotides in Examples 28-36 | |
|---|---|
| Sequence ID | Configuration/Strand |
| X18789 | Monomer Sense |
| X18795 | Monomer Anti-sense |
| XD-09794 | ds Monomer |
| X30833 | Dimer Sense |
| X18795 | Monomer Anti-sense |
| XD-10635 | ds Dimer |
| X34003 | Trimer Sense |
| X18795 | Monomer Anti-sense |
| XD-10636 | ds Trimer |
| X30836 | Tetramer Sense |
| X18795 | Monomer Anti-sense |
| XD-10637 | ds Tetramer |
| X-34004 | Pentamer Sense |
| X18795 | Monomer Anti-sense |
| XD-10638 | ds Pentamer |
| X34005 | Hexamer Sense |
| X18795 | Monomer Anti-sense |
| XD-10639 | ds Hexamer |
| X30837 | Tetramer Sense thiol |
| X30834 | Dimer sense thiol |
| X30835 | Dimer sense-S-DTME |
| X30838 | Hexamer Sense |
| X18795 | Monomer Anti-sense |
| XD-09795 | ds Hexamer |
| X34006 | Pentamer Sense thiol |
| X30834 | Dimer sense thiol |
| X30835 | Dimer sense-S-DTME |
| X34009 | Heptamer Sense |
| X18795 | Monomer Anti-sense |
| XD-10640 | ds Heptamer |
| X34007 | Hexamer Sense thiol |
| X30834 | Dimer sense thiol |
| X30835 | Dimer sense-S-DTME |
| X34010 | Octamer Sense |
| X18795 | Monomer Anti-sense |
| XD-10641 | ds Octamer |

TABLE 16B

FVII siRNA homo-multimers XD-10635, XD-10636, XD-06386, XD-10635

| Duplex ID | SEQ ID NO: | Single Strand ID | Sequence (5'-3') | Configuration |
|---|---|---|---|---|
| XD-10635 | 149 | X30833 | (C6SSC6)gcAfaAfgGfcGfuGfcCfaAfcUfcAf(invdT)dCdAgcAfa AfgGfcGfuGfcCfaAfcUfcAf(invdT)C6NH2) | Dimer |
| | 26 | X18795 | UfsGfaGfuUfgGfcAfcGfcCfuUfuGfcusu | |
| XD-10636 | 150 | X34003 | (C6SSC6)gcAfaAfgGfcGfuGfcCfaAfcUfcAf(invdT)dCdAgcAfa AfgGfcGfuGfcCfaAfcUfcAf(invdT)dCdAgcAfaAfgGfcGfuGfcC faAfcUfcAf(invdT)(C6NH2) | Trimer |
| | 26 | X18795 | UfsGfaGfuUfgGfcAfcGfcCfuUfuGfcusu | |

TABLE 16B-continued

FVII siRNA homo-multimers XD-10635, XD-10636, XD-06386, XD-10635

| Duplex ID | SEQ ID NO: | Single Strand ID | Sequence (5'-3') | Configuration |
|---|---|---|---|---|
| XD-06386 | 151 | X30836 | (C6SSC6)gcAfaAfgGfcGfuGfcCfaAfcUfcAf(invdT)dCdAgcAfa AfgGfcGfuGfcCfaAfcUfcAf(invdT)dCdAgcAfaAfgGfcGfuGfcC faAfcUfcAf(invdT)dCdAgcAfaAfgGfcGfuGfcCfaAfcUfcAf(inv dT)(C6NH2) | Tetramer |
|  | 26 | X18795 | UfsGfaGfuUfgGfcAfcGfcCfuUfuGfcusu |  |
| XD-10635 | 152 | X34004 | (C6SSC6)gcAfaAfgGfcGfuGfcCfaAfcUfcAf(invdT)dCdAgcAfa AfgGfcGfuGfcCfaAfcUfcAf(invdT)dCdAgcAfaAfgGfcGfuGfcC faAfcUfcAf(invdT)dCdAgcAfaAfgGfcGfuGfcCfaAfcUfcAf(inv dT)dCdAgcAfaAfgGfcGfuGfcCfaAfcUfcAf(invdT)C6NH2) | Pentamer |
|  | 26 | X18795 | UfsGfaGfuUfgGfcAfcGfcCfuUfuGfcusu |  |
| XD-06728 | 153 | X34005 | (C6SSC6)gcAfaAfgGfcGfuGfcCfaAfcUfcAf(invdT)dCdAgcAfa AfgGfcGfuGfcCfaAfcUfcAf(invdT)dCdAgcAfaAfgGfcGfuGfcC faAfcUfcAf(invdT)dCdAgcAfaAfgGfcGfuGfcCfaAfcUfcAf(inv dT)dCdAgcAfaAfgGfcGfuGfcCfaAfcUfcAf(invdT)dCdAgcAfa AfgGfcGfuGfcCfaAfcUfcAf(invdT)C6NH2) | Hexamer |
|  | 26 | X18795 | UfsGfaGfuUfgGfcAfcGfcCfuUfuGfcusu |  |

Example 28: Synthesis of FVII Monomer XD-09794

Figure 27A:
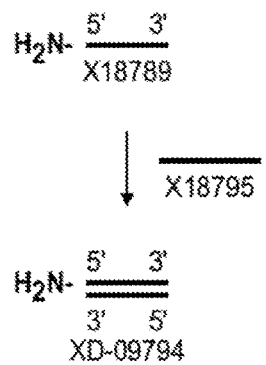
FIG. 27A presents a schematic diagram for a synthesis strategy for monomer of FVII siRNA, which is discussed in connection with Example 28.
Figure 27B:
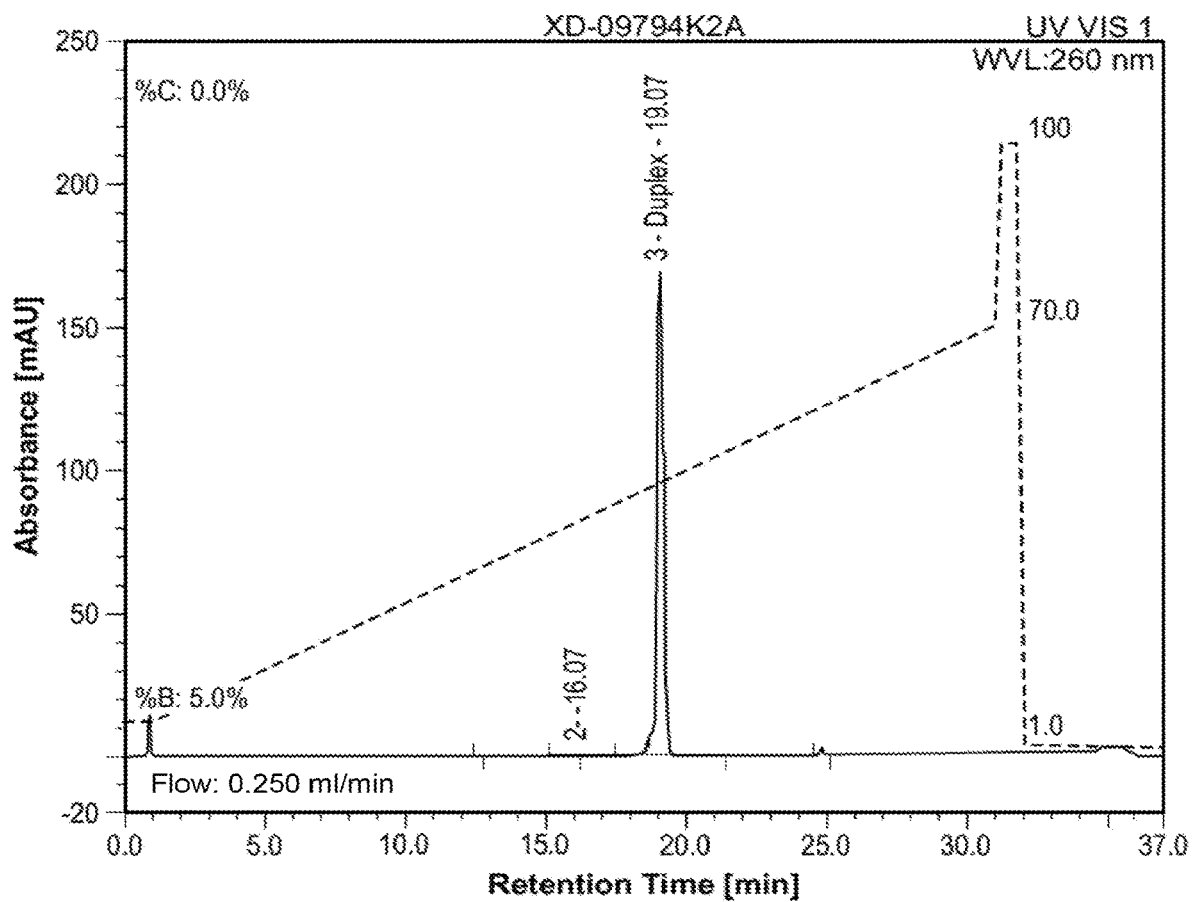
FIG. 27B presents RP-HPLC results for XD-09794, which is discussed in connection with Example 28.

Monomeric sense strand X18789 of FVII siRNA with amino function at the 5'-terminus on the sense strand was synthesized and purified as shown in FIGS. 27A and 27B. Yield, 48.3 mg, 6.694 mmol, 18.6%. The corresponding antisense strand X18795 was likewise synthesized to yield 46.3 mg, 6.35 mmol, 31.9%. 5.35 mg (747.3 nmol) of sense strand and 5.45 mg (747.3 nmol) of anti-sense strand were then annealed to yield 10.8 mg (747.4 nmol) the corresponding double stranded FVII monomer (XD-09794).

Example 29: Synthesis of FVII Dimer XD-10635

Figure 28A:
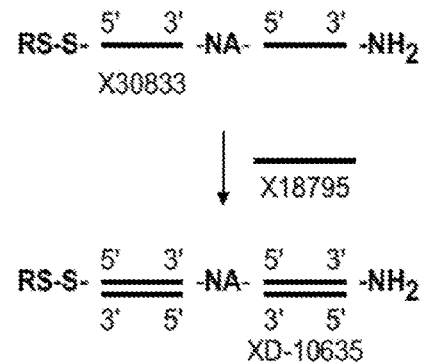
FIG. 28A presents a schematic diagram for a synthesis strategy for homo-dimer of FVII siRNA, which is discussed in connection with Example 29.
Figure 28B:
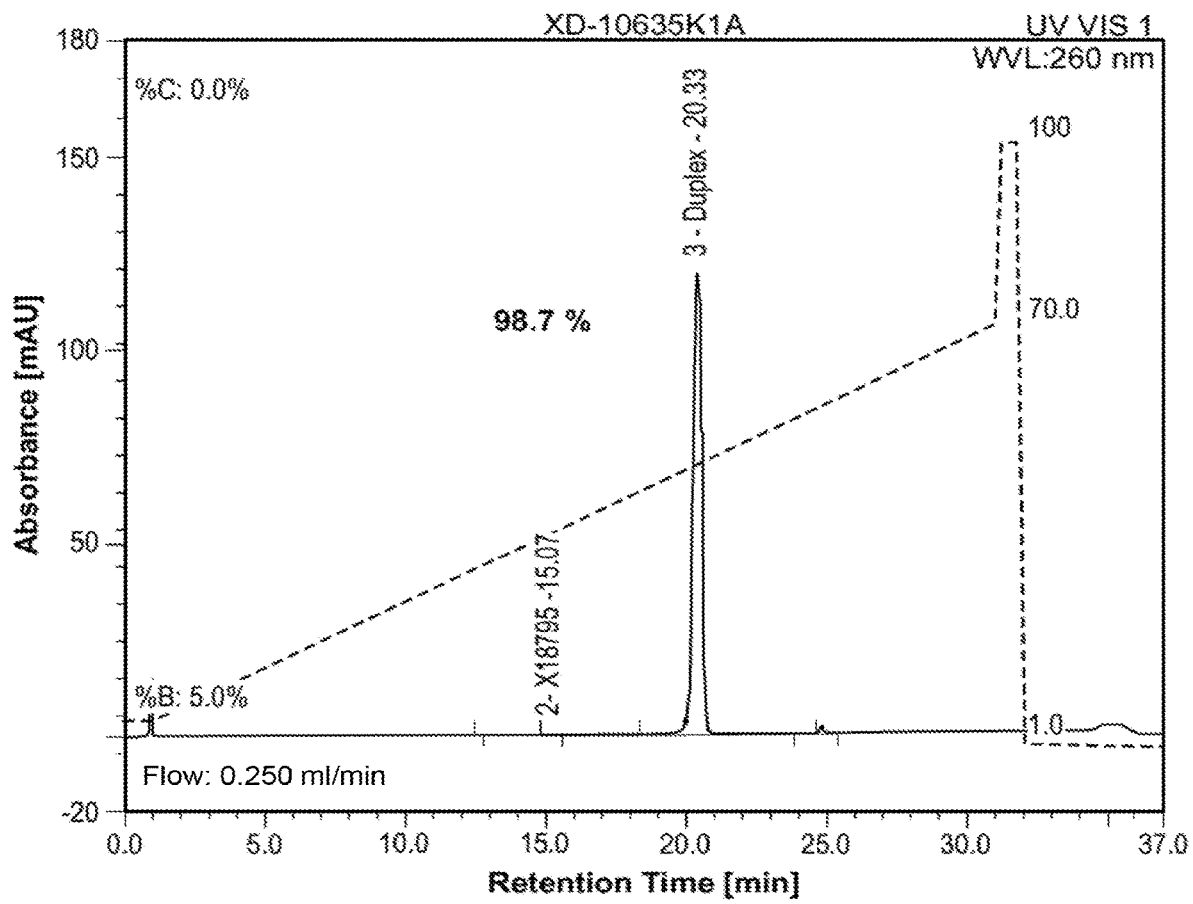
FIG. 28B presents RP-HPLC results for XD-10635, which is discussed in connection with Example 29.

Homodimeric sense-strand of FVII siRNA X30833 with amino and di-sulfide groups at the 3'- and 5'-termini respectively and containing a dCdA cleavable linker was synthesized and purified as shown in FIGS. 28A and 28B. Yield, 35.8 mg, 6.694 mmol, 18.6%.

5.51 mg (362.6 nmol) of sense strand X30833 and 5.29 mg (725.2 nmol) of anti-sense strand X18795 were then annealed to yield 10.8 mg (362.6 nmol) of the corresponding double stranded FVII homo-dimer (XD-10635).

Example 30: Synthesis of FVII Trimer XD-10636

Figure 29A:
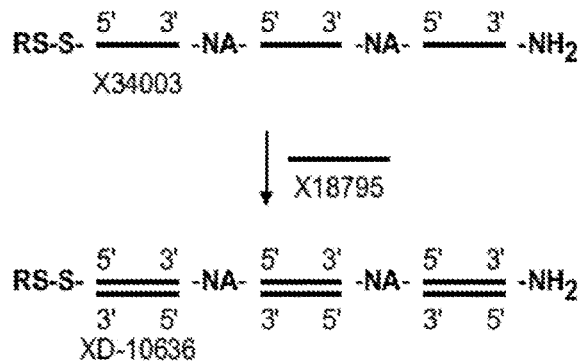
FIG. 29A presents a schematic diagram for a synthesis strategy for homo-trimer of FVII siRNA, which is discussed in connection with Example 30.
Figure 29B:
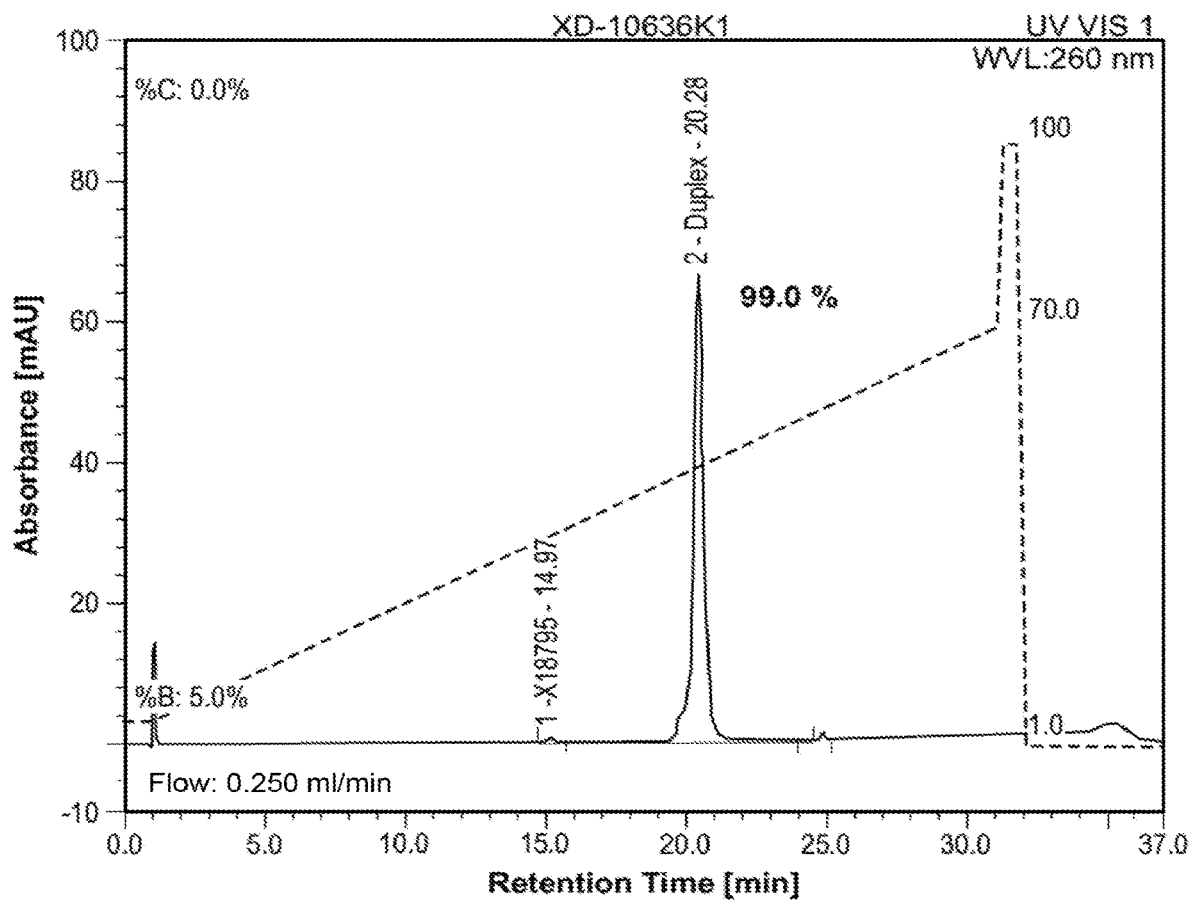
FIG. 29B presents RP-HPLC results for XD-10636, which is discussed in connection with Example 30.

Homo-trimeric sense-strand of FVII siRNA X34003 with amino and di-sulfide groups at the 3'- and 5'-termini respectively and containing two dCdA cleavable linkers was synthesized and purified as shown in FIGS. 29A and 29B. Yield, 19.6 mg (857.9 nmol, 19.3%).

5.16 mg (225.5 nmol) of sense strand X34003 and 4.93 mg (676.5 nmol) of anti-sense strand X18795 were then annealed to yield 10.1 mg (225.5 nmol) of the corresponding double stranded FVII homo-trimer (XD-10636).

Example 31: Synthesis of FVII Tetramer XD-10637

Figure 30A:
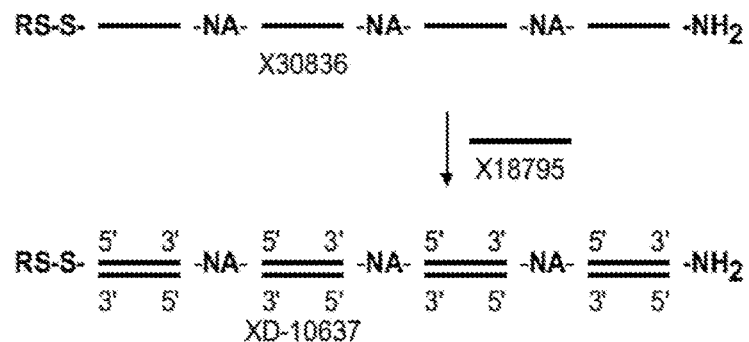
FIG. 30A presents a schematic diagram for a synthesis strategy for homo-tetramer of FVII siRNA, which is discussed in connection with Example 31.
Figure 30B:
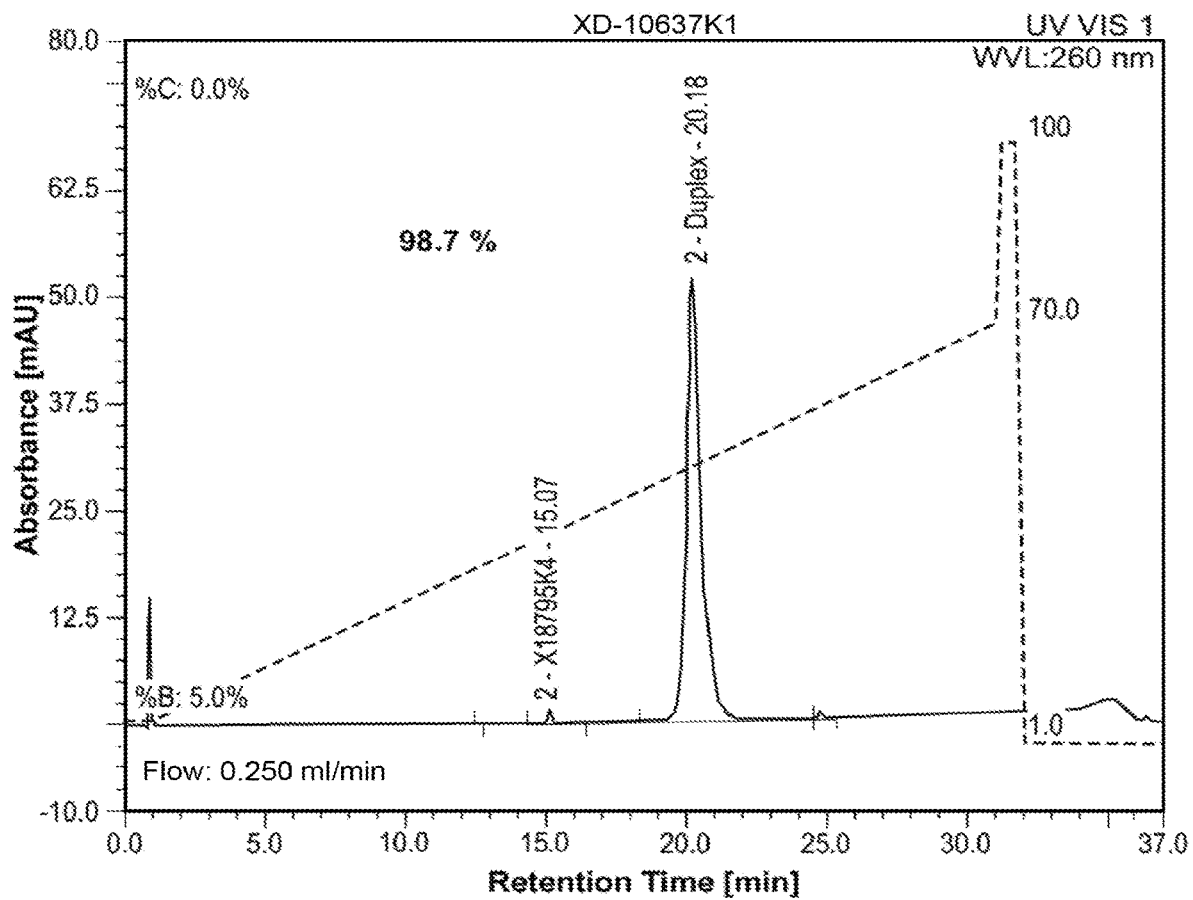
FIG. 30B presents RP-HPLC results for XD-10637, which is discussed in connection with Example 31.

Homo-tetrameric sense-strand of FVII siRNA X30836 with amino and di-sulfide groups at the 3'- and 5'-termini respectively and containing three dCdA cleavable linkers was synthesized and purified as shown in FIGS. 30A and 30B. Yield, 53.1 mg (1734.5 nmol, 13%).

5.53 mg (180.8 nmol) of sense strand X30836 and 5.27 mg (723.2 nmol) of anti-sense strand X18795 were then annealed to yield 10.8 mg (180.8 nmol) of the corresponding double stranded FVII homo-tetramer (XD-10637).

Example 32: Synthesis of FVII Pentamer XD-10638

Figure 31A:
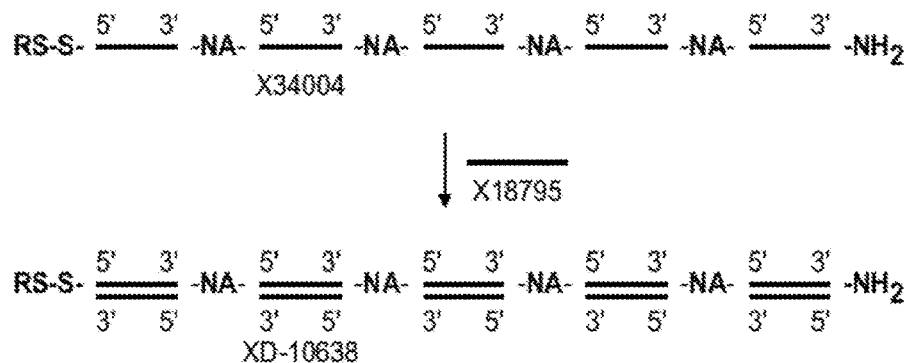
FIG. 31A presents a schematic diagram for a synthesis strategy for homo-pentamer of FVII siRNA, which is discussed in connection with Example 32.
Figure 31B:
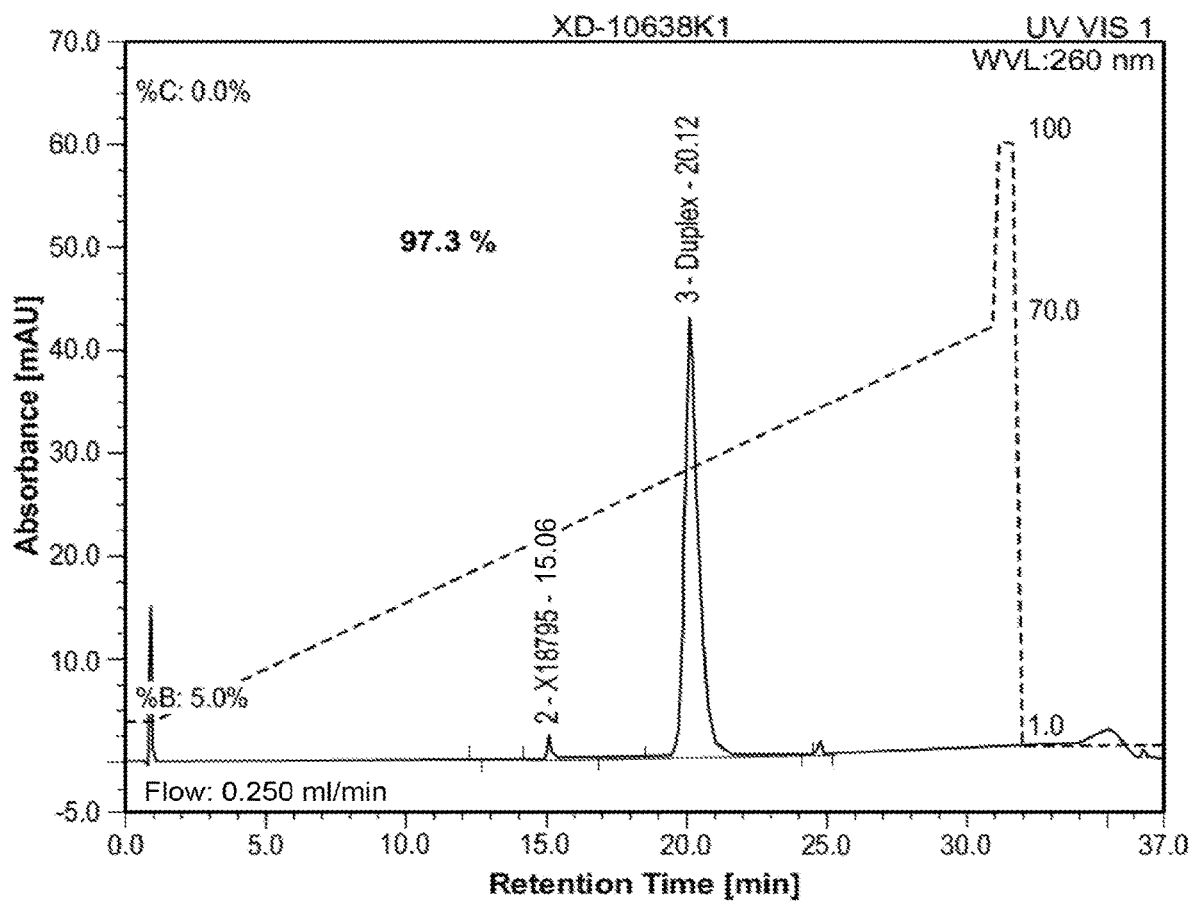
FIG. 31B presents RP-HPLC results for XD-10638, which is discussed in connection with Example 32.

Homo-pentameric sense-strand of FVII siRNA X34004 with amino and di-sulfide groups at the 3'- and 5'-termini respectively and containing four dCdA cleavable linkers was synthesized and purified as shown in FIGS. 31A and 31B. Yield, 35.9 mg (938 nmol, 10.6%).

5.53 mg (144.5 nmol) of sense strand X34004 and 5.27 mg (723.2 nmol) of anti-sense strand X18795 were then annealed to yield 10.8 mg (144.5 nmol) of the corresponding double stranded FVII homo-pentamer (XD-10638).

Example 33: Synthesis of FVII Hexamer XD-10639

Figure 32A:
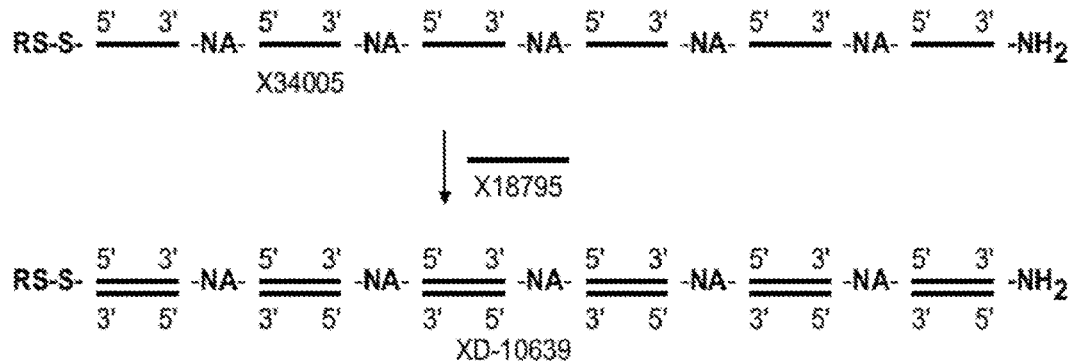
FIG. 32A presents a schematic diagram for a synthesis strategy for homo-hexamer of FVII siRNA, which is discussed in connection with Example 33.
Figure 32B:
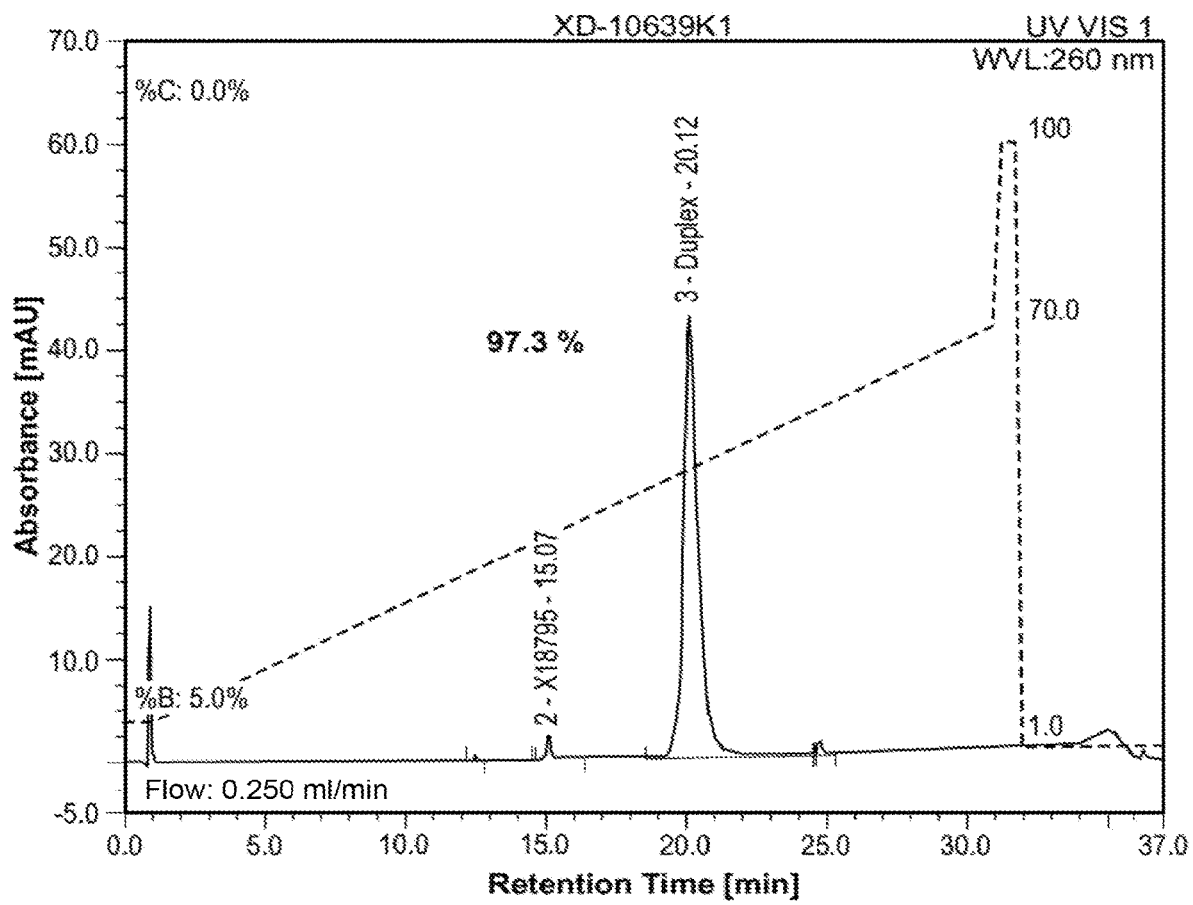
FIG. 32B presents RP-HPLC results for XD-10639, which is discussed in connection with Example 33.

Homo-hexameric sense-strand of FVII siRNA X34005 with amino and di-sulfide groups at the 3'- and 5'-termini respectively and containing five dCdA cleavable linkers was synthesized and purified as shown in FIGS. 32A and 32B. Yield, 21.4 mg (466.1 nmol, 5.3%).

5.15 mg (144.5 nmol) of sense strand X34005 and 4.89 mg (723.2 nmol) of anti-sense strand X18795 were then annealed to yield 10.04 mg (111.9 nmol) of the corresponding double stranded FVII homo-hexamer (XD-10639).

Example 34: Synthesis of FVII Hexamer XD-09795

Figure 33A:
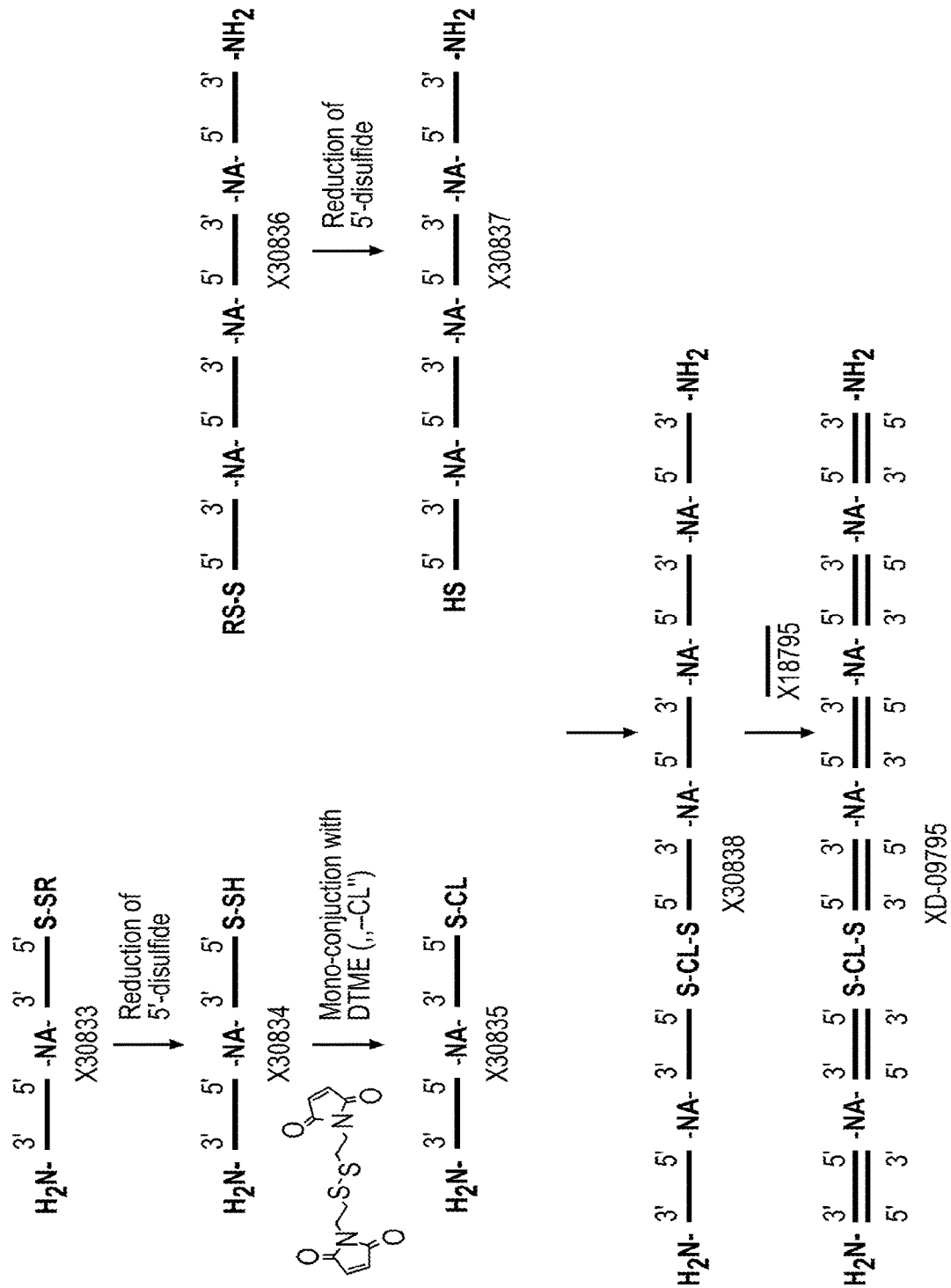
FIG. 33A presents a schematic diagram for a synthesis strategy for homo-hexamer of FVII siRNA via mono-DTME conjugate, which is discussed in connection with Example 34.
Figure 33B:
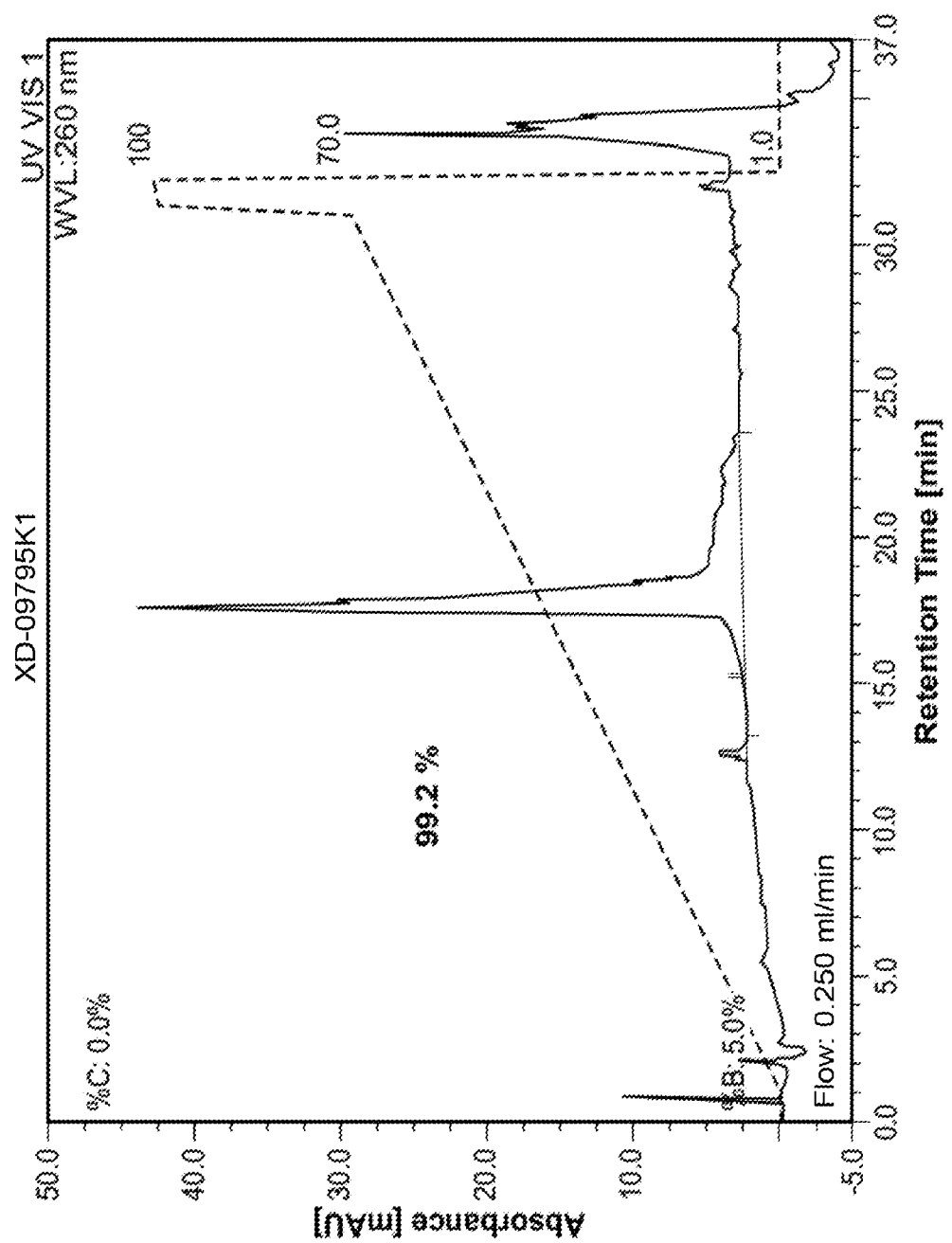
FIG. 33B presents RP-HPLC results for XD-09795, which is discussed in connection with Example 34.

As shown in FIGS. 33A-33B, homo-hexameric sense-strand of FVII siRNA X30838 with amino groups at both of the 3' termini and containing four dCdA cleavable linkers and one reductively cleavable DTME linker was synthesized and purified via the homo-dimeric sense-strand of FVII siRNA X30833 and the homo-tetrameric sense-strand of FVII siRNA X30836 prepared in Examples 28 and 30.

Disulfide group was cleaved from X30833 and X30836 using DTT to give the corresponding 5-thiol derivatives X30834 and X30837 in 97.6% and 91.9% yield respectively. Using the procedure described above 14.9 mg (986.7 nmol) of X30834 was then converted to 10.6 mg (700.5 nmol, 71.0%) of the corresponding mono-DTME derivative X30835 which was reacted with one equivalent of X30837 to give 4.2 mg (90.7 nmol, 64%) of the single stranded homo-hexamer X30838. 3.8 mg (83 nmol) of sense strand X30838 and 3.7 mg (502 nmol, 6 mol. equiv) of anti-sense strand X18795 were then annealed to yield 7.5 mg (83.7 nmol) of the corresponding double stranded FVII homo-hexamer (XD-09795).

Example 35: Synthesis of FVII Heptamer XD-10640

Figure 34A:
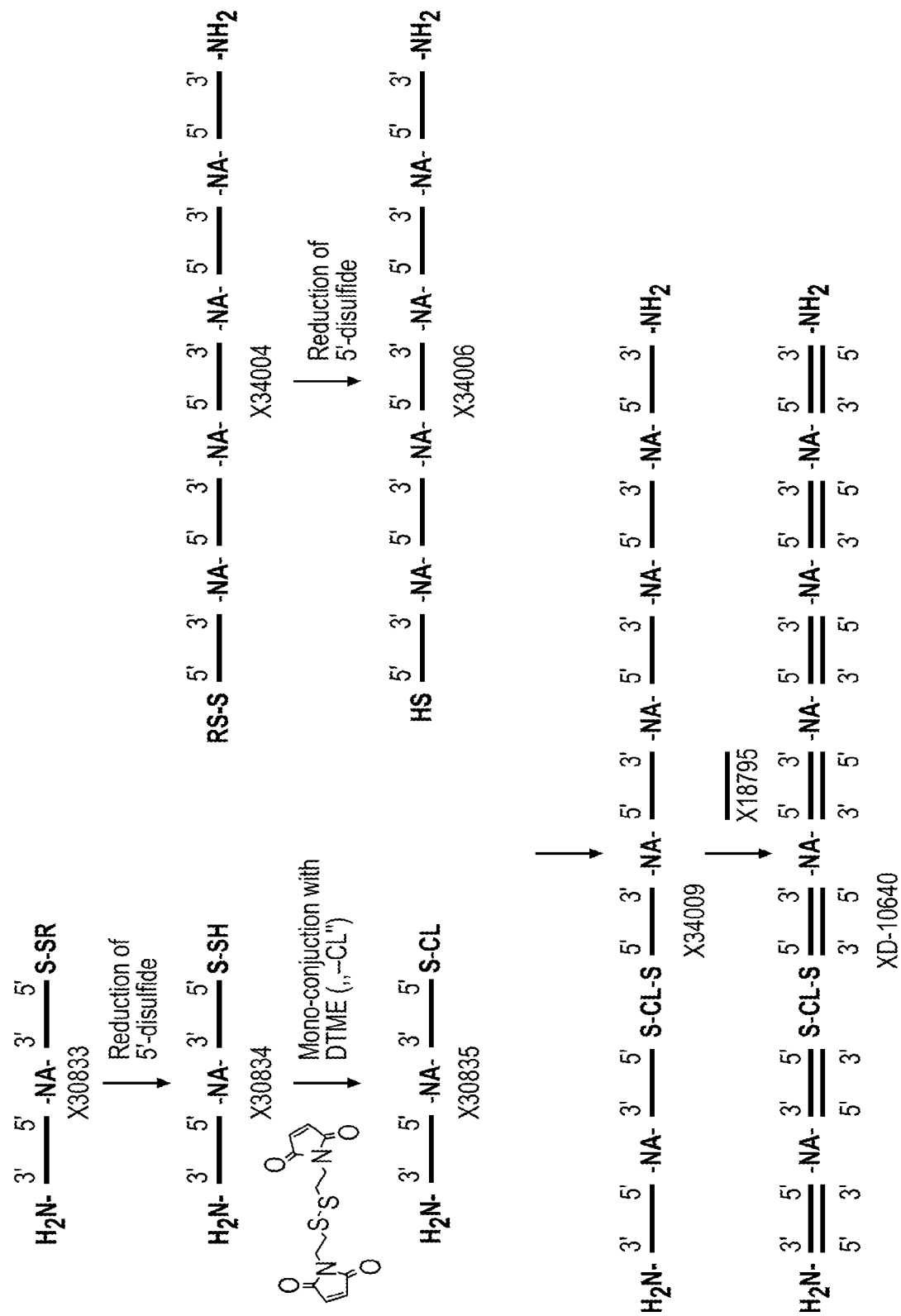
FIG. 34A presents a schematic diagram for a synthesis strategy for homo-heptamer of FVII siRNA via mono-DTME conjugate, which is discussed in connection with Example 35.
Figure 34B:
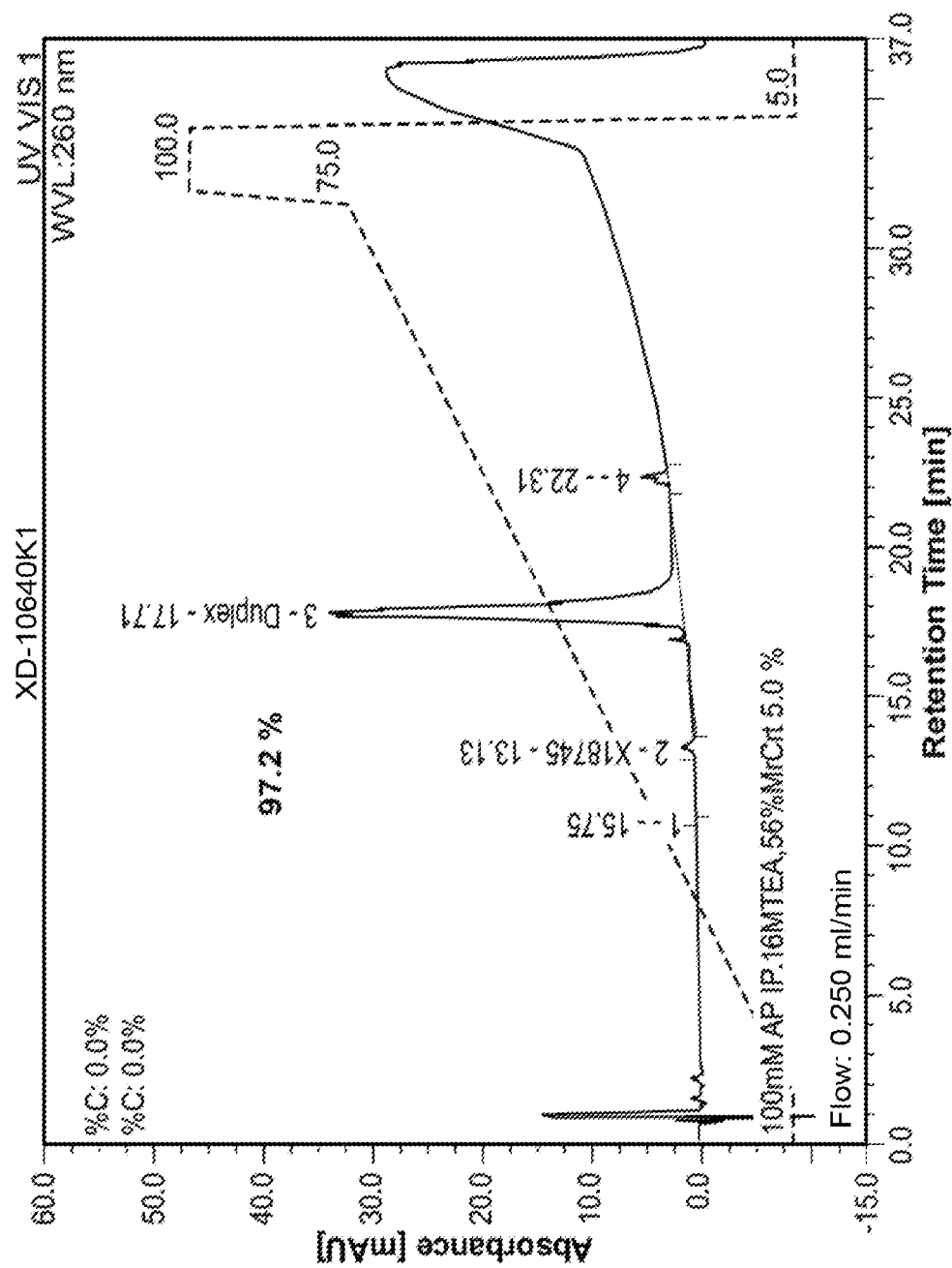
FIG. 34B presents RP-HPLC results for XD-10640, which is discussed in connection with Example 35.

As shown in FIGS. 34A-34B, homo-heptameric sense-strand of FVII siRNA X34009 with amino groups at both of the 3' termini and containing five dCdA cleavable linkers was synthesized and purified via the homo-dimeric sense-strand of FVII siRNA X30833 and the homo-pentameric sense-strand of FVII siRNA X34004. Disulfide group was cleaved from X30833 and X34004 using DTT to give the corresponding 5-thiol derivatives X30834 (28.3 mg, 1877.9 nmol, 86.7%) and X34006 (21.8 mg, 572.2 nmol), respectively. Using the procedure described above X30834 was then converted to the corresponding mono-DTME derivative X30835 (22.6 mg, 1465.2 nmol, 78.1%). 8.8 mg (572.2 nmol) of X30835 was reacted with X34006 (21.8 mg, 572.2 nmol) to give the single stranded homo-heptamer X34009 (8.96 mg, 167.3 nmol, 29.2%). 5.53 mg, (103.3 nmol) of sense strand X34009 and 5.27 mg (723.1 nmol) of anti-sense strand X18795 were then annealed to yield 10.8 mg (103.3 nmol) of the corresponding double stranded FVII homo-heptamer (XD-10640).

Example 36: Synthesis of FVII Octamer XD-10641

Figure 35A:
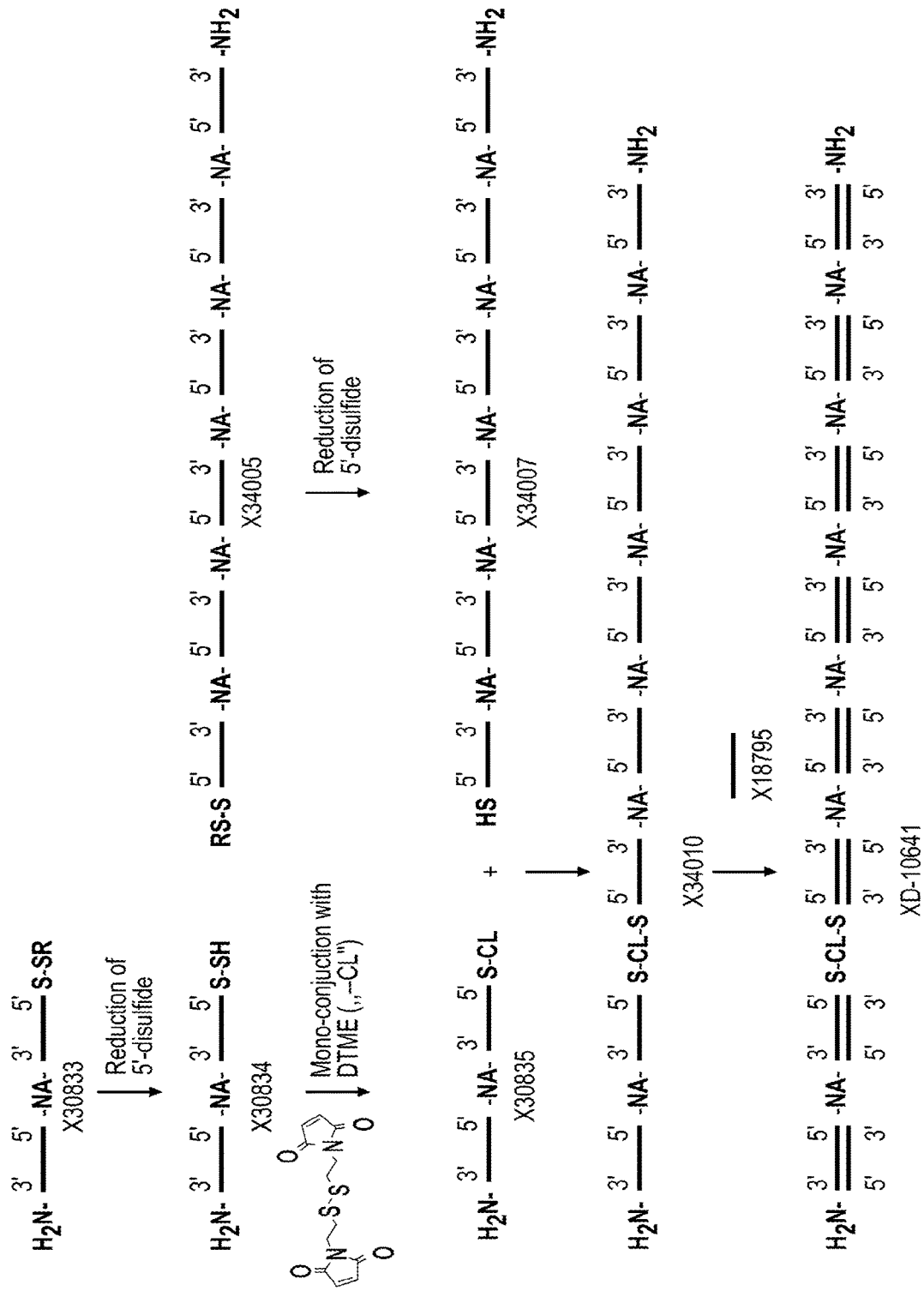
FIG. 35A presents a schematic diagram for a synthesis strategy for homo-octamer of FVII siRNA via mono-DTME conjugate, which is discussed in connection with Example 36.
Figure 35B:
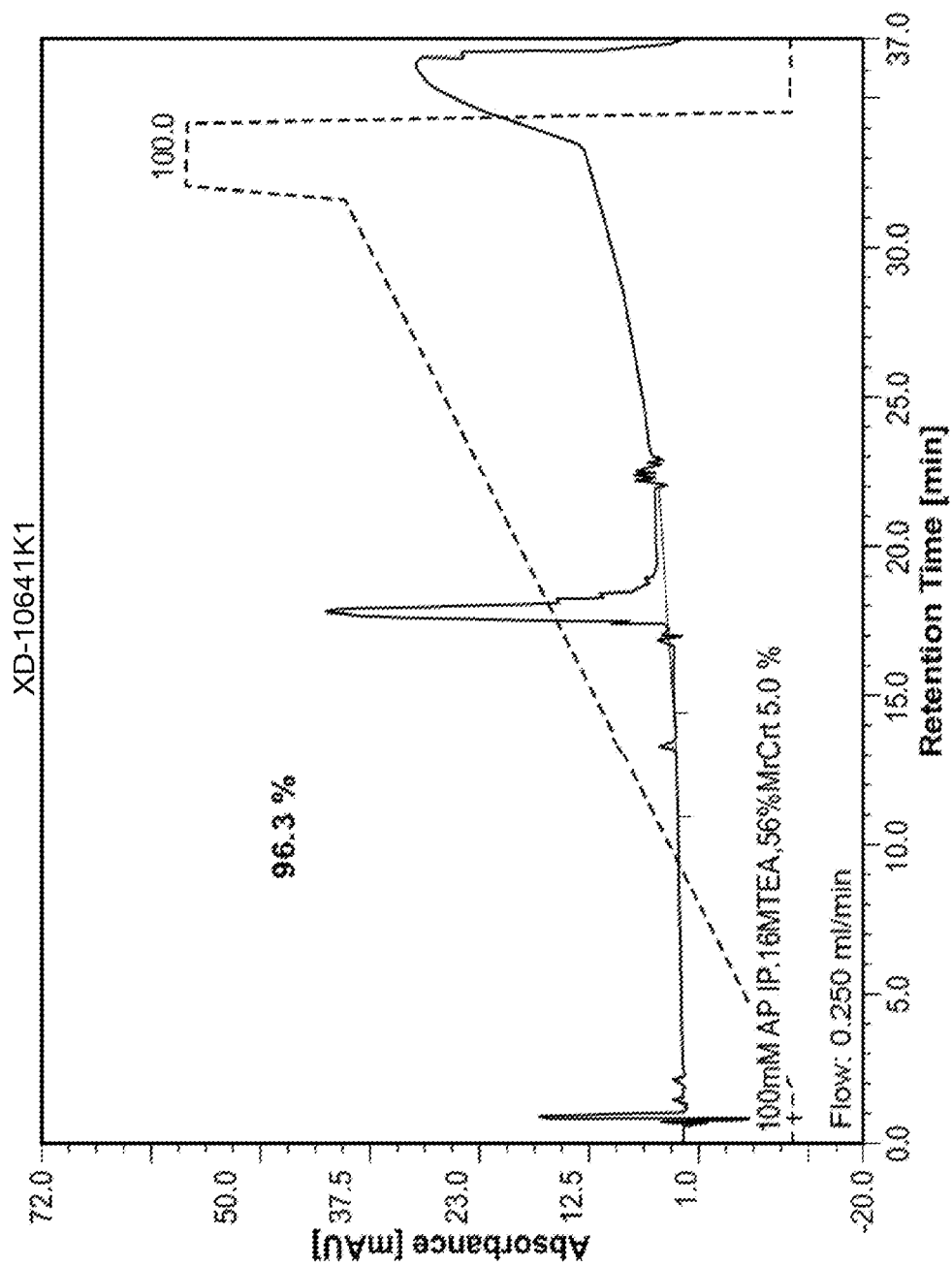
FIG. 35B presents RP-HPLC results for XD-10641, which is discussed in connection with Example 36.

As shown in FIGS. 35A-35B, homo-octameric sense-strand of FVII siRNA X34010 with amino groups at both of the 3' termini and containing six dCdA cleavable linkers was synthesized and purified via the homo-dimeric sense-strand of FVII siRNA X30833 and the homo-hexameric sense-strand of FVII siRNA X34005. Disulfide group was cleaved from X34005 using DTT to give the corresponding 5-thiol derivative X34007 (11.5 mg, 251 nmol, 99.7%) which was reacted with the previously obtained mono-DTME homo-dimer derivative X30835 (3.85 mg, 250.2 nmol) to give the single stranded homo-octamer X34010 (5.2 mg, 85.0 nmol, 34.0%). 4.92 mg (80.33 nmol) of sense strand X34010 and 4.68 mg (642.4 nmol) of anti-sense strand X18795 were then annealed to yield 9.6 mg (80.3 nmol) of the corresponding double stranded FVII homo-octamer (XD-10641).

Example 37: Animal Experiments

Figure 36A:
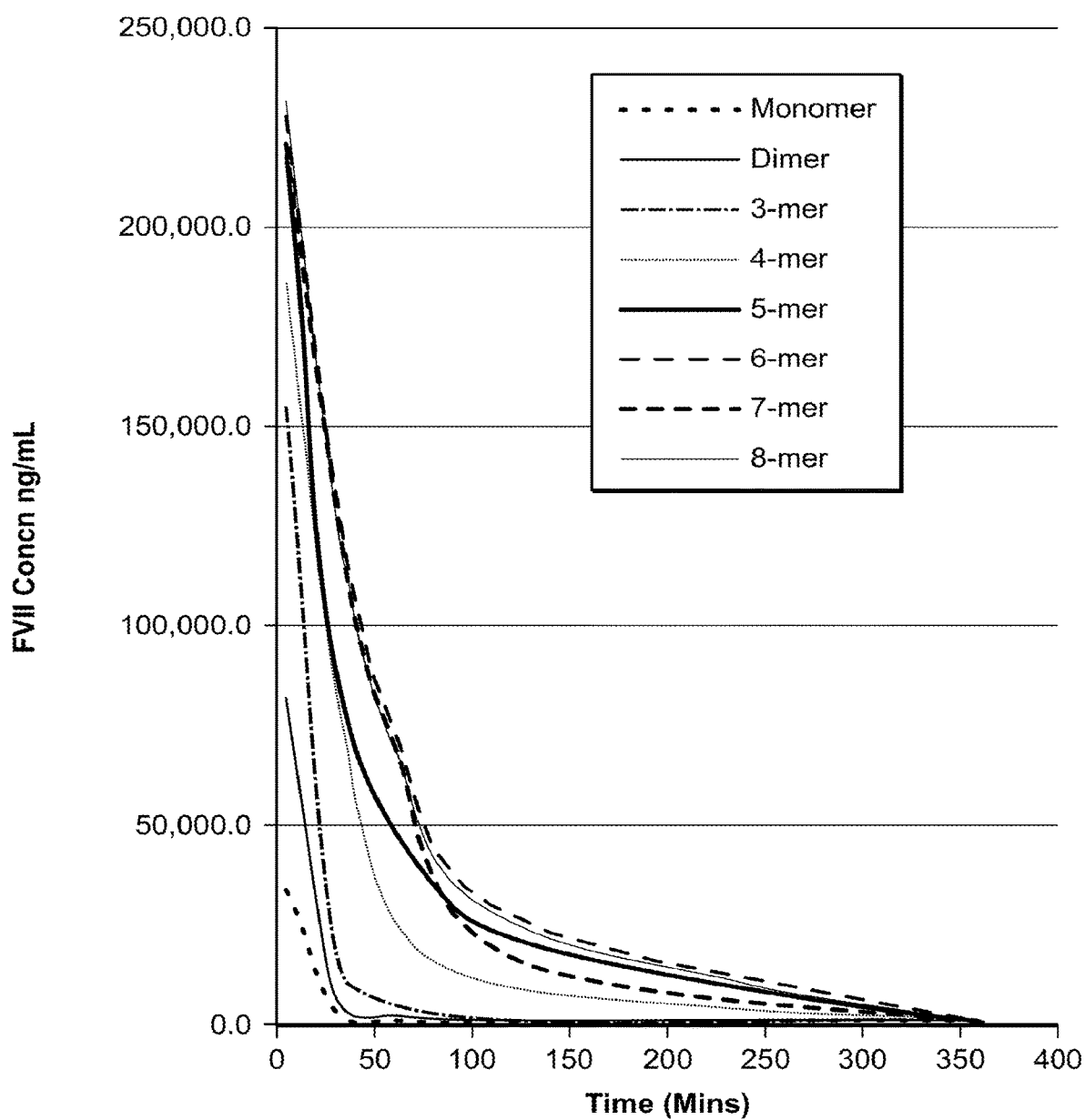
FIG. 36A presents a smooth line scatter plot of FVII siRNA levels in serum for various FVII siRNA multimers over time which is discussed in connection with Example 37.
Figure 36B:
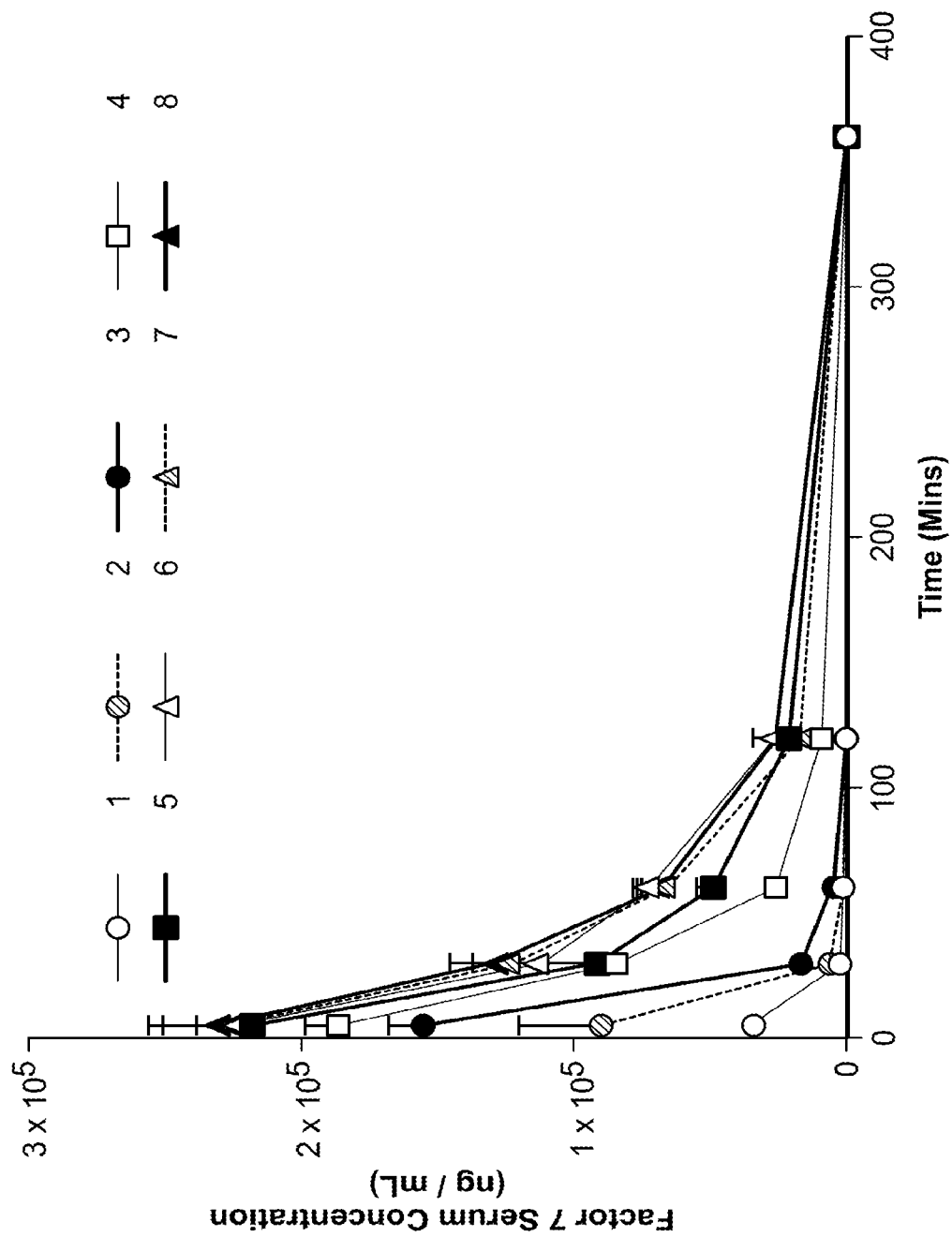
FIG. 36B presents a straight marked scatter plot of FVII siRNA levels in serum for various FVII siRNA multimers over time, which is discussed in connection with Example 37.
Figure 37A:
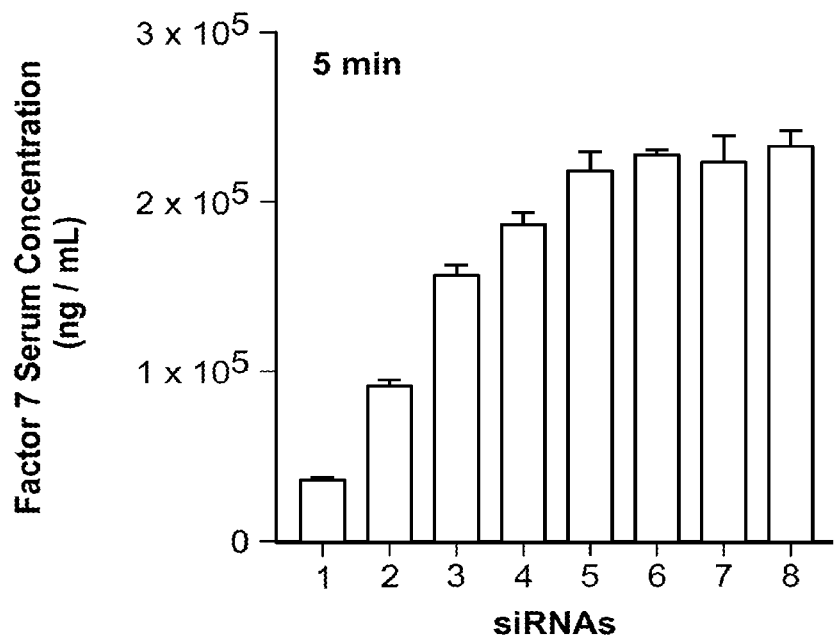
FIGS. 37A-D present bar charts of FVII siRNA levels in serum for FVII siRNA multimers at various times after administration of the respective oligonucleotides, which is discussed in connection with Example 37.
Figure 37B:
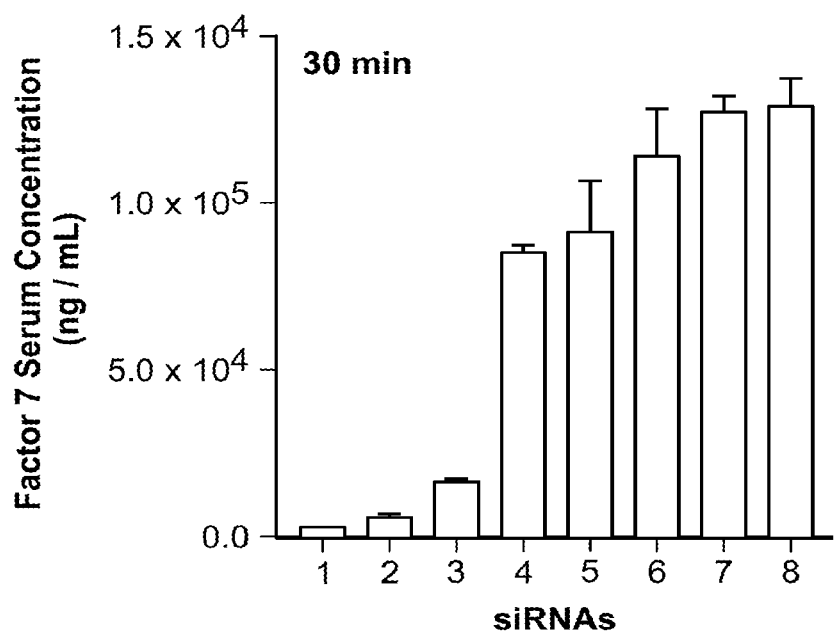
Figure 37C:
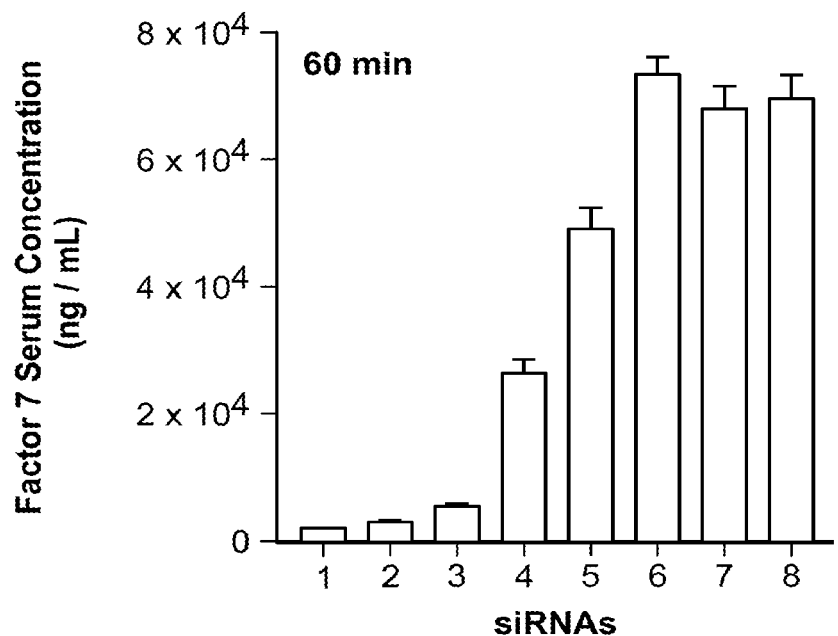
Figure 37D:
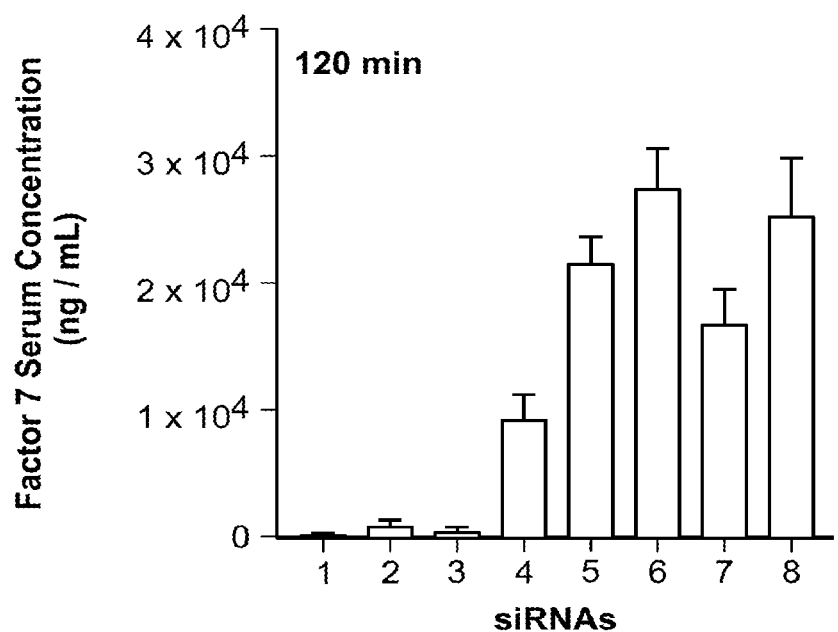

The serum half-lives of the homo-multimers XD-10635, XD-10636, XD-10637, XD-10638, XD-10639, XD-10640 and XD-10641 and the corresponding monomer XD-09794 were determined by iv bolus injection of test material at a concentration of 1 ng/ml in xl PBS via tail vein into 3 cohorts of 4 C57/BL6N female mice aged approx. 11 weeks per cohort. Dosage was 20 mg/kg for both FVII monomer and FVII multimers and blood samples were drawn at 5, 30, 60, 120 and 360 minutes. The serum samples were digested with proteinase K and a specific complementary Atto425-Peptide Nucleic Acid-fluorescent probe was hybridized to the antisense strand. Subsequent AEX-HPLC analysis enabled discrimination of intact antisense strand from metabolites leading to high specificity of the method. Only values for the intact parent compound are shown in Table 17, below and illustrated in FIGS. 36A and 36B as smooth line scatter plot and straight marked scatter plot of FVII siRNA levels in serum for FVII multimers over time, respectively.

TABLE 17

FVII siRNA levels in serum for FVII homo-multimers over time.

| Analyte ID | LLOQ | Animal ID | Group | Dose Level | Sex | Time point | [FVII] ng/mL |
|---|---|---|---|---|---|---|---|
| Saline | 1 ng/mL | S1 | 25 | 0 mg/kg | F | 7 days | BLOQ |
| Saline | 1 ng/mL | S2 | 25 | 0 mg/kg | F | 7 days | BLOQ |
| Saline | 1 ng/mL | S3 | 25 | 0 mg/kg | F | 7 days | BLOQ |
| Saline | 1 ng/mL | S4 | 25 | 0 mg/kg | F | 7 days | BLOQ |
|  |  |  |  |  |  | Mean | BLOQ |
|  |  |  |  |  |  | SD | n.a. |
| Monomer XD-09794 | 1 ng/mL | A1 | 1 | 20 mg/kg | F | 5 min | 30,988.3 |
| Monomer XD-09794 | 1 ng/mL | A2 | 1 | 20 mg/kg | F | 5 min | 32,628.0 |
| Monomer XD-09794 | 1 ng/mL | A3 | 1 | 20 mg/kg | F | 5 min | 37,508.9 |
| Monomer XD-09794 | 1 ng/mL | A4 | 1 | 20 mg/kg | F | 5 min | 35,858.3 |
|  |  |  |  |  |  | Mean | 34,245.9 |
|  |  |  |  |  |  | SD | 2,970.8 |
| Monomer XD-09794 | 1 ng/mL | A5 | 2 | 20 mg/kg | F | 30 min | 3,107.0 |
| Monomer XD-09794 | 1 ng/mL | A6 | 2 | 20 mg/kg | F | 30 min | 3,520.2 |
| Monomer XD-09794 | 1 ng/mL | A7 | 2 | 20 mg/kg | F | 30 min | 3,371.1 |
| Monomer XD-09794 | 1 ng/mL | A8 | 2 | 20 mg/kg | F | 30 min | 2,664.5 |
|  |  |  |  |  |  | Mean | 3,165.7 |
|  |  |  |  |  |  | SD | 375.3 |
| Monomer XD-09794 | 1 ng/mL | A1 | 1 | 20 mg/kg | F | 1 h | 1,339.8 |
| Monomer XD-09794 | 1 ng/mL | A2 | 1 | 20 mg/kg | F | 1 h | 953.0 |
| Monomer XD-09794 | 1 ng/mL | A3 | 1 | 20 mg/kg | F | 1 h | 1,435.8 |
| Monomer XD-09794 | 1 ng/mL | A4 | 1 | 20 mg/kg | F | 1 h | 1,730.9 |
|  |  |  |  |  |  | Mean | 1,364.9 |
|  |  |  |  |  |  | SD | 321.1 |
| Monomer XD-09794 | 1 ng/mL | A5 | 2 | 20 mg/kg | F | 2 h | 598.8 |
| Monomer XD-09794 | 1 ng/mL | A6 | 2 | 20 mg/kg | F | 2 h | 202.7 |
| Monomer XD-09794 | 1 ng/mL | A7 | 2 | 20 mg/kg | F | 2 h | 302.5 |
| Monomer XD-09794 | 1 ng/mL | A8 | 2 | 20 mg/kg | F | 2 h | 124.6 |
|  |  |  |  |  |  | Mean | 307.2 |
|  |  |  |  |  |  | SD | 207.6 |
| Monomer XD-09794 | 1 ng/mL | A9 | 3 | 20 mg/kg | F | 6 h | 4.2 |
| Monomer XD-09794 | 1 ng/mL | A10 | 3 | 20 mg/kg | F | 6 h | 4.0 |
| Monomer XD-09794 | 1 ng/mL | A11 | 3 | 20 mg/kg | F | 6 h | 3.5 |
| Monomer XD-09794 | 1 ng/mL | A12 | 3 | 20 mg/kg | F | 6 h | 14.5 |
|  |  |  |  |  |  | Mean | 6.6 |
|  |  |  |  |  |  | SD | 5.3 |
| Monomer XD-09794 | 1 ng/mL | A9 | 3 | 20 mg/kg | F | 7 days | BLOQ |
| Monomer XD-09794 | 1 ng/mL | A10 | 3 | 20 mg/kg | F | 7 days | BLOQ |
| Monomer XD-09794 | 1 ng/mL | A11 | 3 | 20 mg/kg | F | 7 days | BLOQ |

TABLE 17-continued

FVII siRNA levels in serum for FVII homo-multimers over time.

| Analyte ID | LLOQ | Animal ID | Group | Dose Level | Sex | Time point | [FVII] ng/mL |
|---|---|---|---|---|---|---|---|
| Monomer XD-09794 | 1 ng/mL | A12 | 3 | 20 mg/kg | F | 7 days | BLOQ |
| | | | | | | Mean | BLOQ |
| | | | | | | SD | n.a. |
| | | | | | | SD | |
| Dimer XD-10635 | 1 ng/mL | B1 | 4 | 20 mg/kg | F | 5 min | 82,272.1 |
| Dimer XD-10635 | 1 ng/mL | B2 | 4 | 20 mg/kg | F | 5 min | 90,574.4 |
| Dimer XD-10635 | 1 ng/mL | B3 | 4 | 20 mg/kg | F | 5 min | 94,213.6 |
| Dimer XD-10635 | 1 ng/mL | B4 | 4 | 20 mg/kg | F | 5 min | 92,612.6 |
| | | | | | | Mean | 89,918.2 |
| | | | | | | SD | 5,310.5 |
| Dimer XD-10635 | 1 ng/mL | B5 | 5 | 20 mg/kg | F | 30 min | 6,107.7 |
| Dimer XD-10635 | 1 ng/mL | B6 | 5 | 20 mg/kg | F | 30 min | 5,204.0 |
| Dimer XD-10635 | 1 ng/mL | B7 | 5 | 20 mg/kg | F | 30 min | 7,221.8 |
| Dimer XD-10635 | 1 ng/mL | B8 | 5 | 20 mg/kg | F | 30 min | 6,677.9 |
| | | | | | | Mean | 6,302.9 |
| | | | | | | SD | 862.3 |
| Dimer XD-10635 | 1 ng/mL | B1 | 4 | 20 mg/kg | F | 1 h | 2,114.2 |
| Dimer XD-10635 | 1 ng/mL | B2 | 4 | 20 mg/kg | F | 1 h | 2,911.0 |
| Dimer XD-10635 | 1 ng/mL | B3 | 4 | 20 mg/kg | F | 1 h | 2,722.5 |
| Dimer XD-10635 | 1 ng/mL | B4 | 4 | 20 mg/kg | F | 1 h | 2,092.7 |
| | | | | | | Mean | 2,460.1 |
| | | | | | | SD | 419.0 |
| Dimer XD-10635 | 1 ng/mL | B5 | 5 | 20 mg/kg | F | 2 h | 558.0 |
| Dimer XD-10635 | 1 ng/mL | B6 | 5 | 20 mg/kg | F | 2 h | 348.9 |
| Dimer XD-10635 | 1 ng/mL | B7 | 5 | 20 mg/kg | F | 2 h | 2,718.7 |
| Dimer XD-10635 | 1 ng/mL | B8 | 5 | 20 mg/kg | F | 2 h | 549.0 |
| | | | | | | Mean | 1,043.7 |
| | | | | | | SD | 1,120.9 |
| Dimer XD-10635 | 1 ng/mL | B9 | 6 | 20 mg/kg | F | 6 h | 16.9 |
| Dimer XD-10635 | 1 ng/mL | B10 | 6 | 20 mg/kg | F | 6 h | 19.6 |
| Dimer XD-10635 | 1 ng/mL | B11 | 6 | 20 mg/kg | F | 6 h | 30.3 |
| Dimer XD-10635 | 1 ng/mL | B12 | 6 | 20 mg/kg | F | 6 h | 1,273.8 |
| | | | | | | Mean | 335.2 |
| | | | | | | SD | 625.8 |
| Dimer XD-10635 | 1 ng/mL | B9 | 6 | 20 mg/kg | F | 7 days | BLOQ |
| Dimer XD-10635 | 1 ng/mL | B10 | 6 | 20 mg/kg | F | 7 days | BLOQ |
| Dimer XD-10635 | 1 ng/mL | B11 | 6 | 20 mg/kg | F | 7 days | BLOQ |
| Dimer XD-10635 | 1 ng/mL | B12 | 6 | 20 mg/kg | F | 7 days | BLOQ |
| | | | | | | Mean | BLOQ |
| | | | | | | SD | n.a. |
| Trimer XD-10636 | 1 ng/mL | C1 | 7 | 20 mg/kg | F | 5 min | 144,194.8 |
| Trimer XD-10636 | 1 ng/mL | C2 | 7 | 20 mg/kg | F | 5 min | 172,691.1 |
| Trimer XD-10636 | 1 ng/mL | C3 | 7 | 20 mg/kg | F | 5 min | 155,857.5 |
| Trimer XD-10636 | 1 ng/mL | C4 | 7 | 20 mg/kg | F | 5 min | 147,988.0 |
| | | | | | | Mean | 155,182.9 |
| | | | | | | SD | 12,642.5 |
| Trimer XD-10636 | 1 ng/mL | C5 | 8 | 20 mg/kg | F | 30 min | 15,887.3 |
| Trimer XD-10636 | 1 ng/mL | C6 | 8 | 20 mg/kg | F | 30 min | 16,202.8 |
| Trimer XD-10636 | 1 ng/mL | C7 | 8 | 20 mg/kg | F | 30 min | 17,932.3 |
| Trimer XD-10636 | 1 ng/mL | C8 | 8 | 20 mg/kg | F | 30 min | 17,537.3 |
| | | | | | | Mean | 16,889.9 |
| | | | | | | SD | 997.2 |
| Trimer XD-10636 | 1 ng/mL | C1 | 7 | 20 mg/kg | F | 1 h | 6,276.1 |
| Trimer XD-10636 | 1 ng/mL | C2 | 7 | 20 mg/kg | F | 1 h | 3,939.7 |
| Trimer XD-10636 | 1 ng/mL | C3 | 7 | 20 mg/kg | F | 1 h | 4,018.8 |
| Trimer XD-10636 | 1 ng/mL | C4 | 7 | 20 mg/kg | F | 1 h | 4,884.4 |
| | | | | | | Mean | 4,779.8 |
| | | | | | | SD | 1,085.5 |
| Trimer XD-10636 | 1 ng/mL | C5 | 8 | 20 mg/kg | F | 2 h | 102.7 |
| Trimer XD-10636 | 1 ng/mL | C6 | 8 | 20 mg/kg | F | 2 h | 197.9 |
| Trimer XD-10636 | 1 ng/mL | C7 | 8 | 20 mg/kg | F | 2 h | 1,680.9 |
| Trimer XD-10636 | 1 ng/mL | C8 | 8 | 20 mg/kg | F | 2 h | 469.5 |
| | | | | | | Mean | 612.8 |
| | | | | | | SD | 728.9 |
| Trimer XD-10636 | 1 ng/mL | C9 | 9 | 20 mg/kg | F | 6 h | 32.7 |
| Trimer XD-10636 | 1 ng/mL | C10 | 9 | 20 mg/kg | F | 6 h | 8.0 |
| Trimer XD-10636 | 1 ng/mL | C11 | 9 | 20 mg/kg | F | 6 h | 27.5 |
| Trimer XD-10636 | 1 ng/mL | C12 | 9 | 20 mg/kg | F | 6 h | 12.1 |
| | | | | | | Mean | 20.1 |
| | | | | | | SD | 11.9 |
| Trimer XD-10636 | 1 ng/mL | C9 | 9 | 20 mg/kg | F | 7 days | BLOQ |
| Trimer XD-10636 | 1 ng/mL | C10 | 9 | 20 mg/kg | F | 7 days | BLOQ |
| Trimer XD-10636 | 1 ng/mL | C11 | 9 | 20 mg/kg | F | 7 days | BLOQ |
| Trimer XD-10636 | 1 ng/mL | C12 | 9 | 20 mg/kg | F | 7 days | BLOQ |
| | | | | | | Mean | BLOQ |
| | | | | | | SD | n.a. |
| Tetramer XD-10637 | 1 ng/mL | D1 | 10 | 20 mg/kg | F | 5 min | 174,506.7 |
| Tetramer XD-10637 | 1 ng/mL | D2 | 10 | 20 mg/kg | F | 5 min | 184,149.5 |
| Tetramer XD-10637 | 1 ng/mL | D3 | 10 | 20 mg/kg | F | 5 min | 180,077.0 |
| Tetramer XD-10637 | 1 ng/mL | D4 | 10 | 20 mg/kg | F | 5 min | 204,796.1 |
| | | | | | | Mean | 185,882.3 |
| | | | | | | SD | 13,214.1 |
| Tetramer XD-10637 | 1 ng/mL | D5 | 11 | 20 mg/kg | F | 30 min | 89,104.1 |
| Tetramer XD-10637 | 1 ng/mL | D6 | 11 | 20 mg/kg | F | 30 min | 88,408.8 |
| Tetramer XD-10637 | 1 ng/mL | D7 | 11 | 20 mg/kg | F | 30 min | 79,389.4 |
| Tetramer XD-10637 | 1 ng/mL | D8 | 11 | 20 mg/kg | F | 30 min | 83,820.0 |
| | | | | | | Mean | 85,180.6 |
| | | | | | | SD | 4,516.8 |
| Tetramer XD-10637 | 1 ng/mL | D1 | 10 | 20 mg/kg | F | 1 h | 25,278.6 |
| Tetramer XD-10637 | 1 ng/mL | D2 | 10 | 20 mg/kg | F | 1 h | 24,494.1 |
| Tetramer XD-10637 | 1 ng/mL | D3 | 10 | 20 mg/kg | F | 1 h | 23,070.4 |

TABLE 17-continued

FVII siRNA levels in serum for FVII homo-multimers over time.

| Analyte ID | LLOQ | Animal ID | Group | Dose Level | Sex | Time point | [FVII] ng/mL |
|---|---|---|---|---|---|---|---|
| Tetramer XD-10637 | 1 ng/mL | D4 | 10 | 20 mg/kg | F | 1 h | 31,567.0 |
| | | | | | | Mean | 26,102.5 |
| | | | | | | SD | 3,755.9 |
| Tetramer XD-10637 | 1 ng/mL | D5 | 11 | 20 mg/kg | F | 2 h | 9,191.5 |
| Tetramer XD-10637 | 1 ng/mL | D6 | 11 | 20 mg/kg | F | 2 h | 8,969.4 |
| Tetramer XD-10637 | 1 ng/mL | D7 | 11 | 20 mg/kg | F | 2 h | 5,059.5 |
| Tetramer XD-10637 | 1 ng/mL | D8 | 11 | 20 mg/kg | F | 2 h | 14,666.2 |
| | | | | | | Mean | 9,471.7 |
| | | | | | | SD | 3,948.9 |
| Tetramer XD-10637 | 1 ng/mL | D9 | 12 | 20 mg/kg | F | 6 h | 15.4 |
| Tetramer XD-10637 | 1 ng/mL | D10 | 12 | 20 mg/kg | F | 6 h | 254.3 |
| Tetramer XD-10637 | 1 ng/mL | D11 | 12 | 20 mg/kg | F | 6 h | 58.3 |
| Tetramer XD-10637 | 1 ng/mL | D12 | 12 | 20 mg/kg | F | 6 h | 17.5 |
| | | | | | | Mean | 86.4 |
| | | | | | | SD | 113.7 |
| Tetramer XD-10637 | 1 ng/mL | D9 | 12 | 20 mg/kg | F | 7 days | BLOQ |
| Tetramer XD-10637 | 1 ng/mL | D10 | 12 | 20 mg/kg | F | 7 days | BLOQ |
| Tetramer XD-10637 | 1 ng/mL | D11 | 12 | 20 mg/kg | F | 7 days | BLOQ |
| Tetramer XD-10637 | 1 ng/mL | D12 | 12 | 20 mg/kg | F | 7 days | BLOQ |
| | | | | | | Mean | BLOQ |
| | | | | | | SD | n.a. |
| Pentamer XD-10638 | 1 ng/mL | E1 | 13 | 20 mg/kg | F | 5 min | 201,669.6 |
| Pentamer XD-10638 | 1 ng/mL | E2 | 13 | 20 mg/kg | F | 5 min | 214,525.8 |
| Pentamer XD-10638 | 1 ng/mL | E3 | 13 | 20 mg/kg | F | 5 min | 247,544.7 |
| Pentamer XD-10638 | 1 ng/mL | E4 | 13 | 20 mg/kg | F | 5 min | 207,872.5 |
| | | | | | | Mean | 217,903.2 |
| | | | | | | SD | 20,446.4 |
| Pentamer XD-10638 | 1 ng/mL | E5 | 14 | 20 mg/kg | F | 30 min | 112,318.2 |
| Pentamer XD-10638 | 1 ng/mL | E6 | 14 | 20 mg/kg | F | 30 min | 110,786.0 |
| Pentamer XD-10638 | 1 ng/mL | E7 | 14 | 20 mg/kg | F | 30 min | 94,714.7 |
| Pentamer XD-10638 | 1 ng/mL | E8 | 14 | 20 mg/kg | F | 30 min | 47,610.6 |
| | | | | | | Mean | 91,357.4 |
| | | | | | | SD | 30,231.8 |
| Pentamer XD-10638 | 1 ng/mL | E1 | 13 | 20 mg/kg | F | 1 h | 48,800.2 |
| Pentamer XD-10638 | 1 ng/mL | E2 | 13 | 20 mg/kg | F | 1 h | 46,770.8 |
| Pentamer XD-10638 | 1 ng/mL | E3 | 13 | 20 mg/kg | F | 1 h | 57,711.0 |
| Pentamer XD-10638 | 1 ng/mL | E4 | 13 | 20 mg/kg | F | 1 h | 42,458.4 |
| | | | | | | Mean | 48,935.1 |
| | | | | | | SD | 6,420.4 |
| Pentamer XD-10638 | 1 ng/mL | E5 | 14 | 20 mg/kg | F | 2 h | 19,806.0 |
| Pentamer XD-10638 | 1 ng/mL | E6 | 14 | 20 mg/kg | F | 2 h | 20,633.6 |
| Pentamer XD-10638 | 1 ng/mL | E7 | 14 | 20 mg/kg | F | 2 h | 18,214.2 |
| Pentamer XD-10638 | 1 ng/mL | E8 | 14 | 20 mg/kg | F | 2 h | 27,970.4 |
| | | | | | | Mean | 21,656.1 |
| | | | | | | SD | 4,327.6 |
| Pentamer XD-10638 | 1 ng/mL | E9 | 15 | 20 mg/kg | F | 6 h | 16.4 |
| Pentamer XD-10638 | 1 ng/mL | E10 | 15 | 20 mg/kg | F | 6 h | 15.7 |
| Pentamer XD-10638 | 1 ng/mL | E11 | 15 | 20 mg/kg | F | 6 h | 14.2 |
| Pentamer XD-10638 | 1 ng/mL | E12 | 15 | 20 mg/kg | F | 6 h | 49.4 |
| | | | | | | Mean | 23.9 |
| | | | | | | SD | 17.0 |
| Pentamer XD-10638 | 1 ng/mL | E9 | 15 | 20 mg/kg | F | 7 days | BLOQ |
| Pentamer XD-10638 | 1 ng/mL | E10 | 15 | 20 mg/kg | F | 7 days | BLOQ |
| Pentamer XD-10638 | 1 ng/mL | E11 | 15 | 20 mg/kg | F | 7 days | BLOQ |
| Pentamer XD-10638 | 1 ng/mL | E12 | 15 | 20 mg/kg | F | 7 days | BLOQ |
| | | | | | | Mean | BLOQ |
| | | | | | | SD | n.a. |
| Hexamer XD-10639 | 1 ng/mL | F1 | 16 | 20 mg/kg | F | 5 min | 221,882.0 |
| Hexamer XD-10639 | 1 ng/mL | F2 | 16 | 20 mg/kg | F | 5 min | 227,901.1 |
| Hexamer XD-10639 | 1 ng/mL | F3 | 16 | 20 mg/kg | F | 5 min | 230,969.3 |
| Hexamer XD-10639 | 1 ng/mL | F4 | 16 | 20 mg/kg | F | 5 min | 229,232.9 |
| | | | | | | Mean | 227,496.3 |
| | | | | | | SD | 3,948.1 |
| Hexamer XD-10639 | 1 ng/mL | F5 | 17 | 20 mg/kg | F | 30 min | 125,871.8 |
| Hexamer XD-10639 | 1 ng/mL | F6 | 17 | 20 mg/kg | F | 30 min | 145,598.8 |
| Hexamer XD-10639 | 1 ng/mL | F7 | 17 | 20 mg/kg | F | 30 min | 76,775.7 |
| Hexamer XD-10639 | 1 ng/mL | F8 | 17 | 20 mg/kg | F | 30 min | 107,085.3 |
| | | | | | | Mean | 113,832.9 |
| | | | | | | SD | 29,284.7 |
| Hexamer XD-10639 | 1 ng/mL | F1 | 16 | 20 mg/kg | F | 1 h | 69,114.9 |
| Hexamer XD-10639 | 1 ng/mL | F2 | 16 | 20 mg/kg | F | 1 h | 76,580.8 |
| Hexamer XD-10639 | 1 ng/mL | F3 | 16 | 20 mg/kg | F | 1 h | 68,920.5 |
| Hexamer XD-10639 | 1 ng/mL | F4 | 16 | 20 mg/kg | F | 1 h | 78,412.0 |
| | | | | | | Mean | 73,257.1 |
| | | | | | | SD | 4,952.6 |
| Hexamer XD-10639 | 1 ng/mL | F5 | 17 | 20 mg/kg | F | 2 h | 25,963.0 |
| Hexamer XD-10639 | 1 ng/mL | F6 | 17 | 20 mg/kg | F | 2 h | 33,380.4 |
| Hexamer XD-10639 | 1 ng/mL | F7 | 17 | 20 mg/kg | F | 2 h | 19,372.0 |
| Hexamer XD-10639 | 1 ng/mL | F8 | 17 | 20 mg/kg | F | 2 h | 31,798.1 |
| | | | | | | Mean | 27,628.4 |
| | | | | | | SD | 6,361.7 |
| Hexamer XD-10639 | 1 ng/mL | F9 | 18 | 20 mg/kg | F | 6 h | 52.7 |
| Hexamer XD-10639 | 1 ng/mL | F10 | 18 | 20 mg/kg | F | 6 h | 33.1 |
| Hexamer XD-10639 | 1 ng/mL | F11 | 18 | 20 mg/kg | F | 6 h | 69.4 |
| Hexamer XD-10639 | 1 ng/mL | F12 | 18 | 20 mg/kg | F | 6 h | 47.3 |
| | | | | | | Mean | 50.6 |
| | | | | | | SD | 15.0 |

TABLE 17-continued

FVII siRNA levels in serum for FVII homo-multimers over time.

| Analyte ID | LLOQ | Animal ID | Group | Dose Level | Sex | Time point | [FVII] ng/mL |
|---|---|---|---|---|---|---|---|
| Hexamer XD-10639 | 1 ng/mL | F9 | 18 | 20 mg/kg | F | 7 days | BLOQ |
| Hexamer XD-10639 | 1 ng/mL | F10 | 18 | 20 mg/kg | F | 7 days | BLOQ |
| Hexamer XD-10639 | 1 ng/mL | F11 | 18 | 20 mg/kg | F | 7 days | BLOQ |
| Hexamer XD-10639 | 1 ng/mL | F12 | 18 | 20 mg/kg | F | 7 days | 3.4 |
|  |  |  |  |  |  | Mean | BLOQ |
|  |  |  |  |  |  | SD | n.a. |
| Heptamer XD-10640 | 1 ng/mL | G1 | 19 | 20 mg/kg | F | 5 min | 189,155.8 |
| Heptamer XD-10640 | 1 ng/mL | G2 | 19 | 20 mg/kg | F | 5 min | 203,092.8 |
| Heptamer XD-10640 | 1 ng/mL | G3 | 19 | 20 mg/kg | F | 5 min | 227,234.0 |
| Heptamer XD-10640 | 1 ng/mL | G4 | 19 | 20 mg/kg | F | 5 min | 266,250.0 |
|  |  |  |  |  |  | Mean | 221,433.2 |
|  |  |  |  |  |  | SD | 33,765.8 |
| Heptamer XD-10640 | 1 ng/mL | G5 | 20 | 20 mg/kg | F | 30 min | 123,590.6 |
| Heptamer XD-10640 | 1 ng/mL | G6 | 20 | 20 mg/kg | F | 30 min | 119,556.1 |
| Heptamer XD-10640 | 1 ng/mL | G7 | 20 | 20 mg/kg | F | 30 min | 120,686.6 |
| Heptamer XD-10640 | 1 ng/mL | G8 | 20 | 20 mg/kg | F | 30 min | 142,606.4 |
|  |  |  |  |  |  | Mean | 126,609.9 |
|  |  |  |  |  |  | SD | 10,798.9 |
| Heptamer XD-10640 | 1 ng/mL | G1 | 19 | 20 mg/kg | F | 1 h | 73,022.3 |
| Heptamer XD-10640 | 1 ng/mL | G2 | 19 | 20 mg/kg | F | 1 h | 58,856.0 |
| Heptamer XD-10640 | 1 ng/mL | G3 | 19 | 20 mg/kg | F | 1 h | 64,204.3 |
| Heptamer XD-10640 | 1 ng/mL | G4 | 19 | 20 mg/kg | F | 1 h | 74,596.0 |
|  |  |  |  |  |  | Mean | 67,669.7 |
|  |  |  |  |  |  | SD | 7,445.7 |
| Heptamer XD-10640 | 1 ng/mL | G5 | 20 | 20 mg/kg | F | 2 h | 13,907.3 |
| Heptamer XD-10640 | 1 ng/mL | G6 | 20 | 20 mg/kg | F | 2 h | 12,667.2 |
| Heptamer XD-10640 | 1 ng/mL | G7 | 20 | 20 mg/kg | F | 2 h | 17,123.0 |
| Heptamer XD-10640 | 1 ng/mL | G8 | 20 | 20 mg/kg | F | 2 h | 24,537.2 |
|  |  |  |  |  |  | Mean | 17,058.7 |
|  |  |  |  |  |  | SD | 5,327.6 |
| Heptamer XD-10640 | 1 ng/mL | G9 | 21 | 20 mg/kg | F | 6 h | 45.5 |
| Heptamer XD-10640 | 1 ng/mL | G10 | 21 | 20 mg/kg | F | 6 h | 151.3 |
| Heptamer XD-10640 | 1 ng/mL | G11 | 21 | 20 mg/kg | F | 6 h | 56.1 |
| Heptamer XD-10640 | 1 ng/mL | G12 | 21 | 20 mg/kg | F | 6 h | 58.7 |
|  |  |  |  |  |  | Mean | 77.9 |
|  |  |  |  |  |  | SD | 49.3 |
| Heptamer XD-10640 | 1 ng/mL | G9 | 21 | 20 mg/kg | F | 7 days | BLOQ |
| Heptamer XD-10640 | 1 ng/mL | G10 | 21 | 20 mg/kg | F | 7 days | BLOQ |
| Heptamer XD-10640 | 1 ng/mL | G11 | 21 | 20 mg/kg | F | 7 days | BLOQ |
| Heptamer XD-10640 | 1 ng/mL | G12 | 21 | 20 mg/kg | F | 7 days | BLOQ |
|  |  |  |  |  |  | Mean | BLOQ |
|  |  |  |  |  |  | SD | n.a. |
| Octamer XD-10641 | 1 ng/mL | H1 | 22 | 20 mg/kg | F | 5 min | 203,428.1 |
| Octamer XD-10641 | 1 ng/mL | H2 | 22 | 20 mg/kg | F | 5 min | 231,234.5 |
| Octamer XD-10641 | 1 ng/mL | H3 | 22 | 20 mg/kg | F | 5 min | 243,057.5 |
| Octamer XD-10641 | 1 ng/mL | H4 | 22 | 20 mg/kg | F | 5 min | 246,973.6 |
|  |  |  |  |  |  | Mean | 231,173.4 |
|  |  |  |  |  |  | SD | 19,669.6 |
| Octamer XD-10641 | 1 ng/mL | H5 | 23 | 20 mg/kg | F | 30 min | 152,545.2 |
| Octamer XD-10641 | 1 ng/mL | H6 | 23 | 20 mg/kg | F | 30 min | 116,917.0 |
| Octamer XD-10641 | 1 ng/mL | H7 | 23 | 20 mg/kg | F | 30 min | 127,392.7 |
| Octamer XD-10641 | 1 ng/mL | H8 | 23 | 20 mg/kg | F | 30 min | 119,659.9 |
|  |  |  |  |  |  | Mean | 129,128.7 |
|  |  |  |  |  |  | SD | 16,228.9 |
| Octamer XD-10641 | 1 ng/mL | H1 | 22 | 20 mg/kg | F | 1 h | 59,270.6 |
| Octamer XD-10641 | 1 ng/mL | H2 | 22 | 20 mg/kg | F | 1 h | 67,819.6 |
| Octamer XD-10641 | 1 ng/mL | H3 | 22 | 20 mg/kg | F | 1 h | 74,942.8 |
| Octamer XD-10641 | 1 ng/mL | H4 | 22 | 20 mg/kg | F | 1 h | 75,228.9 |
|  |  |  |  |  |  | Mean | 69,315.5 |
|  |  |  |  |  |  | SD | 7,522.7 |
| Octamer XD-10641 | 1 ng/mL | H5 | 23 | 20 mg/kg | F | 2 h | 37,353.7 |
| Octamer XD-10641 | 1 ng/mL | H6 | 23 | 20 mg/kg | F | 2 h | 16,390.7 |
| Octamer XD-10641 | 1 ng/mL | H7 | 23 | 20 mg/kg | F | 2 h | 27,527.3 |
| Octamer XD-10641 | 1 ng/mL | H8 | 23 | 20 mg/kg | F | 2 h | 20,359.7 |
|  |  |  |  |  |  | Mean | 25,407.9 |
|  |  |  |  |  |  | SD | 9,201.2 |
| Octamer XD-10641 | 1 ng/mL | H9 | 24 | 20 mg/kg | F | 6 h | 81.2 |
| Octamer XD-10641 | 1 ng/mL | H10 | 24 | 20 mg/kg | F | 6 h | 76.9 |
| Octamer XD-10641 | 1 ng/mL | H11 | 24 | 20 mg/kg | F | 6 h | 162.5 |
| Octamer XD-10641 | 1 ng/mL | H12 | 24 | 20 mg/kg | F | 6 h | 138.5 |
|  |  |  |  |  |  | Mean | 114.8 |
|  |  |  |  |  |  | SD | 42.4 |
| Octamer XD-10641 | 1 ng/mL | H9 | 24 | 20 mg/kg | F | 7 days | BLOQ |
| Octamer XD-10641 | 1 ng/mL | H10 | 24 | 20 mg/kg | F | 7 days | BLOQ |
| Octamer XD-10641 | 1 ng/mL | H11 | 24 | 20 mg/kg | F | 7 days | BLOQ |
| Octamer XD-10641 | 1 ng/mL | H12 | 24 | 20 mg/kg | F | 7 days | BLOQ |
|  |  |  |  |  |  | Mean | BLOQ |
|  |  |  |  |  |  | SD | n.a. |

FIGS. 37A, 37B, 37C, and 37D show bar chart graphs of FVII siRNA levels in serum for FVII multimers at 5 minutes, 30 minutes, 60 minutes, and 120 minutes, respectively.

FIGS. 38A and 38B show total FVII siRNA levels in serum, as represented by area under the curve, for FVII multimers, in ng*min/mL and normalized to monomer AUC value.

TABLE 18

Area under the curve values for FVII siRNA monomer and multimers.

|  | Monomer | Dimer | 3-mer | 4-mer | 5-mer | 6-mer | 7-mer | 8-mer |
|---|---|---|---|---|---|---|---|---|
| 5 | 34,245.0 | 82272 | 155182 | 185882 | 217903 | 227496 | 221433 | 231173 |
| 30 | 3,165.0 | 6302 | 16889 | 85180 | 91357 | 133832 | 126609 | 129128 |
| 60 | 1,364.0 | 2460 | 4779 | 26102 | 48935 | 73257 | 67669 | 69315 |
| 120 | 307.0 | 1043 | 612 | 9471 | 21656 | 27268 | 17058 | 25407 |
| 360 | 6.6 | 625 | 20 | 86 | 23.9 | 50.6 | 77 | 115 |
| Total AUC (min * ng/mL) | 621727 | 1604630 | 2713490 | 7271583 | 10689448 | 13420917 | 11862813 | 13384588 |
| AUC, Normalized to Monomer | 1.0 | 2.6 | 4.4 | 11.7 | 17.2 | 21.6 | 19.1 | 21.5 |

The serum half-lives of the multimers were calculated from FVII concentration data using non-linear one phase decay according to the following equation:

$$Y=(Y0-\text{Plateau})*\exp(-k*x)+\text{Plateau}$$

wherein Y is the concentration at time X and the half-life is the natural log of 2/k. 4 different assumptions concerning the initial and final conditions were applied as follows:
1: No assumptions made about the data
2: All siRNAs were injected at the same initial concentration (i.e., the Conc at t=0 is the same for all).
3: All siRNA concentrations all decay to 0 at t=infinity.
4: All siRNAs were injected at the same initial concentration (i.e., the Conc at t=0 is the same for all) and all siRNA concentrations all decay to 0 at t=infinity.

TABLE 19

Calculated serum half-lives of FVII siRNA homo-multimers.

|  | Monomer | Dimer | 3-mer | 4-mer | 5-mer | 6-mer | 7-mer | 8-mer |
|---|---|---|---|---|---|---|---|---|
| ½ life, no assumptions (min) | 7.10 | 6.10 | 7.63 | 20.82 | 20.65 | 29.1 | 31.66 | 30.81 |
| ½ life, all samples plateau to 0 (min) | 7.37 | 6.59 | 7.93 | 21.23 | 23.38 | 31.50 | 31.62 | 31.92 |
| ½ life, all samples start with same initial value = 231173 | 1.80 | 3.61 | 8.39 | 19.29 | 24.21 | 33.65 | 35.07 | 36.63 |
| ½ life, all samples start with same initial value = 123173, and plateau to 0 (min) | 1.81 | 3.68 | 8.45 | 19.88 | 25.83 | 34.72 | 34.39 | 36.49 |

Figure 39:
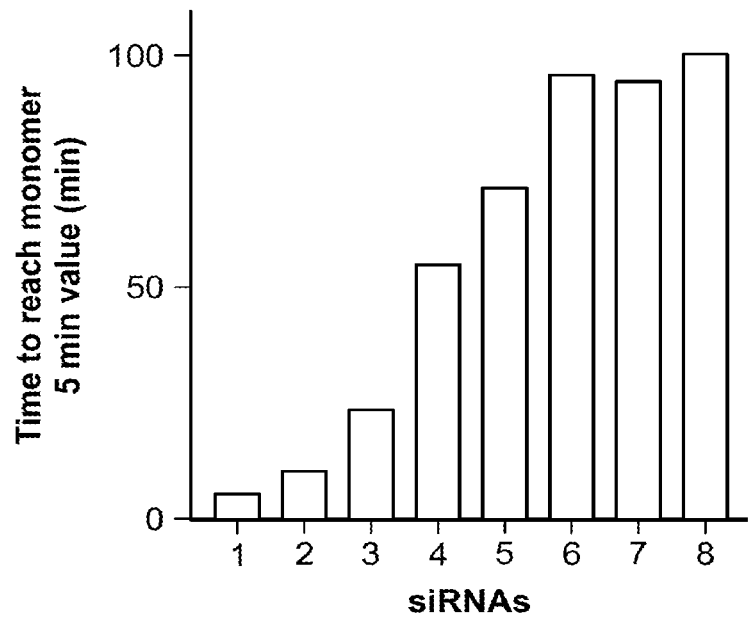
FIG. 39 presents a bar chart of time taken for multimers to reach the same FVII siRNA serum concentrations as the monomer at 5 minutes, which is discussed in connection with Example 38.

Example 38: Calculation of Time Taken for FVII siRNA Homo-Multimers to Reach Same FVII siRNA Concentration as Monomer at 5 Minutes Because the FVII concentration of the monomer was already significantly less than 50% of that injected at the first sample time (5 minutes) the time taken for the serum FVII levels of the multimers to equal that of the monomer at 5 minutes were also calculated using the following equation:

$$Y=(Y0-\text{Plateau})*\exp(-k*x)+\text{Plateau}$$

wherein Plateau was set at the concentration of monomer at 5 minutes (34,245 ng/ml) and shown in FIG. 39.

The following calculations were performed to determine the time in minutes for FVII siRNA homo-multimers to reach concentration of FVII siRNA monomer at 5 minutes:

$Y=(Y0-\text{Plateau})*\exp(-k*x)+\text{Plateau}$, where $x$ is time in minutes $34245=(231173-0)*e^{(-kx)}+0$, where $x$ is minutes $34245=231173*e^{(-kx)}$ $0.14813453=e^{-kx}$ $\ln(0.14813453)=kx$ $-1.909625779=kx$

TABLE 20

Calculated times for FVII siRNA homo-multimers to reach concentration of FVII siRNA monomer at 5 minutes.

|  | Monomer | Dimer | 3-mer | 4-mer | 5-mer | 6-mer | 7-mer | 8-mer |
|---|---|---|---|---|---|---|---|---|
| k values for different constructs | 0.3819 | 0.1882 | 0.08203 | 0.03487 | 0.02683 | 0.01996 | 0.02015 | 0.019 |
| Time (min) | 5.0 | 10.1 | 23.3 | 54.8 | 71.2 | 95.7 | 94.8 | 100.5 |

The invention claimed is:

1. A multimeric oligonucleotide comprising 4 or more subunits -------, wherein:
   each of the subunits ------- is independently a single- or double-stranded oligonucleotide;
   each of the subunits ------- is joined to another subunit by a covalent linker ●;
   at least one of the single- or double-stranded subunits within the multimeric oligonucleotide comprises a covalent linker ● joined to the 3' terminus and a covalent linker ● joined to the 5' terminus of a single strand within the subunit; and
   the molecular weight of the multimeric oligonucleotide is at least 45 kD.

2. The multimeric oligonucleotide of claim 1, wherein the multimeric oligonucleotide has a molecular weight of at least 45-50, 50-55, 55-60, 60-65, 65-70, or 70-75 kD.

3. The multimeric oligonucleotide of claim 1, wherein multimeric oligonucleotide comprises 5 or more subunits.

4. The multimeric oligonucleotide of claim 1, wherein multimeric oligonucleotide comprises 6 or more subunits.

5. The multimeric oligonucleotide of claim 1, further comprising one or more targeting ligands.

6. The multimeric oligonucleotide of claim 5, wherein at least one of the subunits ------- is a targeting ligand.

7. The multimeric oligonucleotide of claim 1, wherein the multimeric oligonucleotide comprises Structure 21:

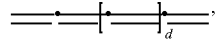
(Structure 21)

wherein n is an integer greater than or equal to 1.

8. The multimeric oligonucleotide of claim 7, wherein n is greater than or equal to 1 and less than or equal to 5.

9. The multimeric oligonucleotide of claim 7, wherein the multimeric oligonucleotide comprises Structure 54:

(Structure 54)

wherein:
   each subunit ------- is independently a double-stranded oligonucleotide ———; and
   d is an integer greater than or equal to 1.

10. The multimeric oligonucleotide of claim 9, wherein Structure 54 is Structure 28:

(Structure 28)

11. The multimeric oligonucleotide of claim 9, wherein Structure 54 is Structure 30:

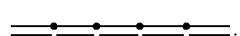
(Structure 30)

12. The multimeric oligonucleotide of claim 1, wherein the multimeric oligonucleotide does not comprise PEG, a polyether compound, or a polymer other than oligonucleotide.

13. The multimeric oligonucleotide of claim 1, comprising two or more different covalent linkers.

14. The multimeric oligonucleotide of claim 7, wherein the multimeric oligonucleotide comprises:

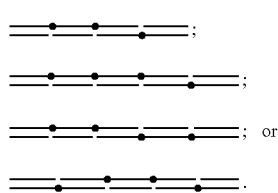

(Structure 29);

(Structure 31);

(Structure 32); or (Structure 33).

15. The multimeric oligonucleotide of claim 7, wherein the multimeric oligonucleotide comprises:

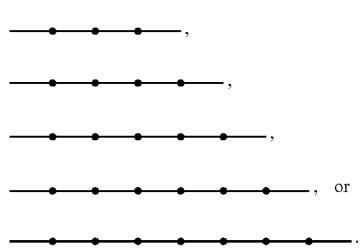

(Structure 34), (Structure 39), (Structure 35), (Structure 40), or (Structure 37).

16. The multimeric oligonucleotide of claim 2, wherein one or more of the covalent linkers in the multimeric oligonucleotide comprises a cleavable covalent linker.

17. The multimeric oligonucleotide of claim 16, wherein the cleavable covalent linker contains an acid cleavable bond, a reductant cleavable bond, a bio-cleavable bond, or an enzyme cleavable bond all of the covalent linkers in the multimeric oligonucleotide are cleavable covalent linkers.

18. A method of synthesizing a multimeric oligonucleotide comprising Structure 51:

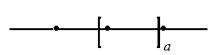

(Structure 51)

wherein each ——— is a single stranded oligonucleotide, each ● is a covalent linker joining adjacent single stranded oligonucleotides, and a is an integer ≥1, the method comprising the steps of:

(i) reacting

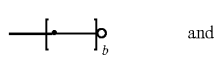

(Structure 52)

and

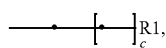

(Structure 53)

wherein ○ is a linking moiety, R1 is a chemical group capable of reacting with the linking moiety ○, b and c are each independently an integer ≥0, b and c cannot both simultaneously be zero, and b+c=a, thereby forming Structure 51:

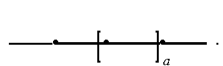

(Structure 51)

19. A method of synthesizing a multimeric oligonucleotide comprising Structure 54:

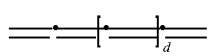

(Structure 54)

wherein each ——— is a single stranded oligonucleotide, each ● is a covalent linker joining adjacent single stranded oligonucleotides, and a >1, the method comprising the steps of:

(i) annealing Structure 51:

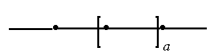

(Structure 51)

with complementary single stranded oligonucleotides ———, thereby forming Structure 54:

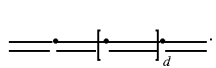

(Structure 54)

* * * * *

SEQUENCE LISTING

<160> NUMBER OF SEQ ID NOS: 155

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
gcaaaggcgu gccaacucat                                                     20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
gcaaaggcgu gccaacucat                                                     20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
gcaaaggcgu gccaacucat                                                     20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
gcaaaggcgu gccaacucat                                                    20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
gcaaaggcgu gccaacucat                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
gcaaaggcgu gccaacucat                                                    20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
ugaguuggca cgccuuugcu ut                                                 22

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ugaguuggca cgccuuugcu u                                                  21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ugaguuggca cgccuuugcu u                                                  21

<210> SEQ ID NO 10
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
cuauuuggag agaaaucgat                                                 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
cuauuuggag agaaaucgat                                                 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
cuauuuggag agaaaucgat                                                 20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
ggaucaucuc aagucuuact t                                               21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
guaagacuug agaugaucct t                                               21

<210> SEQ ID NO 15
```

```
<400> SEQUENCE: 15

000

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
gcaaaggcgu gccaacucat t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
ugaguuggca cgccuuugct t                                              21

<210> SEQ ID NO 18

<400> SEQUENCE: 18

000

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ggaaucuuau auuugaucca a                                              21

<210> SEQ ID NO 20
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uuggaucaaa uauaagauuc ccu                                            23

<210> SEQ ID NO 21

<400> SEQUENCE: 21

000

<210> SEQ ID NO 22
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
cuuacgcuga guacuucgat t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
ucgaaguacu cagcguaagt t                                              21

<210> SEQ ID NO 24

<400> SEQUENCE: 24

000

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
gcaaaggcgu gccaacucat                                                20

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ugaguuggca cgccuuugcu u                                              21

<210> SEQ ID NO 27

<400> SEQUENCE: 27

000

<210> SEQ ID NO 28
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
cuauuuggag agaaaucgat                                                    20

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ucgauuucuc uccaaauagu u                                                  21

<210> SEQ ID NO 30

<400> SEQUENCE: 30

000

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
aacaguguuc uugcucuaua at                                                 22

<210> SEQ ID NO 32
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
uuauagagca agaacacugu uuu                                                23

<210> SEQ ID NO 33

<400> SEQUENCE: 33

000

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 34
```

```
gcaaaggcgu gccaacucat                                          20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
gcaaaggcgu gccaacucat                                          20

<210> SEQ ID NO 36

<400> SEQUENCE: 36

000

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ggaaucuuau auuugaucca a                                        21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
ggaucaucuc aagucuuact t                                        21

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
gcaaaggcgu gccaacucat                                          20

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 40
ugaguuggca cgccuuugcu u                                              21

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
gcaaaggcgu gccaacucat                                                20

<210> SEQ ID NO 42

<400> SEQUENCE: 42

000

<210> SEQ ID NO 43

<400> SEQUENCE: 43

000

<210> SEQ ID NO 44
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
uuauagagca agaacacugu uuu                                            23

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
aacaguguuc uugcucuaua at                                             22

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
gcaaaggcgu gccaacucat                                                20
```

```
<210> SEQ ID NO 47
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
uuauagagca agaacacugu uuu                                              23

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
aacaguguuc uugcucuaua at                                               22

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
gcaaaggcgu gccaacucat                                                  20

<210> SEQ ID NO 53

<400> SEQUENCE: 53

000

<210> SEQ ID NO 54

<400> SEQUENCE: 54
```

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66
<400> SEQUENCE: 66
000

<210> SEQ ID NO 67
<400> SEQUENCE: 67
000

<210> SEQ ID NO 68
<400> SEQUENCE: 68
000

<210> SEQ ID NO 69
<400> SEQUENCE: 69
000

<210> SEQ ID NO 70
<400> SEQUENCE: 70
000

<210> SEQ ID NO 71
<400> SEQUENCE: 71
000

<210> SEQ ID NO 72
<400> SEQUENCE: 72
000

<210> SEQ ID NO 73
<400> SEQUENCE: 73
000

<210> SEQ ID NO 74
<400> SEQUENCE: 74
000

<210> SEQ ID NO 75
<400> SEQUENCE: 75
000

<210> SEQ ID NO 76
<400> SEQUENCE: 76
000

<210> SEQ ID NO 77

```
<400> SEQUENCE: 77
000

<210> SEQ ID NO 78
<400> SEQUENCE: 78
000

<210> SEQ ID NO 79
<400> SEQUENCE: 79
000

<210> SEQ ID NO 80
<400> SEQUENCE: 80
000

<210> SEQ ID NO 81
<400> SEQUENCE: 81
000

<210> SEQ ID NO 82
<400> SEQUENCE: 82
000

<210> SEQ ID NO 83
<400> SEQUENCE: 83
000

<210> SEQ ID NO 84
<400> SEQUENCE: 84
000

<210> SEQ ID NO 85
<400> SEQUENCE: 85
000

<210> SEQ ID NO 86
<400> SEQUENCE: 86
000

<210> SEQ ID NO 87
<400> SEQUENCE: 87
000

<210> SEQ ID NO 88
<400> SEQUENCE: 88
```

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

```
<210> SEQ ID NO 111
<400> SEQUENCE: 111
000

<210> SEQ ID NO 112
<400> SEQUENCE: 112
000

<210> SEQ ID NO 113
<400> SEQUENCE: 113
000

<210> SEQ ID NO 114
<400> SEQUENCE: 114
000

<210> SEQ ID NO 115
<400> SEQUENCE: 115
000

<210> SEQ ID NO 116
<400> SEQUENCE: 116
000

<210> SEQ ID NO 117
<400> SEQUENCE: 117
000

<210> SEQ ID NO 118
<400> SEQUENCE: 118
000

<210> SEQ ID NO 119
<400> SEQUENCE: 119
000

<210> SEQ ID NO 120
<400> SEQUENCE: 120
000

<210> SEQ ID NO 121
<400> SEQUENCE: 121
000

<210> SEQ ID NO 122
```

```
<400> SEQUENCE: 122

000

<210> SEQ ID NO 123

<400> SEQUENCE: 123

000

<210> SEQ ID NO 124

<400> SEQUENCE: 124

000

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 125
ggaucaucuc aagucuuact t                                             21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
guaagacuug agaugaucct t                                             21

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
gcaaaggcgu gccaacucat                                               20

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
ugaguuggca cgccuuugcu u                                             21
```

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 129
cuauuuggag agaaaucgat                        20

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 130
ggaucaucuc aagucuuact t                      21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 131
guaagacuug agaugaucct t                      21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 132
ucgauuucuc uccaaauagu u                      21

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 133
gcaaaggcgu gccaacucat                        20

<210> SEQ ID NO 134

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 134
cuauuuggag agaaaucgat                                                    20

<210> SEQ ID NO 135
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
aacaguguuc uugcucuaua at                                                 22

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
ucgauuucuc uccaaauagu u                                                  21

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 137
gcaaaggcgu gccaacucat                                                    20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 138
gcaaaggcgu gccaacucat                                                    20

<210> SEQ ID NO 139
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 139
ugaguuggca cgccuuugcu u                                              21

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 140
cuauuuggag agaaaucgat                                                20

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
ucgauuucuc uccaaauagu u                                              21

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 142
aacaguguuc uugcucuaua at                                             22

<210> SEQ ID NO 143
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
uuauagagca agaacacugu uuu                                            23

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 144
cuauuuggag agaaaucgat                                                    20

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 145
aacaguguuc uugcucuaua at                                                 22

<210> SEQ ID NO 146
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 146
gcaaaggcgu gccaacucat cagcaaaggc gugccaacuc at                           42

<210> SEQ ID NO 147
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 147
gcaaaggcgu gccaacucat cagcaaaggc gugccaacuc atcagcaaag gcgugccaac        60
ucatcagcaa aggcgugcca acucat                                             86

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 148
gcaaaggcgu gccaacucat                                                    20

<210> SEQ ID NO 149
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Description of Combined DNA/RNA Molecule:
      Synthetic oligonucleotide

<400> SEQUENCE: 149
gcaaaggcgu gccaacucat cagcaaaggc gugccaacuc at                          42

<210> SEQ ID NO 150
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 150
gcaaaggcgu gccaacucat cagcaaaggc gugccaacuc atcagcaaag gcgugccaac       60
ucat                                                                    64

<210> SEQ ID NO 151
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 151
gcaaaggcgu gccaacucat cagcaaaggc gugccaacuc atcagcaaag gcgugccaac       60
ucatcagcaa aggcgugcca acucat                                            86

<210> SEQ ID NO 152
<211> LENGTH: 108
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 152
gcaaaggcgu gccaacucat cagcaaaggc gugccaacuc atcagcaaag gcgugccaac       60
ucatcagcaa aggcgugcca acucatcagc aaaggcgugc caacucat                   108

<210> SEQ ID NO 153
<211> LENGTH: 130
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 153
gcaaaggcgu gccaacucat cagcaaaggc gugccaacuc atcagcaaag gcgugccaac       60
ucatcagcaa aggcgugcca acucatcagc aaaggcgugc caacucatca gcaaaggcgu      120

```
gccaacucat                                                              130

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 154
caguguucuu gcucuauaat t                                                  21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 155
uuauagagca agaacacugt t                                                  21
```